United States Patent
Held et al.

(10) Patent No.: US 12,091,667 B2
(45) Date of Patent: *Sep. 17, 2024

(54) MOLECULAR SWITCHES

(71) Applicant: PRECIGEN, INC., Germantown, MD (US)

(72) Inventors: Mark Anton Held, Germantown, MD (US); Xinhua Zhao, Germantown, MD (US); Lily Yuin Chao, Germantown, MD (US); Na Trinh, Germantown, MD (US); James Kealey, Germantown, MD (US); Kevin Lee Dietzel, Germantown, MD (US)

(73) Assignee: PRECIGEN, INC., Germantown, MD (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/454,060

(22) Filed: Nov. 8, 2021

(65) Prior Publication Data

US 2022/0112506 A1    Apr. 14, 2022

Related U.S. Application Data

(62) Division of application No. 16/481,811, filed as application No. PCT/US2018/015925 on Jan. 30, 2018, now Pat. No. 11,198,877.

(60) Provisional application No. 62/588,985, filed on Nov. 21, 2017, provisional application No. 62/512,312, filed on May 30, 2017, provisional application No. 62/504,626, filed on May 11, 2017, provisional application No. 62/451,819, filed on Jan. 30, 2017.

(51) Int. Cl.

| | | |
|---|---|---|
| C12N 15/52 | (2006.01) | |
| C12N 1/20 | (2006.01) | |
| C12N 9/04 | (2006.01) | |
| C12N 9/10 | (2006.01) | |
| C12N 9/88 | (2006.01) | |
| C12N 15/74 | (2006.01) | |
| C12P 5/02 | (2006.01) | |
| C12P 7/00 | (2006.01) | |
| C12P 7/16 | (2006.01) | |
| C12P 7/18 | (2006.01) | |

(52) U.S. Cl.
CPC .............. *C12N 15/52* (2013.01); *C12N 1/20* (2013.01); *C12N 9/0006* (2013.01); *C12N 9/1022* (2013.01); *C12N 9/88* (2013.01); *C12N 15/74* (2013.01); *C12P 5/023* (2013.01); *C12P 7/16* (2013.01); *C12P 7/18* (2013.01); *C12Y 101/01304* (2013.01); *C12Y 202/01006* (2013.01); *C12Y 401/01004* (2013.01); *C12Y 401/01005* (2013.01)

(58) Field of Classification Search
CPC . C12N 15/74; C12N 15/52; C12P 7/16; C12P 5/023
See application file for complete search history.

(56) References Cited

U.S. PATENT DOCUMENTS

| | | |
|---|---|---|
| 9,267,158 B2 | 2/2016 | Coleman et al. |
| 2011/0008861 A1 | 1/2011 | Berry et al. |
| 2014/0273128 A1 | 9/2014 | Coleman et al. |

FOREIGN PATENT DOCUMENTS

| | | |
|---|---|---|
| WO | 2001073082 A2 | 3/2001 |
| WO | 2014/092562 A1 | 6/2014 |
| WO | 2014089436 A1 | 6/2014 |
| WO | 2015195972 A1 | 12/2015 |
| WO | 2018/200894 A1 | 11/2018 |

OTHER PUBLICATIONS

Vu et al., J. Bacteriol., 198:1250-1259 (2016).
Farhan et al., Appln. Environ. Microbiol., 81:7546-7552 (2015).
Skovran et al., J. Bacteriol., 193:6032-6038 (2011).
International Search Report issued in PCT/US2018/015925.
Written Opinion of the ISA issued in PCT/US2018/015925.
Kopke et al., Applied and Environmental Microbiology, 77: 5467-5475 (2011).
Campbell et al., Cell Calcium, 41: 97-106 (2006).
Chu et al., Journal of Bacteriology, 198:1317-1325 (2016).
Extended European Search Report, issued Dec. 10, 2020, in EP 18 74 4512.
Nguyen et al., Metab Eng (2018), 47:323-333.
Vecherskaya et al., Environmental Microbiology Reports (2009), 1: 442-449.

*Primary Examiner* — Maryam Monshipouri
(74) *Attorney, Agent, or Firm* — Barnes & Thornburg LLP; Gene J. Yao

(57) ABSTRACT

Genetically modified microorganisms that have the ability to convert carbon substrates into chemical products such as 2,3-BDO; 1,4-BDO; isobutyraldehyde; isobutanol; 1-butanol; n-butanol; ethanol; fatty alcohols; and fatty acid methyl ester are disclosed. For example, genetically modified methanotrophs that are capable of generating 2,3-BDO; 1,4-BDO; isobutyraldehyde; isobutanol; 1-butanol; n-butanol; ethanol; fatty alcohols; and fatty acid methyl ester at high titers from a methane source are disclosed. Methods of making these genetically modified microorganisms and methods of using them are also disclosed. These microorganisms and methods make use of molecular switches to regulate gene expression.

13 Claims, 13 Drawing Sheets
Specification includes a Sequence Listing.

MOLECULAR SWITCHES

CROSS-REFERENCE

This application is a division of U.S. Application Ser. No. 16/481,811, filed Jul. 29, 2019, (now U.S. Pat. No. 11,198,877), which claims the priority benefit of U.S. Provisional Application Nos. 62/451,819, filed Jan. 30, 2017; 62/504,626, filed May 11, 2017; 62/512,312, filed May 30, 2017; and 62/588,985, filed Nov. 21, 2017. Each of these applications is hereby incorporated by reference in its entirety.

SEQUENCE LISTING

This application contains a Sequence Listing, which has been submitted electronically in ASCII format and is hereby incorporated by reference in its entirety. The ASCII copy was created on Jan. 29, 2018, is named INX00448_SL.txt and is 250,402 bytes in size.

BACKGROUND OF THE INVENTION

Microbial fermentation of valued chemicals sometimes requires the ability to control the expression of certain genes to efficiently produce the valued chemicals. For example, the ability to reversibly "turn on" or "turn off" expression of certain genes during fermentation by adding substances directly to the fermentation tank can extremely beneficial and can speed the up the fermentation process while decreasing costs.

Here we describe microorganisms and methods that can be used to efficiently produce valued chemicals (e.g., multicarbon products). For example, we described genetically modified microorganisms and methods of fermenting them in such a way that the addition or removal of a particular substance can effectively and efficiently "switch" on or off certain genes, which can ultimately lead to valued chemical production.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

SUMMARY

Disclosed herein are methods of regulating gene expression using a molecular switch in genetically modified microorganisms that are capable of producing a desired organic compound from a carbon source, such as a single carbon containing hydrocarbon molecule such as methane. Various genetically modified microorganisms, vectors, and methods are disclosed throughout.

For example, disclosed herein is a genetically modified microorganism capable of converting a C1 carbon into a multicarbon product, where the microorganism comprises a heterologous gene under the control of a molecular switch.

In some cases, the molecular switch can be responsive to a sugar or rare earth metal. For example, if the molecular switch is responsive to a sugar, the sugar can be arabinose. The molecular switch can be responsive to arabinose at a concentration of at least 0.1 mM, e.g., 1 mM. In some cases, the molecular switch can be response to another type of sugar, isopropyl β-D-1-thiogalactopyranoside (IPTG). The molecular switch can be responsive to IPTG at a concentration of at least 1 µM e.g., 10 µM.

In some cases, the molecular switch can be responsive to a rare earth metal. The rare earth metal can be cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), yttrium (Y), or any combination thereof.

In some cases, the molecular switch is responsive to the rare earth metal cerium (Ce). In some cases, the molecular switch is responsive to cerium (Ce) at a concentration of at least 10 µM. In some cases, maximal response to cerium (Ce) can occur at a concentration of at least 70 µM.

In some cases, the molecular switch is responsive to the rare earth metal lanthanum (La). In some cases, the molecular switch is responsive to lanthanum (La) at a concentration of at least 0.5 µM. In some cases, maximal response to lanthanum (La) can occur at a concentration of at least 35 µM.

In some cases, the molecular switch is responsive to the rare earth metal praseodymium (Pr). In some cases, the molecular switch is responsive to praseodymium (Pr) at a concentration of at least 10 µM. In some cases, maximal response to praseodymium (Pr) can occur at a concentration of at least 140 µM.

In some cases, the molecular switch is responsive to the rare earth metal neodymium (Nd). In some cases, the molecular switch is responsive to neodymium (Nd) at a concentration of at least 10 µM. In some cases, maximal response to neodymium (Nd) can occur at a concentration of at least 70 µM.

In some cases, the expression of the heterologous gene is induced by the molecular switch. In some cases, the expression of the heterologous gene is repressed by the molecular switch. In some cases, the expression of the expression of the heterologous gene is reversed by dilution of the medium.

In some cases, the expression of the heterologous gene is repressed by at least 50%. In some cases, the expression of the heterologous gene is repressed by at least 75%. In some cases, the expression of the heterologous gene is repressed by at least 90%. In some cases, the expression of the heterologous gene is de-repressed by dilution of the medium. In some cases, the dilution is at least a 1.1× dilution.

The genetically modified microorganism can be, in some instances, a methanotroph. The methanotroph can be from the genera *Methylobacter*, *Methylomicrobium*, *Methylomonas*, *Methylocaldum*, *Methylococcus*, *Methylosoma*, *Methylosarcina*, *Methylothermus*, *Methylohalobius*, *Methylogaea*, *Methylovulum*, *Crenothrix*, *Clonothrix*, *Methylosphaera*, *Methylocapsa*, *Methylocella*, *Methylosinus*, *Methylocystis*, or *Methyloacidophdum*. For example, the methanotroph is a *Methylococcus* or more specifically the methanotroph is a *Methylococcus capsulatus*.

In some cases, the genetically modified microorganism produces a multicarbon product that is 2,3-butanediol; 1,4-butanediol; isobutyraldehyde; isobutanol; 1-butanol; n-butanol; ethanol; fatty (or aliphatic long chain) alcohols; fatty acid methyl esters, or any combination thereof.

When the genetically modified microorganism produces a multicarbon product that is 2,3-butanediol, the genetically modified microorganism can comprises a heterologous gene under the control of a molecular switch, where the heterologous gene is acetolactate synthase, alpha-acetolactate decarboxylase, acetoin reductase, or any combination thereof. Should an acetolactate synthase be used, it can be in some cases encoded by a polynucleotide that is substantially similar to any one of SEQ ID NOs: 2, 4, or 6. Should an alpha-acetolactate decarboxylase be used, it can be in some cases encoded by a polynucleotide that is substantially similar to SEQ ID NO: 8 or 10. Should an acetoin reductase be used, it can be in some cases encoded by a polynucleotide that is substantially similar to SEQ ID NO: 12.

When the genetically modified microorganism produces a multicarbon product that is 1,4-butanediol, the genetically modified microorganism can comprises a heterologous gene under the control of a molecular switch, where the heterologous gene is succinyl-CoA synthetase (sucC), CoA-dependent succinate semialdehyde dehydrogenase (sucD), 4-hydroxybutyrate dehydrogenase (4hbD), 4-hydroxybutyryl-CoA transferase (cat2), aldehyde dehydrogenase (ald), alcohol dehydrogenase (adh), or any combination thereof. Should a succinyl-CoA synthetase be used, it can be in some cases encoded by a polynucleotide that is substantially similar to SEQ ID NO: 18. Should a CoA-dependent succinate semialdehyde dehydrogenase be used, it can be in some cases encoded by a polynucleotide that is substantially similar to SEQ ID NO: 20. Should a 4-hydroxybutyrate dehydrogenase be used, it can be in some cases encoded by a polynucleotide that is substantially similar to SEQ ID NO: 22. Should a 4-hydroxybutyryl-CoA transferase be used, it can be in some cases encoded by a polynucleotide that is substantially similar to SEQ ID NO: 24. Should an aldehyde dehydrogenase be used, it can be in some cases encoded by a polynucleotide that is substantially similar to SEQ ID NO: 26. Should an alcohol dehydrogenase be used, it can be in some cases encoded by a polynucleotide that is substantially similar to SEQ ID NO: 28.

When the genetically modified microorganism produces a multicarbon product that is isobutyraldehyde, the genetically modified microorganism can comprises a heterologous gene under the control of a molecular switch, where the heterologous gene is acetolactate synthase (AlsS); ketol-acid reductoisomerase (KARI); dihydroxy-acid dehydratase (DHAD); 2-keto acid decarboxylase (KDC), or any combination thereof. Should an acetolactate synthase be used, it can be in some cases encoded by a polynucleotide that is substantially similar to SEQ ID NO: 30. Should a ketol-acid reductoisomerase be used, it can be in some cases encoded by a polynucleotide that is substantially similar to SEQ ID NO: 32. Should a dihydroxy-acid dehydratase be used, it can be in some cases encoded by a polynucleotide that is substantially similar to SEQ ID NO: 34. Should a 2-keto acid decarboxylase be used, it can be in some cases encoded by a polynucleotide that is substantially similar to any one of SEQ ID NOs: 36, 38, 40, 42, 44, 46 or 48.

When the genetically modified microorganism produces a multicarbon product that is isobutanol, the genetically modified microorganism can comprises a heterologous gene under the control of a molecular switch, where the heterologous gene is acetolactate synthase (AlsS); ketol-acid reductoisomerase (KARI); dihydroxy-acid dehydratase (DHAD); 2-keto acid decarboxylase (KDC), alcohol dehydrogenase (ADH) or any combination thereof. Should an acetolactate synthase be used, it can be in some cases encoded by a polynucleotide that is substantially similar to SEQ ID NO: 30. Should a ketol-acid reductoisomerase be used, it can be in some cases encoded by a polynucleotide that is substantially similar to SEQ ID NO: 32. Should a dihydroxy-acid dehydratase be used, it can be in some cases encoded by a polynucleotide that is substantially similar to SEQ ID NO: 34. Should a 2-keto acid decarboxylase be used, it can be in some cases encoded by a polynucleotide that is substantially similar to any one of SEQ ID NOs: 36, 38, 40, 42, 44, 46 or 48. Should an alcohol dehydrogenase be used, it can be in some cases encoded by a polynucleotide that is substantially similar to any one of SEQ ID NO: 50, 52, 54, 56 or 58.

When the genetically modified microorganism produces a multicarbon product that is 1-butanol, the genetically modified microorganism can comprises a heterologous gene under the control of a molecular switch, where the heterologous gene is L-threonine ammonia lyase, 2-ethylmalate synthase, isopropylmalate isomerase, 2-ketoacid decarboxylase, alcohol dehydrogenase, or any combination thereof. Should an L-threonine ammonia lyase be used, it can be in some cases encoded by a polynucleotide that is substantially similar to SEQ ID NO: 60. Should a 2-ethylmalate synthase be used, it can be in some cases encoded by a polynucleotide that is substantially similar to SEQ ID NO: 62. Should an isopropylmalate isomerase be used, it can be in some cases encoded by a polynucleotide that is substantially similar to SEQ ID NO: 64 or 66. Should a 2-ketoacid decarboxylase be used, it can be in some cases encoded by a polynucleotide that is substantially similar to any one of SEQ ID NOs: 36, 38, 40, 42, 44, 46 or 48. Should an alcohol dehydrogenase be used, it can be in some cases encoded by a polynucleotide that is substantially similar to any one of SEQ ID NOs: 50, 52, 54, 56 or 58.

When the genetically modified microorganism produces a multicarbon product that is ethanol, the genetically modified microorganism can comprises a heterologous gene under the control of a molecular switch, where the heterologous gene is pyruvate decarboxylase (PDC), alcohol dehydrogenase (ADH), or any combination thereof. Should a pyruvate decarboxylase be used, it can be in some cases encoded by a polynucleotide that is substantially similar to SEQ ID NO: 68. Should an alcohol dehydrogenase be used, it can be in some cases encoded by a polynucleotide that is substantially similar to SEQ ID NO: 70.

When the genetically modified microorganism produces a multicarbon product that is fatty alcohol, the genetically modified microorganism can comprises a heterologous gene under the control of a molecular switch, where the heterologous gene is fatty-acyl-CoA reductase (FAR). In these cases, the fatty-acyl-CoA reductase (FAR) can be encoded by a polynucleotide that is substantially similar to SEQ ID NO: 72

When the genetically modified microorganism produces a multicarbon product that is fatty acid methyl ester, the genetically modified microorganism can comprises a heterologous gene under the control of a molecular switch, where the heterologous gene is a WES polypeptide. In these cases, the WES polypeptide can be encoded by a polynucleotide that is substantially similar to any one of SEQ ID NOs: 74, 76, 78, 80, or 82.

In some cases, the C1 carbon is carbon monoxide (CO), carbon dioxide ($CO_2$), methane ($CH_4$), or any combination thereof.

Further disclosed herein is a vector comprising a promoter driving the expression of a gene, where the promoter is responsive to a rare earth metal and is active in a methanotroph.

The rare earth metal can be any disclosed throughout, such as Ce, Dy, Er, Eu, Gd, Ho, La, Lu, Nd, Pr, Pm, Sm, Sc, Tb, Tm, Yb, Y, or any combination thereof.

In some cases, the rare earth metal is cerium. In these cases, the promoter can be responsive to cerium (Ce) at a concentration of at least 10 µM. In some case, the rare earth metal is lanthanum (La). In these cases, the promoter can be responsive to lanthanum (La) at a concentration of at least 0.5 µM. In some case, the rare earth metal is praseodymium (Pr). In these cases, the promoter can be responsive to praseodymium (Pr) at a concentration of at least 10 µM. In some case, the rare earth metal is neodymium (Nd). In these cases, the promoter can be responsive to neodymium (Nd) at a concentration of at least 10 µM.

In some cases, the vector can further comprising a gene. In some cases, the gene can be acetolactate synthase, alpha-acetolactate decarboxylase, acetoin reductase, or any combination thereof. In other cases, the gene can be succinyl-CoA synthetase (sucC), CoA-dependent succinate semialdehyde dehydrogenase (sucD), 4-hydroxybutyrate dehydrogenase (4hbD), 4-hydroxybutyryl-CoA transferase (cat2), aldehyde dehydrogenase (ald), alcohol dehydrogenase (adh), or any combination thereof. In some cases, the gene can be acetolactate synthase (AlsS); ketol-acid reductoisomerase (KARI); dihydroxy-acid dehydratase (DHAD); 2-keto acid decarboxylase (KDC), or any combination thereof. In some cases, the gene can be acetolactate synthase (AlsS); ketol-acid reductoisomerase (KARI); dihydroxy-acid dehydratase (DHAD); 2-keto acid decarboxylase (KDC), alcohol dehydrogenase (ADH), or any combination thereof. In some cases, the gene can be L-threonine ammonia lyase, 2-ethylmalate synthase, isopropylmalate isomerase, 2-ketoacid decarboxylase, alcohol dehydrogenase, or any combination thereof. In some cases, the gene can be pyruvate decarboxylase (PDC), alcohol dehydrogenase (ADH), or any combination thereof. In some cases, the gene can be fatty-acyl-CoA reductase (FAR). In some cases, the gene can be a WES polypeptide.

Additionally disclosed is a method of making a genetically modified microorganism capable of converting a C1 carbon to a multicarbon product comprising transforming a microorganism with the vector as described throughout. In some of these cases, the genetically modified microorganism is capable of producing 2,3-butanediol; 1,4-butanediol; isobutyraldehyde; isobutanol; 1-butanol; n-butanol; ethanol; fatty (or aliphatic long chain) alcohols; and/or fatty acid methyl esters.

Further disclosed herein is a method of making a multicarbon product from a C1 carbon comprising (a) contacting the genetically modified microorganism as described throughout with a C1 carbon; and (b) growing the microorganism to produce the multicarbon product. In some cases, the multicarbon product is 2,3-butanediol; 1,4-butanediol; isobutyraldehyde; isobutanol; 1-butanol; n-butanol; ethanol; fatty (or aliphatic long chain) alcohols; and/or fatty acid methyl esters. In some cases, the C1 carbon is methane. In some cases, the multicarbon product produced is substantially pure. In some cases, the method can further comprising recovering the multicarbon product. In some cases, the method can further comprise contacting the multicarbon product with a catalyst to produce a different product. In some cases, the multicarbon product can be 2,3-BDO. In some cases, the different product can be butadiene. In some cases, the catalyst is a $SiO_2$-supported cesium dihydrogen phosphate ($CsH_2PO_4$) catalyst. In some cases, the different product is methyl ethyl ketone. In some cases, the catalyst is a solid acid catalyst.

In some cases, the method can further comprise contacting the microorganism with a sugar that can activate or repress a molecular switch. The sugar can be within media. In some cases, the sugar can be arabinose. If arabinose is used, the arabinose can be present at a concentration of at least 0.1, e.g., 6.6 mM. In some cases, the sugar can be isopropyl β-D-1-thiogalactopyranoside (IPTG). When IPTG is used, it can be present at a concentration of at least 1 µM, e.g., 10 µM.

In some cases, the method can further comprise contacting the microorganism with media having a rare earth metal that can activate or repress a molecular switch. The rare earth metal can be any disclosed throughout, such as Ce, Dy, Er, Eu, Gd, Ho, La, Lu, Nd, Pr, Pm, Sm, Sc, Tb, Tm, Yb, Y, or any combination thereof. In some cases, the rare earth metal is cerium (Ce). When cerium is the rare earth metal, it can be present at a concentration of at least 10 µM. In some cases, the rare earth metal is lanthanum (La). When lanthanum (La) is the rare earth metal, it can be present at a concentration of at least 0.5 µM. When praseodymium (Pr) is the rare earth metal, it can be present at a concentration of at least 10 µM. When neodymium (Nd) is the rare earth metal, it can be present at a concentration of at least 10 µM.

Also disclosed herein is a method of altering the expression of a gene or set of genes within a microorganism comprising contacting the microorganism with a rare earth metal, where the gene or set of genes are comprised in a heterologous polynucleotide having a molecular switch that is responsive to the rare earth metal. In some cases, the gene or set of genes is acetolactate synthase, alpha-acetolactate decarboxylase, acetoin reductase, or any combination thereof. In some cases, the gene or set of genes is succinyl-CoA synthetase (sucC), CoA-dependent succinate semialdehyde dehydrogenase (sucD), 4-hydroxybutyrate dehydrogenase (4hbD), 4-hydroxybutyryl-CoA transferase (cat2), aldehyde dehydrogenase (ald), alcohol dehydrogenase (adh), or any combination thereof. In some cases, the gene or set of genes is acetolactate synthase (AlsS); ketol-acid reductoisomerase (KARI); dihydroxy-acid dehydratase (DHAD); 2-keto acid decarboxylase (KDC), or any combination thereof. In some cases, the gene or set of genes is acetolactate synthase (AlsS); ketol-acid reductoisomerase (KARI); dihydroxy-acid dehydratase (DHAD); 2-keto acid decarboxylase (KDC); alcohol dehydrogenase (ADH), or any combination thereof. In some cases, the gene or set of genes is L-threonine ammonia lyase, 2-ethylmalate synthase, isopropylmalate isomerase, 2-ketoacid decarboxylase, alcohol dehydrogenase, or any combination thereof. In some cases, the gene or set of genes is pyruvate decarboxylase (PDC), alcohol dehydrogenase (ADH), or any combination thereof. In some cases, the gene is fatty-acyl-CoA reductase (FAR). In some cases, the gene is a WES polypeptide.

The rare earth metal used in the method can be any disclosed throughout, such as Ce, Dy, Er, Eu, Gd, Ho, La, Lu, Nd, Pr, Pm, Sm, Sc, Tb, Tm, Yb, Y, or any combination thereof. In some cases, the rare earth metal is cerium (Ce). When cerium is the rare earth metal, it can be present at a concentration of at least 10 µM. In some cases, the rare earth metal is lanthanum (La). When lanthanum (La) is the rare earth metal, it can be present at a concentration of at least 0.5 µM. When praseodymium (Pr) is the rare earth metal, it can be present at a concentration of at least 10 µM. When neodymium (Nd) is the rare earth metal, it can be present at a concentration of at least 10 μM.

The molecular switch used in the method can comprise pBAD, PmxaF, pTRC, or pXoxF.

In some cases, the expression of the gene or set of genes is reduced upon contact with the rare earth metal. In some cases, the expression of the gene or set of genes is activated upon contact with the rare earth metal.

In some cases, the method further comprises diluting the rare earth metal. In some cases, the microorganism is in contact with the rare earth metal at all times before diluting the rare earth metal. For example, the microorganism is pre-cultured with the rare earth metal.

BRIEF DESCRIPTION OF THE DRAWINGS

FIG. 8A demonstrates acetoin and 2,3-BDO production of 21 different strains after 96 hours following dilution of lanthanum containing media. The strains and genotypes are listed in Table 1 and 2. For strains 1 to 21, production titers were measured 96 hours after a 1:10 (10×) dilution of the culture into fresh medium whereas for strains 22 to 42 production titers were measured after a 1:50 (50×) dilution. Strains 22 to 27 produced high levels of 2,3-BDO, compared to strains subjected less dilution prior to the 2,3-BDO production phase. FIG. 8B demonstrates acetoin and 2,3-BDO production of 21 different strains after 120 hours following dilution of lanthanum containing media. The strains and genotypes of the stains are listed in Table 1 and 2. For strains 1 to 21, production titers were measured 120 hours after a 1:10 (10×) dilution of the culture into fresh medium, whereas for strains 22 to 42 production titers were measured after a 1:50 (50×) dilution. Strains 22 to 27 produced high levels of 2,3-BDO, compared to strains subjected to less dilution prior to the 2,3-BDO production phase.

DETAILED DESCRIPTION OF THE INVENTION

Figure 1:
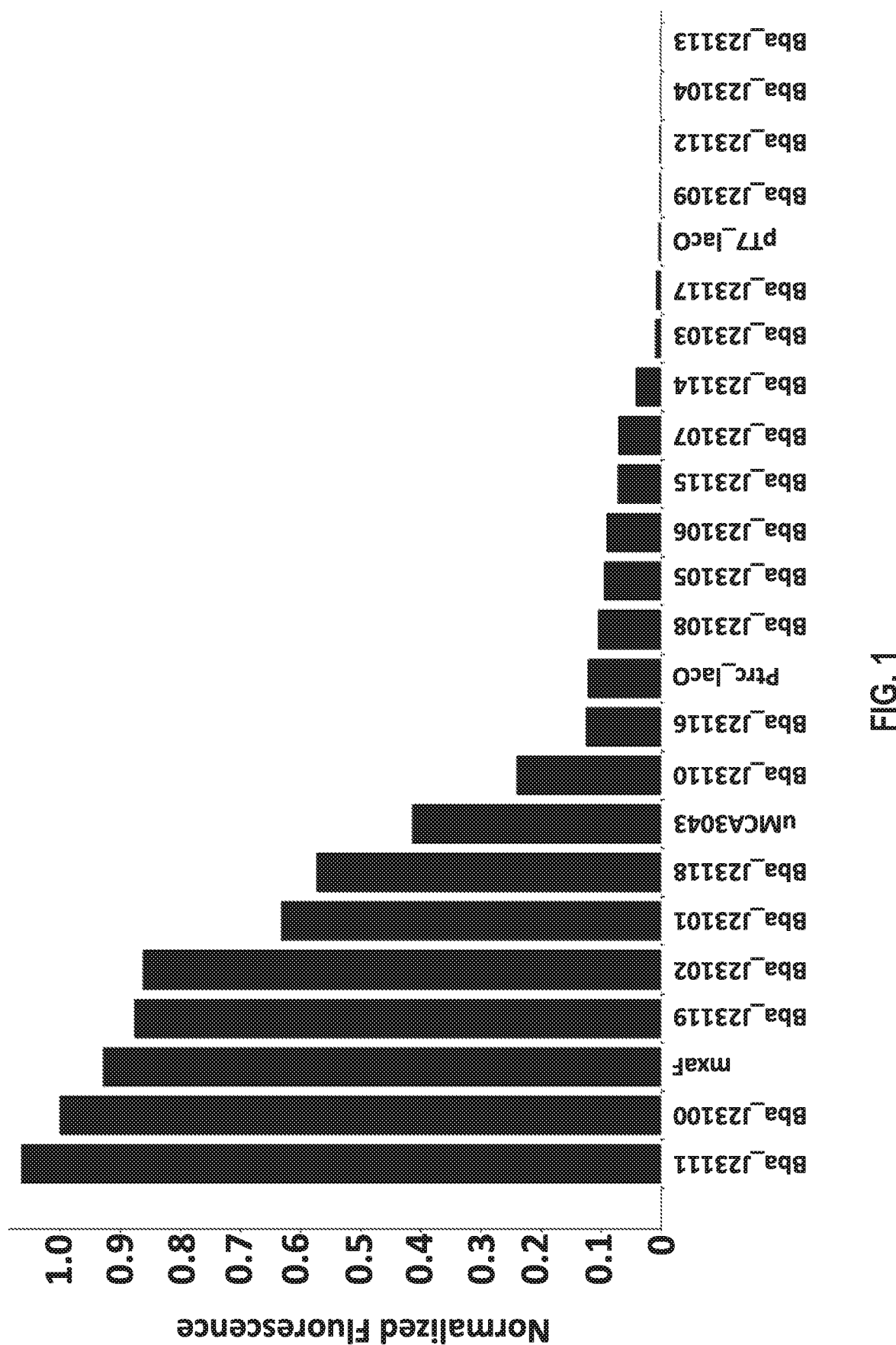
FIG. 1 shows the expression of many promoters within a methanotroph, including but not limited to the promoter pMxaF and J series promoters.

Generally, fermentation using a microorganism that produces a valued chemical, whether naturally occurring or genetically modified, progresses in two stages. The first stage is known as the growth stage. In this growth stage, the microorganism produces minimal valued chemical or in some cases, does not produce any valued chemical at all. The great majority or all of the microbe's energy is devoted to the cellular reproduction mechanism, e.g. cell division. In this case, very few if any, genes that are used to produce the valued chemical are expressed or should be expressed. After enough cells are produced and are matured, the second stage is turned on. This second stage is the stage when the valued chemical is produced. In some cases, the turning on of the second stage naturally occurs after the microorganism is within conditions that promotes the production of the valued chemical. For genetically modified microorganisms, the turning on of the second stage can be "forcefully" induced as-needed and expression of genes can be regulated by a molecular switch.

As discussed, aspects of the invention include molecular switches that can be used to repress or activate the expression of genes within a microorganism. In some cases, the microorganism is genetically modified to produce desired valued chemicals that it would not normally produce or produce naturally producing chemicals but at an increased level. Also disclosed are the microorganisms that comprise the molecular switches, methods of using the microorganisms and/or the molecular switches, as well as making the microorganism and/or molecular switches.

Before the present invention is described in greater detail, it is to be understood that this invention is not limited to particular cases described, as such can, of course, vary. It is also to be understood that the terminology used herein is for the purpose of describing particular cases only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

I. Definitions

The term "switch" and its grammatical equivalents as used herein can mean a regulatory unit of a gene or genes that is capable of responding to a particular stimulus to either induce or repress expression. For example, switches can include regulatory units that respond to sugar (e.g., arabinose) or rare earth metals (e.g., lanthanum).

The term "rare earth metal" and its grammatical equivalent as used herein can mean any chemical element defined as such by the IUPAC, which can include but is not limited to cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value. In some cases, the numerical disclosed throughout can be "about" that numerical value even without specifically mentioning the term "about."

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The term "genetic modification" or "genetically modified" and their grammatical equivalents as used herein can refer to one or more alterations of a nucleic acid, e.g., the nucleic acid within a microorganism's genome. For example, genetic modification can refer to alterations, additions, and/or deletion of nucleic acid (e.g., whole genes or fragments of genes).

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "promoter" and its grammatical equivalents as used herein can refer to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. Some examples of promoters that can be used include but are not limited to pXoxF, pMxaF, pTRC, J23111, J12100, J23102, pBAD, J23110, lacO, J23116, J23106, J23105, J23108, J23107, J23115, J23114, J23118, J23104, J23101, J23119, and uMCA3034.

The term "operably linked" and its grammatical equivalents as used herein can refer to the association of nucleic acid sequences on a single polynucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "codon optimized" and its grammatical equivalents as used herein insofar as it refers to genes or coding regions of nucleic acid molecules (or open reading frames) for transformation of various hosts, can refer to the alteration of codons in the gene or coding regions of the nucleic acid molecules to reflect the typical codon usage of the host organism without altering the polypeptide encoded by the DNA.

The term "open reading frame" ("ORF") and its grammatical equivalents as used herein can refer to a polynucleic acid or nucleic acid sequence (whether naturally occurring, non-naturally occurring, or synthetic) comprising an uninterrupted reading frame consisting of (i) an initiation codon, (ii) a series of two (2) of more codons representing amino acids, and (iii) a termination codon, the ORF being read (or translated) in the 5' to 3' direction.

The term "operon" and its grammatical equivalents as used herein can refer to two or more genes which are transcribed as a single transcriptional unit from a common promoter. In certain cases, the genes, polynucleotides or ORFs comprising the operon are contiguous. It is understood that transcription of an entire operon can be modified (i.e., increased, decreased, or eliminated) by modifying the common promoter. Alternatively, any gene, polynucleotide or ORF, or any combination thereof in an operon can be modified to alter the function or activity of the encoded polypeptide. The modification can result in an increase or a decrease in the activity or function of the encoded polypeptide. Further, the modification can impart new activities on the encoded polypeptide.

The term "vector" and its grammatical equivalents as used herein can refer to any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host microorganism. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

As used herein, the terms "C1 carbon," "C1-carbon substrates" and their grammatical equivalents can refer to any organic compound that contains a single carbon atom. Examples include, but are not limited to, carbon monoxide (CO), methane ($CH_4$), and carbon dioxide ($CO_2$).

As used herein, the term "fermentation" or "fermentation process," and its grammatical equivalents, can be a process in which a host cell is cultivated in a culture medium containing raw materials, such as feedstock and nutrients, wherein the cell converts raw materials, such as a feedstock, into desirable end products, such as multicarbon products.

As used herein, the term "substantially pure" and its grammatical equivalents can refer to a particular substance that does not contain a majority of another substance. For example, "substantially pure product" can mean at least 90% of that product. In some instances, "substantially pure product" can mean at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, or 99.9999% of that product. For example, substantially pure product can mean at least 70% of the product. In some cases, substantially pure product can mean at least 75% of the product. In some cases, substantially pure product can mean at least 80% of the product. In some cases, substantially pure product can mean at least 85% of the product. In some cases, substantially pure product can mean at least 90% of the product. In some cases, substantially pure product can mean at least 91% of the product. In some cases, substantially pure product can mean at least 92% of the product. In some cases, substantially pure product can mean at least 93% of the product. In some cases, substantially pure product can mean at least 94% of the product. In some cases, substantially pure product can mean at least 95% of the product. In some cases, substantially pure product can mean at least 96% of the product. In some cases, substantially pure product can mean at least 97% of the product. In some cases, substantially pure product can mean at least 98% of the product. In some cases, substantially pure product can mean at least 99% of the product.

As used herein, the term "heterologous" and its grammatical equivalents can mean derived from a different species. For example, a "heterologous gene" can mean a gene that is from a species different than the reference species. For example, a methanotroph comprising a "heterologous gene" comprises a gene that is not from the same methanotroph. The gene can be from a different microorganism such as yeast or from a different species such as a different methanotroph species.

As used herein, the term "substantially similar" and its grammatical equivalents, when used in reference to the similarity between a sequence and a reference sequence, means that the sequences are at least 50% (but not 100%) identical. In some cases, the sequences are 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.9%, 99.99%, 99.999%, or 99.9999% identical. In some cases, the term substantially similar refers to a sequence that is at least 50% identical. In some instances, the term substantially similar refers to a sequence that is 55% identical. In some instances, the term substantially similar refers to a sequence that is 60% identical. In some instances, the term substantially similar refers to a sequence that is 65% identical. In some instances, the term substantially similar refers to a sequence that is 70% identical. In some instances, the term substantially similar refers to a sequence that is 75% identical. In some instances, the term substantially similar refers to a sequence that is 80% identical. In other instances, the term substantially similar refers to a sequence that is 81% identical. In other instances, the term substantially similar refers to a sequence that is 82% identical. In other instances, the term substantially similar refers to a sequence that is 83% identical. In other instances, the term substantially similar refers to a sequence that is 84% identical. In other instances, the term substantially similar refers to a sequence that is 85% identical. In other instances, the term substantially similar refers to a sequence that is 86% identical. In other instances, the term substantially similar refers to a sequence that is 87% identical. In other instances, the term substantially similar refers to a sequence that is 88% identical. In other instances, the term substantially similar refers to a sequence that is 89% identical. In some instances, the term substantially similar refers to a sequence that is 90% identical. In some instances, the term substantially similar refers to a sequence that is 91% identical. In some instances, the term substantially similar refers to a sequence that is 92% identical. In some instances, the term substantially similar refers to a sequence that is 93% identical. In some instances, the term substantially similar refers to a sequence that is 94% identical. In some instances, the term substantially similar refers to a sequence that is 95% identical. In some instances, the term substantially similar refers to a sequence that is 96% identical. In some instances, the term substantially similar refers to a sequence that is 97% identical. In some instances, the term substantially similar refers to a sequence that is 98% identical. In some instances, the term substantially similar refers to a sequence that is 99% identical. In some instances, the term substantially similar refers to a sequence that is 100% identical. To determine the percentage of identity between two sequences, the two sequences are aligned, using, for example, the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids/nucleotides is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919) using a gap opening penalty of 10 and a gap extension penalty of 0.1, so that the highest order match obtained between two sequences wherein at least 50% of the total length of one of the two sequences is involved in the alignment.

As will be apparent to those of skill in the art upon reading this disclosure, each of the individual cases described and illustrated herein has discrete components and features which may be readily separated from or combined with the features of any of the other several cases without departing from the scope or spirit of the present invention. Any recited method can be carried out in the order of events recited or in any other order which is logically possible.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

II. Genetically Modified Microorganisms and Methods of Making the Same

The present disclosure is directed, in part, to genetically modified microorganisms that have dramatically improved ability to produce desired chemicals compared to its wild-type counterpart. For example, the genetically modified microorganisms can produce valuable chemicals, including but not limited to, 2,3-butanediol ("2,3-BDO"); 1,4-butanediol ("1,4-BDO"); isobutyraldehyde; isobutanol; 1-butanol; n-butanol; ethanol; fatty (or aliphatic long chain) alcohols; and fatty acid methyl esters. In some cases, the fermentation titers of the desired valuable chemicals are orders of magnitude higher than what could be normally produced. In some instances, the microorganisms that do not naturally produce a specific valuable chemical have been genetically modified to synthesize the valuable chemical. The use of these molecular switches allow for direct control of gene expression at a given time. This control of gene expression by using molecular switches can lead to increased levels of valuable chemical titer production compared to microorganism that do not have these molecular switches.

Microorganisms

In some cases, the microorganisms can use C1 carbon substrates, such as, CO, $CO_2$, and $CH_4$, to synthesize a desired end product (e.g., a multicarbon product). This, however, does not mean that these microorganisms use solely C1 carbons. Some of the microorganisms can be made to utilize additional carbon substrates, including carbon substrates that the microorganism naturally uses. For example, if the microorganism naturally uses sugar for carbon substrates, this microorganism can be made to utilize a different carbon source such as a C1 carbon.

The microorganisms can be a prokaryote or a eukaryote. In some cases, for example, the microorganisms can be bacteria, yeast, or algae.

Microorganisms that can convert C1 carbon substrates into desired products include those capable of using natural gas as a carbon substrate. For example, the microorganism can use methane contained within the natural gas a as a carbon source to make such desired products. Such microorganisms can include methanotrophs. Methanotrophs that can be particularly useful include those from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis, Methyloacidophilum*, or any combinations thereof. In some cases, the methanotroph is from the genus *Methylococcus*. In one instance, the methanotroph can be a methanotroph from the species *Methylococcus capsulatus*.

Some microorganisms are capable of using $CO_2$ as a substrate. Such microorganisms include methanogens. Microorganisms that are capable of using $CO_2$ as a substrate can contain chlorophyll. Examples thereof include algae and cyanobacteria.

Some microorganisms are capable of using CO as a substrate. Examples include anaerobic microorganisms such as *Clostridium*. These microorganism can be genetically modified so as to make substantial amounts of desired valued chemical products.

Nucleic Acids Encoding for Enzymes

Certain enzymes can be used to generate valued chemical products. Some valued chemical products can include, but are not limited to, 2,3-butanediol ("2,3-BDO"); 1,4-butanediol ("1,4-BDO"); isobutyraldehyde; isobutanol; 1-butanol (aka n-butanol); ethanol; fatty (or aliphatic long chain) alcohols; and fatty acid methyl ester. In some cases, the polynucleotide of the promoters encoding these enzymes can be altered so that they are responsive to the substances described herein (e.g., sugars and rare earth metals) and therefore can function as a molecular switch.

2,3-Butanediol ("2,3-BDO")

In some instances, polynucleotides encoding enzymes of the 2,3-BDO pathway can be used. For example, the microorganism can contain (either endogenously or heterologous) one or more polynucleotides encoding for an acetolactate synthase (AlsS), alpha-acetolactate decarboxylase (budA), and/or acetoin reductase. One or more of the polynucleotides can be native to the microorganism. In some cases, one or more of the polynucleotides can be heterologous to the microorganism.

In some cases, the acetolactate synthase can be encoded by a polynucleotide that is substantially similar to any one of SEQ ID NOs: 2, 4, or 6.

In some cases, the alpha-acetolactate decarboxylase can be encoded by a polynucleotide that is substantially similar to SEQ ID NO: 8 or 10.

In some cases, the acetoin reductase can be encoded by a polynucleotide that is substantially similar to any one of SEQ ID NOs: 12, 14, or 16. In some cases, the acetoin reductase can be NADPH-dependent. In some cases, the acetoin reductase can be NADH-dependent.

In order to engineer a microorganism that can produce 2,3-BDO, one or more genes (e.g., heterologous genes) can be transformed or transfected into the microorganism, either transiently or stably. In some cases, one or more of these genes can be episomally expressed. In some cases, one of more of these genes can be integrated into the genome of the microorganism. In some cases, one or more of these genes be can be episomally expressed whereas one or more of these genes can be integrated into the genome of the microorganism. In some cases, the engineered microorganism can utilize one or more of the following enzymes: (i) acetolactate synthase, (ii) alpha-acetolactate decarboxylase, and/or (iii) acetoin reductase. Acetolactate synthase (encoded by the gene AlsS) converts two molecules of pyruvate into 2-acetolactate. Alpha-acetolactate decarboxylase (encoded by the gene BudA) converts 2-acetolactate into acetoin. Acetoin reductase (encoded by the gene ButA) converts acetoin into 2,3-BDO using NADPH or NADH as a reduced cofactor. Acetoin reductases that use NADPH as a cofactor are referred to as "NADPH-dependent acetoin reductase(s)." Acetoin reductases that use NADH as a cofactor are referred to as "NADH-dependent acetoin reductase(s)."

Described herein are methods of making microorganisms used to make 2,3-BDO from a C1 carbon (e.g., methane). In some cases, the microorganism herein can be transformed with a gene encoding one or more of the following enzymes: (i) acetoin reductase (NADPH-dependent and/or NADH-dependent); (ii) alpha-acetolactate decarboxylase; and/or (iii) acetolactate synthase (AlsS). For example, the microorganism can be transformed with a gene encoding a NADPH- or NADH-dependent acetoin reductase. As another example, the microorganism can be transformed with a gene encoding an alpha-acetolactate decarboxylase. As yet another example, the microorganism can be transformed with a gene encoding an acetolactate synthase. These genes can be heterologous to the microorganism. In some cases, these genes can be episomally expressed, or integrated into the genome of the microorganism (e.g., through the use of an integration vector), or any combination of thereof.

In some cases, the microorganism can be transformed with two or more genes such as those encoding NADPH- and/or NADH-dependent acetoin reductase and alpha-acetolactate decarboxylase. As another example, the microorganism can also be transformed with genes encoding NADPH- or NADH-dependent acetoin reductase and acetolactate synthase. As yet another example, the microorganism can be transformed with genes encoding an alpha-acetolactate decarboxylase and acetolactate synthase. One or more of the genes can be heterologous to the microorganism. In some cases, these genes can be episomally expressed, or integrated into the genome of the microorganism, or any combination of thereof.

In some cases, the microorganism can be transformed with at least three or more genes such as those encoding NADPH- and/or NADH-dependent acetoin reductase, alpha-acetolactate decarboxylase, and acetolactate synthase. One or more of the genes can be heterologous to the microorganism. In some cases, these genes can be episomally expressed, or integrated into the genome of the microorganism, or any combination of thereof.

The gene encoding the NADPH-dependent acetoin reductase can be from a bacteria (e.g., a gram positive or gram negative bacterium). The bacterium can be from the genus *Clostridium*, for example, *Clostridium autoethanogenum*.

The NADPH-dependent acetoin reductase can comprise an amino acid sequence that is substantially similar to SEQ ID NO: 11. For example, the NADPH-dependent acetoin reductase may comprise an amino acid sequence that is at least 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 11. In some cases, the NADPH-dependent acetoin reductase can comprise an amino acid sequence that is at least 60% identical to SEQ ID NO: 11. In some cases, the NADPH-dependent acetoin reductase can comprise an amino acid sequence that is at least 65% identical to SEQ ID NO: 11. In some cases, the NADPH-dependent acetoin reductase can comprise an amino acid sequence that is at least 70% identical to SEQ ID NO: 11. In some cases, the NADPH-dependent acetoin reductase can comprise an amino acid sequence that is at least 75% identical to SEQ ID NO: 11. In some cases, the NADPH-dependent acetoin reductase can comprise an amino acid sequence that is at least 80% identical to SEQ ID NO: 11. In some cases, the NADPH-dependent acetoin reductase can comprise an amino acid sequence that is at least 85% identical to SEQ ID NO: 11. In some cases, the NADPH-dependent acetoin reductase can comprise an amino acid sequence that is at least 90% identical to SEQ ID NO: 11. In some cases, the NADPH-dependent acetoin reductase can comprise an amino acid sequence that is at least 91% identical to SEQ ID NO: 11. In some cases, the NADPH-dependent acetoin reductase can comprise an amino acid sequence that is at least 92% identical to SEQ ID NO: 11. In some cases, the NADPH-dependent acetoin reductase can comprise an amino acid sequence that is at least 93% identical to SEQ ID. NO: 11. In some cases, the NADPH-dependent acetoin reductase can comprise an amino acid sequence that is at least 94% identical to SEQ ID NO: 11. In some cases, the NADPH-dependent acetoin reductase can comprise an amino acid sequence that is at least 95% identical to SEQ ID NO: 11. In some cases, the NADPH-dependent acetoin reductase can comprise an amino acid sequence that is at least 96% identical to SEQ ID NO: 11. In some cases, the NADPH-dependent acetoin reductase can comprise an amino acid sequence that is at least 97% identical to SEQ ID NO: 11. In some cases, the NADPH-dependent acetoin reductase can comprise an amino acid sequence that is at least 98% identical to SEQ ID NO: 11. In some cases, the NADPH-dependent acetoin reductase can comprise an amino acid sequence that is at least 99% identical to SEQ ID NO: 11. In some cases, the NADPH-dependent acetoin reductase can comprise an amino acid sequence that is SEQ ID NO: 11. In some cases, the NADPH-dependent acetoin reductase comprise the amino acid sequence SEQ ID NO: 11.

The gene encoding the NADH-dependent acetoin reductase can be from a bacteria (e.g., a gram positive or gram negative bacteria). Examples include those from the genus *Bacillus*, for example *Bacillus subtilis*. The bacteria can be from the genus *Paenibacillus*, for example *Paenibacillus polymyxa*.

In some cases, the NADH-dependent acetoin reductase can comprise an amino acid sequence that is substantially similar to SEQ ID NO: 13 or 15. For example, the NADH-dependent acetoin reductase may comprises an amino acid sequence that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 13 or 15. In some cases, the NADH-dependent acetoin reductase can comprise an amino acid sequence that is at least 60% identical to SEQ ID NO: 13 or 15. In some cases, the NADH-dependent acetoin reductase can comprise an amino acid sequence that is at least 65% identical to SEQ ID NO: 13 or 15. In some cases, the NADH-dependent acetoin reductase can comprise an amino acid sequence that is at least 70% identical to SEQ ID NO: 13 or 15. In some cases, the NADH-dependent acetoin reductase can comprise an amino acid sequence that is at least 75% identical to SEQ ID NO: 13 or 15. In some cases, the NADH-dependent acetoin reductase can comprise an amino acid sequence that is at least 80% identical to SEQ ID NO: 13 or 15. In some cases, the NADH-dependent acetoin reductase can comprise an amino acid sequence that is at least 85% identical to SEQ ID NO: 13 or 15. In some cases, the NADH-dependent acetoin reductase can comprise an amino acid sequence that is at least 90% identical to SEQ ID NO: 13 or 15. In some cases, the NADH-dependent acetoin reductase can comprise an amino acid sequence that is at least 91% identical to SEQ ID NO: 13 or 15. In some cases, the NADH-dependent acetoin reductase can comprise an amino acid sequence that is at least 92% identical to SEQ ID NO: 13 or 15. In some cases, the NADH-dependent acetoin reductase can comprise an amino acid sequence that is at least 93% identical to SEQ ID NO: 13 or 15. In some cases, the NADH-dependent acetoin reductase can comprise an amino acid sequence that is at least 94% identical to SEQ ID NO: 13 or 15. In some cases, the NADH-dependent acetoin reductase can comprise an amino acid sequence that is at least 95% identical to SEQ ID NO: 13 or 15. In some cases, the NADH-dependent acetoin reductase can comprise an amino acid sequence that is at least 96% identical to SEQ ID NO: 13 or 15. In some cases, the NADH-dependent acetoin reductase can comprise an amino acid sequence that is at least 97% identical to SEQ ID NO: 13 or 15. In some cases, the NADH-dependent acetoin reductase can comprise an amino acid sequence that is at least 98% identical to SEQ ID NO: 13 or 15. In some cases, the NADH-dependent acetoin reductase can comprise an amino acid sequence that is at least 99% identical to SEQ ID NO: 13 or 15. In some cases, the NADH-dependent acetoin reductase can comprise the amino acid sequence SEQ ID NO: 13 or 15.

The gene encoding the alpha-acetolactate decarboxylase (budA) can be from a bacterium (e.g., a gram positive bacteria or gram negative bacterium). Examples include those from the genus *Clostridium*, for example *Clostridium autoethanogenum*. Other examples include those from the genus *Klebsiella*, for example *Klebsiella pneumoniae*.

In some cases, the alpha-acetolactate decarboxylase can comprise an amino acid sequence that is substantially similar to SEQ ID NO: 7 or 9. For example, the alpha-acetolactate decarboxylase can comprise an amino acid sequence that is at least 60% 65%, 70%, 75%, 80%, 85%, 90%, 91%, 92%, 93%, 94%, 95%, 96%, 97%, 98%, 99%, 99.9%, 99.99%, 99.999%, or 99.9999% identical to SEQ ID NO: 7 or 9. In some cases, the alpha-acetolactate decarboxylase can comprise an amino acid sequence that is at least 60% identical to SEQ ID NO: 7 or 9. For example, the alpha-acetolactate decarboxylase can comprise an amino acid sequence that is at least 65% identical to SEQ ID NO: 7 or 9. In some cases, the alpha-acetolactate decarboxylase can comprise an amino acid sequence that is at least 70% identical to SEQ ID NO: 7 or 9. For example, the alpha-acetolactate decarboxylase can comprise an amino acid sequence that is at least 75% identical to SEQ ID NO: 7 or 9. In some cases, the alpha-acetolactate decarboxylase can comprise an amino acid sequence that is at least 80% identical to SEQ ID NO: 7 or 9. For example, the alpha-acetolactate decarboxylase can comprise an amino acid sequence that is at least 85% identical to SEQ ID NO: 7 or 9. In some cases, the alpha-acetolactate decarboxylase can comprise an amino acid sequence that is at least 90% identical to SEQ ID NO: 7 or 9. In some cases, the alpha-acetolactate decarboxylase can comprise an amino acid sequence that is at least 91% identical to SEQ ID NO: 7 or 9. In some cases, the alpha-acetolactate decarboxylase can comprise an amino acid sequence that is at least 92% identical to SEQ ID NO: 7 or 9. In some cases, the alpha-acetolactate decarboxylase can comprise an amino acid sequence that is at least 93% identical to SEQ ID NO: 7 or 9. In some cases, the alpha-acetolactate decarboxylase can comprise an amino acid sequence that is at least 94% identical to SEQ ID NO: 7 or 9. In some cases, the alpha-acetolactate decarboxylase can comprise an amino acid sequence that is at least 95% identical to SEQ ID NO: 7 or 9. In some cases, the alpha-acetolactate decarboxylase can comprise an amino acid sequence that is at least 96% identical to SEQ ID NO: 7 or 9. In some cases, the alpha-acetolactate decarboxylase can comprise an amino acid sequence that is at least 97% identical to SEQ ID NO: 7 or 9. In some cases, the alpha-acetolactate decarboxylase can comprise an amino acid sequence that is at least 98% identical to SEQ ID NO: 7 or 9. In some cases, the alpha-acetolactate decarboxylase can comprise an amino acid sequence that is at least 99% identical to SEQ ID NO: 7 or 9. In some cases, the alpha-acetolactate decarboxylase can comprise an amino acid sequence that is identical to SEQ ID NO: 7 or 9. In some cases, the alpha-acetolactate decarboxylase can comprise the amino acid sequence SEQ ID NO: 7 or 9.

The gene encoding the acetolactate synthase (AlsS) can be from a bacterium (e.g., a gram positive bacterium). Examples include those from the genus *Clostridium*, for example *Clostridium autoethanogenum*. Other examples include those from the genus *Bacillus*, for example *Bacillus subtilis*. Additional species example include *Bacillus licheniformis*.

In some cases, the acetolactate synthase can comprise an amino acid sequence that is substantially similar to anyone of SEQ ID NOs: 1, 3, or 5. In some cases, the acetolactate synthase can comprise an amino acid sequence that is at least 60% 65%, 70%, 75%, 80%, 85%, 90%, 91%, 92%, 93%, 94%, 95%, 96%, 97%, 98%, 99%, 99.9%, 99.99%, 99.999%, or 99.9999% identical to anyone of SEQ ID NOs: 1, 3, or 5. In some cases, the acetolactate synthase can comprise an amino acid sequence that is at least 60% identical to anyone of SEQ ID NOs: 1, 3, or 5. In some cases, the acetolactate synthase can comprise an amino acid sequence that is at least 65% identical to anyone of SEQ ID NOs: 1, 3, or 5. In some cases, the acetolactate synthase can comprise an amino acid sequence that is at least 70% identical to anyone of SEQ ID NOs: 1, 3, or 5. In some cases, the acetolactate synthase can comprise an amino acid sequence that is at least 75% identical to anyone of SEQ ID NOs: 1, 3, or 5. In some cases, the acetolactate synthase can comprise an amino acid sequence that is at least 80% identical to anyone of SEQ ID NOs: 1, 3, or 5. In some cases, the acetolactate synthase can comprise an amino acid sequence that is at least 85% identical to anyone of SEQ ID NOs: 1, 3, or 5. In some cases, the acetolactate synthase can comprise an amino acid sequence that is at least 90% identical to anyone of SEQ ID NOs: 1, 3, or 5. In some cases, the acetolactate synthase can comprise an amino acid sequence that is at least 91% identical to anyone of SEQ ID NOs: 1, 3, or 5. In some cases, the acetolactate synthase can comprise an amino acid sequence that is at least 92% identical to anyone of SEQ ID NOs: 1, 3, or 5. In some cases, the acetolactate synthase can comprise an amino acid sequence that is at least 93% identical to anyone of SEQ ID NOs: 1, 3, or 5. In some cases, the acetolactate synthase can comprise an amino acid sequence that is at least 94% identical to anyone of SEQ ID NOs: 1, 3, or 5. In some cases, the acetolactate synthase can comprise an amino acid sequence that is at least 95% identical to anyone of SEQ ID NOs: 1, 3, or 5. In some cases, the acetolactate synthase can comprise an amino acid sequence that is at least 96% identical to anyone of SEQ ID NOs: 1, 3, or 5. In some cases, the acetolactate synthase can comprise an amino acid sequence that is at least 97% identical to anyone of SEQ ID NOs: 1, 3, or 5. In some cases, the acetolactate synthase can comprise an amino acid sequence that is at least 98% identical to anyone of SEQ ID NOs: 1, 3, or 5. In some cases, the acetolactate synthase can comprise an amino acid sequence that is at least 99% identical to anyone of SEQ ID NOs: 1, 3, or 5. In some cases, the acetolactate synthase can comprise an amino acid sequence that is identical to anyone of SEQ ID NOs: 1, 3, or 5.

In some cases, additional enzymes can be provided to the microorganism to yield other desired end products by fermentation.

In some cases, the amino acid sequence can be optimized based on the microorganism in which the genes will be provided or the enzymes will be expressed. In such cases, conservative amino acids substitutions can be made based on whether the microorganism typically uses a specific amino acid or how much of that particular amino acid is available for use within the microorganism.

In some cases, the codons can be optimized based on the microorganism in which the genes will be provided or the enzymes will be expressed. In some cases, one or more the nucleotide sequences encoding for one or more of the enzymes in the 2,3-BDO pathway can be driven by a molecular switch. In some cases, the molecular switch can be turned on or off by a chemical substance as described throughout. In some cases, the chemical substance can be a rare earth metal. In some cases, the rare earth metal can be lanthanum.

1,4-Butanediol ("1,4-BDO")

In some instances, polynucleotides encoding enzymes of the 1,4-BDO pathway can be used. For example, the microorganism can contain (either endogenously or heterologous) one or more polynucleotides encoding for a succinyl-CoA synthetase (sucC), CoA-dependent succinate semialdehyde dehydrogenase (sucD), 4-hydroxybutyrate dehydrogenase (4hbD), 4-hydroxybutyryl-CoA transferase (cat2), aldehyde dehydrogenase (ald), and/or alcohol dehydrogenase (adh).

In some cases, the 4-hydroxybutyrate dehydrogenase (4hbD) can be encoded by a polynucleotide that is substantially similar to SEQ ID NO. 22. In some cases, the 4-hydroxybutyrate dehydrogenase can be encoded by an amino acid sequence that is substantially similar SEQ ID NO: 21.

In some cases, the 4-hydroxybutyrate CoA transferase (Cat2) can be encoded by a polynucleotide that is substantially similar to SEQ ID NO: 24. In some cases, the 4-hydroxybutyrate CoA transferase can be encoded by an amino acid sequence that is substantially similar SEQ ID NO: 23.

In some cases, the aldehyde dehydrogenase gene can be encoded by a polynucleotide that is substantially similar to SEQ ID NO: 26. In some cases, the aldehyde dehydrogenase can be encoded by an amino acid sequence that is substantially similar SEQ ID NO: 25.

In some cases, the alcohol dehydrogenase can be encoded by a polynucleotide that is substantially similar to SEQ ID NO: 28. In some cases, the alcohol dehydrogenase can be encoded by an amino acid sequence that is substantially similar SEQ ID NO: 27.

In some cases, the succinyl CoA synthetase beta subunit (sucC) can be encoded by a polynucleotide that is substantially similar SEQ ID NO: 18. In some cases, the succinyl CoA synthetase beta subunit can be encoded by an amino acid sequence that is substantially similar SEQ ID NO: 17.

In some cases, the CoA-dependent succinate semialdehyde dehydrogenase (sucD) can be encoded by a polynucleotide that is substantially similar to SEQ ID NO: 20. In some cases, the CoA-dependent succinate semialdehyde dehydrogenase can be encoded by an amino acid sequence that is substantially similar SEQ ID NO: 19.

In some cases, the codons can be optimized based on the microorganism in which the genes will be provided or the enzymes will be expressed. In some cases, one or more the nucleotide sequences encoding for one or more of the enzymes in the 1,4-BDO pathway can be driven by a molecular switch. In some cases, the molecular switch can be turned on or off by a chemical substance as described throughout. In some cases, the chemical substance can be a rare earth metal. In some cases, the rare earth metal can be lanthanum.

Isobutyraldehyde

In some instances, polynucleotides encoding enzymes of the isobutyraldehyde pathway can be used. For example, the microorganism can comprise one or more polynucleotides encoding for one or more enzymes from the EC 2.2.1.6, EC 1.1.1.86, EC 4.2.1.9, and/or EC 4.1.1.72. In some cases, the microorganism can comprises one or more polynucleotides (either endogenously or heterologous) encoding for an acetolactate synthase (AlsS); ketol-acid reductoisomerase (KARI); dihydroxy-acid dehydratase (DHAD); and/or 2-keto acid decarboxylase (KDC). One or more of the polynucleotides can be native to the microorganism. In some cases, one or more of the polynucleotides can be heterologous to the microorganism.

In some cases, the AlsS can be encoded by a polynucleotide that is substantially similar to SEQ ID NO: 30. In some cases, the AlsS can be encoded by an amino acid sequence that is substantially similar to SEQ ID NO: 29. In some cases, the ketol-acid reductoisomerase can be encoded by a polynucleotide that is substantially similar to SEQ ID NO: 32. In some cases, the ketol-acid reductoisomerase can be encoded by an amino acid sequence that is substantially similar to SEQ ID NO: 31. In some cases, the dihydroxy-acid dehydratase can be encoded by a polynucleotide that is substantially similar to SEQ ID NO: 34. In some cases, the dihydroxy-acid dehydratase can be encoded by an amino acid sequence that is substantially similar to SEQ ID NO: 33. In some cases, the KDC can be encoded by a polynucleotide that is substantially similar to any one of SEQ ID NOs: 36, 38, 40, 42, 44, 46 or 48. In some cases, the KDC can be encoded by an amino acid sequence that is substantially similar to any one of SEQ ID NOs: 35, 37 39, 41, 43, 45, or 47.

In some cases, the codons can be optimized based on the microorganism in which the genes will be provided or the enzymes will be expressed. In some cases, one or more the nucleotide sequences encoding for one or more of the enzymes in the isobutyraldehyde pathway can be driven by a molecular switch. In some cases, the molecular switch can be turned on or off by a chemical substance as described throughout. In some cases, the chemical substance can be a rare earth metal. In some cases, the rare earth metal can be lanthanum.

Isobutanol

In some instances, polynucleotides encoding enzymes of the isobutanol pathway can be used. For example, the microorganism can comprise one or more polynucleotides encoding for one or more enzymes from the EC 2.2.1.6, EC 1.1.1.86, EC 4.2.1.9, EC 4.1.1.72 and/or EC 1.1.1.1. In some cases, the microorganism can comprises one or more polynucleotides (either endogenously or heterologous) encoding for an acetolactate synthase (AlsS); ketol-acid reductoisomerase (KARI); dihydroxy-acid dehydratase (DHAD); 2-keto acid decarboxylase (KDC), and/or alcohol dehydrogenase (ADH). One or more of the polynucleotides can be native to the microorganism. In some cases, one or more of the polynucleotides can be heterologous to the microorganism.

In some cases, the AlsS can be encoded by a polynucleotide that is substantially similar to SEQ ID NO: 30. In some cases, the AlsS can be encoded by an amino acid sequence that is substantially similar to SEQ ID NO: 29. In some cases, the ketol-acid reductoisomerase can be encoded by a polynucleotide that is substantially similar to SEQ ID NO: 32. In some cases, the ketol-acid reductoisomerase can be encoded by an amino acid sequence that is substantially similar to SEQ ID NO: 31. In some cases, the dihydroxy-acid dehydratase can be encoded by a polynucleotide that is substantially similar to SEQ ID NO: 34. In some cases, the dihydroxy-acid dehydratase can be encoded by an amino acid sequence that is substantially similar to SEQ ID NO: 33. In some cases, the KDC can be encoded by a polynucleotide that is substantially similar to any one of SEQ ID NOs: 36, 38, 40, 42, 44, 46 or 48. In some cases, the KDC can be encoded by an amino acid sequence that is substantially similar to any one of SEQ ID NOs: 35, 37 39, 41, 43, 45, or 47. In some cases, the ADH can be encoded by a polynucleotide that is substantially similar to any one of SEQ ID NOs: 50, 52, 54, 56 or 58. In some cases, the ADH can be encoded by an amino acid that is substantially similar to any one of SEQ ID NOs: 49, 51, 53, 55 or 57.

In some cases, the codons can be optimized based on the microorganism in which the genes will be provided or the enzymes will be expressed. In some cases, one or more the nucleotide sequences encoding for one or more of the enzymes in the isobutanol pathway can be driven by a molecular switch. In some cases, the molecular switch can be turned on or off by a chemical substance as described throughout. In some cases, the chemical substance can be a rare earth metal. In some cases, the rare earth metal can be lanthanum.

1-Butanol (Aka n-Butanol)

In some cases, polynucleotides encoding for enzymes of the 1-butanol pathway can be used. For example, the microorganism can contain (either endogenously or heterologous) one or more polynucleotides encoding for an enzyme from the Enzyme Class EC 4.3.1.19, EC 2.3.3.6, EC 4.2.1.33, EC 4.1.1.72, and/or EC 1.1.1.1. In some cases, the polynucleotides encode for one or more polypeptides that is L-threonine ammonia lyase, 2-ethylmalate synthase, isopropylmalate isomerase, 2-ketoacid decarboxylase (KDC), alcohol dehydrogenase (ADH), or any combination thereof. In some cases, one or more of the polynucleotides can be native to the microorganism. In some cases, one or more of the polynucleotides can be heterologous to the microorganism.

In some cases, L-threonine ammonia lyase can catalyze the conversion of L-threonine to 2-oxybutanoate and ammonia. In some cases, 2-ethylmalate synthase can catalyze the conversion of 2-oxybutanoate and acetyl-CoA to 2-ethylmalate. In some cases, isopropylmalate isomerase can catalyze the conversion of 2-ethylmalate to 3-ethylmalate. In some cases, 3-isopropylmalate dehydrogenase can catalyze the conversion of 3-ethylmalate to 2-ketovalerate, $CO_2$ and NADH. In some cases, KDC can catalyze the conversion of 2-ketovalerate to butryaldehyde. In some cases, ADH can catalyze the conversion of butyraldehyde to 1-butanol. In some cases, the L-threonine ammonia lyase can comprise a nucleotide sequence that is substantially similar to SEQ ID NO: 60. In some cases, the L-threonine ammonia lyase can comprise an amino acid sequence that is substantially similar to SEQ ID NO: 59. In some cases, the 2-ethylmalate synthase can comprise a nucleotide sequence that is substantially similar to SEQ ID NO:62. In some cases, the 2-ethylmalate synthase can comprise an amino acid sequence that is substantially similar to SEQ ID NO: 61. In some cases, the isopropylmalate isomerase can comprise a nucleotide sequence that is substantially similar to SEQ ID NO: 64 or 66. In some cases, the isopropylmalate isomerase can comprise an amino acid sequence that is substantially similar to SEQ ID NO: 63 or 65. In some cases, the KDC can comprise a nucleotide sequence that is substantially similar to any one of SEQ ID NOs: 36, 38, 40, 42, 44, 46 or 48. In some cases, the KDC can comprise an amino acid sequence that is substantially similar to any one of SEQ ID NOs: 35, 37 39, 41, 43, 45, or 47. In some cases, the ADH can be encoded by a polynucleotide that is substantially similar to any one of SEQ ID NOs: 50, 52, 54, 56 or 58. In some cases, the ADH can be encoded by an amino acid that is substantially similar to any one of SEQ ID NOs: 49, 51, 53, 55 or 57.

In some cases, the codons can be optimized based on the microorganism in which the genes will be provided or the enzymes will be expressed. In some cases, one or more the nucleotide sequences encoding for one or more of the enzymes in the 1-butanol pathway can be driven by a molecular switch. In some cases, the molecular switch can be turned on or off by a chemical substance such as the ones described throughout. In some cases, the chemical substance can be a rare earth metal. In some cases, the rare earth metal can be lanthanum.

Ethanol

In some cases, polynucleotides encoding for enzymes of the ethanol pathway can be used. For example, the microorganism can contain (either endogenously or heterologous) one or more polynucleotides encoding for an enzyme from the Enzyme Class EC 1.2.4.1 and/or EC 1.1.1.1. In some cases, the polynucleotides encode for one or more polypeptides that is pyruvate decarboxylase (PDC) and/or alcohol dehydrogenase (ADH). In some cases, one or more of the polynucleotides can be native to the microorganism. In some cases, one or more of the polynucleotides can be heterologous to the microorganism.

In some cases, pyruvate decarboxylase can catalyze the conversion of pyruvate to acetaldehyde. In some cases, the alcohol dehydrogenase can catalyze the conversion of acetaldehyde into ethanol.

In some cases, the pyruvate decarboxylase can comprise a nucleotide sequence that is substantially similar to SEQ ID NO: 68. In some cases, the pyruvate decarboxylase can comprise an amino acid sequence that is substantially similar to SEQ ID NO: 67. In some cases, the alcohol dehydrogenase can comprise a nucleotide sequence that is substantially similar to SEQ ID NO: 70. In some cases, the alcohol dehydrogenase can comprise an amino acid sequence that is substantially similar to SEQ ID NO: 69.

In some cases, the codons can be optimized based on the microorganism in which the genes will be provided or the enzymes will be expressed. In some cases, one or more the nucleotide sequences encoding for one or more of the enzymes in the ethanol pathway can be driven by a molecular switch. In some cases, the molecular switch can be turned on or off by a chemical substance such as described throughout. In some cases, the chemical substance can be a rare earth metal. In some cases, the rare earth metal can be lanthanum.

Fatty (or Aliphatic Long Chain) Alcohols

In some cases, polynucleotides encoding for enzymes of the fatty alcohol pathway can be used. For example, the microorganism can contain (either endogenously or heterologous) one or more polynucleotides encoding for an enzyme from the Enzyme Class EC 1.2.1.50. In some cases, the polynucleotides encode for one or more polypeptides that is a fatty-acyl-CoA reductase (FAR). In some cases, one or more of the polynucleotides can be native to the microorganism. In some cases, one or more of the polynucleotides can be heterologous to the microorganism.

In some cases, the fatty-acyl-CoA reductase can catalyze the conversion of fatty acetyl-CoA to a fatty alcohol.

In some cases, the fatty-acyl-CoA reductase can comprise a nucleotide sequence that is substantially similar to SEQ ID NO: 72. In some cases, the fatty-acyl-CoA reductase can comprise an amino acid sequence that is substantially similar to SEQ ID NO: 71.

In some cases, the codons can be optimized based on the microorganism in which the genes will be provided or the enzymes will be expressed. In some cases, one or more the nucleotide sequences encoding for one or more of the enzymes in the fatty alcohol pathway can be driven by a molecular switch. In some cases, the molecular switch can be turned on or off by a chemical substance such as described throughout. In some cases, the chemical substance can be a rare earth metal. In some cases, the rare earth metal can be lanthanum.

Fatty Acid Methyl Ester

In some cases, polynucleotides encoding for enzymes of the fatty acid methyl ester pathway can be used. For example, the microorganism can contain (either endogenously or heterologous) one or more polynucleotides encoding for an enzyme from the Enzyme Class EC 2.3.1.75. In some cases, the polynucleotides encode for one or more polypeptides that is a WES polypeptide. In some cases, one or more of the polynucleotides can be native to the microorganism. In some cases, one or more of the polynucleotides can be heterologous to the microorganism.

In some cases, the WES polypeptide can catalyze the conversion of fatty acyl-CoA and alcohols to fatty acid esters.

In some cases, the WES polypeptide can comprise a nucleotide sequence that is substantially similar to any one of SEQ ID NOs: 74, 76, 78, 80, or 82. In some cases, the WES polypeptide can comprise an amino acid sequence that is substantially similar to any one of SEQ ID NOs: 73, 75, 77, 79, or 81.

In some cases, the codons can be optimized based on the microorganism in which the genes will be provided or the enzymes will be expressed. In some cases, one or more the nucleotide sequences encoding for one or more of the enzymes in the fatty acid methyl ester pathway can be driven by a molecular switch. In some cases, the molecular switch can be turned on or off by a chemical substance such as described throughout. In some cases, the chemical substance can be a rare earth metal. In some cases, the rare earth metal can be lanthanum.

Vectors

Since some of the enzymes described throughout are not native to some microorganisms, expression vectors can be used to express the desired enzymes within most microorganism and cells. For example, methylotrophs such as methanotrophs, do not naturally express some enzymes of the 2,3-BDO; 1,4-BDO; isobutyraldehyde; isobutanol; 1-butanol; n-butanol; ethanol; fatty alcohols; and fatty acid methyl ester pathways. Therefore, in some cases, the heterologous enzymes can be expressed using certain expression vectors. Vector constructs prepared for introduction into the host microorganisms described throughout can typically, but not always, comprise a replication system (i.e. vector) recognized by the host. In some cases, the vector includes the intended polynucleotide fragment encoding the desired polypeptide and, optionally, transcription and translational initiation regulatory sequences operably linked to the polypeptide-encoding segment. Expression vectors can include, for example, an origin of replication or autonomously replicating sequence (ARS), expression control sequences, a promoter, an enhancer and necessary processing information sites, such as ribosome-binding sites, RNA splice sites, polyadenylation sites, transcriptional terminator sequences, mRNA stabilizing sequences, polynucleotides homologous to host chromosomal DNA, and/or a multiple cloning site. Signal peptides may also be included where appropriate, for example from secreted polypeptides of the same or related species, which allow the protein to cross and/or lodge in cell membranes or be secreted from the cell.

In some cases, the promoter used in the vector can be sensitive to a chemical substance such as described throughout. For example, in the presence of the chemical substance, the promoter is either activated or deactivated. In some cases, the chemical substance can be a rare earth metal. In some cases, the rare earth metal can be lanthanum or cerium. In some cases, the rare earth metal can be praseodymium or neodymium.

The vectors can be constructed using standard methods (see, e.g., Sambrook et al., Molecular Biology: A Laboratory Manual, Cold Spring Harbor, N.Y. 1989; and Ausubel, et al., Current Protocols in Molecular Biology, Greene Publishing, Co. N.Y, 1995).

Manipulation of polynucleotides that encode the enzymes disclosed throughout is typically carried out in recombinant vectors. Vectors which may be employed include bacterial plasmids, bacteriophage, artificial chromosomes, episomal vectors and gene expression vectors. Vectors may be selected to accommodate a polynucleotide encoding a protein of a desired size. Following production of a selected vector, a suitable host cell (e.g., the microorganisms described herein) is transfected or transformed with the vector. Each vector contains various functional components, which generally include a cloning site, an origin of replication and at least one selectable marker gene. A vector may additionally possess one or more of the following elements: an enhancer, promoter, a transcription termination sequence and/or other signal sequences. Such sequence elements may be optimized for the selected host species. Such sequence elements may be positioned in the vicinity of the cloning site, such that they are operatively linked to the gene encoding a preselected enzyme.

Vectors, including cloning and expression vectors, may contain polynucleotides that enable the vector to replicate in one or more selected microorganisms. For example, the sequence may be one that enables the vector to replicate independently of the host chromosomal DNA and may include origins of replication or autonomously replicating sequences. Such sequences are well known for a variety of bacteria, yeast and viruses. For example, the origin of replication from the plasmid pBR322 is suitable for most gram-negative bacteria, the origin of replication for 2 micron plasmid is suitable for yeast, and various viral origins of replication (e.g. SV40, adenovirus) are useful for cloning vectors.

A cloning or expression vector may contain a selection gene, also referred to as a selectable marker. This gene encodes a protein necessary for the survival or growth of transformed microorganisms in a selective culture medium. Microorganisms not transformed with the vector containing the selection gene will therefore not survive in the culture medium. Typical selection genes encode proteins that confer resistance to antibiotics and other toxins, e.g. ampicillin, neomycin, methotrexate, hygromycin, thiostrepton, apramycin or tetracycline, complement auxotrophic deficiencies, or supply critical nutrients not available in the growth media.

The replication of vectors may be performed in *E. coli*. An example of a *E. coli*-selectable marker is the β-lactamase gene, which confers resistance to the antibiotic ampicillin. These selectable markers can be obtained from *E. coli* plasmids, such as pBR322 or a pUC plasmid such as pUC18 or pUC19, or pUC119.

Promoters

Vectors may contain a promoter that is recognized by the host microorganism. The promoter may be operably linked to a coding sequence of interest. Such a promoter may be inducible, repressible, or constitutive. Polynucleotides are operably linked when the polynucleotides are in a relationship permitting them to function in their intended manner.

Different promoters can be used to drive the expression of the genes. For example, if temporary gene expression (i.e., non-constitutively expressed) is desired, expression can be driven by inducible or repressible promoters. The molecular switch can in some cases comprise these inducible or repressible promoters.

In some cases, the desired gene is expressed temporarily. In other words, the desired gene is not constitutively expressed. The expression of the desired gene can be driven by inducible or repressible promoters, which functions as a molecular switch. Examples of inducible or repressible switches include, but are not limited to, those promoters inducible or repressible by: (a) sugars such as arabinose and lactose (or non metabolizable analogs, e.g., isopropyl β-D-1-thiogalactopyranoside (IPTG)); (b) metals such as copper or calcium (or rare earth metals such as lanthanum or cerium); (c) temperature; (d) Nitrogen-source; (e) oxygen; (f) cell state (growth or stationary); (g) metabolites such as phosphate; (h) CRISPRi; (i) jun; (j) fos, (k) metallothionein and/or (l) heat shock. These switches can be used in a methanotroph system. An example of an inducible switch that can be used within methanotrophs is a pBAD, pXoxF or pTRC promoter. An example of a repressible switch that can be used within methanotrophs is a pMxaF promoter.

Inducible or repressible switches that can be particularly useful are switches that are responsive to sugars and rare earth metals. For example, promoters that are sensitive to the sugar arabinose can be used as an inducible switch. In some cases, arabinose switches can be used to drive expression of one or more genes. For example, in the presence arabinose, a desired vector or expression of a gene set can be "turned-on." The arabinose switch can turn on the expression of a desired gene.

Other particularly useful switches can be rare earth metal switches, such as lanthanum sensitive switches (also simply known as a lanthanum switch). In some cases, the lanthanum switch can be a repressible switch that can be used to repress expression of one or more genes, until the repressor is removed (e.g., in this case lanthanum), after which the genes are "turned-on". For example, in the presence the rare earth metal lanthanum, the desired gene set or vector can be "turned-off." The lanthanum switch can be turned off (and expression of the genes induced) by either removing the lanthanum from the media or diluting the lanthanum in the media to levels where its repressible effects are reduced, minimized, or eliminated. Other rare earth metal switches can be used, such as those disclosed throughout.

Constitutively expressed promoters can also be used in the vector systems herein. For example, the expression of one or more desired genes can be controlled by constitutively active promoters. Examples of such promoters include but are not limited to pXoxF, pMxaF and p.Bba.J23111.

Promoters suitable for use with prokaryotic hosts may include, for example, the a-lactamase and lactose promoter systems, alkaline phosphatase, the tryptophan (trp) promoter system, the erythromycin promoter, apramycin promoter, hygromycin promoter, methylenomycin promoter and hybrid promoters such as the tac promoter. Promoters for use in bacterial systems will also generally contain a Shine-Dalgarno sequence operably linked to the coding sequence.

Generally, a strong promoter may be employed to provide for high level transcription and expression of the desired product. For example, promoters that can be used include but are not limited to a pMxaF promoter. In some cases, a mutation can increase the strength of the promoter and therefore result in elevated levels of expression.

In some cases however, a weaker promoter is desired. For example, this is the case where too much expression of a certain gene results in a detrimental effect (e.g., the killing of cells). A weak promoter can be used, for example a pBAD promoter. However, in some cases, a weaker promoter can be made by mutation. For example, the pmxaF promoters can be mutated to be weaker.

One or more promoters of a transcription unit can be an inducible promoter. For example, a GFP can be expressed from a constitutive promoter while an inducible promoter is used to drive transcription of a gene coding for one or more enzymes as disclosed herein and/or the amplifiable selectable marker.

Some vectors may contain prokaryotic sequences that facilitate the propagation of the vector in bacteria. Thus, the vectors may have other components such as an origin of replication (e.g., a polynucleotide that enables the vector to replicate in one or more selected microorganisms), antibiotic resistance genes for selection in bacteria, and/or an amber stop codon which can permit translation to read through the codon. Additional selectable gene(s) may also be incorporated. Generally, in cloning vectors, the origin of replication is one that enables the vector to replicate independently of the host chromosomal DNA, and includes origins of replication or autonomously replicating sequences. Such sequences can include the ColEl origin of replication in bacteria or other known sequences.

Genes

The genes described throughout can all have a promoter driving their expression. The methods described herein, e.g., genome editing and expression inhibition using Cas, can be used to edit the polynucleotide of the promoters or used to inhibit the effectiveness of the promoters. Inhibition can be done by blocking the transcription machinery (e.g., transcription factors) from binding to the promoter or by altering the promoter in such a way that the transcription machinery no longer recognizing the promoter sequence.

The vectors described throughout can also comprise a polynucleotide encoding for one or more of the genes within the 2,3-BDO; 1,4-BDO; isobutyraldehyde; isobutanol; 1-butanol; n-butanol; ethanol; fatty alcohols; and fatty acid methyl ester pathway. These vectors can also contain one or more regulatory elements (inducible and/or repressible promoters) that control the expression of the genes within the vectors. In some cases, the vectors can include switches, including but not limited to inducible or repressible switches, e.g., an arabinose or lanthanum switches. These genes can be heterologous to the microorganism in which the vector is contacted with (and eventually transformed with).

The genes used in the vectors can be any genes described throughout the application. For example, the genes of the 2,3-BDO; 1,4-BDO; isobutyraldehyde; isobutanol; 1-butanol; n-butanol; ethanol; fatty alcohols; and fatty acid methyl ester pathways. These enzymes can be encoded by a polynucleotide or by an polypeptide that is at least 60%, 65%, 70%, 75%, 80%, 85%, 90%, 91%, 92%, 93%, 94%, 95%, 96%, 97%, 98%, 99%, 99.9%, 99.99%, 99.999%, or 99.9999% identical to any one of SEQ ID NOs: 1 to 82.

The genes that are inserted into a microorganism can be heterologous to the microorganism itself. For example, if the microorganism is a methanotroph, the inserted genes can, for example, be from yeast, a bacterium, or a different species of methanotroph. Further, the genes can be endogenously part of the genome of the microorganism.

III. Method of Making the Genetically Modified Microorganisms

The genetically modified microorganisms disclosed throughout can be made by a variety of ways. A microorganism may be modified (e.g., genetically engineered) by any method to comprise and/or express one or more polynucleotides encoding for enzymes in a pathway that catalyze a conversion of a fermentable carbon source (e.g., a C1 carbon) to one or more intermediates in a pathway for the production of desired valuable chemicals, such as 2,3-BDO; 1,4-BDO; isobutyraldehyde; isobutanol; 1-butanol (a.k.a. n-butanol); ethanol; fatty (or aliphatic long chain) alcohols; and fatty acid methyl esters. Such enzymes may include those discussed throughout. For example, one or more of any of the genes discussed throughout can be inserted into a microorganism. The genes can be inserted by an expression vector. The genes can also be under the control of one or more different/same promoters or the one or more genes can be under the control of a switch, such as an inducible or repressible promoter, e.g., an arabinose switch, isopropyl β-D-1-thiogalactopyranoside (IPTG) switch, or a rare earth metal switch. The genes can also be stably integrated into the genome of the microorganism. In some cases, the genes can be expressed in an episomally vector.

The microorganism used in this method can be any described above, including but not limited to a prokaryote. Other microorganisms such as bacteria, yeast, or algae can be used. Microorganisms of particular interest include methanotrophs, such as those from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* or *Methyloacidophilum.* One desired species can include a *Methylococcus capsulatus.*

An exemplary method of making a genetically modified microorganism disclosed herein is contacting (or transforming) a microorganism with a nucleic acid that expresses at least one heterologous gene encoding i) an acetoin reductase; ii) an alpha-acetolactate decarboxylase (budA); iii) a acetolactate synthase, or iv) any combination thereof. The microorganism can be any microorganism that is capable of converting a C1 carbon to a product. In some cases, the product is 2,3-BDO. For example, another exemplary method of making a genetically modified microorganism disclosed herein is contacting (or transforming) a microorganism with a nucleic acid that expresses at least one heterologous gene encoding i) succinyl-CoA synthetase (sucC), ii) CoA-dependent succinate semialdehyde dehydrogenase (sucD), iii) 4-hydroxybutyrate dehydrogenase (4hbD), iv) 4-hydroxybutyryl-CoA transferase (cat2), v) aldehyde dehydrogenase (ald), vi) alcohol dehydrogenase (adh), or vii) any combination thereof. The microorganism can be any microorganism that is capable of converting a C1 carbon to a product. In some cases, the product is 1,4-BDO.

Another exemplary method of making a genetically modified microorganism disclosed herein is contacting (or transforming) a microorganism with a nucleic acid that expresses at least one heterologous gene encoding i) acetolactate synthase (AlsS); ii) ketol-acid reductoisomerase (KARI); iii) dihydroxy-acid dehydratase (DHAD); iv) 2-keto acid decarboxylase (KDC), or v) any combination thereof. The microorganism can be any microorganism that is capable of converting a C1 carbon to a product. In some cases, the product is isobutyraldehyde.

Another exemplary method of making a genetically modified microorganism disclosed herein is contacting (or transforming) a microorganism with a nucleic acid that expresses at least one heterologous gene encoding i) acetolactate synthase (AlsS); ii) ketol-acid reductoisomerase (KARI); iii) dihydroxy-acid dehydratase (DHAD); iv) 2-keto acid decarboxylase (KDC), v) alcohol dehydrogenase (ADH) or vi) any combination thereof. The microorganism can be any microorganism that is capable of converting a C1 carbon to a product. In some cases, the product is isobutanol.

Another exemplary method of making a genetically modified microorganism disclosed herein is contacting (or transforming) a microorganism with a nucleic acid that expresses at least one heterologous gene encoding i) L-threonine ammonia lyase, ii) 2-ethylmalate synthase, isopropylmalate isomerase, iii) 2-ketoacid decarboxylase, iv) alcohol dehydrogenase, or v) any combination thereof. The microorganism can be any microorganism that is capable of converting a C1 carbon to a product. In some cases, the product is 1-butanol.

Another exemplary method of making a genetically modified microorganism disclosed herein is contacting (or transforming) a microorganism with a nucleic acid that expresses at least one heterologous gene encoding i) pyruvate decarboxylase (PDC), ii) alcohol dehydrogenase (ADH), or iii) any combination thereof. The microorganism can be any microorganism that is capable of converting a C1 carbon to a product. In some cases, the product is ethanol.

Another exemplary method of making a genetically modified microorganism disclosed herein is contacting (or transforming) a microorganism with a nucleic acid that expresses at least one heterologous gene encoding fatty-acyl-CoA reductase (FAR). The microorganism can be any microorganism that is capable of converting a C1 carbon to a product. In some cases, the product is a fatty (or aliphatic long chain) alcohol.

Another exemplary method of making a genetically modified microorganism disclosed herein is contacting (or transforming) a microorganism with a nucleic acid that expresses at least one heterologous gene encoding a WES polypeptide. The microorganism can be any microorganism that is capable of converting a C1 carbon to a product. In some cases, the product is a fatty acid methyl ester.

The genes that are inserted into a microorganism can be heterologous to the microorganism itself. For example, if the microorganism is a methanotroph, the inserted genes can, for example, be from yeast, a bacterium, or a different species of methanotroph. Further, the genes can be endogenously part of the genome of the microorganism.

The genes can be inserted into a microorganism through the use of vectors. In some cases, the genes can be inserted into the genome of the microorganism. In some cases, the genes can be episomally expressed within the genome of the microorganism. In some cases, both techniques can be used when two or more genes are inserted into a microorganism. For example, a gene can be inserted into the genome of a microorganism by, for example, use of an integration vector. Subsequently, an additional gene can be transformed into the microorganism through an episomal vector.

Techniques for Genetic Modification

The microorganisms disclosed herein may be genetically engineered by using classic microbiological techniques. Some of such techniques are generally disclosed, for example, in Sambrook et al., 1989, Molecular Cloning: A Laboratory Manual, Cold Spring Harbor Labs Press.

The genetically modified microorganisms disclosed herein may include a polynucleotide that has been inserted, deleted or modified (i.e., mutated; e.g., by insertion, deletion, substitution, and/or inversion of nucleotides), in such a manner that such modifications provide the desired effect of expression (e.g., over-expression) of one or more enzymes as provided herein within the microorganism. Genetic modifications which result in an increase in gene expression or function can be referred to as amplification, overproduction, overexpression, activation, enhancement, addition, or up-regulation of a gene. Addition of a gene to increase gene expression can include maintaining the gene(s) on replicating plasmids or integrating the cloned gene(s) into the genome of the production microorganism. Furthermore, increasing the expression of desired genes can include operatively linking the cloned gene(s) to native or heterologous transcriptional control elements.

Where desired, the expression of one or more of the enzymes provided herein is under the control of a regulatory sequence that controls directly or indirectly the enzyme expression in a time-dependent fashion during the fermentation. Inducible promoters can be used to achieve this.

In some cases, a microorganism is transformed or transfected with a genetic vehicle, such as an expression vector comprising a heterologous polynucleotide sequence coding for the enzymes are provided herein. In some cases, the vector(s) can be an episomal vector, or the gene sequence can be integrated into the genome of the microorganism, or any combination thereof. In some cases, the vectors comprising the heterologous polynucleotide sequence encoding for the enzymes provided herein are integrated into the genome of the microorganism.

To facilitate insertion and expression of different genes coding for the enzymes as disclosed herein from the constructs and expression vectors, the constructs may be designed with at least one cloning site for insertion of any gene coding for any enzyme disclosed herein. The cloning site may be a multiple cloning site, e.g., containing multiple restriction sites.

Transfection

Standard transfection techniques can be used to insert genes into a microorganism. As used herein, the term "transfection" or "transformation" can refer to the insertion of an exogenous nucleic acid or polynucleotide into a host cell. The exogenous nucleic acid or polynucleotide may be maintained as a non-integrated vector, for example, a plasmid or episomal vector, or alternatively, may be integrated into the host cell genome. The term transfecting or transfection is intended to encompass all conventional techniques for introducing nucleic acid or polynucleotide into microorganisms. Examples of transfection techniques include, but are not limited to, calcium phosphate precipitation, DEAE-dextran-mediated transfection, lipofection, electroporation, microinjection, rubidium chloride or polycation mediated transfection, protoplast fusion, and sonication. The transfection method that provides optimal transfection frequency and expression of the construct in the particular host cell line and type is favored. For stable transfectants, the constructs are integrated so as to be stably maintained within the host chromosome. In some cases, the preferred transfection is a stable transfection. In some cases, the integration of the gene occurs at a specific locus within the genome of the microorganism.

Transformation

Expression vectors or other nucleic acids may be introduced to selected microorganisms by any of a number of suitable methods. For example, vector constructs may be introduced to appropriate cells by any of a number of transformation methods for plasmid vectors. Standard calcium-chloride-mediated bacterial transformation is still commonly used to introduce naked DNA to bacteria (see, e.g., Sambrook et al., 1989, Molecular Cloning, A Laboratory Manual, Cold Spring Harbor Laboratory Press, Cold Spring Harbor, N.Y.), but electroporation and conjugation may also be used (see, e.g., Ausubel et al., 1988, Current Protocols in Molecular Biology, John Wiley & Sons, Inc., NY, N.Y.).

For the introduction of vector constructs to yeast or other fungal cells, chemical transformation methods may be used (e.g., Rose et al., 1990, Methods in Yeast Genetics, Cold Spring Harbor Laboratory Press, Cold Spring Harbor, N.Y.). Transformed cells may be isolated on selective media appropriate to the selectable marker used. Alternatively, or in addition, plates or filters lifted from plates may be scanned for GFP fluorescence to identify transformed clones.

For the introduction of vectors comprising differentially expressed sequences to certain types of cells, the method used may depend on the form of the vector. Plasmid vectors may be introduced by any of a number of transfection methods, including, for example, lipid-mediated transfection ("lipofection"), DEAE-dextran-mediated transfection, electroporation or calcium phosphate precipitation (see, e.g., Ausubel et al., 1988, Current Protocols in Molecular Biology, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. Many companies offer kits and ways for this type of transfection.

The host cell may be capable of expressing the construct encoding the desired protein, processing the protein and transporting a secreted protein to the cell surface for secretion. Processing includes co- and post-translational modification such as leader peptide cleavage, GPI attachment, glycosylation, ubiquitination, and disulfide bond formation.

Microorganisms can be transformed or transfected with the above-described expression vectors or polynucleotides coding for one or more enzymes as disclosed herein and cultured in nutrient media modified as appropriate for the specific microorganism, inducing promoters, selecting transformants, or amplifying the genes encoding the desired sequences. In some cases, electroporation methods can be used to deliver an expression vector.

Expression of a vector (and the gene contained in the vector) can be verified by an expression assay, for example, qPCR or by measuring levels of RNA. Expression level can be indicative also of copy number. For example, if expression levels are extremely high, this can indicate that more than one copy of a gene was integrated in a genome. Alternatively, high expression can indicate that a gene was integrated in a highly transcribed area, for example, near a highly expressed promoter. Expression can also be verified by measuring protein levels, such as through Western blotting.

CRISPR/Cas System

The methods disclosed throughout can involve pinpoint insertion of genes or the deletion of genes (or parts of genes). Methods described herein can use a CRISPR/cas system. For example, double-strand breaks (DSBs) can be generated using a CRISPR/cas system, e.g., a type II CRISPR/cas system. A Cas enzyme used in the methods disclosed herein can be Cas9, which catalyzes DNA cleavage. Enzymatic action by Cas9 from *Streptococcus pyogenes* or any closely related Cas9 can generate double stranded breaks at target site sequences which hybridize to 20 nucleotides of a guide sequence and have a protospacer-adjacent motif (PAM) following the 20 nucleotides of the target sequence.

A vector can be operably linked to an enzyme-coding sequence encoding a CRISPR enzyme, such as a Cas protein. Cas proteins that can be used include class 1 and class 2. Non-limiting examples of Cas proteins include Cas1, Cas1B, Cas2, Cas3, Cas4, Cas5, Cas5d, Cas5t, Cas5h, Cas5a, Cash, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within 1, 2, 3, 4, 5, 6, 7, 8, 9, 10, 15, 20, 25, 30, 35, 40, 45, 50, 60, 70, 80, 90, 100, 125, 150, 175, 200, 300, 400, 500, or more base pairs from the first or last nucleotide of a target sequence. A vector that encodes a CRISPR enzyme that is mutated to with respect, to a corresponding wild-type enzyme such that the mutated CRISPR enzyme lacks the ability to cleave one or both strands of a target polynucleotide containing a target sequence can be used.

A vector that encodes a CRISPR enzyme comprising one or more nuclear localization sequences (NLSs) can be used. For example, there can be 1, 2, 3, 4, 5, 6, 7, 8, 9, 10 NLSs used. A CRISPR enzyme can comprise the NLSs at or near the ammo-terminus (e.g., 1, 2, 3, 4, 5, 6, 7, 8, 9, 10 NLSs), or at or near the carboxy-terminus (e.g., 1, 2, 3, 4, 5, 6, 7, 8, 9, 10 NLSs), or any combination of these (e.g., one or more NLS at the ammo-terminus and one or more NLS at the carboxy terminus). When more than one NLS is present, each can be selected independently of others, such that a single NLS can be present in more than one copy and/or in combination with one or more other NLSs present in one or more copies.

CRISPR enzymes used in the methods can comprise at most 6 NLSs. An NLS is considered near the N- or C-terminus when the nearest amino acid to the NLS is within 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" and its grammatical equivalents can refer to an RNA which can be specific for a target DNA and can form a complex with Cas protein. An RNA/Cas complex can assist in "guiding" Cas protein to a target DNA.

A method disclosed herein also can comprise introducing into a cell or embryo at least one guide RNA or nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a cell or microorganism by transfecting the cell or microorganism with an isolated guide RNA or plasmid DNA comprising a sequence coding for the guide RNA and a promoter. A guide RNA can also be transferred into a cell or microorganism in other way, such as using virus-mediated gene delivery.

A guide RNA can be isolated. For example, a guide RNA can be transfected in the form of an isolated RNA into a cell or microorganism. A guide RNA can be prepared by in vitro transcription using any in vitro transcription system. A guide RNA can be transferred to a cell in the form of isolated RNA rather than in the form of plasmid comprising encoding sequence for a guide RNA.

A guide RNA can comprise three regions: a first region at the 5' end that can be complementary to a target site in a chromosomal sequence, a second internal region that can form a stem loop structure, and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from 10 nucleotides to 25 nucleotides (i.e., from 10 nts to 25 nts; or 10 nts to 25 nts; or from 10 nts to 25 nts; or from 10 nts to 25 nts) or more. For example, a region of base pairing between a first region of a guide RNA and a target site in a chromosomal sequence can be 10, 11, 12, 13, 14, 15, 16, 17, 18, 19, 20, 22, 23, 24, 25, or more nucleotides in length. Sometimes, a first region of a guide RNA can be 19, 20, or 21 nucleotides in length.

A guide RNA can also comprises a second region that forms a secondary structure. For example, a secondary structure formed by a guide RNA can comprise a stem (or hairpin) and a loop. A length of a loop and a stem can vary. For example, a loop can range from 3 to 10 nucleotides in length, and a stem can range from 6 to 20 base pairs in length. A stem can comprise one or more bulges of 1 to 10 nucleotides. The overall length of a second region can range from 16 to 60 nucleotides in length. For example, a loop can be 4 nucleotides in length and a stem can be 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than 4 nucleotides in length. For example, the length of a third region can range from 5 to 60 nucleotides in length.

A guide RNA can be introduced into a cell or embryo as an RNA molecule. For example, a RNA molecule can be transcribed in vitro and/or can be chemically synthesized. An RNA can be transcribed from a synthetic DNA molecule, e.g., a gBlocks® gene fragment. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III). Plasmid vectors that can be used to express guide RNA include, but are not limited to, px330 vectors and px333 vectors. In some cases, a plasmid vector (e.g., px333 vector) can comprise two guide RNA-encoding DNA sequences.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Site-Specific Insertion

Insertion of the genes can be site-specific. For example, one or more genes can be inserted adjacent to a promoter.

Modification of a targeted locus of a microorganism can be produced by introducing DNA into microorganisms, where the DNA has homology to the target locus. DNA can include a marker gene, allowing for selection of cells comprising the integrated construct. Homologous DNA in a target vector can recombine with DNA at a target locus. A marker gene can be flanked on both sides by homologous DNA sequences, a 3' recombination arm, and a 5' recombination arm.

A variety of enzymes can catalyze insertion of foreign DNA into a microorganism genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, $\Phi$C31 integrase (a serine recombinase derived from Streptomyces phage $\Phi$C31), or bacteriophage derived site-specific recombinases (including Flp, lambda integrase, bacteriophage HK022 recombinase, bacteriophage R4 integrase and phage TP901-1 integrase).

The CRISPR/Cas system can be used to perform site specific insertion. For example, a nick on an insertion site in the genome can be made by CRISPR/cas to facilitate the insertion of a transgene at the insertion site.

The methods described herein, can utilize techniques which can be used to allow a DNA or RNA construct entry into a host cell include, but are not limited to, calcium phosphate/DNA coprecipitation, microinjection of DNA into a nucleus, electroporation, bacterial protoplast fusion with intact cells, transfection, lipofection, infection, particle bombardment, sperm mediated gene transfer, or any other technique.

Certain aspects disclosed herein can utilize vectors (including the ones described above). Any plasmids and vectors can be used as long as they are replicable and viable in a selected host microorganism. Vectors known in the art and those commercially available (and variants or derivatives thereof) can be engineered to include one or more recombination sites for use in the methods. Vectors that can be used include, but not limited to eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), pXT1, pSG5, pPbac, pMbac, pMClneo, and pOG44 (Stratagene, Inc.), and pYES2, pAC360, pBlueBa-cHis A, B, and C, pVL1392, pBlueBac111, pCDM8, pcDNA1, pZeoSV, pcDNA3, pREP4, pCEP4, and pEBVHis (Invitrogen, Corp.), and variants or derivatives thereof.

These vectors can be used to express a gene or portion of a gene of interest. A gene of portion or a gene can be inserted by using known methods, such as restriction enzyme-based techniques.

IV. Other Methods

Methods of Making Valued Chemicals

The genetically modified microorganisms described herein can be used to make valued chemicals, including but not limited to 2,3-BDO; 1,4-BDO; isobutyraldehyde; isobutanol; 1-butanol; n-butanol; ethanol; fatty (or aliphatic long chain) alcohols; and fatty acid methyl esters.

The microorganism can be any of the microorganisms discussed throughout including but not limited to a prokaryote, such as a methanotroph.

The carbon substrate can be any carbon substrate discussed throughout including but not limited to a C1 carbon substrate, such as methane.

The fermentation conditions used during the making of the valued chemicals can be any condition described throughout, such as in the presence or absence of a sugar or rare earth metal and a molecular switch. For example, the media can contain a sugar or rare earth metal when expression of a gene or genes is controlled by a molecular switch.

2,3-BDO

Disclosed herein is a method of making 2,3-BDO comprising contacting a genetically modified microorganism with a carbon substrate, where the microorganism comprises at least one heterologous gene under the control of a molecular switch encoding: i) an acetoin reductase; ii) an alpha-acetolactate decarboxylase (budA); iii) an AlsS; or iv) any combination thereof. In some cases, the at least one heterologous gene is integrated into the genome of the microorganism. The method can further comprise growing the microorganism to produce 2,3-BDO. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce 2,3-BDO.

The 2,3-BDO that is produced from these methods can be substantially pure. The 2,3-BDO produced can be recovered. Additionally, non-2,3-BDO products (i.e., by-products) can also be recovered, such as 2-acetolactate and acetoin.

1,4-BDO

Disclosed herein is a method of making 1,4-BDO comprising contacting a genetically modified microorganism with a carbon substrate, where the microorganism comprises at least one heterologous gene under the control of a molecular switch encoding: i) succinyl-CoA synthetase (sucC), ii) CoA-dependent succinate semialdehyde dehydrogenase (sucD), iii) 4-hydroxybutyrate dehydrogenase (4hbD), iv) 4-hydroxybutyryl-CoA transferase (cat2), v) aldehyde dehydrogenase (ald), vi) alcohol dehydrogenase (adh), or vii) any combination thereof. In some cases, the at least one heterologous gene is integrated into the genome of the microorganism. The method can further comprise growing the microorganism to produce 1,4-BDO. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce 1,4-BDO.

The 1,4-BDO that is produced from these methods can be substantially pure. The 1,4-BDO produced can be recovered. Additionally, non-1,4-BDO products (i.e., by-products) can also be recovered, such as succinyl coA, succinyl semialdehyde, γ-hydroxybutyrate, 4-hydroxybutyryl coA, and/or 4-hydroxybutyraldehyde.

Isobutyraldehyde

Disclosed herein is a method of making isobutyraldehyde comprising contacting a genetically modified microorganism with a carbon substrate, where the microorganism comprises at least one heterologous gene under the control of a molecular switch encoding: i) acetolactate synthase (AlsS); ii) ketol-acid reductoisomerase (KARI); iii) dihydroxy-acid dehydratase (DHAD); iv) 2-keto acid decarboxylase (KDC), or v) any combination thereof. In some cases, the at least one heterologous gene is integrated into the genome of the microorganism. The method can further comprise growing the microorganism to produce isobutyraldehyde. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce isobutyraldehyde.

The isobutyraldehyde that is produced from these methods can be substantially pure. The isobutyraldehyde produced can be recovered. Additionally, non-isobutyraldehyde products (i.e., by-products) can also be recovered, such as pyruvate, 2-acetolactate, 2,3-dihydroxyisovalerate, and ketoisovalerate.

Isobutanol

Disclosed herein is a method of making isobutanol comprising contacting a genetically modified microorganism with a carbon substrate, where the microorganism comprises at least one heterologous gene under the control of a molecular switch encoding: i) acetolactate synthase (AlsS); ii) ketol-acid reductoisomerase (KARI); iii) dihydroxy-acid dehydratase (DHAD); iv) 2-keto acid decarboxylase (KDC), v) alcohol dehydrogenase (ADH) or vi) any combination thereof. In some cases, the at least one heterologous gene is integrated into the genome of the microorganism. The method can further comprise growing the microorganism to produce isobutanol. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce isobutanol.

The isobutanol that is produced from these methods can be substantially pure. The isobutanol produced can be recovered. Additionally, non-isobutanol products (i.e., by-products) can also be recovered, such as pyruvate, 2-acetolactate, 2,3-dihydroxyisovalerate, and ketoisovalerate, isobutyraldehyde.

1-Butanol (a.k.a. n-Butanol)

Disclosed herein is a method of making 1-butanol comprising contacting a genetically modified microorganism with a carbon substrate, where the microorganism comprises at least one heterologous gene under the control of a molecular switch encoding: i) L-threonine ammonia lyase, ii) 2-ethylmalate synthase, isopropylmalate isomerase, iii) 2-ketoacid decarboxylase, iv) alcohol dehydrogenase, or v) any combination thereof. In some cases, the at least one heterologous gene is integrated into the genome of the microorganism. The method can further comprise growing the microorganism to produce 1-butanol. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce 1-butanol.

The 1-butanol that is produced from these methods can be substantially pure. The 1-butanol produced can be recovered. Additionally, non-1-butanol products (i.e., by-products) can also be recovered, such as acetyl-CoA, acetoacetyl-CoA, 3-hydroxybutyryl-CoA, crotonyl-CoA, butyryl-CoA, and butyraldehyde.

Ethanol

Disclosed herein is a method of making ethanol comprising contacting a genetically modified microorganism with a carbon substrate, where the microorganism comprises at least one heterologous gene under the control of a molecular switch encoding: i) pyruvate decarboxylase (PDC), ii) alcohol dehydrogenase (ADH), or iii) any combination thereof. In some cases, at least one heterologous gene is integrated into the genome of the microorganism. The method can further comprise growing the microorganism to produce ethanol. At least one heterologous gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce ethanol.

The ethanol that is produced from these methods can be substantially pure. The ethanol produced can be recovered. Additionally, non-ethanol products (i.e., by-products) can also be recovered, such as acetaldehyde.

Fatty (or Aliphatic Long Chain) Alcohol

Disclosed herein is a method of making fatty (or aliphatic long chain) alcohol comprising contacting a genetically modified microorganism with a carbon substrate, where the microorganism comprises at least one heterologous gene under the control of a molecular switch encoding a fatty-acyl-CoA reductase (FAR). In some cases, the at least one heterologous gene is integrated into the genome of the microorganism. The method can further comprise growing the microorganism to produce fatty (or aliphatic long chain) alcohol. The FAR gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce fatty (or aliphatic long chain) alcohol.

The fatty (or aliphatic long chain) alcohol that is produced from these methods can be substantially pure. The fatty (or aliphatic long chain) alcohol produced can be recovered. Additionally, non-fatty (or aliphatic long chain) alcohol products (i.e., by-products) can also be recovered.

Fatty Acid Methyl Ester

Disclosed herein is a method of making fatty acid methyl ester comprising contacting a genetically modified microorganism with a carbon substrate, where the microorganism comprises at least one heterologous gene under the control of a molecular switch encoding a WES polypeptide. In some cases, the at least one heterologous gene is integrated into the genome of the microorganism. The method can further comprise growing the microorganism to produce fatty acid methyl ester. The WES polypeptide gene can be under the control of a switch, such as an inducible or repressible promoter that is responsive to the presence or absence of a component in the media, e.g., a sugar such as arabinose or a rare earth element such as lanthanum. Also the microorganism can be first grown in media that contains a rare earth metal (e.g., at least 1 µM lanthanum) and then subsequently the rare earth metal can be removed (e.g., by being diluted out of the media). This removal can occur before growing the microorganism to produce fatty acid methyl ester.

The fatty acid methyl ester that is produced from these methods can be substantially pure. The fatty acid methyl ester produced can be recovered. Additionally, non-fatty acid methyl ester products (i.e., by-products) can also be recovered.

V. Fermentation

In general, the microorganisms disclosed herein should be used in fermentation conditions that are appropriate to convert a C1 carbon (such as methane) to 2,3-BDO; 1,4-BDO; isobutyraldehyde; isobutanol; 1-butanol; n-butanol; ethanol; fatty (or aliphatic long chain) alcohols; and fatty acid methyl esters (or other desired product). Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition.

The optimum reaction conditions will depend partly on the particular microorganism of used. However, in some cases, it is preferred that the fermentation be performed at a pressure higher than ambient pressure. Operating at increased pressures can allow for a significant increase in the rate of C1-carbon transfer from the gas phase to the liquid phase where it can be taken up by the microorganism as a carbon source for the production of the multicarbon products. This in turn can mean that the retention time (defined as the liquid volume in the bioreactor divided by the input gas flow rate) can be reduced when bioreactors are maintained at elevated pressure rather than atmospheric pressure.

The use of pressurized systems can greatly reduce the volume of the bioreactor required, and consequently the capital cost of the fermentation equipment. In some cases, reactor volume can be reduced in linear proportion to increases in reactor operating pressure, i.e. bioreactors operated at 10 atmospheres of pressure need only be one tenth the volume of those operated at 1 atmosphere of pressure.

It is also desirable that the rate of introduction of the C1-carbon substrate (such as methane) containing gaseous substrate is such as to ensure that the concentration of the C1-carbon substrate (such as methane) in the liquid phase does not become limiting. This is because a consequence of C1-carbon substrate (e.g., methane) limited conditions may be that the multicarbon product is consumed by the culture.

Fermentation Conditions pH can be optimized based on the microorganism used. For example, the pH used during methanotroph fermentation of methane to a desired product (such as a multicarbon product), can be from 4 to 10. In other instances, the pH can be from 5 to 9; 6 to 8; 6.1 to 7.9; 6.2 to 7.8; 6.3 to 7.7; 6.4 to 7.6; or 6.5 to 7.5. For example, the pH can be from 6.6 to 7.4. In some cases, the pH can be from 5 to 9. In some cases, the pH can be from 6 to 8. In some cases, the pH can be from 6.1 to 7.9. In some cases, the pH can be from 6.2 to 7.8. In some cases, the pH can be from 6.3 to 7.7. In some cases, the pH can be from 6.4 to 7.6. In some cases, the pH can be from 6.5 to 7.5. In some cases the pH used for methanotroph fermentation can be greater than 6.

Temperature can also be adjusted based on the microorganism used. For example, the temperature used during methanotroph fermentation of methane to a desired product (such as a multicarbon product), can be from 30° C. to 45° C. In other instances, the temperature of the fermentation can be from 30° C. to 45° C.; 31° C. to 44° C.; 32° C. to 43° C.; 33° C. to 42° C.; 34° C. to 41° C.; 35° C. to 40° C. For example, the temperature can be from 36° C. to 39° C. (e.g., 36° C., 37° C., 38° C., or 39° C. In some cases, the temperature can be from 30° C. to 45° C. (e.g., 30° C., 31° C., 32° C., 33° C., 34° C., 35° C., 36° C., 37° C., 38° C., 39° C., 40° C., 41° C., 42° C., 43° C., 44° C., or 45° C.). In some cases, the temperature can be from 31° C. to 44° C. (e.g., 31° C., 32° C., 33° C., 34° C., 35° C., 36° C., 37° C., 38° C., 39° C., 40° C., 41° C., 42° C., 43° C., or 44° C. In some cases, the temperature can be from 32° C. to 43° C. In some cases, the temperature can be from 33° C. to 42° C. (e.g., 33° C., 34° C., 35° C., 36° C., 37° C., 38° C., 39° C., 40° C., 41° C., or 42° C. In some cases, the temperature can be from 34° C. to 41° C. (e.g., 34° C., 35° C., 36° C., 37° C., 38° C., 39° C., 40° C., or 41° C.). In some cases, the temperature can be from 35° C. to 40° C. (e.g., 35° C., 36° C., 37° C., 38° C., 39° C., or 40° C.

In some cases, the temperature of fermentation can be from 37.0° C. to 47.9° C. In some cases, the temperature of fermentation can be from 37.1° C. to 47.8° C. In some cases, the temperature of fermentation can be from 37.2° C. to 47.7° C. In some cases, the temperature of fermentation can be from 37.3° C. to 47.6° C. In some cases, the temperature of fermentation can be from 37.4° C. to 47.5° C. In some cases, the temperature of fermentation can be from 37.5° C. to 47.4° C. In some cases, the temperature of fermentation can be from 37.6° C. to 47.3° C. In some cases, the temperature of fermentation can be from 37.7° C. to 47.2° C. In some cases, the temperature of fermentation can be from 37.8° C. to 47.1° C. In some cases, the temperature of fermentation can be from 37.9° C. to 47.0° C. In some cases, the temperature of fermentation can be from 38.0° C. to 46.9° C. In some cases, the temperature of fermentation can be from 38.1° C. to 46.8° C. In some cases, the temperature of fermentation can be from 38.2° C. to 46.7° C. In some cases, the temperature of fermentation can be from 38.3° C. to 46.6° C. In some cases, the temperature of fermentation can be from 38.4° C. to 46.5° C. In some cases, the temperature of fermentation can be from 38.5° C. to 46.4° C. In some cases, the temperature of fermentation can be from 38.6° C. to 46.3° C. In some cases, the temperature of fermentation can be from 38.7° C. to 46.2° C. In some cases, the temperature of fermentation can be from 38.8° C. to 46.1° C. In some cases, the temperature of fermentation can be from 38.9° C. to 46.0° C. In some cases, the temperature of fermentation can be from 39.0° C. to 45.9° C. In some cases, the temperature of fermentation can be from 39.1° C. to 45.8° C. In some cases, the temperature of fermentation can be from 39.2° C. to 45.7° C. In some cases, the temperature of fermentation can be from 39.3° C. to 45.6° C. In some cases, the temperature of fermentation can be from 39.4° C. to 45.5° C. In some cases, the temperature of fermentation can be from 39.5° C. to 45.4° C. In some cases, the temperature of fermentation can be from 39.6° C. to 45.3° C. In some cases, the temperature of fermentation can be from 39.7° C. to 45.2° C. In some cases, the temperature of fermentation can be from 39.8° C. to 45.1° C. In some cases, the temperature of fermentation can be from 39.9° C. to 45.0° C. In some cases, the temperature of fermentation can be from 40.0° C. to 44.9° C. In some cases, the temperature of fermentation can be from 40.1° C. to 44.8° C. In some cases, the temperature of fermentation can be from 40.2° C. to 44.7° C. In some cases, the temperature of fermentation can be from 40.3° C. to 44.6° C. In some cases, the temperature of fermentation can be from 40.4° C. to 44.5° C. In some cases, the temperature of fermentation can be from 40.5° C. to 44.4° C. In some cases, the temperature of fermentation can be from 40.6° C. to 44.3° C. In some cases, the temperature of fermentation can be from 40.7° C. to 44.2° C. In some cases, the temperature of fermentation can be from 40.8° C. to 44.1° C. In some cases, the temperature of fermentation can be from 40.9° C. to 44.0° C. In some cases, the temperature of fermentation can be from 41.0° C. to 43.9° C. In some cases, the temperature of fermentation can be from 41.1° C. to 43.8° C. In some cases, the temperature of fermentation can be from 41.2° C. to 43.7° C. In some cases, the temperature of fermentation can be from 41.3° C. to 43.6° C. In some cases, the temperature of fermentation can be from 41.4° C. to 43.5° C. In some cases, the temperature of fermentation can be from 41.5° C. to 43.4° C. In some cases, the temperature of fermentation can be from 41.6° C. to 43.3° C. In some cases, the temperature of fermentation can be from 41.7° C. to 43.2° C. In some cases, the temperature of fermentation can be from 41.8° C. to 43.1° C. In some cases, the temperature of fermentation can be from 41.9° C. to 43.0° C. In some cases, the temperature of fermentation can be from 42.0° C. to 42.9° C. In some cases, the temperature of fermentation can be from 42.1° C. to 42.8° C. In some cases, the temperature of fermentation can be from 42.2° C. to 42.7° C. In some cases, the temperature of fermentation can be from 42.3° C. to 42.6° C. In some cases, the temperature of fermentation can be from 42.4° C. to 42.5° C.

Availability of oxygen and other gases such as gaseous C1-carbon substrates (such as methane) can affect yield and fermentation rate. For example, when considering oxygen availability, the percent of dissolved oxygen (DO) within the fermentation media can be from 1% to 40%. In certain instances, the DO concentration can be from 1.5% to 35%; 2% to 30%; 2.5% to 25%; 3% to 20%; 4% to 19%; 5% to 18%; 6% to 17%; 7% to 16%; 8% to 15%; 9% to 14%; 10% to 13%; or 11% to 12%. For example, in some cases the DO concentration can be from 2% to 30%. In other cases, the DO can be from 3% to 20%. In some cases, the DO can be from 4% to 10%. In some cases, the DO can be from 1.5% to 35%. In some cases, the DO can be from 2.5% to 25%. In some cases, the DO can be from 4% to 19%. In some cases, the DO can be from 5% to 18%. In some cases, the DO can be from 6% to 17%. In some cases, the DO can be from 7% to 16%. In some cases, the DO can be from 8% to 15%. In some cases, the DO can be from 9% to 14%. In some cases, the DO can be from 10% to 13%. In some cases, the DO can be from 11% to 12%.

When using a methanotroph, the type of methane substances can have an effect on yield and fermentation rates. For example, natural gas can be used, which typically has a methane content of above 85% (e.g., above 90%) methane. Other components within natural gas can include but is not limited to ethane, propane, iso-butane, normal-butane, iso-pentane, normal pentane, hexanes plus, nitrogen, carbon dioxide, oxygen, hydrogen, and hydrogen sulfides.

"Pure" methane can be used as well. In these cases, the methane typically comes from a tank. The methane contained within these tanks can range from 90% or greater methane content and the remaining gas are other gases (such as carbon dioxide). For example, gas having a methane content of greater than 90% can be used during the fermentation process. In certain instances, the methane concentration can be greater than 90%; 91%; 92%; 93%; 94%; 95%; 96%; 97%; 98%; 99%; or 99.9%. In some cases, the methane concentration can be 90% methane and 10% are other gases (such as carbon dioxide). In other instances, the methane concentration can be 91% methane and 9% are other gases (such as carbon dioxide). In some cases, the methane concentration can be 92% methane and 8% are other gases (such as carbon dioxide). In some cases, the methane concentration can be 93% methane and 7% are other gases (such as carbon dioxide). In some cases, the methane concentration can be 94% methane and 6% are other gases (such as carbon dioxide). In some cases, the methane concentration can be 95% methane and 5% are other gases (such as carbon dioxide). In other instances, the methane concentration can be 96% methane and 4% are other gases (such as carbon dioxide). In some cases, the methane concentration can be 97% methane and 3% are other gases (such as carbon dioxide). In some cases, the methane concentration can be 98% methane and 2% are other gases (such as carbon dioxide). In some cases, the methane concentration can be 99% methane and 1% are other gases (such as carbon dioxide). In some cases, the methane concentration can be 99.9% methane and 0.1% are other gases (such as carbon dioxide).

Switches

Some switches can be used in order to repress expression. For example, a rare earth metal with the atomic number of less than 63 can be used to repress expression. In some cases, a rare earth metal with an atomic number of less than 62 can be used to repress expression. In some cases, a rare earth metal with an atomic number of less than 61 can be used. In some cases, a rare earth metal with an atomic number of less than 60 can be used to repress expression. Some switches can be used to activate expression. For example, in some cases, a rare earth metal with the atomic number of greater than 63 can be used to induce expression.

Lanthanum

In cases where a switch is used, the media can comprise a molecule that induces or represses the switch. For example, when a lanthanum sensitive switch is used to repress the expression of one or more of the genes described herein, the media can comprise lanthanum, which will repress expression of the one or more genes under the control of the switch. In the case of lanthanum any one of the following concentrations can effectively repress expression of the one or more genes: 0.1 µM; 0.5 µM; 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 50 µM; 100 µM or more. In one case, 0.1 µM lanthanum can be used to repression expression of the one or more genes under the control of a lanthanum switch. In other cases, at least 0.5 µM lanthanum can be used. In other cases, at least 1 µM lanthanum can be used. In other cases, at least 2 µM lanthanum can be used. In other cases, at least 3 µM lanthanum can be used. In other cases, at least 4 µM lanthanum can be used. In other cases, at least 5 µM lanthanum can be used. In other cases, at least 6 µM lanthanum can be used. In other cases, at least 7 µM lanthanum can be used. In other cases, at least 8 µM lanthanum can be used. In other cases, at least 9 µM lanthanum can be used. In other cases, at least 10 µM lanthanum can be used. In other cases, at least 12.5 µM lanthanum can be used. In other cases, at least 15 µM lanthanum can be used. In other cases, at least 17.5 µM lanthanum can be used. In other cases, at least 20 µM lanthanum can be used. In other cases, at least 25 µM lanthanum can be used. In other cases, at least 50 µM lanthanum can be used. In other cases, at least 100 µM lanthanum can be used. In some cases, a range of 0.5 µM lanthanum to 100 µM lanthanum will effectively repress gene expression. In some cases, a range of 0.5 µM lanthanum to 50 µM lanthanum will repress gene expression. In other cases, a range of 1 µM lanthanum to 20 µM lanthanum will repress gene expression. In some cases, a range of 2 µM lanthanum to 15 µM lanthanum will repress gene expression. In some cases, a range of 3 µM lanthanum to 12.5 µM lanthanum will repress gene expression. In some cases, a range of 4 µM lanthanum to 12 µM lanthanum will repress gene expression. In some cases, a range of 5 µM lanthanum to 11.5 µM lanthanum will repress gene expression. In some cases, a range of 6 µM lanthanum to 11 µM lanthanum will repress gene expression. In some cases, a range of 7 µM lanthanum to 10.5 µM lanthanum will repress gene expression. In some cases, a range of 8 µM lanthanum to 10 µM lanthanum will repress gene expression. In some cases, the maximal repressive effect of lanthanum is from 10 µM to 35 µM of lanthanum. In some cases, the maximal repressive effective of lanthanum is at about 35 µM.

In some cases, the lanthanum in the media can be diluted to turn on expression of the one or more lanthanum repressed genes. For example, in some cases, the dilution of lanthanum containing media can be 1:1 (1 part lanthanum containing media to 1 part non-lanthanum containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising lanthanum. The media can then be diluted to effectively turn on the expression of the lanthanum repressed genes. The microorganism can be then grown in conditions to promote the production of desired products, such as the multicarbon products (or others disclosed throughout).

Cerium

In certain cases, a cerium sensitive switch can be used to repress or induce the expression of one or more of the genes described herein. In some cases, the media can comprise cerium, which can in some instances repress expression of the one or more genes under the control of the switch. In the case of cerium any one of the following concentrations can effectively repress expression of the one or more genes: 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 30 µM; 35 µM; 40 µM; 45 µM; 50 µM; 55 µM; 60 µM; 65 µM; 70 µM; 75 µM; 80 µM; 85 µM; 90 µM; 95 µM; 100 µM; 105 µM; 110 µM; 115 µM; 120 µM; 125 µM; 130 µM; 135 µM; 140 µM; 145 µM; 150 µM; 155 µM; 160 µM; 165 µM; 170 µM; 175 µM; 180 µM; 185 µM; 190 µM; 195 µM; 200 µM or more. In one case, at least 1 µM cerium can be used. In other cases, at least 2 µM cerium can be used. In other cases, at least 3 µM cerium can be used. In other cases, at least 4 µM cerium can be used. In other cases, at least 5 µM cerium can be used. In other cases, at least 6 µM cerium can be used. In other cases, at least 7 µM cerium can be used. In other cases, at least 8 µM cerium can be used. In other cases, at least 9 µM cerium can be used. In other cases, at least 10 µM cerium can be used. In other cases, at least 12.5 µM cerium can be used. In other cases, at least 15 µM cerium can be used. In other cases, at least 17.5 µM cerium can be used. In other cases, at least 20 µM cerium can be used. In other cases, at least 25 µM cerium can be used. In other cases, at least 25 µM cerium can be used. In other cases, at least 30 µM cerium can be used. In other cases, at least 35 µM cerium can be used. In other cases, at least 40 µM cerium can be used. In other cases, at least 45 µM cerium can be used. In other cases, at least 50 µM cerium can be used. In other cases, at least 55 µM cerium can be used. In other cases, at least 60 µM cerium can be used. In other cases, at least 65 µM cerium can be used. In other cases, at least 70 µM cerium can be used. In other cases, at least 75 µM cerium can be used. In other cases, at least 80 µM cerium can be used. In other cases, at least 85 µM cerium can be used. In other cases, at least 90 µM cerium can be used. In other cases, at least 95 µM cerium can be used. In other cases, at least 100 µM cerium can be used. In other cases, at least 105 µM cerium can be used. In other cases, at least 110 µM cerium can be used. In other cases, at least 115 µM cerium can be used. In other cases, at least 120 µM cerium can be used. In other cases, at least 125 µM cerium can be used. In other cases, at least 130 µM cerium can be used. In other cases, at least 135 µM cerium can be used. In other cases, at least 140 µM cerium can be used. In other cases, at least 145 µM cerium can be used. In other cases, at least 150 µM cerium can be used. In other cases, at least 155 µM cerium can be used. In other cases, at least 160 µM cerium can be used. In other cases, at least 165 µM cerium can be used. In other cases, at least 170 µM cerium can be used. In other cases, at least 175 µM cerium can be used. In other cases, at least 180 µM cerium can be used. In other cases, at least 185 µM cerium can be used. In other cases, at least 190 µM cerium can be used. In other cases, at least 195 µM cerium can be used. In other cases, at least 200 µM or more cerium can be used.

In some cases, a range of 1 µM cerium to 200 µM cerium will effectively repress gene expression. In some cases, a range of 5 µM cerium to 175 µM cerium will repress gene expression. In other cases, a range of 7.5 µM cerium to 150 µM cerium will repress gene expression. In some cases, a range of 10 µM cerium to 145 µM cerium will repress gene expression. In some cases, a range of 15 µM cerium to 140 µM cerium will repress gene expression. In some cases, a range of 20 µM cerium to 125 µM cerium will repress gene expression. In some cases, a range of 25 µM cerium to 100 µM cerium will repress gene expression. In some cases, a range of 30 µM cerium to 90 µM cerium will repress gene expression. In some cases, a range of 35 µM cerium to 75 µM cerium will repress gene expression. In some cases, a range of 40 µM cerium to 65 µM cerium will repress gene expression. In some cases, the maximal repressive effect of cerium is from 35 µM to 70 µM of cerium. In some cases, the maximal repressive effective of lanthanum is at about 70 µM.

In some cases, the cerium in the media can be diluted to turn on expression of the one or more cerium repressed genes. For example, in some cases, the dilution of cerium containing media can be 1:1 (1 part cerium containing media to 1 part non-cerium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising cerium. The media can then be diluted to effectively turn on the expression of the cerium repressed genes. The microorganism can be then grown in conditions to promote the production of desired products, such as the multicarbon products (or others disclosed throughout).

Praseodymium

In certain cases, a praseodymium switch can be used to induce or repress the expression of one or more of the genes described herein. In some cases, the media can comprise praseodymium, which will in certain instances repress expression of the one or more genes under the control of the switch. In the case of praseodymium any one of the following concentrations can effectively repress expression of the one or more genes: 1 µM; 2 µM; 3 µM; 4 µM; 5 µM; 6 µM; 7 µM; 8 µM; 9 µM; 10 µM; 12.5 µM; 15 µM; 17.5 µM; 20 µM; 25 µM; 30 µM; 35 µM; 40 µM; 45 µM; 50 µM; 55 µM; 60 µM; 65 µM; 70 µM; 75 µM; 80 µM; 85 µM; 90 µM; 95 µM; 100 µM; 105 µM; 110 µM; 115 µM; 120 µM; 125 µM; 130 µM; 135 µM; 140 µM; 145 µM; 150 µM; 155 µM; 160 µM; 165 µM; 170 µM; 175 µM; 180 µM; 185 µM; 190 µM; 195 µM; 200 µM or more. In one case, at least 1 µM praseodymium can be used. In other cases, at least 2 µM praseodymium can be used. In other cases, at least 3 µM praseodymium can be used. In other cases, at least 4 µM praseodymium can be used. In other cases, at least 5 μM praseodymium can be used. In other cases, at least 6 μM praseodymium can be used. In other cases, at least 7 μM praseodymium can be used. In other cases, at least 8 μM praseodymium can be used. In other cases, at least 9 μM praseodymium can be used. In other cases, at least 10 μM praseodymium can be used. In other cases, at least 12.5 μM praseodymium can be used. In other cases, at least 15 μM praseodymium can be used. In other cases, at least 17.5 μM praseodymium can be used. In other cases, at least 20 μM praseodymium can be used. In other cases, at least 25 μM praseodymium can be used. In other cases, at least 25 μM praseodymium can be used. In other cases, at least 30 μM praseodymium can be used. In other cases, at least 35 μM praseodymium can be used. In other cases, at least 40 μM praseodymium can be used. In other cases, at least 45 μM praseodymium can be used. In other cases, at least 50 μM praseodymium can be used. In other cases, at least 55 μM praseodymium can be used. In other cases, at least 60 μM praseodymium can be used. In other cases, at least 65 μM praseodymium can be used. In other cases, at least 70 μM praseodymium can be used. In other cases, at least 75 μM praseodymium can be used. In other cases, at least 80 μM praseodymium can be used. In other cases, at least 85 μM praseodymium can be used. In other cases, at least 90 μM praseodymium can be used. In other cases, at least 95 μM praseodymium can be used. In other cases, at least 100 μM praseodymium can be used. In other cases, at least 105 μM praseodymium can be used. In other cases, at least 110 μM praseodymium can be used. In other cases, at least 115 μM praseodymium can be used. In other cases, at least 120 μM praseodymium can be used. In other cases, at least 125 μM praseodymium can be used. In other cases, at least 130 μM praseodymium can be used. In other cases, at least 135 μM praseodymium can be used. In other cases, at least 140 μM praseodymium can be used. In other cases, at least 145 μM praseodymium can be used. In other cases, at least 150 μM praseodymium can be used. In other cases, at least 155 μM praseodymium can be used. In other cases, at least 160 μM praseodymium can be used. In other cases, at least 165 μM praseodymium can be used. In other cases, at least 170 μM praseodymium can be used. In other cases, at least 175 μM praseodymium can be used. In other cases, at least 180 μM praseodymium can be used. In other cases, at least 185 μM praseodymium can be used. In other cases, at least 190 μM praseodymium can be used. In other cases, at least 195 μM praseodymium can be used. In other cases, at least 200 μM or more praseodymium can be used.

In some cases, a range of 1 μM praseodymium to 200 μM praseodymium will effectively repress gene expression. In some cases, a range of 5 μM praseodymium to 175 μM praseodymium will repress gene expression. In other cases, a range of 7.5 μM praseodymium to 150 μM praseodymium will repress gene expression. In some cases, a range of 10 μM praseodymium to 145 μM praseodymium will repress gene expression. In some cases, a range of 15 μM praseodymium to 140 μM praseodymium will repress gene expression. In some cases, a range of 20 μM praseodymium to 125 μM praseodymium will repress gene expression. In some cases, a range of 25 μM praseodymium to 100 μM praseodymium will repress gene expression. In some cases, a range of 30 μM praseodymium to 90 μM praseodymium will repress gene expression. In some cases, a range of 35 μM praseodymium to 75 μM praseodymium will repress gene expression. In some cases, a range of 40 μM praseodymium to 65 μM praseodymium will repress gene expression. In some cases, the maximal repressive effect of praseodymium is at least 140 μM.

In some cases, the praseodymium in the media can be diluted to turn on expression of the one or more praseodymium repressed genes. For example, in some cases, the dilution of praseodymium containing media can be 1:1 (1 part praseodymium containing media to 1 part non-praseodymium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising praseodymium. The media can then be diluted to effectively turn on the expression of the praseodymium repressed genes. The microorganism can be then grown in conditions to promote the production of desired products, such as the multicarbon products (or others disclosed throughout).

Neodymium

In certain cases, a neodymium switch can be used to repress or induce the expression of one or more of the genes described herein. In some cases, the media can comprise neodymium, which will repress expression of the one or more genes under the control of the switch. In the case of neodymium any one of the following concentrations can effectively repress expression of the one or more genes: 1 μM; 2 μM; 3 μM; 4 μM; 5 μM; 6 μM; 7 μM; 8 μM; 9 μM; 10 μM; 12.5 μM; 15 μM; 17.5 μM; 20 μM; 25 μM; 30 μM; 35 μM; 40 μM; 45 μM; 50 μM; 55 μM; 60 μM; 65 μM; 70 μM; 75 μM; 80 μM; 85 μM; 90 μM; 95 μM; 100 μM; 105 μM; 110 μM; 115 μM; 120 μM; 125 μM; 130 μM; 135 μM; 140 μM; 145 μM; 150 μM; 155 μM; 160 μM; 165 μM; 170 μM; 175 μM; 180 μM; 185 μM; 190 μM; 195 μM; 200 μM or more. In one case, at least 1 μM neodymium can be used. In other cases, at least 2 μM neodymium can be used. In other cases, at least 3 μM neodymium can be used. In other cases, at least 4 μM neodymium can be used. In other cases, at least 5 μM neodymium can be used. In other cases, at least 6 μM neodymium can be used. In other cases, at least 7 μM neodymium can be used. In other cases, at least 8 μM neodymium can be used. In other cases, at least 9 μM neodymium can be used. In other cases, at least 10 μM neodymium can be used. In other cases, at least 12.5 μM neodymium can be used. In other cases, at least 15 μM neodymium can be used. In other cases, at least 17.5 μM neodymium can be used. In other cases, at least 20 μM neodymium can be used. In other cases, at least 25 μM neodymium can be used. In other cases, at least 25 µM neodymium can be used. In other cases, at least 30 µM neodymium can be used. In other cases, at least 35 µM neodymium can be used. In other cases, at least 40 µM neodymium can be used. In other cases, at least 45 µM neodymium can be used. In other cases, at least 50 µM neodymium can be used. In other cases, at least 55 µM neodymium can be used. In other cases, at least 60 µM neodymium can be used. In other cases, at least 65 µM neodymium can be used. In other cases, at least 70 µM neodymium can be used. In other cases, at least 75 µM neodymium can be used. In other cases, at least 80 µM neodymium can be used. In other cases, at least 85 µM neodymium can be used. In other cases, at least 90 µM neodymium can be used. In other cases, at least 95 µM neodymium can be used. In other cases, at least 100 µM neodymium can be used. In other cases, at least 105 µM neodymium can be used. In other cases, at least 110 µM neodymium can be used. In other cases, at least 115 µM neodymium can be used. In other cases, at least 120 µM neodymium can be used. In other cases, at least 125 µM neodymium can be used. In other cases, at least 130 µM neodymium can be used. In other cases, at least 135 µM neodymium can be used. In other cases, at least 140 µM neodymium can be used. In other cases, at least 145 µM neodymium can be used. In other cases, at least 150 µM neodymium can be used. In other cases, at least 155 µM neodymium can be used. In other cases, at least 160 µM neodymium can be used. In other cases, at least 165 µM neodymium can be used. In other cases, at least 170 µM neodymium can be used. In other cases, at least 175 µM neodymium can be used. In other cases, at least 180 µM neodymium can be used. In other cases, at least 185 µM neodymium can be used. In other cases, at least 190 µM neodymium can be used. In other cases, at least 195 µM neodymium can be used. In other cases, at least 200 µM or more neodymium can be used.

In some cases, a range of 1 µM neodymium to 200 µM neodymium will effectively repress gene expression. In some cases, a range of 5 µM neodymium to 175 µM neodymium will repress gene expression. In other cases, a range of 7.5 µM neodymium to 150 µM neodymium will repress gene expression. In some cases, a range of 10 µM neodymium to 145 µM neodymium will repress gene expression. In some cases, a range of 15 µM neodymium to 140 µM neodymium will repress gene expression. In some cases, a range of 20 µM neodymium to 125 µM neodymium will repress gene expression. In some cases, a range of 25 µM neodymium to 100 µM neodymium will repress gene expression. In some cases, a range of 30 µM neodymium to 90 µM neodymium will repress gene expression. In some cases, a range of 35 µM neodymium to 75 µM neodymium will repress gene expression. In some cases, a range of 40 µM neodymium to 65 µM neodymium will repress gene expression. In some cases, the maximal repressive effect of neodymium is at least 140 µM.

In some cases, the neodymium in the media can be diluted to turn on expression of the one or more neodymium repressed genes. For example, in some cases, the dilution of neodymium containing media can be 1:1 (1 part neodymium containing media to 1 part non-neodymium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising neodymium. The media can then be diluted to effectively turn on the expression of the neodymium repressed genes. The microorganism can be then grown in conditions to promote the production of desired products, such as the multicarbon products (or others disclosed throughout).

Scandium

In certain cases, a scandium switch can be used to repress or induce the expression of one or more of the genes described herein. In some cases, the media can comprise scandium, which will repress or induce expression of the one or more genes under the control of the switch. In the case of scandium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM scandium can be used. In other cases, at least 20 µM scandium can be used. In other cases, at least 30 µM scandium can be used. In other cases, at least 40 µM scandium can be used. In other cases, at least 50 µM scandium can be used. In other cases, at least 60 µM scandium can be used. In other cases, at least 70 µM scandium can be used. In other cases, at least 80 µM scandium can be used. In other cases, at least 90 µM scandium can be used. In other cases, at least 100 µM scandium can be used. In other cases, at least 120 µM scandium can be used. In other cases, at least 140 µM scandium can be used. In other cases, at least 150 µM scandium can be used. In other cases, at least 175 µM scandium can be used. In other cases, at least 200 µM or more scandium can be used.

In some cases, a range of 10 µM scandium to 200 µM scandium will effectively repress gene expression. In some cases, a range of 20 µM scandium to 175 µM scandium will repress or induce gene expression. In other cases, a range of 30 µM scandium to 150 µM scandium will repress or induce gene expression. In some cases, a range of 40 µM scandium to 140 µM scandium will repress or induce gene expression. In some cases, a range of 50 µM to 120 µM scandium will repress or induce gene expression. In some cases, a range of 60 µM scandium to 100 µM scandium will repress or induce gene expression. In some cases, a range of 70 µM scandium to 90 µM scandium will repress or induce gene expression.

In some cases, the scandium in the media can be diluted to reverse the effect of scandium. For example, in some cases, the dilution of scandium containing media can be 1:1 (1 part scandium containing media to 1 part non-scandium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Yttrium

In certain cases, a yttrium switch can be used to repress or induce the expression of one or more of the genes described herein. In some cases, the media can comprise yttrium, which will repress or induce expression of the one or more genes under the control of the switch. In the case of yttrium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM yttrium can be used. In other cases, at least 20 µM yttrium can be used. In other cases, at least 30 µM yttrium can be used. In other cases, at least 40 µM yttrium can be used. In other cases, at least 50 µM yttrium can be used. In other cases, at least 60 µM yttrium can be used. In other cases, at least 70 µM yttrium can be used. In other cases, at least 80 µM yttrium can be used. In other cases, at least 90 µM yttrium can be used. In other cases, at least 100 µM yttrium can be used. In other cases, at least 120 µM yttrium can be used. In other cases, at least 140 µM yttrium can be used. In other cases, at least 150 µM yttrium can be used. In other cases, at least 175 µM yttrium can be used. In other cases, at least 200 µM or more yttrium can be used.

In some cases, a range of 10 µM yttrium to 200 µM yttrium will effectively repress gene expression. In some cases, a range of 20 µM yttrium to 175 µM yttrium will repress or induce gene expression. In other cases, a range of 30 µM yttrium to 150 µM yttrium will repress or induce gene expression. In some cases, a range of 40 µM yttrium to 140 µM yttrium will repress or induce gene expression. In some cases, a range of 50 µM yttrium to 120 µM yttrium will repress or induce gene expression. In some cases, a range of 60 µM yttrium to 100 µM yttrium will repress or induce gene expression. In some cases, a range of 70 µM yttrium to 90 µM yttrium will repress or induce gene expression.

In some cases, the yttrium in the media can be diluted to reverse the effect of yttrium. For example, in some cases, the dilution of yttrium containing media can be 1:1 (1 part yttrium containing media to 1 part non-yttrium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Samrium

In certain cases, a samrium switch can be used to repress or induce the expression of one or more of the genes described herein. In some cases, the media can comprise samrium, which will repress or induce expression of the one or more genes under the control of the switch. In the case of samrium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM samrium can be used. In other cases, at least 20 µM samrium can be used. In other cases, at least 30 µM samrium can be used. In other cases, at least 40 µM samrium can be used. In other cases, at least 50 µM samrium can be used. In other cases, at least 60 µM samrium can be used. In other cases, at least 70 µM samrium can be used. In other cases, at least 80 µM samrium can be used. In other cases, at least 90 µM samrium can be used. In other cases, at least 100 µM samrium can be used. In other cases, at least 120 µM samrium can be used. In other cases, at least 140 µM samrium can be used. In other cases, at least 150 µM samrium can be used. In other cases, at least 175 µM samrium can be used. In other cases, at least 200 µM or more samrium can be used.

In some cases, a range of 10 µM samrium to 200 µM samrium will effectively repress or induce gene expression. In some cases, a range of 20 µM samrium to 175 µM samrium will repress or induce gene expression. In other cases, a range of 30 µM samrium to 150 µM samrium will repress or induce gene expression. In some cases, a range of 40 µM samrium to 140 µM samrium will repress or induce gene expression. In some cases, a range of 50 µM samrium to 120 µM samrium will repress or induce gene expression. In some cases, a range of 60 µM samrium to 100 µM samrium will repress or induce gene expression. In some cases, a range of 70 µM samrium to 90 µM samrium will repress or induce gene expression.

In some cases, the samrium in the media can be diluted to reverse the effect of samrium. For example, in some cases, the dilution of samrium containing media can be 1:1 (1 part samrium containing media to 1 part non-samrium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Europium

In certain cases, a europium switch can be used to repress or induce the expression of one or more of the genes described herein. In some cases, the media can comprise europium, which will repress or induce expression of the one or more genes under the control of the switch. In the case of europium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM europium can be used. In other cases, at least 20 µM europium can be used. In other cases, at least 30 µM europium can be used. In other cases, at least 40 µM europium can be used. In other cases, at least 50 µM europium can be used. In other cases, at least 60 µM europium can be used. In other cases, at least 70 µM europium can be used. In other cases, at least 80 µM europium can be used. In other cases, at least 90 µM europium can be used. In other cases, at least 100 µM europium can be used. In other cases, at least 120 µM europium can be used. In other cases, at least 140 µM europium can be used. In other cases, at least 150 µM europium can be used. In other cases, at least 175 µM europium can be used. In other cases, at least 200 µM or more europium can be used.

In some cases, a range of 10 µM europium to 200 µM europium will effectively repress or induce gene expression. In some cases, a range of 20 µM europium to 175 µM europium will repress or induce gene expression. In other cases, a range of 30 µM europium to 150 µM europium will repress or induce gene expression. In some cases, a range of 40 µM europium to 140 µM europium will repress or induce gene expression. In some cases, a range of 50 µM europium to 120 µM europium will repress or induce gene expression. In some cases, a range of 60 µM europium to 100 µM europium will repress or induce gene expression. In some cases, a range of 70 µM europium to 90 µM europium will repress or induce gene expression.

In some cases, the europium in the media can be diluted to reverse the effect of europium. For example, in some cases, the dilution of europium containing media can be 1:1 (1 part europium containing media to 1 part non-europium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Gadolinium

In certain cases, a gadolinium switch can be used to repress or induce the expression of one or more of the genes described herein. In some cases, the media can comprise gadolinium, which will repress or induce expression of the one or more genes under the control of the switch. In the case of gadolinium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM gadolinium can be used. In other cases, at least 20 µM gadolinium can be used. In other cases, at least 30 µM gadolinium can be used. In other cases, at least 40 µM gadolinium can be used. In other cases, at least 50 µM gadolinium can be used. In other cases, at least 60 µM gadolinium can be used. In other cases, at least 70 µM gadolinium can be used. In other cases, at least 80 µM gadolinium can be used. In other cases, at least 90 µM gadolinium can be used. In other cases, at least 100 µM gadolinium can be used. In other cases, at least 120 µM gadolinium can be used. In other cases, at least 140 µM gadolinium can be used. In other cases, at least 150 µM gadolinium can be used. In other cases, at least 175 µM gadolinium can be used. In other cases, at least 200 µM or more gadolinium can be used.

In some cases, a range of 10 µM gadolinium to 200 µM gadolinium will effectively repress or induce gene expression. In some cases, a range of 20 µM gadolinium to 175 µM gadolinium will repress or induce gene expression. In other cases, a range of 30 µM gadolinium to 150 µM gadolinium will repress or induce gene expression. In some cases, a range of 40 µM gadolinium to 140 µM gadolinium will repress or induce gene expression. In some cases, a range of 50 µM gadolinium to 120 µM gadolinium will repress or induce gene expression. In some cases, a range of 60 µM gadolinium to 100 µM gadolinium will repress or induce gene expression. In some cases, a range of 70 µM gadolinium to 90 µM gadolinium will repress or induce gene expression.

In some cases, the gadolinium in the media can be diluted to reverse the effect of gadolinium. For example, in some cases, the dilution of gadolinium containing media can be 1:1 (1 part gadolinium containing media to 1 part non-gadolinium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Terbium

In certain cases, a terbium switch can be used to repress or induce the expression of one or more of the genes described herein. In some cases, the media can comprise terbium, which will repress or induce expression of the one or more genes under the control of the switch. In the case of terbium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM terbium can be used. In other cases, at least 20 µM terbium can be used. In other cases, at least 30 µM terbium can be used. In other cases, at least 40 µM terbium can be used. In other cases, at least 50 µM terbium can be used. In other cases, at least 60 µM terbium can be used. In other cases, at least 70 µM terbium can be used. In other cases, at least 80 µM terbium can be used. In other cases, at least 90 µM terbium can be used. In other cases, at least 100 µM terbium can be used. In other cases, at least 120 µM terbium can be used. In other cases, at least 140 µM terbium can be used. In other cases, at least 150 µM terbium can be used. In other cases, at least 175 µM terbium can be used. In other cases, at least 200 µM or more terbium can be used.

In some cases, a range of 10 µM terbium to 200 µM terbium will effectively repress or induce gene expression. In some cases, a range of 20 µM terbium to 175 µM terbium will repress or induce gene expression. In other cases, a range of 30 µM terbium to 150 µM terbium will repress or induce gene expression. In some cases, a range of 40 µM terbium to 140 µM terbium will repress or induce gene expression. In some cases, a range of 50 µM terbium to 120 µM terbium will repress or induce gene expression. In some cases, a range of 60 µM terbium to 100 µM terbium will repress or induce gene expression. In some cases, a range of 70 µM terbium to 90 µM terbium will repress or induce gene expression.

In some cases, the terbium in the media can be diluted to reverse the effect of terbium. For example, in some cases, the dilution of terbium containing media can be 1:1 (1 part terbium containing media to 1 part non-terbium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Dysprosium

In certain cases, a dysprosium switch can be used to repress or induce the expression of one or more of the genes described herein. In some cases, the media can comprise dysprosium, which will repress or induce expression of the one or more genes under the control of the switch. In the case of dysprosium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM dysprosium can be used. In other cases, at least 20 µM dysprosium can be used. In other cases, at least 30 µM dysprosium can be used. In other cases, at least 40 µM dysprosium can be used. In other cases, at least 50 µM dysprosium can be used. In other cases, at least 60 µM dysprosium can be used. In other cases, at least 70 µM dysprosium can be used. In other cases, at least 80 µM dysprosium can be used. In other cases, at least 90 µM dysprosium can be used. In other cases, at least 100 µM dysprosium can be used. In other cases, at least 120 µM dysprosium can be used. In other cases, at least 140 µM dysprosium can be used. In other cases, at least 150 µM dysprosium can be used. In other cases, at least 175 µM dysprosium can be used. In other cases, at least 200 µM or more dysprosium can be used.

In some cases, a range of 10 µM dysprosium to 200 µM dysprosium will effectively repress or induce gene expression. In some cases, a range of 20 µM dysprosium to 175 µM dysprosium will repress or induce gene expression. In other cases, a range of 30 µM dysprosium to 150 µM dysprosium will repress or induce gene expression. In some cases, a range of 40 µM dysprosium to 140 µM dysprosium will repress or induce gene expression. In some cases, a range of 50 μM dysprosium to 120 μM dysprosium will repress or induce gene expression. In some cases, a range of 60 μM dysprosium to 100 μM dysprosium will repress or induce gene expression. In some cases, a range of 70 μM dysprosium to 90 μM dysprosium will repress or induce gene expression.

In some cases, the dysprosium in the media can be diluted to reverse the effect of dysprosium. For example, in some cases, the dilution of dysprosium containing media can be 1:1 (1 part dysprosium containing media to 1 part non-dysprosium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Holmium

In certain cases, a holmium switch can be used to repress or induce the expression of one or more of the genes described herein. In some cases, the media can comprise holmium, which will repress or induce expression of the one or more genes under the control of the switch. In the case of holmium any one of the following concentrations can effectively repress expression of the one or more genes: 10 μM; 20 μM; 30 μM; 40 μM; 50 μM; 60 μM; 70 μM; 80 μM; 90 μM; 100 μM; 120 μM; 140 μM; 150 μM; 175 μM; 200 μM or more. In other cases, at least 10 μM holmium can be used. In other cases, at least 20 μM holmium can be used. In other cases, at least 30 μM holmium can be used. In other cases, at least 40 μM holmium can be used. In other cases, at least 50 μM holmium can be used. In other cases, at least 60 μM holmium can be used. In other cases, at least 70 μM holmium can be used. In other cases, at least 80 μM holmium can be used. In other cases, at least 90 μM holmium can be used. In other cases, at least 100 μM holmium can be used. In other cases, at least 120 μM holmium can be used. In other cases, at least 140 μM holmium can be used. In other cases, at least 150 μM holmium can be used. In other cases, at least 175 μM holmium can be used. In other cases, at least 200 μM or more holmium can be used.

In some cases, a range of 10 μM holmium to 200 μM holmium will effectively repress or induce gene expression. In some cases, a range of 20 μM holmium to 175 μM holmium will repress or induce gene expression. In other cases, a range of 30 μM holmium to 150 μM holmium will repress or induce gene expression. In some cases, a range of 40 μM holmium to 140 μM holmium will repress or induce gene expression. In some cases, a range of 50 μM holmium to 120 μM holmium will repress or induce gene expression. In some cases, a range of 60 μM holmium to 100 μM holmium will repress or induce gene expression. In some cases, a range of 70 μM holmium to 90 μM holmium will repress or induce gene expression.

In some cases, the holmium in the media can be diluted to reverse the effect of holmium. For example, in some cases, the dilution of holmium containing media can be 1:1 (1 part holmium containing media to 1 part non-holmium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Erbium

In certain cases, an erbium switch can be used to repress or induce the expression of one or more of the genes described herein. In some cases, the media can comprise erbium, which will repress or induce expression of the one or more genes under the control of the switch. In the case of erbium any one of the following concentrations can effectively repress expression of the one or more genes: 10 μM; 20 μM; 30 μM; 40 μM; 50 μM; 60 μM; 70 μM; 80 μM; 90 μM; 100 μM; 120 μM; 140 μM; 150 μM; 175 μM; 200 μM or more. In other cases, at least 10 μM erbium can be used. In other cases, at least 20 μM erbium can be used. In other cases, at least 30 μM erbium can be used. In other cases, at least 40 μM erbium can be used. In other cases, at least 50 μM erbium can be used. In other cases, at least 60 μM erbium can be used. In other cases, at least 70 μM erbium can be used. In other cases, at least 80 μM erbium can be used. In other cases, at least 90 μM erbium can be used. In other cases, at least 100 μM erbium can be used. In other cases, at least 120 μM erbium can be used. In other cases, at least 140 μM erbium can be used. In other cases, at least 150 μM erbium can be used. In other cases, at least 175 μM erbium can be used. In other cases, at least 200 μM or more erbium can be used.

In some cases, a range of 10 μM erbium to 200 μM erbium will effectively repress or induce gene expression. In some cases, a range of 20 μM erbium to 175 μM erbium will repress or induce gene expression. In other cases, a range of 30 µM erbium to 150 µM erbium will repress or induce gene expression. In some cases, a range of 40 µM erbium to 140 µM erbium will repress or induce gene expression. In some cases, a range of 50 µM erbium to 120 µM erbium will repress or induce gene expression. In some cases, a range of 60 µM erbium to 100 µM erbium will repress or induce gene expression. In some cases, a range of 70 µM erbium to 90 µM erbium will repress or induce gene expression.

In some cases, the erbium in the media can be diluted to reverse the effect of erbium. For example, in some cases, the dilution of erbium containing media can be 1:1 (1 part erbium containing media to 1 part non-erbium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Thulium

In certain cases, a thulium switch can be used to repress or induce the expression of one or more of the genes described herein. In some cases, the media can comprise thulium, which will repress or induce expression of the one or more genes under the control of the switch. In the case of thulium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM thulium can be used. In other cases, at least 20 µM thulium can be used. In other cases, at least 30 µM thulium can be used. In other cases, at least 40 µM thulium can be used. In other cases, at least 50 µM thulium can be used. In other cases, at least 60 µM thulium can be used. In other cases, at least 70 µM thulium can be used. In other cases, at least 80 µM thulium can be used. In other cases, at least 90 µM thulium can be used. In other cases, at least 100 µM thulium can be used. In other cases, at least 120 µM thulium can be used. In other cases, at least 140 µM thulium can be used. In other cases, at least 150 µM thulium can be used. In other cases, at least 175 µM thulium can be used. In other cases, at least 200 µM or more thulium can be used.

In some cases, a range of 10 µM thulium to 200 µM thulium will effectively repress or induce gene expression. In some cases, a range of 20 µM thulium to 175 µM thulium will repress or induce gene expression. In other cases, a range of 30 µM thulium to 150 µM thulium will repress or induce gene expression. In some cases, a range of 40 µM thulium to 140 µM thulium will repress or induce gene expression. In some cases, a range of 50 µM thulium to 120 µM thulium will repress or induce gene expression. In some cases, a range of 60 µM thulium to 100 µM thulium will repress or induce gene expression. In some cases, a range of 70 µM thulium to 90 µM thulium will repress or induce gene expression.

In some cases, the thulium in the media can be diluted to reverse the effect of thulium. For example, in some cases, the dilution of thulium containing media can be 1:1 (1 part thulium containing media to 1 part non-thulium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Yterrbium

In certain cases, a yterrbium switch can be used to repress or induce the expression of one or more of the genes described herein. In some cases, the media can comprise yterrbium, which will repress or induce expression of the one or more genes under the control of the switch. In the case of yterrbium any one of the following concentrations can effectively repress expression of the one or more genes: 10 µM; 20 µM; 30 µM; 40 µM; 50 µM; 60 µM; 70 µM; 80 µM; 90 µM; 100 µM; 120 µM; 140 µM; 150 µM; 175 µM; 200 µM or more. In other cases, at least 10 µM yterrbium can be used. In other cases, at least 20 µM yterrbium can be used. In other cases, at least 30 µM yterrbium can be used. In other cases, at least 40 µM yterrbium can be used. In other cases, at least 50 µM yterrbium can be used. In other cases, at least 60 µM yterrbium can be used. In other cases, at least 70 µM yterrbium can be used. In other cases, at least 80 µM yterrbium can be used. In other cases, at least 90 µM yterrbium can be used. In other cases, at least 100 µM yterrbium can be used. In other cases, at least 120 µM yterrbium can be used. In other cases, at least 140 µM yterrbium can be used. In other cases, at least 150 µM yterrbium can be used. In other cases, at least 175 µM yterrbium can be used. In other cases, at least 200 µM or more yterrbium can be used.

In some cases, a range of 10 µM yterrbium to 200 µM yterrbium will effectively repress or induce gene expression. In some cases, a range of 20 µM yterrbium to 175 µM yterrbium will repress or induce gene expression. In other cases, a range of 30 µM yterrbium to 150 µM yterrbium will repress or induce gene expression. In some cases, a range of 40 µM yterrbium to 140 µM yterrbium will repress or induce gene expression. In some cases, a range of 50 µM yterrbium to 120 µM yterrbium will repress or induce gene expression. In some cases, a range of 60 µM yterrbium to 100 µM yterrbium will repress or induce gene expression. In some cases, a range of 70 µM yterrbium to 90 µM yterrbium will repress or induce gene expression.

In some cases, the yterrbium in the media can be diluted to reverse the effect of yterrbium. For example, in some cases, the dilution of yterrbium containing media can be 1:1 (1 part yterrbium containing media to 1 part non-yterrbium containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

After dilution, the microorganism can be then grown in conditions to promote the production of desired products, such as the multicarbon products (or others disclosed throughout).

Arabinose

In some cases, an arabinose sensitive switch can be used to induce/repress the expression of one or more of the genes described herein. In these cases, the media can comprise arabinose, which will in some cases, induce the expression of the one or more genes under the control of the switch. In the case of arabinose any one of the following concentrations can effectively induce/repress expression of the one or more genes: 0.1 g/L; 0.5 g/L; 1 g/L; 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; g/L; 20 g/L; 25 g/L; 30 g/L; 35 g/L; 40 g/L; 45 g/L; 50 g/L; 55 g/L; 60 g/L; 65 g/L; 70 g/L; 75 g/L; 80 g/L; 85 g/L; 90 g/L; 95 g/L; 100 g/L or more. In one case, 0.1 g/L arabinose can be used to induce/repress expression of the one or more genes under the control of an arabinose switch. In other cases, at least 0.5 g/L arabinose can be used. In other cases, at least 1 g/L arabinose can be used. In other cases, at least 2 g/L arabinose can be used. In other cases, at least 3 g/L arabinose can be used. In other cases, at least 4 g/L arabinose can be used. In other cases, at least 5 g/L arabinose can be used. In other cases, at least 6 g/L arabinose can be used. In other cases, at least 7 g/L arabinose can be used. In other cases, at least 8 g/L arabinose can be used. In other cases, at least 9 g/L arabinose can be used. In other cases, at least 10 g/L arabinose can be used. In other cases, at least 11 g/L arabinose can be used. In other cases, at least 12 g/L arabinose can be used. In other cases, at least 13 g/L arabinose can be used. In other cases, at least 14 g/L arabinose can be used. In other cases, at least 15 g/L arabinose can be used. In other cases, at least 16 g/L arabinose can be used. In other cases, at least 17 g/L arabinose can be used. In other cases, at least 18 g/L arabinose can be used. In other cases, at least 19 g/L arabinose can be used. In other cases, at least 20 g/L arabinose can be used. In other cases, at least 25 g/L arabinose can be used. In other cases, at least 30 g/L arabinose can be used. In other cases, at least 35 g/L arabinose can be used. In other cases, at least 40 g/L arabinose can be used. In other cases, at least 45 g/L arabinose can be used. In other cases, at least 50 g/L arabinose can be used. In other cases, at least 55 g/L arabinose can be used. In other cases, at least 60 g/L arabinose can be used. In other cases, at least 65 g/L arabinose can be used. In other cases, at least 70 g/L arabinose can be used. In other cases, at least 75 g/L arabinose can be used. In other cases, at least 80 g/L arabinose can be used. In other cases, at least 85 g/L arabinose can be used. In other cases, at least 90 g/L arabinose can be used. In other cases, at least 95 g/L arabinose can be used. In other cases, at least 100 g/L arabinose can be used. In some cases, a range of 0.5 g/L arabinose to 100 g/L arabinose will effectively induce/repress gene expression. In some cases, a range of 0.5 g/L arabinose to 50 g/L arabinose will induce/repress gene expression. In other cases, a range of 1 g/L arabinose to 20 g/L arabinose will induce/repress gene expression. In some cases, a range of 2 g/L arabinose to 15 g/L arabinose will induce/repress gene expression. In some cases, a range of 3 g/L arabinose to 12.5 g/L arabinose will induce/repress gene expression. In some cases, a range of 4 g/L arabinose to 12 g/L arabinose will induce/repress gene expression. In some cases, a range of 5 g/L arabinose to 11.5 g/L arabinose will induce/repress gene expression. In some cases, a range of 6 g/L arabinose to 11 g/L arabinose will induce/repress gene expression. In some cases, a range of 7 g/L arabinose to 10.5 g/L arabinose will induce/repress gene expression. In some cases, a range of 8 g/L arabinose to 10 g/L arabinose will induce/repress gene expression.

In some cases, any one of the following concentrations of arabinose can effectively induce/repress gene expression of the one or more genes: 0.1 mM; 0.2 mM; 0.3 mM; 0.4 mM; 0.5 mM; 0.6 mM; 0.7 mM; 0.8 mM; 0.9 mM; 1 mM; 1.5 mM; 2 mM; 2.5 mM; 3 mM; 3.5 mM; 4 mM; 4.5 mM; 5 mM; 5.5 mM; 6 mM; 6.6 mM; 7 mM; 7.5 mM; 8 mM; 8.5 mM; 9 mM; 9.5 mM; 10 mM; 12.5 mM; 15 mM; 17.5 mM; 20 mM; 25 mM; 50 mM; 100 mM or more. In one case, 0.1 mM arabinose can be used to repress/induce expression of the one or more genes under the control of an arabinose switch. In other cases, at least 0.2 mM arabinose can be used. In other cases, at least 0.3 mM arabinose can be used. In other cases, at least 0.4 mM arabinose can be used. In other cases, at least 0.5 mM arabinose can be used. In other cases, at least 0.6 mM arabinose can be used. In other cases, at least 0.7 mM arabinose can be used. In other cases, at least 0.8 mM arabinose can be used. In other cases, at least 0.9 mM arabinose can be used. In other cases, at least 1 mM arabinose can be used. In other cases, at least 1.5 mM arabinose can be used. In other cases, at least 2 mM arabinose can be used. In other cases, at least 2.5 mM arabinose can be used. In other cases, at least 3 mM arabinose can be used. In other cases, at least 3.5 mM arabinose can be used. In other cases, at least 4 mM arabinose can be used. In other cases, at least 4.5 mM arabinose can be used. In other cases, at least 5 mM arabinose can be used. In other cases, at least 5.5 mM arabinose can be used. In other cases, at least 6 mM arabinose can be used. In other cases, at least 6.6 mM arabinose can be used. In other cases, at least 7 mM arabinose can be used. In other cases, at least 7.5 mM arabinose can be used. In other cases, at least 8 mM arabinose can be used. In other cases, at least 8.5 mM arabinose can be used. In other cases, at least 9 mM arabinose can be used. In other cases, at least 9.5 mM arabinose can be used. In other cases, at least 10 mM arabinose can be used. In other cases, at least 12.5 mM arabinose can be used. In other cases, at least 15 mM arabinose can be used. In other cases, at least 17.5 mM arabinose can be used. In other cases, at least 20 mM arabinose can be used. In other cases, at least 25 mM arabinose can be used. In other cases, at least 50 mM arabinose can be used. In other cases, at least 100 mM arabinose can be used. In some cases, a range of 0.5 mM arabinose to 100 mM arabinose will effectively induce gene expression. In some cases, a range of 0.5 mM arabinose to 50 mM arabinose will induce gene expression. In other cases, a range of 1 mM arabinose to 20 mM arabinose will induce gene expression. In some cases, a range of 2 mM arabinose to 15 mM arabinose will induce gene expression. In some cases, a range of 3 mM arabinose to 12.5 mM arabinose will induce gene expression. In some cases, a range of 4 mM arabinose to 12 mM arabinose will induce gene expression. In some cases, a range of 5 mM arabinose to 11.5 mM arabinose will induce gene expression. In some cases, a range of 6 mM arabinose to 11 mM arabinose will induce gene expression. In some cases, a range of 7 mM arabinose to 10.5 mM arabinose will induce gene expression. In some cases, a range of 8 mM arabinose to 10 mM arabinose will induce gene expression.

In some cases, the arabinose in the media can be diluted to turn on/off the expression of the one or more arabinose repressed/induced genes. For example, in some cases, the dilution of arabinose containing media can be 1:1 (1 part arabinose containing media to 1 part non-arabinose containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

isopropyl β-D-1-thiogalactopyranoside

In certain cases, an IPTG sensitive switch can be used to induce or repress the expression of one or more of the genes described herein. In some cases, the media can comprise IPTG, which can in some instances induce expression of the one or more genes under the control of the switch. In the case of IPTG any one of the following concentrations can effectively induce or repress expression of the one or more genes: 1 μM; 2 μM; 3 μM; 4 μM; 5 μM; 6 μM; 7 μM; 8 μM; 9 μM; 10 μM; 12.5 μM; 15 μM; 17.5 μM; 20 μM; 25 μM; 30 μM; 35 μM; 40 μM; 45 μM; 50 μM; 55 μM; 60 μM; 65 μM; 70 μM; 75 μM; 80 μM; 85 μM; 90 μM; 95 μM; 100 μM; 105 μM; 110 μM; 115 μM; 120 μM; 125 μM; 130 μM; 135 μM; 140 μM; 145 μM; 150 μM; 155 μM; 160 μM; 165 μM; 170 μM; 175 μM; 180 μM; 185 μM; 190 μM; 195 μM; 200 μM or more. In one case, at least 1 μM IPTG can be used. In other cases, at least 2 μM IPTG can be used. In other cases, at least 3 μM IPTG can be used. In other cases, at least 4 μM IPTG can be used. In other cases, at least 5 μM IPTG can be used. In other cases, at least 6 μM IPTG can be used. In other cases, at least 7 μM IPTG can be used. In other cases, at least 8 μM IPTG can be used. In other cases, at least 9 μM IPTG can be used. In other cases, at least 10 μM IPTG can be used. In other cases, at least 12.5 μM IPTG can be used. In other cases, at least 15 μM IPTG can be used. In other cases, at least 17.5 μM IPTG can be used. In other cases, at least 20 μM IPTG can be used. In other cases, at least 25 μM IPTG can be used. In other cases, at least 25 μM IPTG can be used. In other cases, at least 30 μM IPTG can be used. In other cases, at least 35 μM IPTG can be used. In other cases, at least 40 μM IPTG can be used. In other cases, at least 45 μM IPTG can be used. In other cases, at least 50 μM IPTG can be used. In other cases, at least 55 μM IPTG can be used. In other cases, at least 60 μM IPTG can be used. In other cases, at least 65 μM IPTG can be used. In other cases, at least 70 μM IPTG can be used. In other cases, at least 75 μM IPTG can be used. In other cases, at least 80 μM IPTG can be used. In other cases, at least 85 μM IPTG can be used. In other cases, at least 90 μM IPTG can be used. In other cases, at least 95 μM IPTG can be used. In other cases, at least 100 μM IPTG can be used. In other cases, at least 105 μM IPTG can be used. In other cases, at least 110 μM IPTG can be used. In other cases, at least 115 μM IPTG can be used. In other cases, at least 120 μM IPTG can be used. In other cases, at least 125 μM IPTG can be used. In other cases, at least 130 μM IPTG can be used. In other cases, at least 135 μM IPTG can be used. In other cases, at least 140 μM IPTG can be used. In other cases, at least 145 μM IPTG can be used. In other cases, at least 150 μM IPTG can be used. In other cases, at least 155 μM IPTG can be used. In other cases, at least 160 μM IPTG can be used. In other cases, at least 165 μM IPTG can be used. In other cases, at least 170 μM IPTG can be used. In other cases, at least 175 μM IPTG can be used. In other cases, at least 180 μM IPTG can be used. In other cases, at least 185 μM IPTG can be used. In other cases, at least 190 μM IPTG can be used. In other cases, at least 195 μM IPTG can be used. In other cases, at least 200 μM or more IPTG can be used.

In some cases, a range of 1 μM IPTG to 200 μM IPTG will effectively induce or repress gene expression. In some cases, a range of 5 μM IPTG to 175 μM IPTG will induce or repress gene expression. In other cases, a range of 7.5 μM IPTG to 150 μM IPTG will induce or repress gene expression. In some cases, a range of 10 μM IPTG to 145 μM IPTG will induce or repress gene expression. In some cases, a range of 15 μM IPTG to 140 μM IPTG will induce or repress gene expression. In some cases, a range of 20 μM IPTG to 125 μM IPTG will induce or repress gene expression. In some cases, a range of 25 µM IPTG to 100 µM IPTG will induce or repress gene expression. In some cases, a range of 30 µM IPTG to 90 µM IPTG will induce or repress gene expression. In some cases, a range of 35 µM IPTG to 75 µM IPTG will induce or repress gene expression. In some cases, a range of 40 µM IPTG to 65 µM IPTG will induce or repress gene expression.

In some cases, the IPTG in the media can be diluted to turn on or off expression of the one or more IPTG induced or repressed genes. For example, in some cases, the dilution of IPTG containing media can be 1:1 (1 part IPTG containing media to 1 part non-IPTG containing media). In some cases, the dilution can be at least 1:2; 1:3; 1:4; 1:5; 1:7.5; 1:10; 1:15; 1:20; 1:25; 1:30; 1:35; 1:40; 1:45; 1:50; 1:75; 1:100; 1:200; 1:300; 1:400; 1:500; 1:1,000; or 1:10,000. For example, in some cases, a 1:2 dilution can be used. In some cases, at least a 1:3 dilution can be used. In some cases, at least a 1:4 dilution can be used. In some cases, at least a 1:5 dilution can be used. In some cases, at least a 1:7.5 dilution can be used. In some cases, at least a 1:10 dilution can be used. In some cases, at least a 1:15 dilution can be used. In some cases, at least a 1:20 dilution can be used. In some cases, at least a 1:25 dilution can be used. In some cases, at least a 1:30 dilution can be used. In some cases, at least a 1:35 dilution can be used. In some cases, at least a 1:40 dilution can be used. In some cases, at least a 1:45 dilution can be used. In some cases, at least a 1:50 dilution can be used. In some cases, at least a 1:75 dilution can be used. In some cases, at least a 1:100 dilution can be used. In some cases, at least a 1:200 dilution can be used. In some cases, at least a 1:300 dilution can be used. In some cases, at least a 1:400 dilution can be used. In some cases, at least a 1:500 dilution can be used. In some cases, at least a 1:1,000 dilution can be used. In some cases, at least a 1:10,000 dilution can be used.

In some cases, the microorganism can be grown in media comprising IPTG. IPTG can be added to the media to turn on the expression of IPTG induced genes. The microorganism can be then grown in conditions to promote the production of desired products, such as the multicarbon products (or others disclosed throughout). The media can then be diluted to effectively turn off the expression of the IPTG induced genes.

Bioreactor

Fermentation reactions may be carried out in any suitable bioreactor. In some cases, the bioreactor may comprise a first, growth reactor in which the microorganisms are cultured, and a second, fermentation reactor, to which broth from the growth reactor is fed and in which most of the fermentation product is produced.

Product Recovery

The fermentation of the microorganisms disclosed herein can produce a broth comprising a desired product (e.g., a multicarbon product), one or more by-products, and/or the microorganism itself (e.g., a genetically modified methanotroph).

The microorganisms and the methods herein can produce multicarbon products such as 2,3-BDO; 1,4-BDO; isobutyraldehyde; isobutanol; 1-butanol; n-butanol; ethanol; fatty (or aliphatic long chain) alcohols; and/or fatty acid methyl esters at surprisingly high efficiency, more so than other known fermentation processes. For example, the microorganisms and the methods disclosed herein can convert a C1-carbon substrate (such as methane) at a rate of greater than 50%. This means that at least 50% of the C1-carbons within the systems are converted into product, such as 2,3-BDO; 1,4-BDO; isobutyraldehyde; isobutanol; 1-butanol; n-butanol; ethanol; fatty (or aliphatic long chain) alcohols; and/or fatty acid methyl esters. In some cases, the conversion of a C1-carbon substrate into multicarbon products can be at least 60%, 70%, 80%, 81%, 83%, 84%, 85%, 86%, 87%, 88%, 89%, 90%, 91%, 93%, 94%, 95%, 96%, 97%, 98%, or 99%. In some cases, the conversion of a C1-carbon substrate into multicarbon products can be at least 60%. In some cases, the conversion of a C1-carbon substrate into multicarbon products can be at least 70%. In some cases, the conversion of a C1-carbon substrate into multicarbon products can be at least 80%. In some cases, the conversion of a C1-carbon substrate into multicarbon products can be at least 81%. In some cases, the conversion of a C1-carbon substrate into multicarbon products can be at least 82%. In some cases, the conversion of a C1-carbon substrate into multicarbon products can be at least 83%. In some cases, the conversion of a C1-carbon substrate into multicarbon products can be at least 84%. In some cases, the conversion of a C1-carbon substrate into multicarbon products can be at least 85%. In some cases, the conversion of a C1-carbon substrate into multicarbon products can be at least 86%. In some cases, the conversion of a C1-carbon substrate into multicarbon products can be at least 87%. In some cases, the conversion of a C1-carbon substrate into multicarbon products can be at least 88%. In some cases, the conversion of a C1-carbon substrate into multicarbon products can be at least 89%. In some cases, the conversion of a C1-carbon substrate into multicarbon products can be at least 90%. In some cases, the conversion of a C1-carbon substrate into multicarbon products can be at least 91%. In some cases, the conversion of a C1-carbon substrate into multicarbon products can be at least 92%. In some cases, the conversion of a C1-carbon substrate into multicarbon products can be at least 93%. In some cases, the conversion of a C1-carbon substrate into multicarbon products can be at least 94%. In some cases, the conversion of a C1-carbon substrate into multicarbon products can be at least 95%. In some cases, the conversion of a C1-carbon substrate into multicarbon products can be at least 96%. In some cases, the conversion of a C1-carbon substrate into multicarbon products can be at least 97%. In some cases, the conversion of a C1-carbon substrate into multicarbon products can be at least 98%. In some cases, the conversion of a C1-carbon substrate into multicarbon products can be at least 99%.

In certain methods when producing multicarbon products, the concentration of multicarbon products in the fermentation broth is at least 1 g/L. For example, the concentration of multicarbon products produced in the fermentation broth can be from 1 g/L to 5 g/L, 2 g/L to 6 g/L, 3 g/L to 7 g/L, 4 g/L to 8 g/L, 5 g/L to 9 g/L, or 6 g/L to 10 g/L. In some cases, the concentration of multicarbon products can be at least 9 g/L. In some cases, the concentration of multicarbon products can be from 1 g/L to 5 g/L. In some cases, the concentration of multicarbon products can be from 2 g/L to 6 g/L. In some cases, the concentration of multicarbon products can be from 3 g/L to 7 g/L. In some cases, the concentration of multicarbon products can be from 4 g/L to 8 g/L. In some cases, the concentration of multicarbon products can be from 5 g/L to 9 g/L. In some cases, the concentration of multicarbon products can be from 6 g/L to 10 g/L.

In other cases, when microorganisms are used that normally produce at least some of the same multicarbon product such as 2,3-BDO; 1,4-BDO; isobutyraldehyde; isobutanol; 1-butanol; n-butanol; ethanol; fatty (or aliphatic long chain) alcohols; and/or fatty acid methyl esters, after genetic modification and fermentation, the genetically modified microorganism can produce the same multicarbon product in concentrations that are at least 1.1× the amount that is normally produced. In some cases, the genetically modified microorganism can produce at least 2×, 3×, 4×, 5×, 6×, 7×, 8×, 9×, 10×, 15×, 20×, 25×, 30×, 35×, 40×, 45×, 50×, 60×, 70×, 80×, 90× or 100× the amount that is normally produced (e.g., produced by a microorganism that is unmodified and of the same species as the genetically modified microorganism). In some cases, the genetically modified microorganism can produce at least 2×, 3×, 4×, 5×, 10×, 25×, 50×, and or 100× the amount that is normally produced. In some cases, the genetically modified microorganism can produce at least 2× the amount that is normally produced. In some cases, the genetically modified microorganism can produce at least 3× the amount that is normally produced. In some cases, the genetically modified microorganism can produce at least 4× the amount that is normally produced. In some cases, the genetically modified microorganism can produce at least 5× the amount that is normally produced. In some cases, the genetically modified microorganism can produce at least 10× the amount that is normally produced. In some cases, the genetically modified microorganism can produce at least 25× the amount that is normally produced. In some cases, the genetically modified microorganism can produce at least 50× the amount that is normally produced. In some cases, the genetically modified microorganism can produce at least 100× the amount that is normally produced.

As discussed above, in certain cases the multicarbon product produced in the fermentation reaction is converted to a different product such as MEK, butene, butadiene, or other products directly from the fermentation broth. In other cases, the multicarbon product is first recovered from the fermentation broth before conversion to a different product.

In some cases, multicarbon product can be continuously removed from a portion of broth and recovered as purified. In particular cases, the recovery of the multicarbon product includes passing the removed portion of the broth containing the multicarbon product through a separation unit to separate the microorganisms (e.g., genetically modified methanotroph) from the broth, to produce a cell-free multicarbon product permeate, and returning the microorganisms to the bioreactor. The cell-free multicarbon product containing permeate may then can be stored or be used for subsequent conversion to a different desired product.

The recovering of the desired multicarbon product and/or one or more other products or by-products produced in the fermentation reaction can comprise continuously removing a portion of the broth and recovering separately the multicarbon product and one or more other products from the removed portion of the broth. In some cases, the recovery of the multicarbon product and/or one or more other products includes passing the removed portion of the broth containing the multicarbon product and/or one or more other products through a separation unit to separate microorganisms from the multicarbon product and/or one or more other products, to produce a cell-free multicarbon product and one or more other product-containing permeate, and returning the microorganisms to the bioreactor.

In the above cases, the recovery of the multicarbon product and one or more other products can include first removing the multicarbon product from the cell-free permeate followed by removing the one or more other products from the cell-free permeate. The cell-free permeate can also then returned to the bioreactor.

The multicarbon product, or a mixed product stream containing the multicarbon product, can be recovered from the fermentation broth. For example, methods that can be used can include but are not limited to, fractional distillation or evaporation, pervaporation, and extractive fermentation. Further examples include: recovery using steam from whole fermentation broths; reverse osmosis combined with distillation; liquid-liquid extraction techniques involving solvent extraction of the multicarbon product; aqueous two-phase extraction of the multicarbon product in PEG/dextran system; solvent extraction using alcohols or esters, e.g., ethyl acetate, tributylphosphate, diethyl ether, n-butanol, dodecanol, oleyl alcohol, and an ethanol/phosphate system; aqueous two-phase systems composed of hydrophilic solvents and inorganic salts. See generally, Voloch, M., et al., (1985) and U.S. Pat. Pub. Appl. No. 2012/0045807.

In some cases prior to exposure to solvent, the fermentation broth is dewatered by evaporation or both microfiltration and reverse osmosis because of the low partition coefficient and the low selectivity of the multicarbon product. Repulsive extraction or salting out using potassium chloride (KCl) or dehydrated $K_2CO_3$ has also been investigated on the recovery of multicarbon products such as 2,3-BDO (Syu, M. J., "Biological production of 2,3-butanediol, Appl Microbiol Biotechnol., 55(1):10-8 (2001)) like the salting-out effect of K2CO3 on extraction of butanol in acetone-O butanol-ethanol fermentation. The removal of water from the fermentation broth was also tested before salting out because the concentration of the multicarbon product, such as 2,3-BDO in the broth was too low to be salted out even if at a saturated KCl or $K_2CO_3$ solution. See generally, U.S. Pat. Pub. Appl. No. 2012/0045807.

A yet further example of a method to recover a multicarbon product such as 2,3-BDO is to react it with formaldehyde to form a formal under catalysis of acid. The multicarbon product such as 2,3-BDO formal is collected in the top oil phase and allowed to react with acid methanol to form multicarbon product such as 2,3-BDO and methylal. Methylal can be hydrolyzed to methanol and formaldehyde. See generally, U.S. Pat. Pub. Appl. No. 2012/0045807.

A further example, may be the use of ionic liquids to extract the multicarbon product such as ethanol/2,3-BDO from clarified broth. Ionic liquids can be tailored in many ways to change physical properties. An advantage of this approach is that ionic liquids are not volatile. Some are water sensitive but others are not.

Pervaporation or vacuum membrane distillation can be used for multicarbon product fermentation such as ethanol, butanol, and 2,3-BDO in water as an extract from the fermentation broth. A microporous polytetrafluoroethylene (PTFE) membrane is used in the integrated process, while a silicone membrane is usually used in pervaporative ethanol or butanol fermentations. See generally, U.S. Pat. Pub. Appl. No. 2012/0045807.

By-products such as acids including acetate and butyrate may also be recovered from the fermentation broth using known methods. For example, an adsorption system involving an activated charcoal filter or electrodialysis may be used.

In certain cases of the invention, the multicarbon product and other by-products are recovered from the fermentation broth by continuously removing a portion of the broth from the bioreactor, separating microbial cells from the broth (conveniently by filtration, for example), and recovering the multicarbon product and others such as alcohols and acids from the broth. Alcohols may conveniently be recovered for example by distillation, and acids may be recovered for example by adsorption on activated charcoal. The separated microbial cells are returned to the fermentation bioreactor.

The cell-free permeate remaining after the alcohol(s) and acid(s) have been removed is also preferably returned to the fermentation bioreactor. Additional nutrients may be added to the cell-free permeate to replenish the nutrient medium before it is returned to the bioreactor.

Also, if the pH of the broth was adjusted during recovery of the multicarbon product and/or by-products, the pH should be re-adjusted to a similar pH to that of the broth in the fermentation bioreactor, before being returned to the bioreactor.

In certain cases, the multicarbon product is continuously recovered from the fermentation broth or bioreactor and fed directly for chemical conversion to one or more of butene, butadiene, and/or methyl ethyl ketone. For example, the multicarbon product may be fed directly through a conduit to one or more vessel suitable for chemical synthesis of one or more of downstream products such as butene, butadiene, and/or methyl ethyl ketone or other down-stream chemical products in the case of 2,3-BDO.

While some cases have been shown and described herein, such cases are provided by way of example only. Numerous variations, changes, and substitutions will now occur to those skilled in the art without departing from the invention. It should be understood that various alternatives to the cases of the invention described herein will be employed in practicing the invention.

EXAMPLES

Example 1: Lanthanum Effect on Promoters

Figure 2:
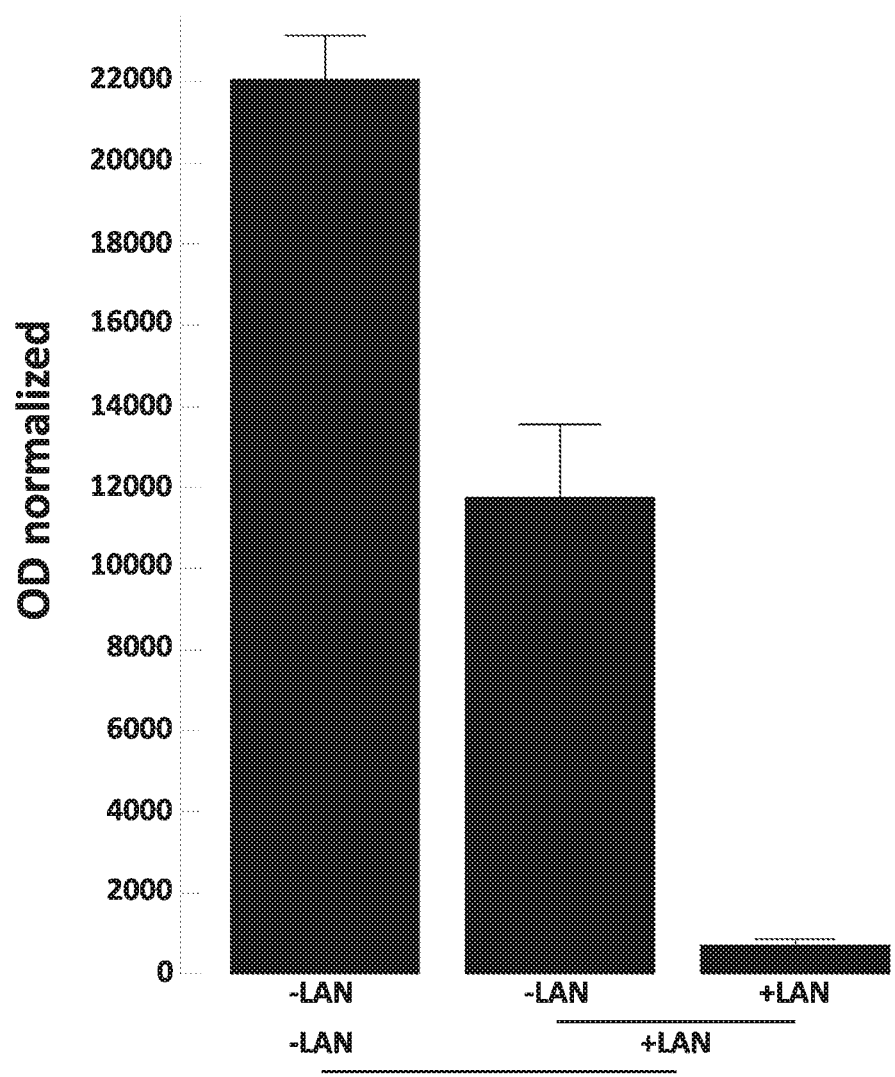
FIG. 2 shows the effect of lanthanum on pMxaF expression as measured by mCherry levels. In the presence of 35 μM lanthanum, expression is repressed by approximately 90%. After removal of the 35 μM lanthanum, approximately 50% activity is recovered.

Constructs having different promoters driving the expression of mCherry were transformed into *Methylococcus capsulatus*. Single colonies were plasmid tested and confirmed as being mutation free. These clones were further tested for activity. See FIG. 1. The following promoters were tested for activity pMxaF, J23111, J12100, J23102, pBAD, J23110, lacO, J23116, J23106, J23105, J23108, J23107, J23115, J23114, J23118, J23104, J23101, J23119, and uMCA3034. pMxaF was chosen for further testing in the presence of lanthanum. *Methylococcus capsulatus* transformed with pMxaF-mCherry showed that in the presence of 35 µM lanthanum, expression is repressed by approximately 90%. See FIG. 2. After removal of the 35 µM lanthanum, approximately 50% activity is recovered after 24 hours.

Example 2: Lanthanum Titration

*Methylococcus capsulatus* transformed with pMxaF-mCherry were used to determine the optimal concentration necessary for repression of the pMxaF promoter. A *Methylococcus capsulatus* with a pMxaF-mCherry promoter was grown in the presence of 0, 0.5, 1.1, 2.2, 4.4, 8.8, 17.5, and 35 µM lanthanum. At 0.5 µM, pMxaF is repressed by approximately 70%. At 8.8 µM, repression is seen at approximately 87%, similar to that seen at 17.5, and 35 µM. See FIG. 3.

Example 3: Reactivation

Figure 3:
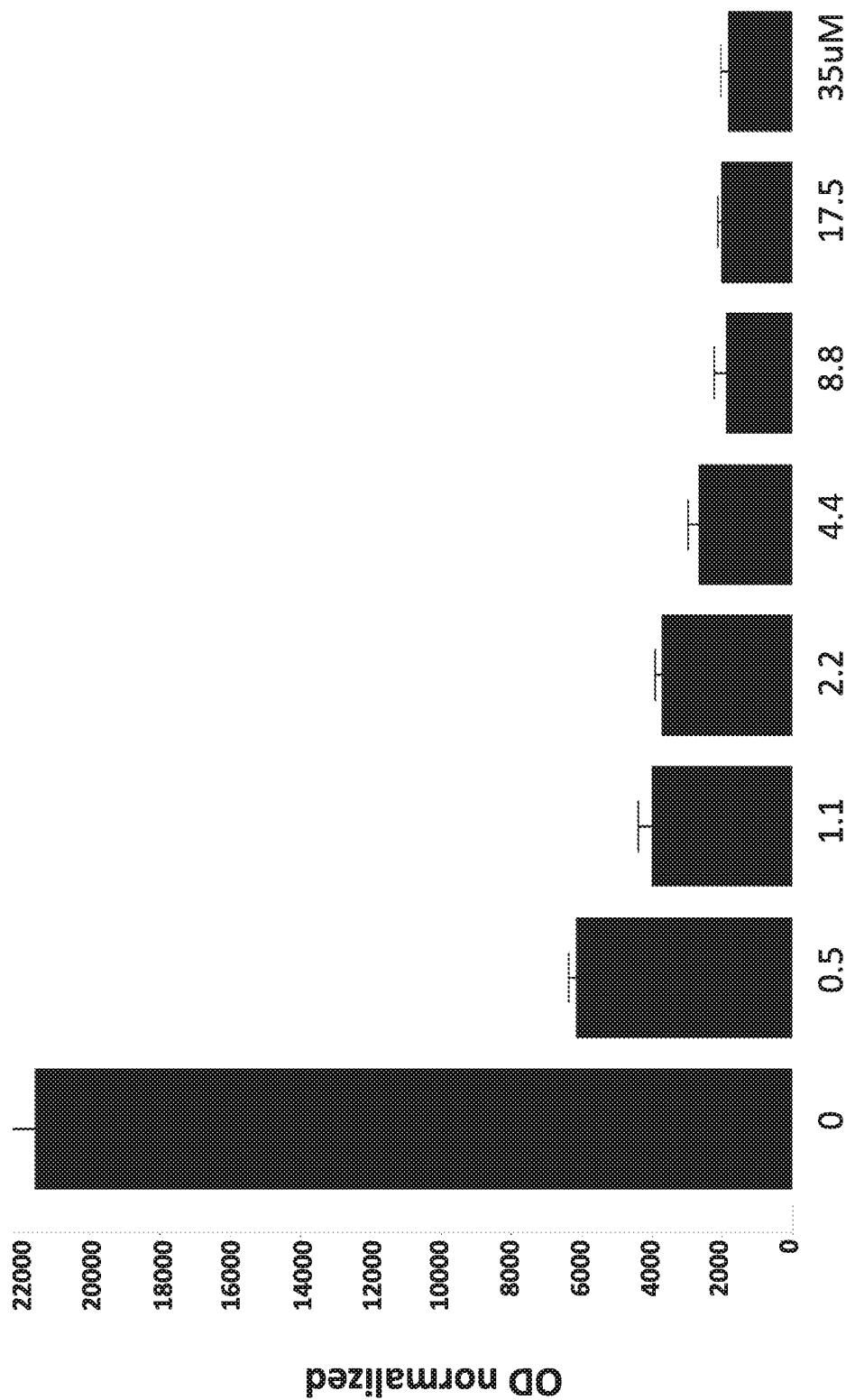
FIG. 3 shows the effect of different concentrations of lanthanum on pMxaF expression as measured by mCherry levels. Maximal repression is seen at a concentration of above 8.8 μM lanthanum.
Figure 4:
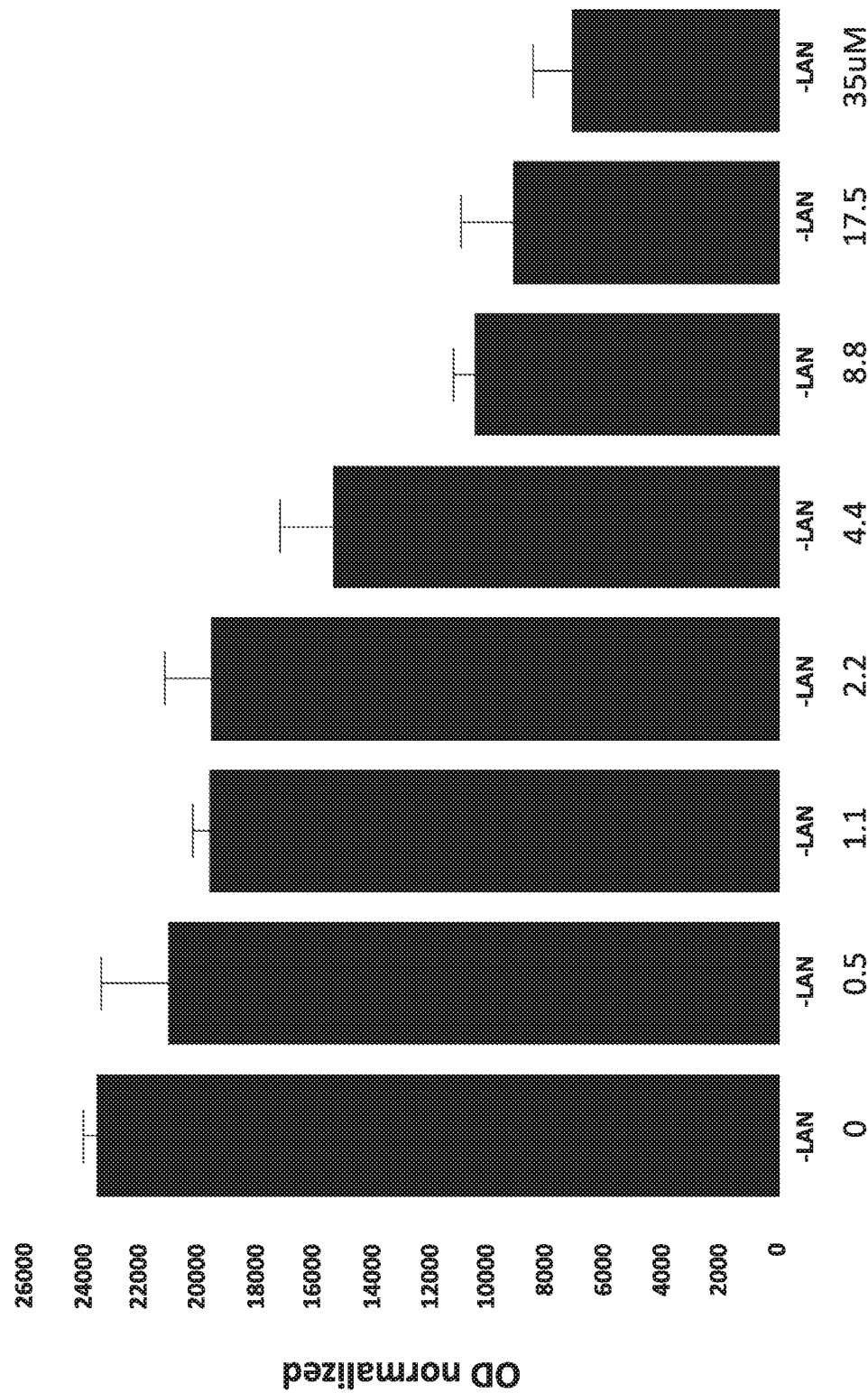
FIG. 4 shows the effect of de-repression after lanthanum treatment at various concentrations as measured by mCherry levels. Generally, the more lanthanum used to repress pMxaF, the less expression is recovered after lanthanum is removed from the system.

The methanotrophs from FIG. 3 were used in a "depression" experiment, where the media containing the various amount of lanthanum in FIG. 3, were diluted to the point where there is effectively no lanthanum left in the media, e.g. (a 30-fold dilution). mCherry expression was measured 24 hours after dilution. Generally, the more lanthanum used to repress pMxaF, the less expression is recovered after lanthanum is removed from the system. See FIG. 4. For example, in the samples that received 8.8 µM lanthanum initially and later depressed by dilution, mCherry expression recovered approximately 50%.

In order to ensure that the cells were sufficiently diluted and no lanthanum was present extracellularly, the methanotrophs were washed an additional three times. The amount of expression following three additional washings did not change. Thus, the lack of recovery is likely due to residual intracellular lanthanum, which could not be diluted out even after multiple washing/dilutions.

Example 4: pBAD and Arabinose

Figure 5:
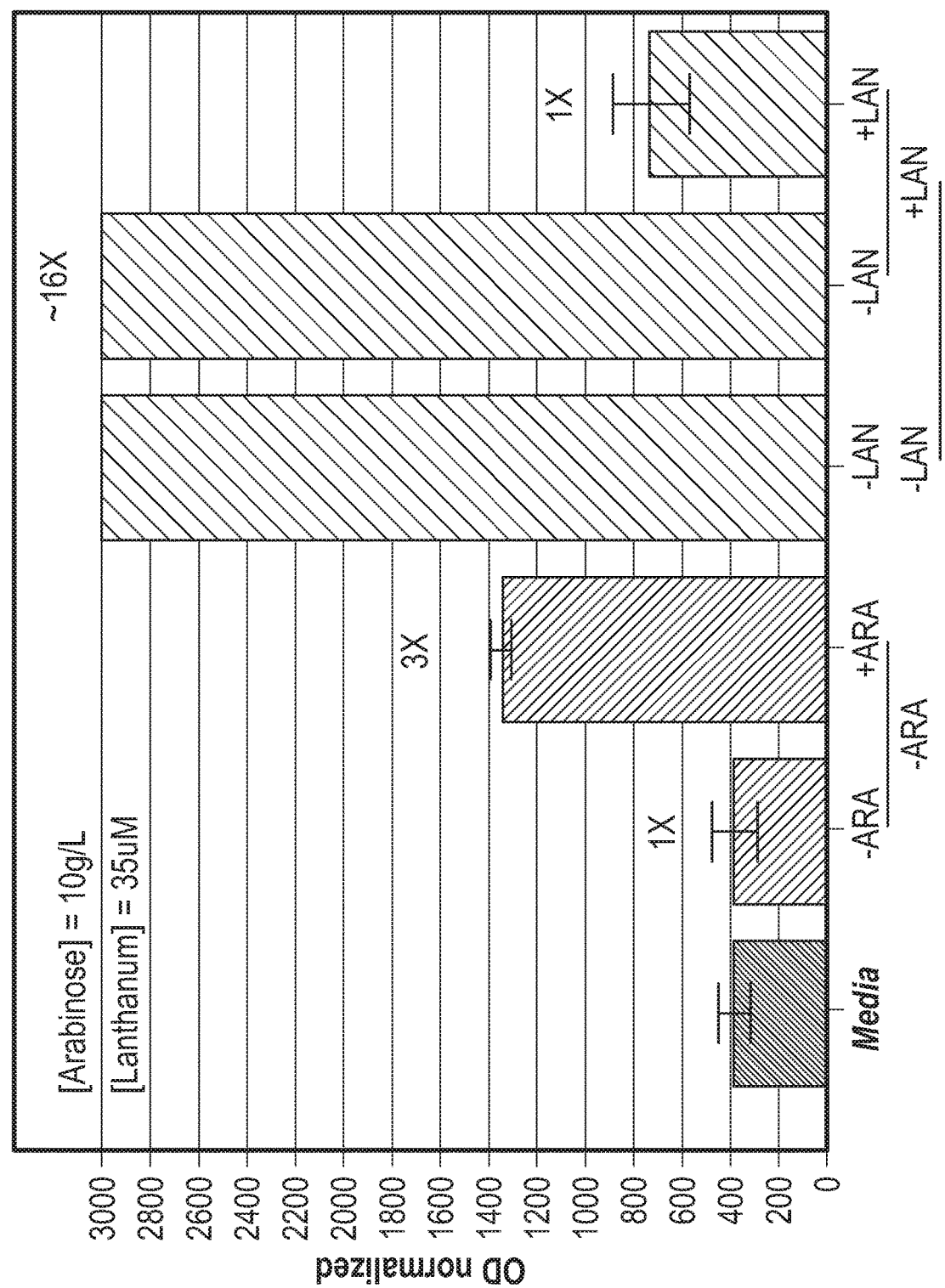
FIG. 5 shows that the pBAD promoter is turned on by the addition of 10 g/L of arabinose as measured by mCherry levels. Further, mCherry levels without any arabinose is identical to the levels seen in the background media. Also, in the presence of 35 μM lanthanum, there is still some background activity of pMxaF (compared to the media), indicating a bit of "leakiness."

*Methylococcus capsulatus* transformed with pBAD driving mCherry expression were tested for the ability to be induced by other compounds such as sugars. For example, pBAD in the presence of 10 g/L of arabinose was induced by approximately 300% (i.e., 3 fold). See FIG. 5. mCherry levels without any arabinose is identical to the levels seen in the background media.

Example 5: pXoxF and Lanthanum

Figure 6:
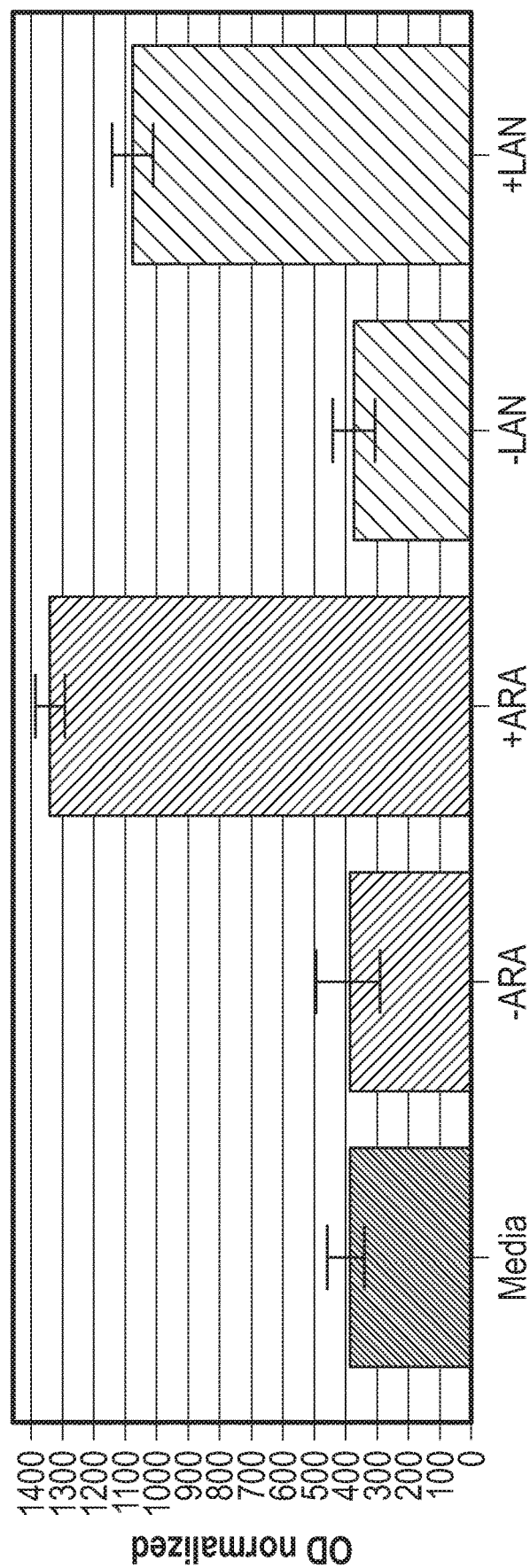
FIG. 6 shows that the pXoxF promoter is inducible in the presence of lanthanum to almost the same extent that pBAD is induced by arabinose. pXoxF in the absence of lanthanum does not exhibit any measurable leakiness.

*Methylococcus capsulatus* transformed with pXoxF driving mCherry expression was tested for its ability to respond to lanthanum. In the presence of 35 µM lanthanum, pXoxF was activated, increasing the expression of pXoxF by approximately 300% (3 fold), similar to levels exhibited by arabinose on the pBAD promoter. See FIG. 6 (arabinose treatment was conducted on a pBAD promoter while lanthanum treatment was conducted on a pXoxF promoter). This study indicates that pXoxF has a tight "off" state, with minimal leaky expression. It also indicates that pXoxF can be induced by lanthanum.

Example 6: Isobutanol Producing Strains

Figure 7:
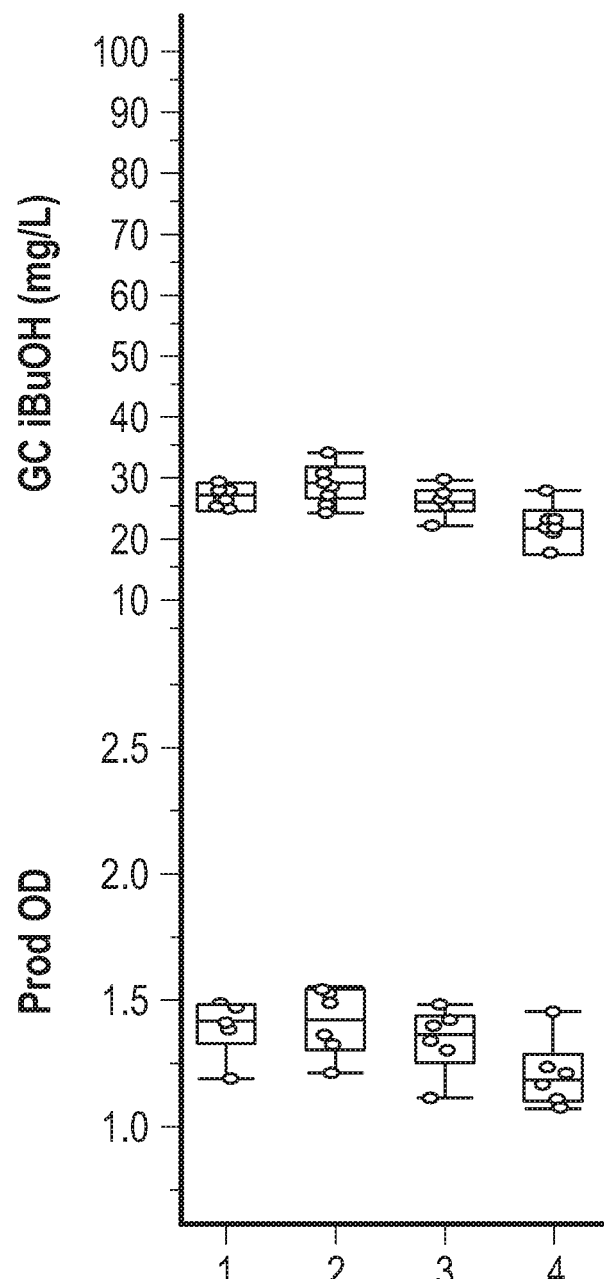
FIG. 7 shows the ability of strains using a lanthanum response molecular switch to produce isobutanol. Four different strains having isobutanol enzymes driven by pMxaF showed production of isobutanol after lanthanum was diluted out from the initial medium.

*Methylococcus capsulatus* strains expressing isobutanol production pathway enzymes driven by a pMxaF promoter shows the ability of using a lanthanum switch to produce isobutanol. Four different strains having isobutanol enzymes driven by pMxaF were able to produce of isobutanol after lanthanum was diluted out from the initial medium. See FIG. 7. As seen, OD levels were similar among the four different strains.

Example 7: 2,3-Butanediol Producing Strains

In order to produce 2,3-BDO, *Methylococcus capsulatus* was transformed with genes that gave it the ability to produce 2,3-BDO. These genes were also placed under the control of a lanthanum "switch" where lanthanum repressed the expression of genes in its presence. Upon removal or dilution of lanthanum in the media, the repressed genes were "switched" on.

*Methylococcus capsulatus* expressing the various genes described below in Table 1 were pre-culturing in the presence of 10 µM lanthanum.

TABLE 1

| Number | Strain | Genotype |
|---|---|---|
| 1 & 22 | XZ685 | pmxaF>Bsu.alsA>rbs.GTW0001__Kpn.BudA>rbs.GTW0001__Cau.ButA |
| 2 & 23 | XZ686 | |
| 3 & 24 | XZ687 | |
| 4 & 25 | XZ688 | pmxaF>Bsu.alsA>rbs.Mca.mxaF__Kpn.BudA>rbs.Mca.mxaF__Cau.ButA |
| 5 & 26 | XZ689 | |
| 6 & 27 | XZ690 | |
| 7 & 28 | XZ691 | pmxaF>Blic.alsA>rbs.GTW0001__Kpn.BudA>rbs.GTW0001__Cau.ButA |
| 8 & 29 | XZ692 | |
| 9 & 30 | XZ693 | |
| 10 & 31 | XZ694 | pmxaF>Blic.alsA>rbs.Mca.mxaF__Kpn.BudA>rbs.Mca.mxaF__Cau.ButA |
| 11 & 32 | XZ695 | |
| 12 & 33 | XZ696 | |
| 13 & 34 | XZ697 | pmxaF>Bsu.alsA>rbs.GTW0001__Kpn.BudA>rbs.GTW0001__Cau.ButA |
| 14 & 35 | XZ698 | |
| 15 & 36 | XZ699 | |
| 16 & 37 | XZ700 | pmxaF>Bsu.alsA>rbs.Mca.mxaF__Kpn.BudA>rbs.Mca.mxaF__Cau.ButA |
| 17 & 38 | XZ701 | |
| 18 & 39 | XZ702 | |
| 19 & 40 | XZ703 | pmxaF>Blic.alsA>rbs.Mca.mxaF__Kpn.BudA>rbs.Mca.mxaF__Cau.ButA |
| 20 & 41 | XZ704 | |
| 21 & 42 | XZ705 | |

After growing precultures to ~3 OD600, the medium containing lanthanum was diluted at a ratio of 1:10 (lanthanum containing media: non-lanthanum containing media) or 1:50. After 96 or 120 hours, the cultures assessed for production of 2,3-BDO and acetoin (FIG. 8A, 96 hours) or (FIG. 8B, 120 hours). Shown below in Table 2 are strains, dilution levels, acetoin production titers after 96 hours, 2,3-BDO production titers after 96 hours, acetoin production titers after 120 hours, and 2,3-BDO production titers after 120 hours.

TABLE 2

| | Strain | Dilution | Acetoin (mg/L)_96 h | 2,3BDO (mg/L)_96 h | Acetoin (mg/L)_120 h | 2,3BDO (mg/L)_120 h |
|---|---|---|---|---|---|---|
| 1 | XZ685 | 10X | 5.847 | 71.342 | 8.617 | 150.864 |
| 2 | XZ686 | 10X | 4.86 | 51.439 | 10.539 | 135.871 |
| 3 | XZ687 | 10X | 6.306 | 53.591 | 10.475 | 137.104 |
| 4 | XZ688 | 10X | 5.311 | 73.08 | 8.79 | 158.947 |
| 5 | XZ689 | 10X | 5.282 | 71.059 | 6.944 | 149.219 |
| 6 | XZ690 | 10X | 5.679 | 51.291 | 13.412 | 165.688 |
| 7 | XZ691 | 10X | 4.014 | 0 | 0 | 19.231 |
| 8 | XZ692 | 10X | 3.719 | 4.679 | 7.984 | 23.991 |
| 9 | XZ693 | 10X | 3.778 | 4.082 | 6.2 | 18.78 |
| 10 | XZ694 | 10X | 43.925 | 0 | 54.582 | 4.871 |
| 11 | XZ695 | 10X | 44.734 | 0 | 55.632 | 3.363 |
| 12 | XZ696 | 10X | 46.473 | 0 | 57.444 | 5.39 |
| 13 | XZ697 | 10X | 5.982 | 48.549 | 12.221 | 131.618 |
| 14 | XZ698 | 10X | 3.441 | 52.775 | 12.594 | 137.996 |
| 15 | XZ699 | 10X | 5.747 | 44.14 | 12.937 | 131.699 |
| 16 | XZ700 | 10X | 5.101 | 50.998 | 12.26 | 117.653 |
| 17 | XZ701 | 10X | 4.82 | 52.523 | 12.167 | 120.369 |
| 18 | XZ702 | 10X | 5.802 | 54.763 | 12.119 | 133.294 |
| 19 | XZ703 | 10X | 38.501 | 0 | 51.296 | 6.482 |
| 20 | XZ704 | 10X | 33.64 | 0 | 44.195 | 5.021 |
| 21 | XZ705 | 10X | 40.326 | 0 | 52.443 | 5.978 |
| 22 | XZ685 | 50X | 4.245 | 95.288 | 8.993 | 184.974 |
| 23 | XZ686 | 50X | 3.028 | 87.876 | 0 | 173.315 |
| 24 | XZ687 | 50X | 4.341 | 85.562 | 10.06 | 193.196 |
| 25 | XZ688 | 50X | 4.088 | 73.804 | 8.181 | 156.027 |
| 26 | XZ689 | 50X | 4.273 | 78.782 | 0 | 156.435 |
| 27 | XZ690 | 50X | 4.383 | 79.226 | 7.879 | 155.869 |
| 28 | XZ691 | 50X | 3.178 | 10.35 | 8.197 | 32.164 |
| 29 | XZ692 | 50X | 2.838 | 14.16 | 7.839 | 38.733 |
| 30 | XZ693 | 50X | 2.865 | 12.942 | 9.163 | 41.967 |
| 31 | XZ694 | 50X | 53.138 | 0 | 64.47 | 4.259 |
| 32 | XZ695 | 50X | 66.256 | 0 | 79.665 | 4.736 |
| 33 | XZ696 | 50X | 66.139 | 0 | 78.46 | 4.746 |
| 34 | XZ697 | 50X | 4.664 | 57.939 | 9.411 | 122.655 |
| 35 | XZ698 | 50X | 5.749 | 67.055 | 10.424 | 151.002 |
| 36 | XZ699 | 50X | 4.182 | 63.379 | 10.386 | 137.577 |
| 37 | XZ700 | 50X | 3.558 | 59.187 | 9.519 | 121.163 |
| 38 | XZ701 | 50X | 3.085 | 63.574 | 10.265 | 140.806 |
| 39 | XZ702 | 50X | 5.039 | 66.163 | 11.252 | 131.931 |
| 40 | XZ703 | 50X | 58.687 | 0 | 72.718 | 6.653 |

TABLE 2-continued

|    | Strain | Dilution | Acetoin (mg/L)_96 h | 2,3BDO (mg/L)_96 h | Acetoin (mg/L)_120 h | 2,3BDO (mg/L)_120 h |
|----|--------|----------|---------------------|--------------------|----------------------|---------------------|
| 41 | XZ704  | 50X      | 55.523              | 0                  | 70.855               | 6.577               |
| 42 | XZ705  | 50X      | 59.577              | 0                  | 76.618               | 4.793               |

Figure 8A:
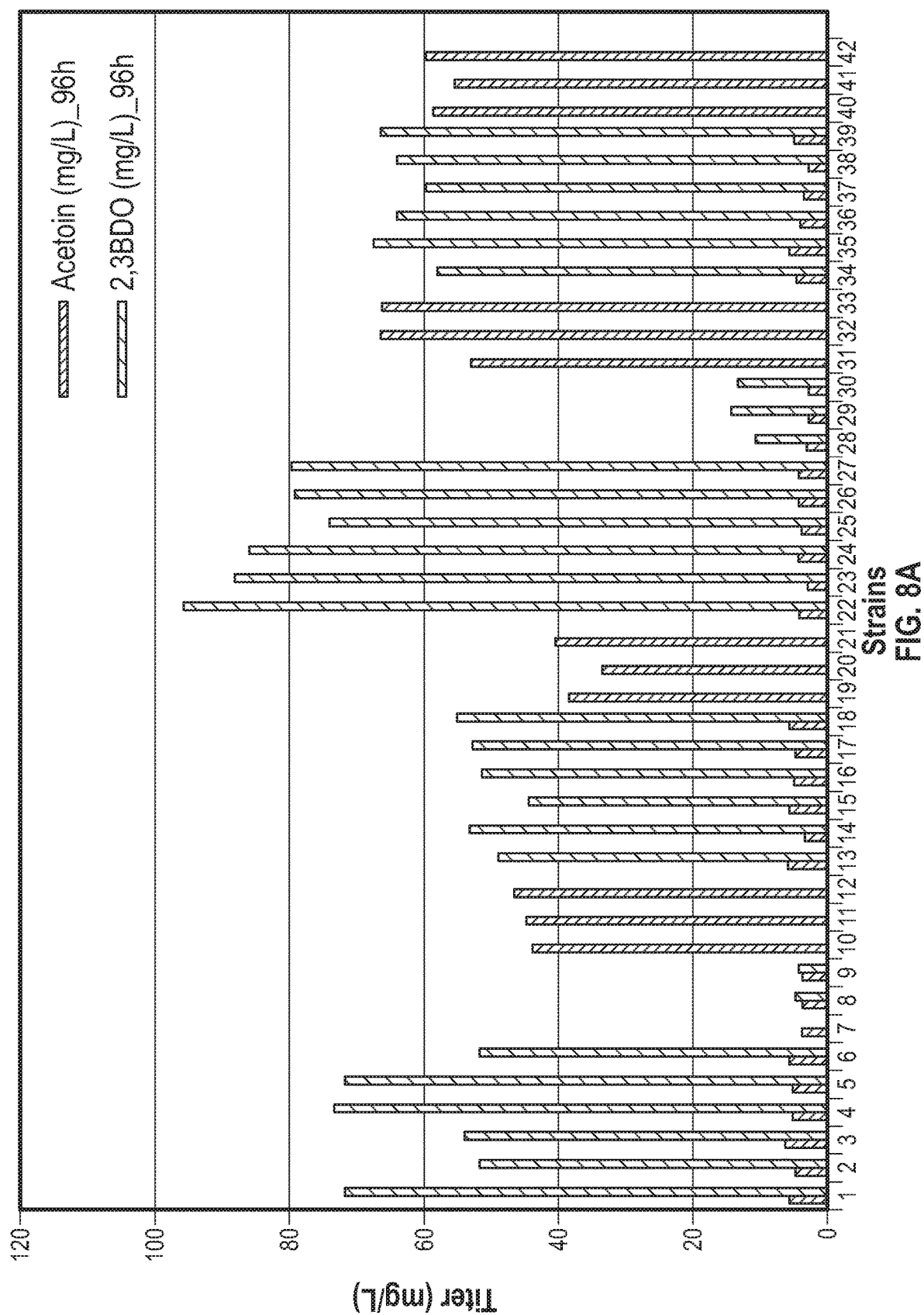
FIGS. 8A and 8B.
Figure 8B:
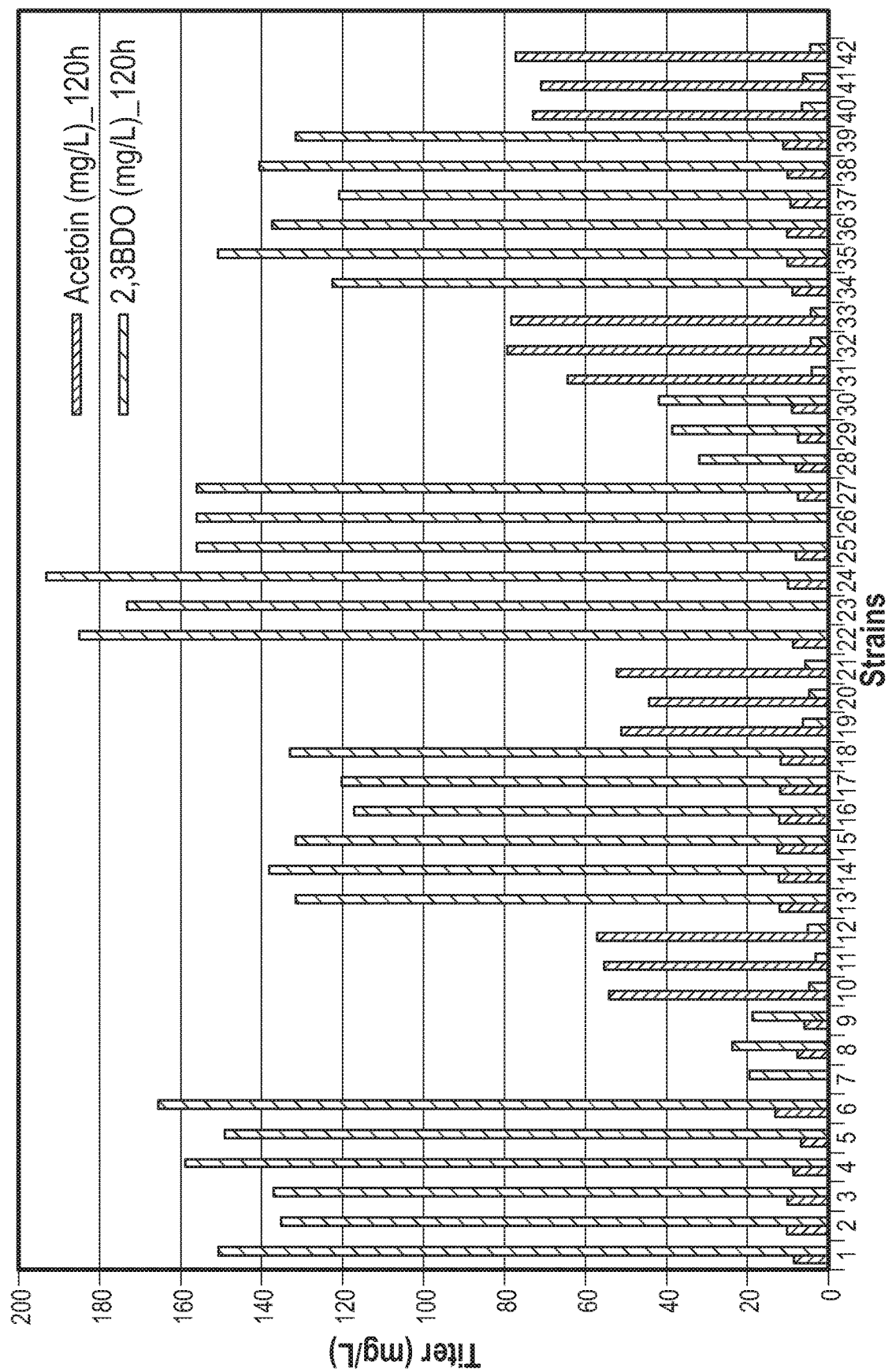

As shown FIGS. 8A, 8B, and Table 2, strains XZ685, XZ686, XZ687, XZ688, XZ689, and XZ690 (referring to 22 to 27, respectively in FIGS. 8A and 8B) produced the highest titers of 2,3-BDO at both 96 and 120 hours when diluting the lanthanum containing medium 1:50 (50×). Using a 1:10 dilution protocol also resulted in significant production of 2,3-BDO but the titers were lower than those using the 1:50 dilution protocol at both 96 and 120 hours. Strains XZ697, XZ698, XZ699, XZ700, XZ701, and XZ702 (referring to 34 to 39, respectively in FIGS. 8A and 8B) produced lower titers at both 1:10 and 1:50 dilutions at both 96 and 120 hours.

Example 8: Other Rare Earth Metals

Figure 9:
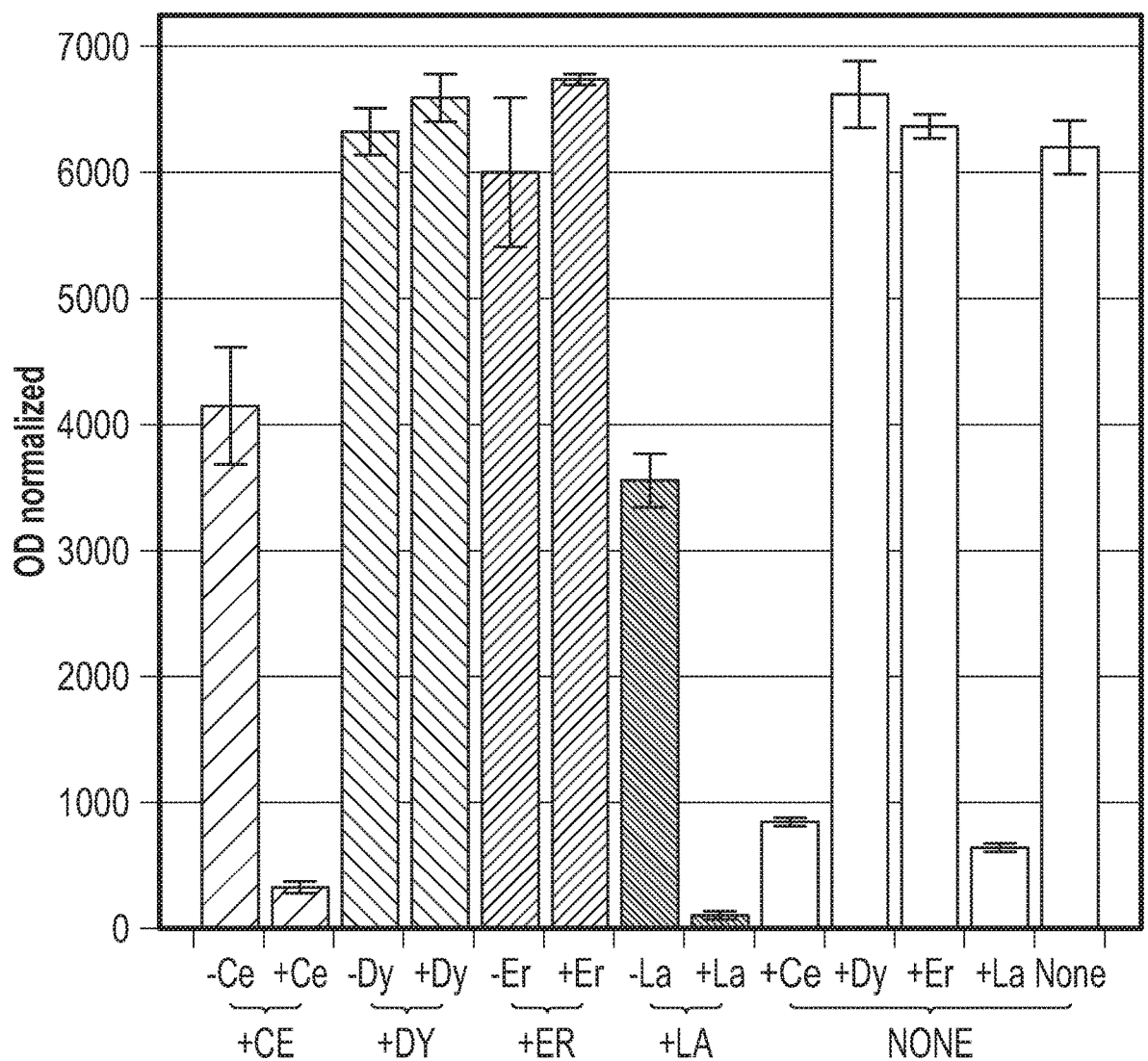
FIG. 9 shows the ability of other rare earth metals to activate or repress the pMxaF promoter as measured by mCherry levels. Cerium (Ce) and Lanthanum (La) were able to repress the pMxaF promoter whether or not they were present in the media during pre-culture or added after the pre-culture period. Further, dysprosium (Dy) or erbium (Er) were not able to repress the pMxaF promoter at any time.

In order to determine whether other rare earth metals can be used to modify the expression of genes, Cerium (Ce), dysprosium (Dy), and erbium (Er) were placed into the media in the presence of a *Methylococcus capsulatus* having a pMxaF promoter driving mCherry expression. FIG. 9 shows the ability of other rare earth metals to activate or repress the pMxaF promoter as measured by mCherry levels. Cerium (Ce) and Lanthanum (La) were able to repress the pMxaF promoter whether or not they were present in the media during pre-culture or added after the pre-culture period. Further, dysprosium (Dy) or erbium (Er) were not able to repress the pMxaF promoter at any time. See FIG. 9.

Also as shown in FIG. 9, repression of the promoter by lanthanum or cerium were more effective if initially present. Addition of lanthanum or cerium at a later time lead to decreased expression of mCherry, however the repression was not as effective. The addition of dysprosium or erbium at either time point did not lead to activation of repression of the pMxaF promoter.

Figure 10:
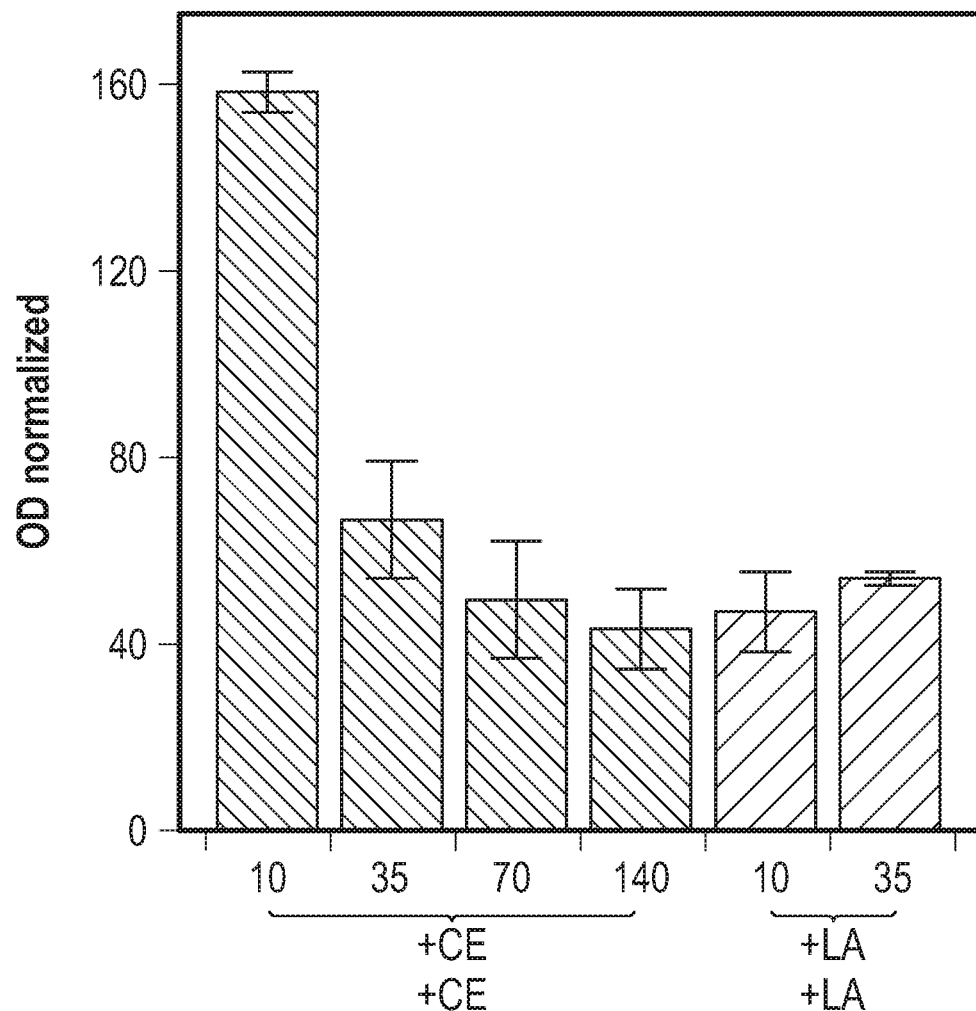
FIG. 10 shows that a titration of different levels of cerium on the effect of its ability to repress the pMxaF promoter. Full repression of the pMxaF promoter occur at approximately 70 μM of cerium. At this level, repression is similar to that of 10 or 35 μM of lanthanum.

A titration study was also performed using 10, 35, 70, and 140 µM cerium. As shown in FIG. 10, full repression of the pMxaF promoter occur at approximately 70 µM of cerium. At this level, repression is similar to that of 10 or 35 µM of lanthanum.

Figure 11:
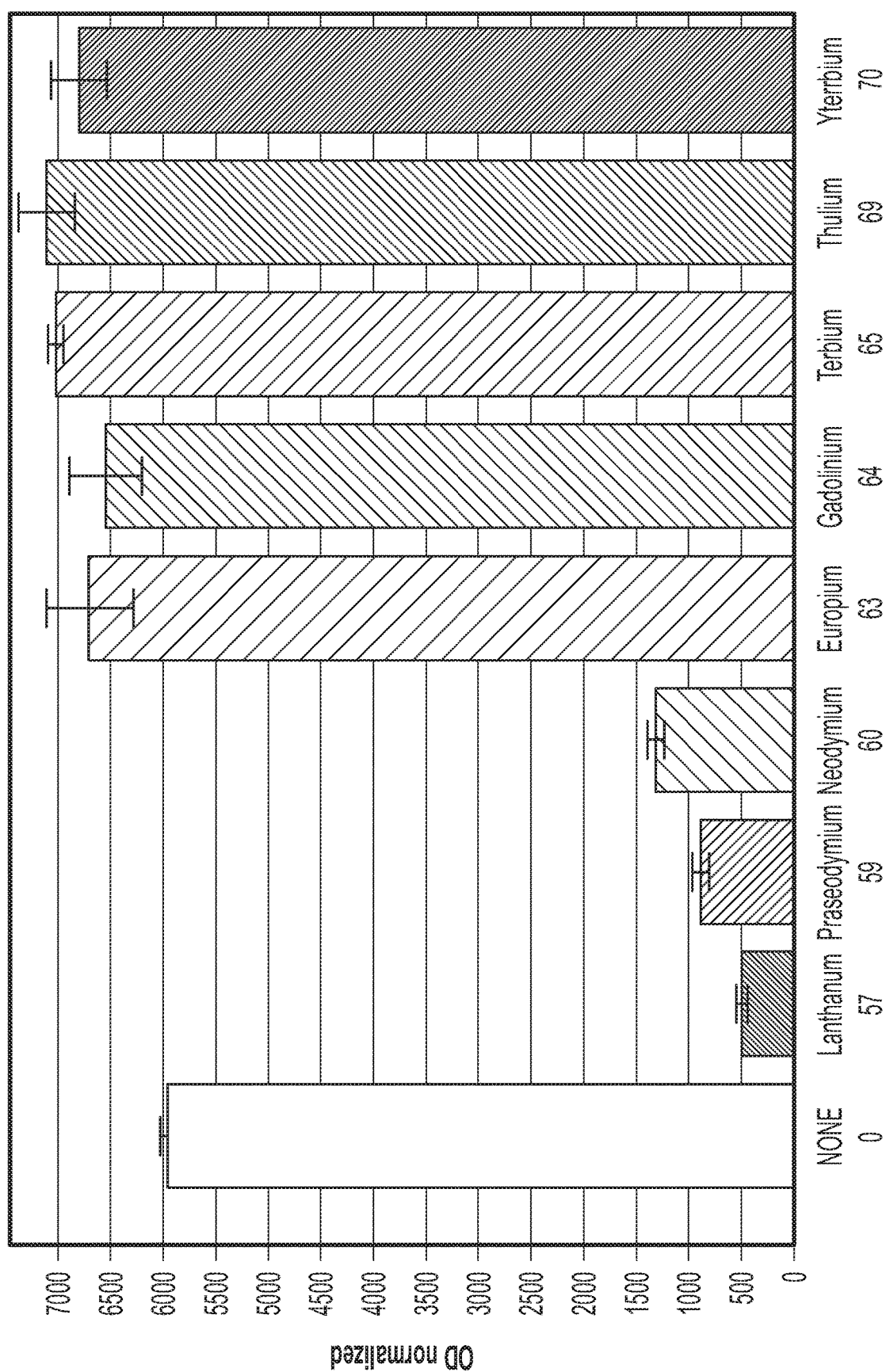
FIG. 11 shows the ability of different rare earth metals to activate or repress the pMxaF promoter as measured by mCherry. Lanthanum (La), praseodymium (Pr), and neodymium (Nd) repressed the pMxaF promoter. Additionally, europium (Eu), gadolinium (Gd), terbium (Tb), thulium (Tm), and ytterbium (Yb), did not repress the pMxaF promoter. In fact, these later rare earth metals activated the expression of the pMxaF promoter.

Other rare earth metals were also tested. As seen in FIG. 11, lanthanum (La), praseodymium (Pr), and neodymium (Nd), repressed the pMxaF promoter. However, europium (Eu), gadolinium (Gd), terbium (Tb), thulium (Tm), and ytterbium (Yb), did not repress the pMxaF promoter, but rather activated the expression of the pMxaF promoter.

Figure 12:
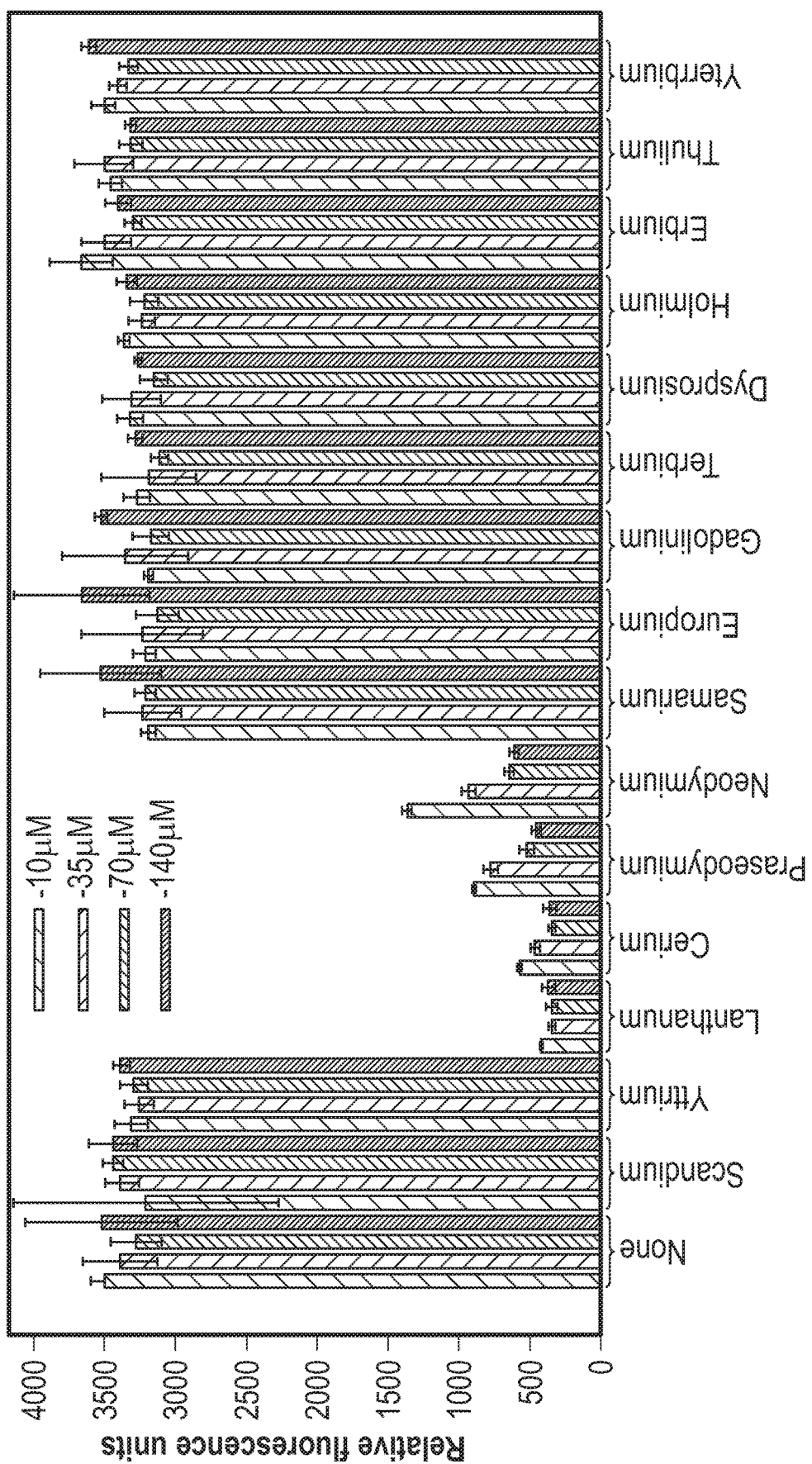
FIG. 12 shows the ability of various rare earth metals at a concentration of 10 μM 70 μM or 140 μM to activate or repress the pMxaF promoter as measured by mCherry. Scandium (Sc), yttrium (Y), samarium (Sm), europium (Eu), gadolinium (Gd), terbium (Tb), dysprosium (Dy), holmium (Ho), erbium (Er), thulium (Tm), and ytterbium (Yb) minimally activated or repressed the pMxaF promoter at 10 μM, 35 μM, 70 μM or 140 μM. However, lanthanum (La), cerium (Ce), praseodymium (Pr), and neodymium (Nd) significantly repressed the expression of the pMxaF promoter at all concentrations. Maximal repression was observed starting at 35 μM for lanthanum, 70 μM for cerium, and 140 μM for praseodymium and neodymium.

An additional experiment was conducted using scandium (Sc), yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), and ytterbium (Yb). Four concentrations of these rare earth metals (10 µM, 35 µM, 70 µM, or 140 µM) were tested for its ability to activate or repress the pMxaF promoter as measured by mCherry. The cultures were treated with for 24 hours with the respective rare earth metal. As seen in FIG. 12, scandium (Sc), yttrium (Y), samarium (Sm), europium (Eu), gadolinium (Gd), terbium (Tb), dysprosium (Dy), holmium (Ho), erbium (Er), thulium (Tm), and ytterbium (Yb) minimally activated or repressed the pMxaF promoter at 10 µM, 35 µM, 70 µM, or 140 µM. On the other hand, lanthanum (La), cerium (Ce), praseodymium (Pr), and neodymium (Nd) significantly repressed the expression of the pMxaF promoter at all concentrations. As previously shown and verified here, lanthanum repressed the pMxaF promoter and maximal repression was observed at 35 µM. Additionally, cerium repressed the pMxaF promoter and maximal repression was observed at 70 µM. Further, praseodymium and neodymium repressed the pMxaF promoter and maximal repression was observed at 140 µM.

What is claimed is:

1. A vector comprising:
   (a) genes encoding the following polypeptides: (i) an acetolactate synthase comprising an amino acid sequence that is at least 90% identical to SEQ ID NO: 1; (ii) an alpha-acetolactate decarboxylase comprising an amino acid sequence that is at least 90% identical to SEQ ID NO: 9; and (iii) an acetoin reductase comprising an amino acid sequence that is at least 90% identical to SEQ ID NO: 11; and
   (b) a promoter driving the expression of such genes, the promoter being pMxAF or pXoxF.

2. The vector of claim 1, wherein the genes encode the following polypeptides: an acetolactate synthase comprising an amino acid sequence that is at least 95% identical to SEQ ID NO: 1; an alpha-acetolactate decarboxylase comprising an amino acid sequence that is at least 95% identical to SEQ ID NO: 9; and an acetoin reductase comprising an amino acid sequence that is at least 95% identical to SEQ ID NO: 11.

3. A method of making a genetically modified methanotroph capable of converting a C1 carbon to a multicarbon product, the method comprising transforming a methanotroph with the vector of claim 1, wherein the methanotroph is selected from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* or *Methyloacidophilum*.

4. A method of making a multicarbon product, the method comprising:
   a) contacting a methanotroph with the vector of claim 1, thereby generating a genetically-modified methanotroph; and
   b) growing the genetically-modified methanotroph to produce the multicarbon product;
   wherein the methanotroph is selected from the genera *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis,* or *Methyloacidophilum*.

5. The method of claim 4, wherein the multicarbon product is 2,3-butanediol.

6. The method of claim 4, further comprising contacting the multicarbon product with a $SiO_2$-supported cesium dihydrogen phosphate ($CsH_2PO_4$) catalyst to produce a second multicarbon product.

7. The method of claim 4, wherein step a) further comprises contacting the genetically-modified methanotroph with media comprising a rare earth metal that can activate or repress the promoter.

8. The method of claim 7, wherein the rare earth metal is lanthanum.

9. The method of claim 8, wherein the lanthanum is present at a concentration of at least 0.5 µM.

10. The vector of claim 2, wherein:
    (a) the acetolactate synthase comprises an amino acid sequence that is at least 98% identical to SEQ ID NO: 1; (b) the alpha-acetolactate decarboxylase comprises an amino acid sequence that is at least 98% identical to SEQ ID NO: 9; and (c) the acetoin reductase comprises an amino acid sequence that is at least 98% identical to SEQ ID NO: 11.

11. The method of claim 3, wherein the methanotroph is from the species *Methylococcus capsulatus*.

12. The method of claim 4, wherein the methanotroph is from the species *Methylococcus capsulatus*.

13. The vector of claim 2, wherein:
    (a) the acetolactate synthase comprises the amino acid sequence of SEQ ID NO: 1; (b) the alpha-acetolactate decarboxylase comprises the amino acid sequence of SEQ ID NO: 9; and (c) the acetoin reductase comprises the amino acid sequence of SEQ ID NO: 11.

* * * * *

SEQUENCE LISTING

```
<160> NUMBER OF SEQ ID NOS: 82

<210> SEQ ID NO 1
<211> LENGTH: 570
<212> TYPE: PRT
<213> ORGANISM: Bacillus subtilis

<400> SEQUENCE: 1

Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
            20                  25                  30

Phe Gly Ile Pro Gly Ala Lys Ile Asp Ala Val Phe Asp Ala Leu Gln
        35                  40                  45

Asp Lys Gly Pro Glu Ile Ile Val Ala Arg His Glu Gln Asn Ala Ala
    50                  55                  60

Phe Met Ala Gln Ala Val Gly Arg Leu Thr Gly Lys Pro Gly Val Val
65                  70                  75                  80
```

-continued

```
Leu Val Thr Ser Gly Pro Gly Ala Ser Asn Leu Ala Thr Gly Leu Leu
                 85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
            115                 120                 125

Ala Leu Phe Gln Pro Ile Thr Lys Tyr Ser Val Glu Val Gln Asp Val
130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
                180                 185                 190

Gly Pro Ala Ala Asp Asp Ala Ile Ser Ala Ala Ile Ala Lys Ile Gln
                195                 200                 205

Thr Ala Lys Leu Pro Val Val Leu Val Gly Met Lys Gly Gly Arg Pro
210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
                260                 265                 270

Leu Leu Leu Glu Gln Ala Asp Val Leu Thr Ile Gly Tyr Asp Pro
                275                 280                 285

Ile Glu Tyr Asp Pro Lys Phe Trp Asn Ile Asn Gly Asp Arg Thr Ile
290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
                325                 330                 335

His Asp Ala Val Lys Val Glu Phe Ala Glu Arg Glu Gln Lys Ile Leu
                340                 345                 350

Ser Asp Leu Lys Gln Tyr Met His Glu Gly Glu Gln Val Pro Ala Asp
                355                 360                 365

Trp Lys Ser Asp Arg Ala His Pro Leu Glu Ile Val Lys Glu Leu Arg
370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                405                 410                 415

Met Ile Ser Asn Gly Met Gln Thr Leu Gly Val Ala Leu Pro Trp Ala
                420                 425                 430

Ile Gly Ala Ser Leu Val Lys Pro Gly Glu Lys Val Val Ser Val Ser
                435                 440                 445

Gly Asp Gly Gly Phe Leu Phe Ser Ala Met Glu Leu Glu Thr Ala Val
                450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495
```

```
Val Asp Phe Gly Asn Ile Asp Ile Val Lys Tyr Ala Glu Ser Phe Gly
            500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Ile Asp Val Pro Val
    530                 535                 540

Asp Tyr Ser Asp Asn Ile Asn Leu Ala Ser Asp Lys Leu Pro Lys Glu
545                 550                 555                 560

Phe Gly Glu Leu Met Lys Thr Lys Ala Leu
            565                 570

<210> SEQ ID NO 2
<211> LENGTH: 1713
<212> TYPE: DNA
<213> ORGANISM: Bacillus subtilis

<400> SEQUENCE: 2
```

| | | | | | |
|---|---|---|---|---|---|
| atgaccaagg | ccaccaagga | acagaaaagc | ctggtcaaga | accgcggtgc | tgaactggtt | 60 |
| gtggactgcc | tcgtggaaca | gggcgtgacc | catgtcttcg | gcatcccggg | cgccaagatc | 120 |
| gacgccgtct | tcgacgccct | gcaggataaa | ggtccggaaa | tcatcgtggc | acgccatgag | 180 |
| cagaacgcag | ccttcatggc | ccaggccgtc | ggtcggctga | cgggtaagcc | cggcgtggtg | 240 |
| ctggtcaccc | tccggtccgg | gagcctcgaa | ctggccacgg | gactgctcac | cgccaacacc | 300 |
| gaaggcgacc | cggtggtcgc | cctggccggt | aatgtcatcc | gggcggatcg | cctgaagcgc | 360 |
| acccatcagt | ccctggataa | cgcggccctg | ttccagccaa | tcaccaaata | tagtgtcgaa | 420 |
| gtgcaggatg | tgaagaacat | cccggaagcc | gtcaccaatg | cgttccgaat | cgcgtccgcc | 480 |
| ggccaagcag | gggcagcatt | cgtgagcttc | ccccaggacg | tggtcaatga | agtgaccaac | 540 |
| accaaaaacg | tcagagccgt | agccgccccg | aagctgggcc | ctgcagcaga | tgacgccatc | 600 |
| tccgctgcca | tcgcgaagat | ccagaccgca | aagctgccgg | tcgtgctggt | cggaatgaag | 660 |
| ggcggacgcc | cggaggccat | caaggccgtg | cgtaaactgc | tgaagaaggt | gcagctaccg | 720 |
| ttcgtggaaa | cctaccaggc | cgccggcacc | ctgagtcggg | acttggaaga | ccagtatttc | 780 |
| ggccgtatcg | gcctgttccg | caaccagccg | ggcgacctgc | cctggaaca | agccgatgtg | 840 |
| gtgctgacca | tcggctacga | cccgatcgaa | tatgacccga | agttctggaa | catcaatggc | 900 |
| gaccgcacga | tcatccatct | ggacgaaatc | atcgccgaca | tcgaccatgc | ctatcagccg | 960 |
| gacctggaac | tgatcggcga | catcccgagc | accatcaacc | acatcgaaca | cgatgccgtg | 1020 |
| aaggtggaat | tgccgaacg | cgaacagaag | atcctgtcgg | acctgaagca | gtatatgcat | 1080 |
| gagggcgaac | aggtgcctgc | cgactggaag | tcggacagag | cccatccgct | ggaaatcgtg | 1140 |
| aaggaactgc | gtaacgccgt | cgacgaccat | gtcaccgtca | cctgcgatat | cggcagccat | 1200 |
| gccatttgga | tgagccgcta | cttccggagc | tatgaaccgc | tgaccctgat | gatctccaac | 1260 |
| ggtatgcaga | ccctcggcgt | cgccctcccg | tgggccatcg | gcgcaagtct | ggtgaagccg | 1320 |
| ggcgaaaaag | tggtcagcgt | gtccggcgac | ggcggcttcc | tgttctccgc | tatggaactg | 1380 |
| gaaaccgcgg | tccgcctgaa | ggccccgatc | gtgcatatcg | tgtggaacga | cagcacctac | 1440 |
| gacatggtcg | ccttccagca | gctgaaaaag | tacaaccgca | ccagcgccgt | ggacttcggc | 1500 |
| aatatcgaca | tcgtgaagta | tgccgaatcc | ttcggagcca | ccggactgcg | cgtggaatcc | 1560 |
| ccggaccagc | tggcggacgt | tctgcgtcag | ggcatgaatg | ccgaaggtcc | cgtgattatc | 1620 |
| gatgtgcccg | tcgactacag | cgacaacatc | aacctggcct | cggacaaatt | gccgaaggag | 1680 |

```
ttcggcgaac tgatgaaaac aaaagcacta taa                              1713
```

<210> SEQ ID NO 3
<211> LENGTH: 556
<212> TYPE: PRT
<213> ORGANISM: Clostridium autoethanogenum

<400> SEQUENCE: 3

```
Met Asn Arg Asp Ile Lys Lys Glu Val Gln Leu Asn Thr Ala Gln Met
1               5                   10                  15

Leu Val Lys Cys Leu Glu Ala Glu Gly Val Lys Tyr Ile Phe Gly Ile
            20                  25                  30

Pro Gly Glu Glu Asn Leu Glu Ile Met Asn Ala Ile Ser Asp Ser Thr
        35                  40                  45

Ile Glu Phe Ile Thr Thr Arg His Glu Gln Gly Ala Ala Phe Met Ala
    50                  55                  60

Asp Val Tyr Gly Arg Leu Thr Gly Lys Ala Gly Val Cys Leu Ser Thr
65                  70                  75                  80

Leu Gly Pro Gly Ala Thr Asn Leu Val Thr Gly Val Ala Asp Ala Asp
                85                  90                  95

Ser Asp Gly Ala Pro Val Val Ala Ile Thr Gly Gln Val Gly Thr Glu
            100                 105                 110

Arg Met His Ile Thr Ser His Gln Phe Leu Asp Leu Cys Lys Met Phe
        115                 120                 125

Glu Pro Ile Thr Lys Arg Ser Lys Gln Ile Val Arg Pro Asp Thr Val
    130                 135                 140

Ser Glu Ile Ile Arg Leu Val Phe Lys Tyr Ala Glu Ser Glu Lys Pro
145                 150                 155                 160

Gly Ala Cys His Ile Asp Leu Pro Val Asn Ile Ala Lys Met Pro Val
                165                 170                 175

Gly Ala Leu Glu Lys Pro Leu Glu Lys Lys Ile Pro Lys Glu His
            180                 185                 190

Ala Asp Leu Ser Thr Ile Glu Glu Ala Ala Ser Glu Ile Phe Lys Ala
        195                 200                 205

Lys Asn Pro Ile Ile Leu Ala Gly Ser Gly Ala Ile Arg Gly Asn Ser
    210                 215                 220

Ser Lys Ala Val Thr Glu Phe Ala Thr Lys Leu Lys Ile Pro Val Ile
225                 230                 235                 240

Asn Thr Met Met Ala Lys Gly Ile Ile Pro Met Asp Asn Lys Tyr Ser
                245                 250                 255

Met Trp Thr Ile Gly Ile Pro Gln Lys Asp Tyr Val Asn Lys Ile Ile
            260                 265                 270

Glu Glu Ala Asp Leu Val Ile Thr Ile Gly Tyr Asp Ile Val Glu Tyr
        275                 280                 285

Ala Pro Ser Lys Trp Asn Ile Asn Gly Asp Ile Lys Ile Val His Ile
    290                 295                 300

Asp Ala Arg Pro Ser His Ile Asn Lys Leu Tyr Gln Pro Ile Val Glu
305                 310                 315                 320

Val Val Gly Asp Ile Ser Asp Ala Leu Tyr Asn Ile Leu Arg Arg Thr
                325                 330                 335

Ser Ser Lys Asp Glu Pro Val Lys Ala Leu Glu Ile Lys Ser Glu Met
            340                 345                 350

Leu Ala Glu His Glu Ser Tyr Ala Asn Asp Asn Ala Phe Pro Met Lys
        355                 360                 365
```

Pro Gln Arg Ile Leu Asn Asp Val Arg Lys Val Met Gly Pro His Asp
    370                 375                 380

Ile Val Ile Ser Asp Val Gly Ala His Lys Met Trp Ile Ala Arg His
385                 390                 395                 400

Tyr Asn Cys Tyr Glu Pro Asn Thr Cys Ile Ile Ser Asn Gly Phe Ala
                405                 410                 415

Thr Met Gly Ile Gly Val Pro Gly Ala Ile Ala Lys Leu Ile Asn
                420                 425                 430

Pro Asp Lys Lys Val Leu Ala Ile Val Gly Asp Gly Phe Met Met
                435                 440                 445

Asn Asn Gln Glu Leu Glu Thr Ala Leu Arg Ile Lys Thr Pro Ile Val
    450                 455                 460

Val Leu Ile Phe Asn Asp Ser Asn Tyr Gly Leu Ile Lys Trp Lys Gln
465                 470                 475                 480

Glu Glu His Tyr Gly Lys Ser Cys Tyr Val Asp Phe Thr Asn Pro Asp
                485                 490                 495

Phe Val Lys Leu Ala Glu Ser Met Tyr Ala Lys Gly Tyr Arg Val Glu
                500                 505                 510

Lys Ala Glu Asp Leu Ile Pro Thr Leu Glu Glu Ala Phe Lys Gln Asn
                515                 520                 525

Val Pro Ala Val Ile Asp Cys Gln Val Asp Tyr Gly Glu Asn Ile Lys
                530                 535                 540

Leu Thr Lys His Leu Lys Glu Val Tyr Glu Asn Met
545                 550                 555

<210> SEQ ID NO 4
<211> LENGTH: 1671
<212> TYPE: DNA
<213> ORGANISM: Clostridium autoethanogenum

<400> SEQUENCE: 4

```
atgaatcggg atatcaagaa agaggtgcag ctcaacacgg cccagatgct ggtcaagtgt      60
ctggaagccg agggcgtcaa gtatatcttc ggcatcccgg gcgaggagaa tctcgaaatc     120
atgaacgcca tctcggattc cacgatcgag ttcatcacca cccgccatga acagggcgcg     180
gccttcatgg ccgacgtgta cggccggctg accggcaagg cgggcgtgtg tctgagcacc     240
ctcggcccg cgcgaccaa cctggtcacc ggcgtggccg acgccgactc cgacggcgcc     300
cccgtggtcg cgatcaccgg ccaggtgggc acggagcgga tgcacatcac ctcccatcag     360
ttcctcgacc tctgcaagat gttcgagccg atcaccaagc ggagcaagca gatcgtccgc     420
ccggacacgg tgtcggagat catccgcctg gtgttcaagt acgccgaaag cgaaaagccc     480
ggcgcctgtc atatcgacct gccggtcaac atcgccaaga tgcccgtcgg cgccctggag     540
aagccgctgg agaaaaaaat cccgccgaag gaacacgcgg acctgtccac catcgaggaa     600
gcggcgtccg agatcttcaa ggccaaaaac cccatcatcc tggccggcag cggcgccatc     660
cgcggcaaca gcagcaaggc ggtcaccgag ttcgccacca gctgaagat ccccgtcatc     720
aacacgatga tggccaaggg catcatcccg atggacaaca gtatagcat gtggaccatc     780
ggcatccccc agaaggacta tgtgaacaag atcatcgaag aggccgacct ggtcatcacc     840
atcggctacg acatcgtgga atatgccccg tcgaaatgga catcaacgg cgacatcaag     900
atcgtccata tcgacgcccg ccctcgcac atcaacaaac tctaccagcc catcgtggag     960
gtggtcggcg acatcagcga cgcgctgtat aacatcctgc gccgcaccag ctcgaaagac    1020
gagccggtca aggcgctgga gatcaagtcg gaaatgctgg cggagcacga gtcctacgcg    1080
```

```
aacgacaatg cgttcccgat gaagccgcag cgcatcctca acgatgtgcg caaagtcatg    1140
ggcccgcacg acatcgtgat ctccgatgtg ggcgcccata aaatgtggat cgcccgccac    1200
tataactgct acgagccgaa tacctgcatc atctcgaacg gcttcgccac gatgggcatc    1260
ggcgtcccgg gcgcgatcgc cgccaaactc atcaacccgg ataagaaggt cctggccatc    1320
gtcggcgacg gcggcttcat gatgaataac caggaactgg agacggcgct gcgcatcaaa    1380
acgcccatcg tggtcctcat cttcaacgac tccaattacg gcctcatcaa gtggaagcag    1440
gaggagcatt atggcaaatc gtgctatgtg gacttcacca acccggactt cgtgaagctg    1500
gccgagagca tgtacgccaa aggctatcgc gtggagaaag ccgaggatct gatcccgacc    1560
ctcgaagagg ccttcaagca gaatgtcccg gcggtcatcg actgccaggt ggactatggc    1620
gagaatatca agctcaccaa gcacctcaag gaggtctatg aaaacatgtg a            1671
```

<210> SEQ ID NO 5
<211> LENGTH: 572
<212> TYPE: PRT
<213> ORGANISM: Bacillus licheniformis

<400> SEQUENCE: 5

```
Met Asn Asn Val Ala Ala Lys Asn Glu Thr Leu Thr Val Arg Gly Ala
1               5                   10                  15

Glu Leu Val Val Asp Ser Leu Ile Gln Gln Gly Val Thr His Val Phe
            20                  25                  30

Gly Ile Pro Gly Ala Lys Ile Asp Ala Val Phe Asp Val Leu Lys Asp
        35                  40                  45

Lys Gly Pro Glu Leu Ile Val Cys Arg His Glu Gln Asn Ala Ala Phe
    50                  55                  60

Met Ala Ala Val Gly Arg Leu Thr Gly Lys Pro Gly Val Cys Leu
65                  70                  75                  80

Val Thr Ser Gly Pro Gly Ala Ser Asn Leu Ala Thr Gly Leu Val Thr
                85                  90                  95

Ala Asn Thr Glu Gly Asp Pro Val Val Ala Leu Ala Gly Ala Val Lys
            100                 105                 110

Arg Ala Asp Arg Leu Lys Lys Thr His Gln Ser Met Asp Asn Ala Ala
        115                 120                 125

Leu Phe Gln Pro Ile Thr Lys Tyr Ser Ala Glu Val Glu Asp Ala Asn
    130                 135                 140

Asn Ile Pro Glu Ala Val Thr Asn Ala Phe Arg Ala Ala Ala Ser Gly
145                 150                 155                 160

Gln Ala Gly Ala Ala Phe Leu Ser Phe Pro Gln Asp Val Thr Ala Gly
                165                 170                 175

Pro Ala Thr Ala Lys Pro Val Lys Thr Met Pro Ala Pro Lys Leu Gly
            180                 185                 190

Ala Ala Ser Asp Glu Gln Ile Ser Ala Ala Ile Ala Lys Ile His Asn
        195                 200                 205

Ala Asn Leu Pro Val Val Leu Val Gly Met Lys Gly Gly Arg Pro Glu
    210                 215                 220

Ala Ile Glu Ala Val Arg Arg Leu Leu Arg Lys Val Lys Leu Pro Phe
225                 230                 235                 240

Val Glu Thr Tyr Gln Ala Ala Gly Thr Leu Ser His Asp Leu Glu Asp
                245                 250                 255

Gln Tyr Phe Gly Arg Ile Gly Leu Phe Arg Asn Gln Pro Gly Asp Met
            260                 265                 270
```

Leu Leu Glu Lys Ala Asp Val Val Leu Thr Val Gly Tyr Asp Pro Ile
        275                 280                 285

Glu Tyr Asp Pro Val Phe Trp Asn Gly Lys Gly Glu Arg Ser Val Ile
    290                 295                 300

His Leu Asp Glu Ile Gln Ala Asp Ile Asp His Asp Tyr Gln Pro Glu
305                 310                 315                 320

Ile Glu Leu Ile Gly Asp Ile Ala Glu Thr Leu Asn His Ile Glu His
                325                 330                 335

Asp Ser Leu Pro Val Ser Ile Asp Glu Ser Phe Ala Pro Val Leu Asp
                340                 345                 350

Tyr Leu Lys Lys Ala Leu Glu Gln Ser Glu Pro Pro Lys Glu Thr
            355                 360                 365

Lys Thr Asp Leu Val His Pro Leu Gln Ile Val Arg Asp Leu Arg Glu
    370                 375                 380

Leu Leu Ser Asp Asp Ile Thr Val Thr Cys Asp Ile Gly Ser His Ala
385                 390                 395                 400

Ile Trp Met Ser Arg Tyr Phe Arg Thr Tyr Arg Pro His Gly Leu Leu
                405                 410                 415

Ile Ser Asn Gly Met Gln Thr Leu Gly Val Ala Leu Pro Trp Ala Ile
                420                 425                 430

Ala Ala Thr Leu Val Asn Pro Gly Gln Lys Val Val Ser Val Ser Gly
            435                 440                 445

Asp Gly Gly Phe Leu Phe Ser Ala Met Glu Leu Glu Thr Ala Val Arg
    450                 455                 460

Leu Lys Ala Pro Ile Val His Ile Val Trp Asn Asp Ser Thr Tyr Asp
465                 470                 475                 480

Met Val Ala Phe Gln Gln Glu Met Lys Tyr Lys Arg Thr Ser Gly Val
                485                 490                 495

Asp Phe Gly Gly Ile Asp Ile Val Lys Tyr Ala Glu Ser Phe Gly Ala
                500                 505                 510

Lys Gly Leu Arg Val Asn Ser Pro Asp Glu Leu Ala Glu Val Leu Lys
            515                 520                 525

Ala Gly Leu Asp Ala Glu Gly Pro Val Val Ile Asp Ile Pro Val Asp
    530                 535                 540

Tyr Ser Asp Asn Ile His Leu Ala Asp Gln Arg Phe Pro Lys Lys Phe
545                 550                 555                 560

Glu Glu His Phe Asn Lys Glu Ala Ser Lys Gln Ser
                565                 570

<210> SEQ ID NO 6
<211> LENGTH: 1719
<212> TYPE: DNA
<213> ORGANISM: Bacillus licheniformis

<400> SEQUENCE: 6

```
atgaataacg tcgcggccaa gaacgaaacc ctgaccgtcc ggggcgccga actcgtggtg      60
gatagcctga tccagcaggg cgtgacccat gtcttcggca tcccgggcgc caaaatcgac     120
gcggtcttcg acgtgctgaa ggataagggc cccgaactga tcgtctgccg ccatgagcag     180
aacgcggcct tcatggccgc cgccgtcggc cgcctgacgg gcaagccggg cgtctgcctg     240
gtcacctccg gcccgggcgc ctcgaatctc gcgaccggcc tggtcaccgc gaacacggaa     300
ggcgaccccg tggtcgccct ggcgggcgcc gtgaagcggg cggatcggct gaagaagacg     360
caccagtcga tggataacgc cgccctgttc cagcccatca cgaagtacag cgcggaggtg     420
```

-continued

```
gaagacgcga acaacatccc ggaggccgtg acgaacgcct tccgcgccgc ggcgtccggc     480
caggccggcg cggccttcct cagcttcccc caggatgtca ccgccggccc ggccaccgcc     540
aagccggtca aaaccatgcc cgccccgaag ctgggcgccg cgagcgatga acagatctcc     600
gccgcgatcg cgaagatcca caacgcgaat ctgccggtgg tcctcgtggg catgaagggc     660
ggccggccgg aagccatcga agccgtgcgc cgcctgctcc gcaaggtcaa gctcccgttc     720
gtggaaacct accaggcggc cggcacgctg tcgcacgatc tggaggatca gtacttcggc     780
cggatcggcc tgttccggaa ccagccgggc gacatgctcc tggaaaaggc cgacgtggtc     840
ctgaccgtgg gctacgaccc gatcgagtac gatccggtgt tctggaatgg caaaggcgaa     900
cgctcggtca tccacctcga cgaaatccag gccgatatcg atcacgacta ccagcccgag     960
atcgaactca tcggcgacat cgcggaaacc ctcaatcaca tcgagcatga ctcgctgccg    1020
gtgtccatcg acgaatcctt cgcgcccgtg ctcgactatc tcaagaaggc gctcgaagaa    1080
cagtcggagc ccccgaagga aacgaagacc gatctggtcc acccgctcca gatcgtgcgc    1140
gacctgcgcg agctgctctc cgatgacatc accgtcacct gcgacatcgg cagccacgcc    1200
atctggatgt cccgctattt ccgcacctat cgcccgcatg gcctcctgat ctccaacggc    1260
atgcagacgc tgggcgtcgc cctgccgtgg gcgatcgccg cgaccctggt gaacccgggc    1320
cagaaggtgg tgtcggtcag cggcgatggc ggcttcctct tctccgcgat ggaactcgaa    1380
accgccgtcc gcctcaaggc gccgatcgtg cacatcgtgt ggaacgactc cacgtacgac    1440
atggtcgcgt tccagcagga aatgaagtac aagcgcacct ccggcgtcga tttcggcggc    1500
atcgacatcg tcaagtatgc ggaatccttc ggcgccaaag gcctccgcgt gaatagcccc    1560
gatgaactgg ccgaggtcct gaaggccggc ctcgacgcgg agggcccggt ggtcatcgac    1620
atccccgtcg actactcgga taacatccac ctggccgacc agcgcttccc gaagaagttc    1680
gaggagcact tcaacaagga agcgtcgaag cagtcctga                           1719
```

<210> SEQ ID NO 7
<211> LENGTH: 239
<212> TYPE: PRT
<213> ORGANISM: Clostridium autoethanogenum

<400> SEQUENCE: 7

```
Met Asp Asp Glu Val Lys Val Pro Asn His Ile Tyr Gln Met Ser Thr
1               5                  10                  15

Ile Asn Ala Leu Val Ser Gly Leu Tyr Asp Gly Cys Val Ser Leu Ser
            20                  25                  30

Lys Leu Leu Lys Lys Gly Asn Phe Gly Ile Gly Thr Phe Lys Gly Leu
        35                  40                  45

Asp Gly Glu Leu Thr Leu Leu Asn Gly Thr Phe Tyr Arg Thr Lys Pro
    50                  55                  60

Asp Gly Ser Val Tyr Val Cys Ser Lys Asn Val Ser Val Pro Phe Ala
65                  70                  75                  80

Val Val Thr Glu Leu Glu Asn Tyr Asn Thr Tyr Asn Ile Gln Asn Arg
                85                  90                  95

Thr Ser Tyr Glu Asp Ile Arg Lys Glu Leu Asp Ser Phe Ile Glu Ser
            100                 105                 110

Lys Asn Ile Phe Tyr Ala Phe Tyr Met Glu Gly Lys Phe Asn Tyr Val
        115                 120                 125

Lys Thr Arg Thr Val Val Lys Gln Asn Met Pro Tyr Lys Pro Met Ala
    130                 135                 140
```

```
Glu Val Val Lys Asp Gln Pro Met Phe Glu Tyr Asn Gly Val Asp Gly
145                 150                 155                 160

Tyr Val Val Gly Phe Arg Cys Pro Asp Tyr Val Glu Gly Leu Asn Val
                165                 170                 175

Pro Gly Tyr His Phe His Phe Ile Asn Lys Asp Lys Lys Phe Gly Gly
            180                 185                 190

His Ile Ser Glu Phe Ser Ile Glu Asn Ala Lys Val Tyr Val Gln Asn
        195                 200                 205

Cys Ser Cys Phe Arg Met Glu Leu Pro Lys Asn Glu Ser Phe Tyr Asn
    210                 215                 220

Met Glu Val Gln Asp Arg Asn Asp Glu Ile Thr Ser Val Glu Lys
225                 230                 235

<210> SEQ ID NO 8
<211> LENGTH: 720
<212> TYPE: DNA
<213> ORGANISM: Clostridium autoethanogenum

<400> SEQUENCE: 8
atggatgatg aggtgaaagt cccgaaccac atctaccaga tgtcgaccat caatgccctg      60
gtcagcggcc tctacgacgg ctgtgtgtcg ctctcgaagc tcctgaaaaa gggcaatttc     120
ggcatcggca cgttcaaggg cctggatggc gagctgaccc tcctgaacgg cacgttctat     180
cgcaccaaac cggatggctc cgtgtacgtg tgcagcaaga acgtgagcgt ccccttcgcg     240
gtcgtcaccg agctggagaa ctacaatacc tataacatcc agaatcgcac ctcctatgag     300
gacatccgca aggagctgga ctcgttcatc gagtcgaaga acatcttcta tgccttctat     360
atggaaggca aattcaacta cgtcaaaacc cgcaccgtcg tgaagcagaa catgccgtac     420
aagccgatgg ccgaggtggt caaagaccag ccgatgttcg aatacaacgg cgtcgatggc     480
tacgtcgtcg gcttccggtg cccggattat gtggaaggcc tcaatgtgcc cggctaccat     540
ttccacttca tcaacaagga caaaaagttc ggcggccaca tctccgagtt ctcgatcgag     600
aacgccaaag tctacgtcca gaactgctcc tgtttccgca tggagctccc gaagaatgag     660
agcttctaca catatggagt tcaggaccgc aacgacgaaa tcacgtccgt ggagaaatga     720

<210> SEQ ID NO 9
<211> LENGTH: 259
<212> TYPE: PRT
<213> ORGANISM: Klebsiella pneumoniae

<400> SEQUENCE: 9

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110
```

His Pro Val Ser Arg Gln Gln Leu His Glu Val Ile Asp Gln Gln Ile
            115                 120                 125

Pro Ser Asp Asn Leu Phe Cys Ala Leu Arg Ile Asp Gly His Phe Arg
        130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 10
<211> LENGTH: 780
<212> TYPE: DNA
<213> ORGANISM: Klebsiella pneumoniae

<400> SEQUENCE: 10

```
atgaaccact cggccgaatg cacctgcgaa gagagcctct gcgaaaccct ccgggccttc      60
tcggcccagc acccggagag cgtcctgtac cagacgagcc tgatgtcggc gctgctgtcg     120
ggcgtgtatg aaggctcgac gaccatcgcc gacctgctga agcatggcga cttcggcctg     180
ggcaccttca tgaactgga cggcgagctc atcgccttca gctcgcaggt gtatcagctc     240
cgggccgatg gctccgcccg gaaggcccag cccgaacaga gaccccgtt cgccgtgatg     300
acctggttcc agccgcagta tcggaagacc ttcgaccacc ccgtgagccg ccagcagctc     360
cacgaggtga tcgaccagca gatcccgagc gacaacctct tctgcgccct cgcatcgac     420
ggccatttcc gccacgcgca tacccgcacc gtcccgcggc agaccccgcc ctaccgcgcc     480
atgaccgatg tcctggatga ccagccggtc ttccggttca accagcgcga gggcgtcctg     540
gtcggcttcc gcaccccgca gcacatgcag ggcatcaacg tcgcgggcta tcatgaacac     600
ttcatcaccg atgatcgcaa gggcggcggc cacctcctcg actaccagct ggaccacggc     660
gtcctgacct tcggcgaaat ccataagctg atgatcgacc tccccgccga cagcgccttc     720
ctgcaggcga atctgcatcc ggacaacctc gatgccgcca tccgctccgt cgagtcgtga     780
```

<210> SEQ ID NO 11
<211> LENGTH: 357
<212> TYPE: PRT
<213> ORGANISM: Clostridium autoethanogenum

<400> SEQUENCE: 11

Met Lys Ala Val Leu Trp Tyr Asp Lys Lys Asp Val Arg Val Glu Glu
1               5                   10                  15

Ile Glu Glu Pro Lys Val Lys Glu Asn Ala Val Lys Ile Lys Val Lys
            20                  25                  30

Trp Cys Gly Ile Cys Gly Ser Asp Leu His Glu Tyr Leu Gly Gly Pro

```
        35                  40                  45

Ile Phe Ile Pro Val Gly Thr Pro His Pro Leu Ser Lys Ser Thr Ala
    50                  55                  60

Pro Val Val Leu Gly His Glu Phe Ser Gly Glu Val Val Glu Ile Gly
65                  70                  75                  80

Ser Lys Val Thr Lys Phe Lys Ala Gly Asp Arg Val Ile Val Glu Pro
                85                  90                  95

Ile Val Ala Cys Gly Lys Cys Pro Ala Cys Leu Glu Gly Lys Tyr Asn
            100                 105                 110

Leu Cys Glu Ala Leu Gly Phe His Gly Leu Cys Gly Ser Gly Gly Gly
        115                 120                 125

Phe Ala Glu Tyr Thr Val Phe Pro Glu Asp Phe Val His Lys Ile Pro
    130                 135                 140

Asp Thr Met Asp Tyr Glu Gln Ala Ala Leu Val Glu Pro Met Ala Val
145                 150                 155                 160

Ala Leu His Ser Leu Arg Val Gly Asn Phe Thr Thr Gly Asn Thr Ala
                165                 170                 175

Leu Val Leu Gly Ala Gly Pro Ile Gly Leu Ala Thr Ile Gln Cys Leu
            180                 185                 190

Lys Ala Ser Gly Ala Arg Ile Val Ile Val Phe Gln Arg Lys Ser Val
        195                 200                 205

Arg Gln Glu Tyr Ala Lys Lys Phe Gly Ala Asp Val Val Leu Asp Pro
    210                 215                 220

Asn Glu Val Asp Val Ile Glu Glu Ile Lys Lys Leu Thr Gly Gly Val
225                 230                 235                 240

Gly Val Asp Thr Ser Phe Glu Thr Thr Gly Ala Asn Val Gly Ile Asn
                245                 250                 255

Thr Ala Ile Gln Ala Leu Lys Tyr Glu Gly Thr Ala Val Ile Thr Ser
            260                 265                 270

Val Trp Glu Lys Asn Ala Glu Ile Asn Pro Asn Asp Leu Val Phe Thr
        275                 280                 285

Glu Lys Lys Val Val Gly Thr Leu Ala Tyr Arg His Glu Phe Pro Ser
    290                 295                 300

Thr Ile Ala Leu Met Asn Asp Gly Arg Ile Lys Thr Asp Gly Tyr Ile
305                 310                 315                 320

Thr Lys Arg Ile Ala Leu Glu Asp Ile Val Lys Glu Gly Phe Glu Thr
                325                 330                 335

Leu Thr Gly Pro Glu Lys Lys Lys His Val Lys Ile Ile Val Thr Pro
            340                 345                 350

Asp Lys Ser Leu Leu
        355

<210> SEQ ID NO 12
<211> LENGTH: 1074
<212> TYPE: DNA
<213> ORGANISM: Clostridium autoethanogenum

<400> SEQUENCE: 12
atgaaggccg tcctgtggta cgacaaaaag gatgtccgcg tggaagaaat cgaggaaccg      60
aaggtgaaag aaaacgccgt gaagatcaaa gtcaagtggt gcggcatctg cggctcggac     120
ctgcatgagt atctcggcgg cccgatcttc atcccggtcg gcaccccccca cccgctgtcg     180 aagagcaccg cgcccgtcgt gctgggccac gagttctcgg gcgaagtggt ggagatcggc     240
agcaaagtga ccaagttcaa ggcgggcgac cgcgtcatcg tggaaccgat cgtcgcctgc     300
```

```
ggcaaatgcc cggcctgcct ggaaggcaag tacaatctgt gcgaggcgct gggcttccac    360
ggcctgtgcg gcagcggcgg cggcttcgcc gagtacacgg tgttcccgga agatttcgtg    420
cacaagatcc ccgacacgat ggattatgaa caggccgcgc tggtggagcc gatggcggtc    480
gcgctgcact ccctgcgggt gggcaacttc accacgggca acaccgccct ggtcctgggc    540
gcgggcccga tcggcctggc caccatccag tgcctcaaag cgtcgggcgc ccggatcgtc    600
atcgtcttcc agcgcaaatc ggtgcggcag gaatacgcca gaagttcgg cgcggacgtg    660 gtcctcgacc cgaatgaggt ggacgtgatc gaggaaatca aaaagctgac cggcggcgtg    720
ggcgtggaca cgagcttcga accaccggc gccaacgtcg gcatcaacac cgcgatccag    780
gcgctgaaat atgagggcac cgccgtcatc acctccgtct gggagaagaa cgccgagatc    840
aatccgaacg acctggtctt caccgaaaag aaggtcgtcg gcaccctcgc gtaccggcac    900
gagttcccgt cgaccatcgc cctgatgaac gacggccgca tcaagaccga tggctatatc    960
accaagcgga tcgccctgga agacatcgtc aaggagggct tcgaaaccct gaccggcccg    1020
gagaagaaaa agcacgtcaa aatcatcgtc acgcccgata aaagcctcct gtga         1074
```

<210> SEQ ID NO 13
<211> LENGTH: 400
<212> TYPE: PRT
<213> ORGANISM: Bacillus subtilis

<400> SEQUENCE: 13

```
Met Lys Ala Leu Leu Trp His Asn Gln Arg Asp Val Arg Val Glu Glu
1               5                   10                  15

Val Pro Glu Pro Ala Val Arg Ser Gly Ala Val Lys Ile Lys Val Lys
            20                  25                  30

Trp Cys Gly Ile Cys Gly Thr Asp Leu His Glu Tyr Leu Ala Gly Pro
        35                  40                  45

Ile Phe Ile Pro Thr Glu Glu His Pro Leu Thr His Val Lys Ala Pro
    50                  55                  60

Val Ile Leu Gly His Glu Phe Ser Gly Glu Val Val Glu Ile Gly Glu
65                  70                  75                  80

Gly Val Thr Asn His Lys Val Gly Asp Arg Val Val Glu Pro Ile
                85                  90                  95

Tyr Ser Cys Gly Lys Cys Glu Ala Cys Lys His Gly His Tyr Asn Val
            100                 105                 110

Cys Glu Gln Leu Val Phe His Gly Leu Gly Gly Asp Gly Gly Gly Phe
        115                 120                 125

Ser Glu Tyr Thr Val Val Pro Ala Asp Met Val His His Ile Pro Asp
    130                 135                 140

Glu Met Thr Tyr Glu Gln Gly Ala Leu Val Glu Pro Ala Ala Val Ala
145                 150                 155                 160

Val His Ala Val Arg Gln Ser Lys Leu Lys Glu Gly Glu Ala Val Ala
                165                 170                 175

Val Phe Gly Cys Gly Pro Ile Gly Leu Leu Val Ile Gln Ala Ala Lys
            180                 185                 190

Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
    210                 215                 220

Glu Gln Asp Val Val Ala Glu Ile Arg Asn Leu Thr Asn Gly Leu Gly
225                 230                 235                 240
```

```
Val Asn Val Ser Phe Glu Val Thr Gly Val Glu Val Leu Arg Gln
                245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
        275                 280                 285

Lys Glu Val Val Gly Ile Leu Gly Tyr Arg His Ile Phe Pro Ser Val
    290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Glu Gly Phe Glu Ala Leu
                325                 330                 335

Val Lys Asp Lys Lys Gln Val Lys Ile Leu Val Ser Pro Lys Gly His
            340                 345                 350

Leu Leu Asp Tyr Gln Leu Asp His Gly Val Leu Thr Phe Gly Glu Ile
        355                 360                 365

His Lys Leu Met Ile Asp Leu Pro Ala Asp Ser Ala Phe Leu Gln Ala
    370                 375                 380

Asn Leu His Pro Asp Asn Leu Asp Ala Ala Ile Arg Ser Val Glu Ser
385                 390                 395                 400

<210> SEQ ID NO 14
<211> LENGTH: 1053
<212> TYPE: DNA
<213> ORGANISM: Bacillus subtilis

<400> SEQUENCE: 14
atgaaagccc tgctgtggca taaccagcgc gacgtgcggg tggaagaggt cccggagccc      60
gccgtccgca gcggcgcggt gaaaatcaaa gtgaaatggt gcggcatctg tggcaccgac     120
ctgcatgaat atctggccgg ccccatcttc atcccgacgg aggaacatcc gctgacgcac     180
gtcaaggccc cggtcatcct cggccatgag ttcagcggcg aggtggtgga gatcggcgaa     240
ggcgtcacca tcacaaaagt cggcgatcgc gtggtcgtcg aaccgatcta ctcgtgcggc     300
aagtgtgagg cgtgcaagca cggccactat aatgtctgcg agcagctggt gttccacggc     360
ctgggcggcg acggcggcgg cttctcggag tacaccgtgg tgccggcgga tatggtccac     420
cacatcccgg atgaaatgac ctacgagcag ggcgccctgg tcgagccggc cgccgtggcg     480
gtgcacgcgg tgcgccagag caaactcaag gagggcgaag ccgtggccgt cttcggctgc     540
ggcccgatcg gcctgctggt catccaggcg gccaaagcgg cgggcgcgac cccgtcatc      600 gcggtcgagc tgtcgaagga acgccaggag ctcgccaagc tggcgggcgc ggattatgtc     660
ctgaaccccg ccaacaggga cgtggtggcg gaaatccgga acctgaccaa cggcctgggc     720
gtcaacgtct ccttcgaggt caccggcgtg gaagtcgtcc tgcggcaggc gatcgaatcg     780
acctcgttcg agggccagac ggtcatcgtg tcggtctggg agaaggacgc caccatcacg     840
cccaataatc tggtcctgaa agagaaggaa gtggtcggca tcctcggcta ccggcatatc     900
ttcccgtccg tcatcaagct gatctcgtcg ggccagatcc aggccgagaa actcatcacc     960
aagaagatca cggtggacca ggtggtcgaa gaaggcttcg aagcgctggt caaggataag    1020
aagcaggtga agatcctcgt gtcgccgaag tga                                1053

<210> SEQ ID NO 15
<211> LENGTH: 350
<212> TYPE: PRT
```

<213> ORGANISM: Paenibacillus polymyxa

<400> SEQUENCE: 15

Met Gln Ala Leu Arg Trp His Gly Ile Lys Asp Leu Arg Leu Glu Asn
1               5                   10                  15

Ile Glu Gln Pro Ala Ala Leu Pro Gly Lys Val Lys Ile Lys Val Glu
            20                  25                  30

Trp Cys Gly Ile Cys Gly Ser Asp Leu His Glu Tyr Val Ala Gly Pro
        35                  40                  45

Ile Phe Ile Pro Glu Asn Ala Gln His Pro Leu Thr Gly Glu Lys Ser
    50                  55                  60

Pro Ile Val Met Gly His Glu Phe Ser Gly Gln Phe Phe Asp Phe Gly
65                  70                  75                  80

Glu Gly Val Thr Lys Ile Gln Val Gly Asp Arg Glu Val Val Glu Pro
                85                  90                  95

Val Phe Ala Cys Gly Glu Cys Asp Ala Cys Arg Gln Gly Lys Tyr Asn
            100                 105                 110

Leu Cys Asp Lys Met Gly Phe Leu Gly Leu Ala Gly Gly Gly Gly Gly
        115                 120                 125

Phe Ser Glu Tyr Val Ala Ala Asp Glu His Met Val His Lys Ile Pro
    130                 135                 140

Glu Ser Val Ser Phe Glu Gln Gly Ala Leu Val Glu Pro Ser Ala Val
145                 150                 155                 160

Ala Leu Tyr Ala Val Arg Gln Ile Gln Leu Lys Val Asp Asp Lys Ala
                165                 170                 175

Val Val Phe Gly Ala Gly Pro Ile Gly Leu Leu Val Ile Glu Ala Leu
            180                 185                 190

Asn Ala Ser Gly Ala Ser Glu Ile Tyr Ala Glu Glu Leu Ser Glu Glu
        195                 200                 205

Arg Thr Ala Lys Ala Glu Asp Leu Gly Ala Ile Val Leu Asp Pro Asn
    210                 215                 220

Thr Tyr Asp Val Val Glu Glu Leu His Lys Arg Thr Asn Gly Gly Val
225                 230                 235                 240

Tyr Val Pro Tyr Glu Val Thr Glu Val Pro Pro Val Leu Thr Gln Ala
                245                 250                 255

Ile Glu Ser Ala Lys Ile Ser Gly Glu Ile Met Ile Val Ile Ile Phe
            260                 265                 270

Glu Lys Glu Ala Leu Ile Lys Pro Asn Asn Ile Val Met Asn Glu Arg
        275                 280                 285

Asn Leu Thr Gly Leu Ile Cys Tyr Asp Asp Val Phe Pro Ala Leu Ile
    290                 295                 300

Ser Leu Met Glu Asn Gly Tyr Phe Pro Ala Asp Lys Leu Val Ile Lys
305                 310                 315                 320

Arg Ile Lys Leu Val Asp Val Ile Glu Ala Ala Phe Glu Ser Leu Leu
                325                 330                 335

Ile Glu Glu Tyr Gln Val Thr Ile Leu Val Ser Pro His Ala
            340                 345                 350

<210> SEQ ID NO 16
<211> LENGTH: 1053
<212> TYPE: DNA
<213> ORGANISM: Paenibacillus polymyxa

<400> SEQUENCE: 16
atgcaggcgc tgcgctggca cggcatcaag gacctgcggc tggagaacat cgagcagccc     60

```
gccgccctcc cgggcaaggt gaagatcaag gtggaatggt gcggcatctg cggcagcgac    120
ctgcatgaat atgtcgccgg cccgatcttc atccccgaaa acgcgcagca tccgctcacg    180
ggcgagaagt cgcccatcgt gatgggccat gagttctccg ccagttcttc gacttcggc     240 gaaggcgtga cgaaaatcca ggtgggcgac cgcgaagtgg tggagccggt cttcgcgtgt    300
ggcgaatgcg atgcgtgccg gcagggcaaa tataacctgt gcgataagat gggcttcctg    360
ggcctggccg gcggcggcgg cggcttctcg gaatatgtcg ccgcggatga gcatatggtg    420
cacaaaatcc ccgagtccgt gtccttcgaa cagggcgccc tggtcgagcc gtccgccgtc    480
gccctctacg cggtccgcca gatccagctg aaggtcgatg acaaggcggt ggtcttcggc    540
gccggcccca tcggcctgct cgtcatcgaa gcgctgaacg ccagcggcgc gagcgaaatc    600
tatgcggaag agctcagcga agagcgcacc gccaaagccg aagacctggg cgccatcgtg    660
ctcgacccca cacgtacga tgtcgtcgag gaactccata agcgcacgaa tggcggcgtc      720 tacgtccccct atgaggtcac ggaagtcccg cccgtgctga cccaggccat cgagtccgcc    780
aagatctccg gcgaaatcat gatcgtcatc atcttcgaaa aggaggccct catcaagccg    840
aacaacatcg tcatgaatga acggaacctg acgggcctga tctgctacga cgatgtgttc    900
ccggccctga tctccctcat ggagaatggc tacttccccg ccgacaagct ggtcatcaaa    960
cggatcaagc tggtggatgt catcgaagcg gccttcgagt cgctcctgat cgaggagtac    1020
caggtgacca tcctcgtgtc gccgcacgcc tga                                  1053
```

<210> SEQ ID NO 17
<211> LENGTH: 387
<212> TYPE: PRT
<213> ORGANISM: Escherichia coli

<400> SEQUENCE: 17

```
Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
                20                  25                  30

Glu Ala Ala Ser Lys Ile Gly Ala Gly Pro Trp Val Val Lys Cys Gln
            35                  40                  45

Val His Ala Gly Gly Arg Gly Lys Ala Gly Gly Val Lys Val Val Asn
        50                  55                  60

Ser Lys Glu Asp Ile Arg Ala Phe Ala Glu Asn Trp Leu Gly Lys Arg
65                  70                  75                  80

Leu Val Thr Tyr Gln Thr Asp Ala Asn Gly Gln Pro Val Asn Gln Ile
                85                  90                  95

Leu Val Glu Ala Ala Thr Asp Ile Ala Lys Glu Leu Tyr Leu Gly Ala
            100                 105                 110

Val Val Asp Arg Ser Ser Arg Arg Val Val Phe Met Ala Ser Thr Glu
        115                 120                 125

Gly Gly Val Glu Ile Glu Lys Val Ala Glu Glu Thr Pro His Leu Ile
    130                 135                 140

His Lys Val Ala Leu Asp Pro Leu Thr Gly Pro Met Pro Tyr Gln Gly
145                 150                 155                 160

Arg Glu Leu Ala Phe Lys Leu Gly Leu Glu Gly Lys Leu Val Gln Gln
                165                 170                 175

Phe Thr Lys Ile Phe Met Gly Leu Ala Thr Ile Phe Leu Glu Arg Asp
            180                 185                 190
```

```
Leu Ala Leu Ile Glu Ile Asn Pro Leu Val Ile Thr Lys Gln Gly Asp
            195                 200                 205

Leu Ile Cys Leu Asp Gly Lys Leu Gly Ala Asp Gly Asn Ala Leu Phe
        210                 215                 220

Arg Gln Pro Asp Leu Arg Glu Met Arg Asp Gln Ser Gln Glu Asp Pro
225                 230                 235                 240

Arg Glu Ala Gln Ala Ala Gln Trp Glu Leu Asn Tyr Val Ala Leu Asp
            245                 250                 255

Gly Asn Ile Gly Cys Met Val Asn Gly Ala Gly Leu Ala Met Gly Thr
        260                 265                 270

Met Asp Ile Val Lys Leu His Gly Gly Glu Pro Ala Asn Phe Leu Asp
        275                 280                 285

Val Gly Gly Gly Ala Thr Lys Glu Arg Val Thr Glu Ala Phe Lys Ile
    290                 295                 300

Ile Leu Ser Asp Asp Lys Val Lys Ala Val Leu Val Asn Ile Phe Gly
305                 310                 315                 320

Gly Ile Val Arg Cys Asp Leu Ile Ala Asp Gly Ile Ile Gly Ala Val
                325                 330                 335

Ala Glu Val Gly Val Asn Val Pro Val Val Val Arg Leu Glu Gly Asn
            340                 345                 350

Asn Ala Glu Leu Gly Ala Lys Lys Leu Ala Asp Ser Gly Leu Asn Ile
        355                 360                 365

Ile Ala Ala Lys Gly Leu Asp Ala Ala Gln Gln Val Val Ala Ala Val
        370                 375                 380

Glu Gly Lys
385

<210> SEQ ID NO 18
<211> LENGTH: 2036
<212> TYPE: DNA
<213> ORGANISM: Escherichia coli

<400> SEQUENCE: 18
atgaacttac atgaatatca ggcaaaacaa cttttttgccc gctatggctt accagcaccg      60
gtgggttatg cctgtactac tccgcgcgaa gcagaagaag ccgcttcaaa atcggtgcc      120 ggtccgtggg tagtgaaatg tcaggttcac gctggtggcc gcggtaaagc gggcggtgtg     180
aaagttgtaa acagcaaaga agacatccgt gcttttgcag aaaactggct gggcaagcgt     240
ctggtaacgt atcaaacaga tgccaatggc caaccggtta accagattct ggttgaagca     300
gcgaccgata tcgctaaaga gctgtatctc ggtgccgttt tgaccgtag ttcccgtcgt      360 gtggtcttta tggcctccac cgaaggcggc gtggaaatcg aaaaagtggc ggaagaaact     420
ccgcacctga tccataaagt tgcgcttgat ccgctgactg cccgatgcc gtatcaggga     480 cgcgagctgg cgttcaaact gggtctggaa ggtaaactgg ttcagcagtt caccaaaatc     540
ttcatgggcc tggcgaccat tttcctggag cgcgacctgg cgttgatcga atcaacccg     600 ctggtcatca ccaaacaggg cgatctgatt tgcctcgacg gcaaactggg cgctgacggc     660
aacgcactgt tccgccagcc tgatctgcgc gaaatgcgtg accagtcgca ggaagatccg     720
cgtgaagcac aggctgcaca gtgggaactg aactacgttg cgctggacgg taacatcggt     780
tgtatggtta acggcgcagg tctggcgatg gtacgatgg acatcgttaa actgcacggc     840
ggcgaaccgg ctaacttcct tgacgttggc ggcggcgcaa ccaaagaacg tgtaaccgaa     900
gcgttcaaaa tcatcctctc tgacgacaaa gtgaaagccg ttctggttaa catcttcggc     960
```

```
ggtatcgttc gttgcgacct gatcgctgac ggtatcatcg gcgcggtagc agaagtgggt   1020
gttaacgtac cggtcgtggt acgtctggaa ggtaacaacg ccgaactcgg cgcgaagaaa   1080
ctggctgaca gcggcctgaa tattattgca gcaaaaggtc tgacggatgc agctcagcag   1140
gttgttgccg cagtggaggg gaaataatgt ccatttttaat cgataaaaac accaaggtta   1200
tctgccaggg ctttaccggt agccagggga ctttccactc agaacaggcc attgcatacg   1260
gcactaaaat ggttggcggc gtaaccccag gtaaaggcgg caccacccac ctcggcctgc   1320
cggtgttcaa caccgtgcgt gaagccgttg ctgccactgg cgctaccgct tctgttatct   1380
acgtaccagc accgttctgc aaagactcca ttctggaagc catcgacgca ggcatcaaac   1440
tgattatcac catcactgaa ggcatcccga cgctggatat gctgaccgtg aaagtgaagc   1500
tggatgaagc aggcgttcgt atgatcggcc cgaactgccc aggcgttatc actccgggtg   1560
aatgcaaaat cggtatccag cctggtcaca ttcacaaacc gggtaaagtg ggtatcgttt   1620
cccgttccgg tacactgacc tatgaagcgt taaacagac cacgattac ggtttcggtc   1680 agtcgacctg tgtcggtatc ggcggtgacc cgatcccggg ctctaacttt atcgacattc   1740
tcgaaatgtt cgaaaaagat ccgcagaccg aagcgatcgt gatgatcggt gagatcggcg   1800
gtagcgctga agaagaagca gctgcgtaca tcaaagagca cgttaccaag ccagttgtgg   1860
gttacatcgc tggtgtgact gcgccgaaag gcaaacgtat gggccacgcg ggtgccatca   1920
ttgccggtgg gaagggact gcggatgaga aattcgctgc tctggaagcc gcaggcgtga   1980
aaaccgttcg cagcctggcg gatatcggtg aagcactgaa aactgttctg aaataa        2036
```

<210> SEQ ID NO 19
<211> LENGTH: 451
<212> TYPE: PRT
<213> ORGANISM: Porphyromonas gingivalis

<400> SEQUENCE: 19

```
Met Glu Leu Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
        35                  40                  45

Val Asp Glu Thr Gly Met Gly Val Tyr Glu His Lys Val Ala Lys Asn
    50                  55                  60

Gln Gly Lys Ser Lys Gly Val Trp Tyr Asn Leu His Asn Lys Lys Ser
65                  70                  75                  80

Ile Gly Ile Leu Asn Ile Asp Glu Arg Thr Gly Met Ile Glu Ile Ala
                85                  90                  95

Lys Pro Ile Gly Val Val Gly Ala Val Thr Pro Thr Thr Asn Pro Ile
            100                 105                 110

Val Thr Pro Met Ser Asn Ile Ile Phe Ala Leu Lys Thr Cys Asn Ala
        115                 120                 125

Ile Ile Ile Ala Pro His Pro Arg Ser Lys Lys Cys Ser Ala His Ala
    130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
                165                 170                 175

Met Gly Ala Val Asp Val Val Ala Thr Gly Gly Met Gly Met Val
            180                 185                 190
```

```
Lys Ser Ala Val Ser Ser Gly Lys Pro Ser Phe Gly Val Gly Ala Gly
            195                 200                 205

Asn Val Gln Val Ile Val Asp Ser Asn Ile Asp Phe Glu Ala Ala Ala
        210                 215                 220

Glu Lys Ile Ile Thr Gly Arg Ala Phe Asp Asn Gly Ile Ile Cys Ser
225                 230                 235                 240

Gly Glu Gln Ser Ile Ile Tyr Asn Glu Ala Asp Lys Glu Ala Val Phe
                245                 250                 255

Thr Ala Phe Arg Asn His Gly Ala Tyr Phe Cys Asp Glu Ala Glu Gly
            260                 265                 270

Asp Arg Ala Arg Ala Ala Ile Phe Glu Asn Gly Ala Ile Ala Lys Asp
        275                 280                 285

Val Val Gly Gln Ser Val Ala Phe Ile Ala Lys Lys Ala Asn Ile Asn
        290                 295                 300

Ile Pro Glu Gly Thr Arg Ile Leu Val Val Glu Ala Arg Gly Val Gly
305                 310                 315                 320

Ala Glu Asp Val Ile Cys Lys Glu Lys Met Cys Pro Val Met Cys Ala
                325                 330                 335

Leu Ser Tyr Lys His Phe Glu Glu Gly Val Glu Ile Ala Arg Thr Asn
            340                 345                 350

Leu Ala Asn Glu Gly Asn Gly His Thr Cys Ala Ile His Ser Asn Asn
        355                 360                 365

Gln Ala His Ile Ile Leu Ala Gly Ser Glu Leu Thr Val Ser Arg Ile
    370                 375                 380

Val Val Asn Ala Pro Ser Ala Thr Thr Ala Gly Gly His Ile Gln Asn
385                 390                 395                 400

Gly Leu Ala Val Thr Asn Thr Leu Gly Cys Gly Ser Trp Gly Asn Asn
                405                 410                 415

Ser Ile Ser Glu Asn Phe Thr Tyr Lys His Leu Leu Asn Ile Ser Arg
            420                 425                 430

Ile Ala Pro Leu Asn Ser Ser Ile His Ile Pro Asp Asp Lys Glu Ile
        435                 440                 445

Trp Glu Leu
    450

<210> SEQ ID NO 20
<211> LENGTH: 1356
<212> TYPE: DNA
<213> ORGANISM: Porphyromonas gingivalis

<400> SEQUENCE: 20
atggaaatca aagaaatggt gagccttgca cgcaaggctc agaaggagta tcaagctacc    60
cataaccaag aagcagttga caacatttgc cgagctgcag caaaagttat ttatgaaaat   120
gcagctattc tggctcgcga agcagtagac gaaaccggca tgggcgttta cgaacacaaa   180
gtggccaaga atcaaggcaa atccaaaggt gtttggtaca acctccacaa taaaaaatcg   240
attggtatcc tcaatataga cgagcgtacc ggtatgatcg agattgcaaa gcctatcgga   300
gttgtaggag ccgtaacgcc gacgaccaac ccgatcgtta ctccgatgag caatatcatc   360
tttgctctta agacctgcaa tgccatcatt attgcccccc accccagatc caaaaaatgc   420
tctgcacacg cagttcgtct gatcaaagaa gctatcgctc cgttcaacgt accggaaggt   480
atggttcaga tcatcgaaga acccagcatc gagaagacgc aggaactcat gggcgccgta   540
gacgtagtag ttgctacggg tggtatgggc atggtgaagt ctgcatattc ttcaggaaag   600
```

```
ccttctttcg gtgttggagc cggtaacgtt caggtgatcg tggatagcaa catcgatttc    660
gaagctgctg cagaaaaaat catcaccggt cgtgctttcg acaacggtat catctgctca    720
ggcgaacaga gcatcatcta caacgaggct gacaaggaag cagttttcac agcattccgc    780
aaccacggtg catatttctg tgacgaagcc gaaggagatc gggctcgtgc agctatcttc    840
gaaaatggag ccatcgcgaa agatgtagta ggtcagagcg ttgccttcat tgccaagaaa    900
gcaaacatca atatccccga gggtacccgt attctcgttg ttgaagctcg cggcgtagga    960
gcagaagacg ttatctgtaa ggaaaagatg tgtcccgtaa tgtgcgccct cagctacaag   1020
cacttcgaaa aggtgtagaa atcgcacgt acgaacctcg ccaacgaagg taacggccac   1080
acctgtgcta tccactccaa caatcaggca cacatcatcc tcgcaggatc agagctgacg   1140
gtatctcgta tcgtagtgaa tgctccgagt gccactacag caggcggtca catccaaaac   1200
ggtcttgccg taaccaatac gctcggatgc ggatcatggg gtaataactc tatctccgag   1260
aacttcactt acaagcacct cctcaacatt tcacgcatcg caccgttgaa ttcaagcatt   1320
cacatccccg atgacaaaga aatctgggaa ctctaa                              1356
```

<210> SEQ ID NO 21
<211> LENGTH: 371
<212> TYPE: PRT
<213> ORGANISM: Porphyromonas gingivalis

<400> SEQUENCE: 21

```
Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
                20                  25                  30

Thr Asn Glu Phe Ile Tyr Glu Pro Tyr Met Lys Ala Cys Gln Leu Pro
            35                  40                  45

Cys His Phe Val Met Gln Glu Lys Tyr Gly Gln Gly Glu Pro Ser Asp
        50                  55                  60

Glu Met Met Asn Asn Ile Leu Ala Asp Ile Arg Asn Ile Gln Phe Asp
65                  70                  75                  80

Arg Val Ile Gly Ile Gly Gly Gly Thr Val Ile Asp Ile Ser Lys Leu
                85                  90                  95

Phe Val Leu Lys Gly Leu Asn Asp Val Leu Asp Ala Phe Asp Arg Lys
                100                 105                 110

Ile Pro Leu Ile Lys Glu Lys Glu Leu Ile Ile Val Pro Thr Thr Cys
            115                 120                 125

Gly Thr Gly Ser Glu Val Thr Asn Ile Ser Ile Ala Glu Ile Lys Ser
        130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
                180                 185                 190

Ser Pro Lys Ala Ser Pro Tyr Ser Arg Leu Phe Ser Glu Ala Ala Trp
            195                 200                 205

Asp Ile Ile Leu Glu Val Phe Lys Lys Ile Ala Glu His Gly Pro Glu
        210                 215                 220

Tyr Arg Phe Glu Lys Leu Gly Glu Met Ile Met Ala Ser Asn Tyr Ala
225                 230                 235                 240
```

Gly Ile Ala Phe Gly Asn Ala Gly Val Gly Val His Ala Leu Ser
                245                 250                 255

Tyr Pro Leu Gly Gly Asn Tyr His Val Pro His Gly Glu Ala Asn Tyr
            260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
    290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
            340                 345                 350

Asn Asn Tyr Val Glu Leu Thr Val Asp Glu Ile Glu Gly Ile Tyr Arg
        355                 360                 365

Arg Leu Tyr
    370

<210> SEQ ID NO 22
<211> LENGTH: 1114
<212> TYPE: DNA
<213> ORGANISM: Porphyromonas gingivalis

<400> SEQUENCE: 22

```
atgcaacttt tcaaactcaa gagtgtaaca catcactttg acactttgc agaatttgcc     60 aaggaattct gtcttggaga cgcgacttg gtaattacca acgagttcat ctatgaaccg    120
tatatgaagg catgccagct ccctgccat tttgttatgc aggagamtat gggcaaggcg    180
agccttctga cgaaatgatg aataacatct tggcagacat ccgtaatatc cagttcgacc    240
gcgtaatcgg tatcggagga ggtacggtta ttgacatctc taaactttc gttctgaaag    300 gattaaatga tgtactcgat gcattcgacc gcaaaatacc tcttatcaaa gagaaagaac    360
tgatcattgt gcccacaaca tgcggaacgg gtagcgaggt gacgaacatt tctatcgcag    420
aaatcaaaag ccgtcacacc aaaatgggat tggctgacga tgccattgtt gcagaccatg    480
ccatcatcat acctgaactt ctgaagagct tgcctttcca cttctacgca tgcagtgcaa    540
tcgatgctct tatccatgcc atcgagtcat acgtatctcc taaagccagt ccatattctc    600
gtctgttcag tgaggcggct tgggacatta tcctggaagt attcaagaaa atcgccgaac    660
acggccctga ataccgcttc gaaaagctgg gagaaatgat catggccagc mctatgccgg    720
tatagccttc ggaaatgcag gagtaggagc cgtccacgca ctatcctacc cgttgggagg    780
caactatcac gtgccgcatg gagaagcaaa ctatcagttc ttcacagagg tattcaaagt    840
ataccaaaag aagaatcctt tcggctatat agtcgaactc aactggaagc tctccaagat    900
actgaactgc cagcccgaat acgtatatcc gaagctggat gaacttctcg gatgccttct    960
taccaagaaa cctttgcacg aatacggcat gaaggacgaa gaggtaagag ctttgcgga   1020 atcagtgctt aagacacagc aaagattgct cgccaacaac tacgtagagc ttactgtaga   1080
tgagatcgaa ggtatctaca gaagactcta ctaa                               1114
```

<210> SEQ ID NO 23
<211> LENGTH: 431
<212> TYPE: PRT
<213> ORGANISM: Porphyromonas gingivalis -continued

<400> SEQUENCE: 23

```
Met Lys Asp Val Leu Ala Glu Tyr Ala Ser Arg Ile Val Ser Ala Glu
1               5                   10                  15

Glu Ala Val Lys His Ile Lys Asn Gly Glu Arg Val Ala Leu Ser His
            20                  25                  30

Ala Ala Gly Val Pro Gln Ser Cys Val Asp Ala Leu Val Gln Gln Ala
        35                  40                  45

Asp Leu Phe Gln Asn Val Glu Ile Tyr His Met Leu Cys Leu Gly Glu
    50                  55                  60

Gly Lys Tyr Met Ala Pro Glu Met Ala Pro His Phe Arg His Ile Thr
65                  70                  75                  80

Asn Phe Val Gly Gly Asn Ser Arg Lys Ala Val Glu Glu Asn Arg Ala
                85                  90                  95

Asp Phe Ile Pro Val Phe Phe Tyr Glu Val Pro Ser Met Ile Arg Lys
            100                 105                 110

Asp Ile Leu His Ile Asp Val Ala Ile Val Gln Leu Ser Met Pro Asp
        115                 120                 125

Glu Asn Gly Tyr Cys Ser Phe Gly Val Ser Cys Asp Tyr Ser Lys Pro
    130                 135                 140

Ala Ala Glu Ser Ala His Leu Val Ile Gly Glu Ile Asn Arg Gln Met
145                 150                 155                 160

Pro Tyr Val His Gly Asp Asn Leu Ile His Ile Ser Lys Leu Asp Tyr
                165                 170                 175

Ile Val Met Ala Asp Tyr Pro Ile Tyr Ser Leu Ala Lys Pro Lys Ile
            180                 185                 190

Gly Glu Val Glu Glu Ala Ile Gly Arg Asn Cys Ala Glu Leu Ile Glu
        195                 200                 205

Asp Gly Ala Thr Leu Gln Leu Gly Ile Gly Ala Ile Pro Asp Ala Ala
    210                 215                 220

Leu Leu Phe Leu Lys Asp Lys Asp Leu Gly Ile His Thr Glu Met
225                 230                 235                 240

Phe Ser Asp Gly Val Val Glu Leu Val Arg Ser Gly Val Ile Thr Gly
                245                 250                 255

Lys Lys Lys Thr Leu His Pro Gly Lys Met Val Ala Thr Phe Leu Met
            260                 265                 270

Gly Ser Glu Asp Val Tyr His Phe Ile Asp Lys Asn Pro Asp Val Glu
        275                 280                 285

Leu Tyr Pro Val Asp Tyr Val Asn Asp Pro Arg Val Ile Ala Gln Asn
    290                 295                 300

Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
                325                 330                 335

Gly Gln Val Asp Tyr Val Arg Gly Ala Ala Trp Ser Lys Asn Gly Lys
            340                 345                 350

Ser Ile Met Ala Ile Pro Ser Thr Ala Lys Asn Gly Thr Ala Ser Arg
        355                 360                 365

Ile Val Pro Ile Ile Ala Glu Gly Ala Ala Val Thr Thr Leu Arg Asn
    370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
```

```
                405                 410                 415
Asp Phe Arg Glu Glu Leu Thr Lys His Leu Arg Lys Arg Phe Gly
            420                 425                 430

<210> SEQ ID NO 24
<211> LENGTH: 1296
<212> TYPE: DNA
<213> ORGANISM: Porphyromonas gingivalis

<400> SEQUENCE: 24
atgaaagacg tattagcgga atatgcctcc cgaattgttt cggccgaaga agccgtaaaa      60
catatcaaaa atggagaacg ggtagctttg tcacatgctg ccggagttcc tcagagttgt     120
gttgatgcac tggtacaaca ggccgacctt ttccagaatg tcgaaattta tcacatgctt     180
tgtctcggcg aaggaaaata tatggcacct gaaatggccc ctcacttccg cacataaacc     240
aattttgtag gtggtaattc tcgtaaagca gttgaggaaa atagagccga cttcattccg     300
gtattctttt atgaagtgcc atcaatgatt cgcaaagaca tccttcacat agatgtcgcc     360
atcgttcagc tttcaatgcc tgatgagaat ggttactgta gttttggagt atcttgcgat     420
tatagcaaac cggcagcaga aagcgctcat ttagttatag ggaaatcaa ccgtcaaatg      480 ccatatgtac atggcgacaa cttgattcac atatcgaagt tggattacat cgtgatggca     540
gactacccta tctattctct tgcaaagccc aaaatcggag aagtagaaga agctatcggg     600
cgtaattgtg ccgagcttat tgaagatggt gccacactcc aactcggtat cggcgcgatt     660
cctgatgcag ccctgttatt cctcaaggac aaaaaagatc tggggatcca taccgagatg     720
ttctccgatg gtgttgtcga attagttcgc agtggagtaa ttacaggaaa gaaaaagaca     780 cttcacccg gaaagatggt cgcaaccttc ttaatgggaa gcgaagacgt atatcatttc      840
atcgacaaaa atcccgatgt agaactttat ccggtagatt acgtcaatga tccgcgagta     900
atcgctcaaa atgataatat ggtcagcatc aatagctgta tcgaaatcga tcttatggga     960
caagtcgtgt ccgaatgtat aggaagcaag caattcagcg gaaccggcgg tcaagtagat    1020
tatgttcgtg gagcagcatg gtctaaaaac ggcaaaagca tcatggcaat tccctcaaca    1080
gccaaaaacg gtactgcatc tcgaattgta cctataattg cagagggagc tgctgtaaca    1140
accctccgca acgaagtcga ttacgttgta ccgaatacg gtatagcaca actcaaagga     1200
aagagtttgc gccagcgagc agaagctctt attgccatag cccacccgga tttcagagag    1260
gaactaacga aacatctccg caaacgtttc ggataa                              1296

<210> SEQ ID NO 25
<211> LENGTH: 468
<212> TYPE: PRT
<213> ORGANISM: Clostridium beijerinckii

<400> SEQUENCE: 25

Met Asn Lys Asp Thr Leu Ile Pro Thr Thr Lys Asp Leu Lys Leu Lys
1               5                   10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Asn Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Val
65                  70                  75                  80
```

Leu Ala Thr Met Ile Leu Glu Thr His Met Gly Arg Tyr Glu Asp
                85                  90                  95

Lys Ile Leu Lys His Glu Leu Val Ala Lys Tyr Thr Pro Gly Thr Glu
                100                 105                 110

Asp Leu Thr Thr Thr Ala Trp Ser Gly Asp Asn Gly Leu Thr Val Val
                115                 120                 125

Glu Met Ser Pro Tyr Gly Val Ile Gly Ala Ile Thr Pro Ser Thr Asn
            130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Ile Glu Met Ile Asn Lys Ala Ile Ile Ser Cys Gly Gly Pro
                180                 185                 190

Glu Asn Leu Val Thr Thr Ile Lys Asn Pro Thr Met Glu Ser Leu Asp
                195                 200                 205

Ala Ile Ile Lys His Pro Leu Ile Lys Leu Leu Cys Gly Thr Gly Gly
            210                 215                 220

Pro Gly Met Val Lys Thr Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
                260                 265                 270

Leu Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Ser Asp Glu Ile Asp Val Glu Ser Pro Ser Asn Ile Lys
            340                 345                 350

Cys Ile Val Cys Glu Val Asn Ala Asn His Pro Phe Val Met Thr Glu
            355                 360                 365

Leu Met Met Pro Ile Leu Pro Ile Val Arg Val Lys Asp Ile Asp Glu
370                 375                 380

Ala Val Lys Tyr Thr Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 26
<211> LENGTH: 2696

<212> TYPE: DNA
<213> ORGANISM: Clostridium beijerinckii

<400> SEQUENCE: 26
tctagaggtt catcatcatc cataggaaat aatacacgta tttcataatc atcgctatta 60
atatattcaa ttaatttttc aggagtcttt actctctccc aaagaattaa ctcagttgat 120
ctggattcac caatttcaat aatctagcgg tatttgaagg cctactaaat tctctttctg 180
ttgataatat caatatcttt gcttttgtct ctattttagg cacaatatcg cagatacaat 240
ttattattgg caacccacat ttattgcagc tctcatataa cttagtaatt tgcttaactt 300
taaattcaga ctccatttta cctccattat tagttggtta gtgtgtcata tcttcttgct 360
attactaact gattataaca tatgtattca atatatcact cctagttttc aaagcactgg 420
caatacgaat tacaaattaa tttctggatt tatgtcagta tttcattaat aaaaggtcgg 480
acttttaaga tacttgtttt agctattgat catatttatt aaagactatg catttaatgt 540
ataattataa tgaatattat caataatatt tattttatat tacaatctta cagtctttat 600
tctaaatttc actcaaatac caaacgagct ttattcataa acaatatata acaataattc 660
caaaataata cgatatttta tctgtaacag ccatataaaa aaaatatcat atagtcttgt 720
catttgataa cgttttgtct tccttatatt tactttttcg gtttaatagg ttgattctgt 780
aaattttagt gataacatat atttgatgac attaaaaatt taatatttca tataaatttt 840
taatgtctat taatttttaa atcacaagga ggaatagttc atgaataaag acacactaat 900
acctacaact aaagatttaa aattaaaaac aaatgttgaa aacattaatt taaagaacta 960
caaggataat tcttcatgtt tcggagtatt cgaaaatgtt gaaaatgcta taaacagcgc 1020
tgtacacgcg caaaagatat tatcccttca ttatacaaaa gaacaaagag aaaaaatcat 1080
aactgagata agaaaggccg cattagaaaa taaagaggtt ttagctacca tgattctgga 1140
agaaacacat atgggaaggt atgaagataa aatattaaag catgaattag tagctaaata 1200
tactcctggt acagaagatt taactactac tgcttggtca ggtgataatg gtcttacagt 1260
tgtagaaatg tctccatatg gcgttatagg tgcaataact ccttctacga atccaactga 1320
aactgtaata tgtaatagca tcggcatgat agctgctgga aatgctgtag tatttaacgg 1380
acacccaggc gctaaaaaat gtgttgcttt tgctattgaa atgataaata aagcaattat 1440
ttcatgtggc ggtcctgaga atttagtaac aactataaaa aatccaacta tggaatccct 1500
agatgcaatt attaagcatc ctttaataaa acttctttgc ggaactggag gtccaggaat 1560
ggtaaaaacc ctcttaaatt ctggcaagaa agctataggt gctggtgctg gaaatccacc 1620
agttattgta gatgataccg ctgatataga aaaggctggt aagagtatca ttgaaggctg 1680
ttcttttgat aataatttac cttgtattgc agaaaaagaa gtatttgttt ttgagaatgt 1740
tgcagatgat ttaatatcta acatgctaaa aaataatgct gtaattataa atgaagatca 1800
agtatcaaaa ttaatagatt tagtattaca aaaaaataat gaaactcaag aatactttat 1860
aaacaaaaaa tgggtaggaa aagatgcaaa attattctca gatgaaatag atgttgagtc 1920
tccttcaaat attaaatgca tagtctgcga agtaaatgca aatcatccat ttgtcatgac 1980
agaactcatg atgccaatat taccaattgt aagagttaaa gatatagatg aagctgttaa 2040
atatacaaag atagcagaac aaaatagaaa acatagtgcc tatatttatt ctaaaaatat 2100
agacaaccta aatagatttg aaagagaaat tgatactact atttttgtaa agaatgctaa 2160
atcttttgct ggtgttggtt atgaagctga aggatttaca actttcacta ttgctggatc 2220

```
tactggtgaa ggcataacct ctgcaagaaa ttttacaaga caaagaagat gtgtacttgc   2280
cggctaactt cttgctaaat ttatacattt attcacataa ctttaatatg caatgttccc   2340
acaaaatatt aaaactatt tagaagggag atattaaatg aataaattag taaaattaac   2400
agatttaaag cgcattttca agatggtat gacaattatg gttggggtt ttttagattg     2460 tggaactcct gaaaatatta tagatatgct agttgattta aatataaaaa atctgactat   2520
tataagcaat gatacagctt ttcctaataa aggaatagga aaacttattg taaatggtca   2580
agtttctaaa gtaattgctt cacatattgg aactaatcct gaaactggga aaaaatgag    2640 ctctggtgaa cttaaagttg agctttctcc acaaggaaca ctgatcgaaa gaattc       2696
```

```
<210> SEQ ID NO 27
<211> LENGTH: 348
<212> TYPE: PRT
<213> ORGANISM: Saccharomyces cerevisiae

<400> SEQUENCE: 27

Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Val Lys Ser
        275                 280                 285

Ile Ser Ile Val Gly Ser Tyr Val Gly Asn Arg Ala Asp Thr Arg Glu
```

```
            290                 295                 300
Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
            340                 345

<210> SEQ ID NO 28
<211> LENGTH: 3627
<212> TYPE: DNA
<213> ORGANISM: Saccharomyces cerevisiae

<400> SEQUENCE: 28
gatccttcaa tatgcgcaca tacgctgtta tgttcaaggt cccttcgttt aagaacgaaa      60
gcggtcttcc ttttgaggga tgtttcaagt tgttcaaatc tatcaaattt gcaaatcccc     120
agtctgtatc tagagcgttg aatcggtgat gcgatttgtt aattaaattg atggtgtcac     180
cattaccagg tctagatata ccaatggcaa actgagcaca caataccag tccggatcaa      240 ctggcaccat ctctcccgta gtctcatcta attttcttc cggatgaggt tccagatata      300
ccgcaacacc tttattatgg tttccctgag ggataatag aatgtcccat tcgaaatcac      360
caattctaaa cctgggcgaa ttgtatttcg ggtttgttaa ctcgttccag tcaggaatgt     420
tccacgtgaa gctatcttcc agcaaagtct ccacttcttc atcaaattgt ggagaatact     480
cccaatgctc ttatctatgg gacttccggg aaacacagta ccgatacttc ccaattcgtc     540
ttcagagctc attgtttgtt tgaagagact aatcaaagaa tcgttttctc aaaaaaatta     600
atatcttaac tgatagtttg atcaaagggg caaaacgtag gggcaaacaa acggaaaaat     660
cgtttctcaa attttctgat gccaagaact ctaaccagtc ttatctaaaa attgccttat     720
gatccgtctc tccggttaca gcctgtgtaa ctgattaatc ctgcctttct aatcaccatt     780
ctaatgtttt aattaaggga ttttgtcttc attaacggct ttcgctcata aaaatgttat     840
gacgttttgc ccgcaggcgg gaaaccatcc acttcacgag actgatctcc tctgccggaa     900
caccgggcat ctccaactta aagttggag aaataagaga atttcagatt gagagaatga      960
aaaaaaaaaa aaaaaaaag gcagaggaga gcatagaaat ggggttcact ttttggtaaa    1020
gctatagcat gcctatcaca tataaataga gtgccagtag cgactttttt cacactcgaa    1080
atactcttac tactgctctc ttgttgtttt tatcacttct tgtttcttct tggtaaatag    1140
aatatcaagc tacaaaaagc atacaatcaa ctatcaacta ttaactatat cgtaatacac    1200
aatgtctatt ccagaaactc aaaaagccat tatcttctac gaatccaacg gcaagttgga    1260
gcataaggat atcccagttc caaagccaaa gcccaacgaa ttgttaatca acgtcaagta    1320
ctctggtgtc tgccacaccg atttgcacgc ttggcatggt gactggccat tgccaactaa    1380
gttaccatta gttggtggtc acgaaggtgc cggtgtcgtt gtcggcatgg gtgaaaacgt    1440
taagggctgg aagatcggtg actacgccgg tatcaaatgg ttgaacggtt cttgtatggc    1500
ctgtgaatac tgtgaattgg gtaacgaatc caactgtcct cacgctgact tgtcaggtta    1560
cacccacgac ggttctttcc aagaatacgc taccgctgac gctgttcaag ccgctcacat    1620
tcctcaaggt actgacttgg ctgaagtcgc gccaatcttg tgtgctggta tcaccgtata    1680
caaggctttg aagtctgcca acttgagagc aggccactgg gcggccattt ctggtgctgc    1740
tggtggtcta ggttctttgg ctgttcaata tgctaaggcg atgggttaca gagtcttagg    1800
```

```
tattgatggt ggtccaggaa aggaagaatt gtttacctcg ctcggtggtg aagtattcat    1860
cgacttcacc aaagagaagg acattgttag cgcagtcgtt aaggctacca acggcggtgc    1920
ccacggtatc atcaatgttt ccgtttccga agccgctatc gaagcttcta ccagatactg    1980
tagggcgaac ggtactgttg tcttggttgg tttgccagcc ggtgcaaagt gctcctctga    2040
tgtcttcaac cacgttgtca agtctatctc cattgtcggc tcttacgtgg ggaacagagc    2100
tgataccaga gaagccttag atttctttgc cagaggtcta gtcaagtctc aataaaggt     2160
agttggctta tccagtttac cagaaattta cgaaagatg gagaagggcc aaattgctgg     2220
tagatacgtt gttgacactt ctaaataagc ggatctccta tgccttcacg atttatagtt    2280
tccattatca agtatgccta tattagtata tagcatcttt agatgacagt gttcgaagtt    2340
tcacgaataa agataatat tctactttt gctcccagcg cgtttgctag cacgagtgaa      2400
caccatccct cgcctgtgag ttgtacccat tcctctaaac tgtagacatg gtagcttcag    2460
cagtgttcgt tatgtacggc atcctccaac aaacagtcgg ttatagtttg tcctgctcct    2520
ctgaatcgtc tccctcgata tttctcattt tccttcgcat gccagcattg aaatgatcga    2580
agttcaatga tgaaacggta attcttctgt catttactca tctcatctca tcaagttata    2640
taattctata cggatgtaat tttcacttt tcgtcttgac gtccacccta taatttcaat     2700
tattgaaccc tcacaaatga tgcactgcaa tgtacacacc ctcatatagt ttctcagggc    2760
ttgatcaggg ttccgtagat gggaattga gaagtataag ggagataacg gtaatgttat     2820
attgagaaaa tgaaagatga actcagtatt gacaggatct aaaaccaaaa tatagcgggc    2880
ctatacagga agtagtattt gtaaaagtaa accatgttgc tagtacgaac gacttccctg    2940
aatgtgtcaa ggatgccagt gccatgcctc gccagaggaa taggcatcct caagggcaaa    3000
tatagactag cgaacctgat gaatgcccaa cctcagtgag acatgtgtcg agcgagatcc    3060
agcaaaagga tcagcaggca ggagagtcaa acaccgccac cgatactggt gttattcaca    3120
aatcagatga agaaactctg atatatttcg ataatgttta cgctagaacc acctcggttt    3180
ggaatccaac actgtggtac aatctcctgc taagaaacca gtcacgggat gcagtgaggg    3240
agaaaataag gaatttagcc agtccaccca ataaccccat ttatggactg gagttgaagt    3300
ctaccattcc agtgaaaagg gatggtggtg tatttgccac atttgtcgtt ccacccaagt    3360
atacaaaagc tcaggtaaat tctctaatcc aacagaatac agccagagaa tcctctaaaa    3420
acttactctc gtacttcact cgagcttctg ccttcccagt aaagggttcg ccttggattg    3480
aggatttaag aagactacca agtaccacta tagtcatcaa gttccaaggg cccgccttaa    3540
cagaagaaga aatatactct ttattcagaa gatatgggac aattattgat atttcccctc    3600
ccactgctgc taacaacaat gtggcaa                                        3627
```

<210> SEQ ID NO 29
<211> LENGTH: 553
<212> TYPE: PRT
<213> ORGANISM: Methylococcus capsulatus

<400> SEQUENCE: 29

```
Met Arg Glu Thr Ile Pro Pro Arg Thr Gly Ala Asp Leu Leu Val Asp
1               5                   10                  15

Ser Leu Gln Ala Leu Gly Val Glu Tyr Val Phe Gly Val Pro Gly Gly
                20                  25                  30

Ala Ile Leu Pro Ile Leu Asn Val Leu Ala Asp Arg Gly Pro Arg Phe
            35                  40                  45
```

```
Ile Val Cys Arg Asp Glu Thr Gly Ala Ala Phe Met Ala Gln Ser Trp
 50                  55                  60
Gly Arg Ile Thr Gly Arg Pro Gly Val Val Leu Thr Thr Ser Gly Pro
 65                  70                  75                  80
Gly Leu Ile Asn Ala Val Cys Gly Val Ala Thr Ala Thr Glu Asp Arg
                 85                  90                  95
Asp Pro Leu Val Val Ile Thr Gly Gln Val Pro Arg Ala Val Gln Phe
                100                 105                 110
Lys Gln Ser His Met Asn Leu Asp Ser Val Gly Leu Phe Ala Pro Ile
            115                 120                 125
Thr Lys Trp Ser Val Glu Val Glu Pro Asn Thr Val Ser Glu Ile
        130                 135                 140
Leu Val Asn Ala Phe Arg Thr Ala Gln Thr Pro Cys Ala Gly Ala Val
145                 150                 155                 160
His Val Ser Val Pro Asn Asp Met Leu Thr Ala Pro Val Thr Ala Gln
                165                 170                 175
Ala Leu Ala Pro Ala Glu Pro Ala Val Trp Gly Thr Ala Pro Ala Ala
                180                 185                 190
Val Val Glu Arg Ala Ala Ser Leu Leu Asn Asp Ala Lys Ala Pro Ala
            195                 200                 205
Ile Leu Leu Gly Leu Arg Ala Ser Thr Pro Gly Ala Ala Ala Val
        210                 215                 220
Arg Arg Phe Leu Glu Arg His Pro Leu Pro Val Ala Met Thr Phe Glu
225                 230                 235                 240
Ala Ala Gly Thr Leu Ser Arg Asp Leu Val Asp Gln Phe Val Gly Arg
                245                 250                 255
Val Gly Tyr Val Leu Asn Gln Pro Gly Asp Glu Val Leu Arg Gln Ala
                260                 265                 270
Asp Leu Val Leu Thr Ile Gly Tyr Asp Pro Ile Glu Tyr Glu Pro Ser
            275                 280                 285
Ala Trp Ile Ser Pro Gln Ser Gln Ala Ile His Leu Asp Ala Leu Pro
        290                 295                 300
Ala Ala Val Asp Arg Ala Tyr His Pro Ala Ala Glu Leu Val Gly Asp
305                 310                 315                 320
Ile Ala Ala Asn Leu Ala Ala Leu Gly Ser Leu Leu Arg Ile Glu Asp
                325                 330                 335
Arg Ala Gly Arg Pro Ala Val Ala Ala Arg Arg Leu Leu Glu
                340                 345                 350
Glu Gln Ala Arg Gly Ala Ala Leu Thr Gly Met Pro Ile His Pro Leu
            355                 360                 365
Arg Phe Ile His Asp Leu Arg Ala Thr Leu Asp Asp Glu Ala Thr Val
        370                 375                 380
Thr Cys Asp Val Gly Ala His Glu Ile Trp Met Ala Arg Tyr Phe Phe
385                 390                 395                 400
Cys Tyr Ala Pro Arg His Leu Leu Phe Ser Met Gly His Gln Thr Met
                405                 410                 415
Gly Val Ala Leu Pro Trp Ala Ile Gly Ala Ala Leu Ala Arg Pro Gly
                420                 425                 430
Lys Lys Val Val Ser Val Ser Gly Asp Gly Ser Phe Leu Met Thr Cys
            435                 440                 445
Met Glu Leu Glu Thr Ala Val Arg Leu Lys Leu Pro Ile Val His Ile
        450                 455                 460
Val Trp Lys Asp Gly Gly Tyr Asn Leu Ile His Ser Leu Gln Met Arg
```

```
                465                 470                 475                 480
Asp Tyr Gly Arg Ser Phe Gly Ala Glu Phe Gly Pro Thr Asp Phe Val
                    485                 490                 495

Lys Leu Ala Glu Ala Phe Gly Ala Ile Gly Tyr Arg Ile Glu Ser Ala
                500                 505                 510

Asp Gly Ile Val Pro Val Leu Asn Arg Ala Leu Ala Ala Asp Ala Pro
            515                 520                 525

Val Leu Ile Glu Val Pro Ile Asp Tyr Ser Asp Asn Val His Leu Val
530                 535                 540

Glu Ala Ile Asp Ala Ser Ala Gln His
545                 550

<210> SEQ ID NO 30
<211> LENGTH: 1662
<212> TYPE: DNA
<213> ORGANISM: Methylococcus capsulatus

<400> SEQUENCE: 30
atgcgtgaaa cgatacctcc ccgcaccggc gccgacctgc tggtcgactc cctccaggcg    60
ctgggcgtcg aatacgtctt cggcgtgccc ggcggcgcga tactcccgat cctgaacgtg   120
ctggccgacc gcggcccgcg cttcatcgtt tgccgggacg aaaccggcgc cgccttcatg   180
gcccagtcct ggggccggat caccggccgg cccggcgtgg tgctcaccac ctccggcccc   240
ggcctcatca acgccgtctg tggcgtcgct accgccacag aggaccgcga cccgctggtc   300
gtcatcaccg ccaggtgcc gcgggccgtg caattcaagc agagccacat gaacctggat   360
tcggtcggcc tgttcgcgcc gatcaccaaa tggagcgtcg aggtcgagga accgaatact   420
gtatcggaaa tcctggtcaa cgccttccgc accgcgcaga cgccgtgcgc cggagccgtc   480
cacgtctcgg taccgaacga catgctcacc gcgccggtca ccgcgcaggc cctggcgccg   540
gccgaacccg ccgtctgggg aacggccccg gccgccgtcg tcgaacgcgc ggcgtccctg   600
ctgaacgatg ccaaagcccc ggccatcctg ctcggattgc gggccagcac acctggagcg   660
gcggcggcgg tccggcgttt cctggagcgg catccgctgc cggtggcgat gaccttcgaa   720
gccgccggca ccctgtcccg cgatctggtc gatcagttcg tcggccgggt cggctacgtg   780
ctcaaccagc cggcgacga ggtgctcgcg caagccgatc tggtactcac gatcggctac   840
gacccgatcg aatacgaacc ttccgcctgg atctcaccgc agtcgcaggc gatccacctg   900
gatgccctgc cgccgccgt cgaccgggcc taccaccctg ccgccgaact ggtcggcgac   960
atcgccgcca acctggccgc gctcggcagc ctgctccgaa tcgaggatcg agccggacgc  1020
cccgccgtcg ccgcggcgcg gcggcgtctg ctggaggagc aagcccgcgg cgcagcactg  1080
accggtatgc cgatccaccc cttgcgcttc attcacgacc ttcgggccac gctggacgac  1140
gaggcgacgg tgacctgcga cgtcggcgcc cacgagatct ggatggcccg ctacttcttc  1200
tgctacgccc cgcgtcacct gctgttcagc atggccacc agaccatggg cgtcgccctg  1260
ccctgggcca tcggcgcggc cctggcccgg cccggcaaga agtggtttc ggtatccggc  1320
gacggctcct tcctcatgac ctgcatggaa ctggaaaccg cggtgcgcct caaactgccg  1380
atcgtgcaca tcgtctggaa agacggcggc tacaacctga tccacagcct gcagatgcgc  1440
gactatgggc gcagcttcgg cgccgagttc ggccccaccg acttcgtcaa actggcggag  1500
gccttcggcg cgatcgggta ccggatcgag tccgcggacg gatcgtcccc tgtgctgaac  1560
cgggcgctcg cggccgacgc gccggtgctg atcgaagtgc ccatcgacta cagcgacaac  1620
```
gtccacctgg tcgaggcgat cgacgcctcg gcgcagcact ga                1662

<210> SEQ ID NO 31
<211> LENGTH: 338
<212> TYPE: PRT
<213> ORGANISM: Methylococcus capsulatus

<400> SEQUENCE: 31

Met Gln Ile Tyr Tyr Asp Lys Asp Ala Asp Leu Ser Ile Ile Gln Gly
1               5                   10                  15

Lys Lys Val Ala Ile Ile Gly Tyr Gly Ser Gln Gly His Ala His Ala
            20                  25                  30

Asn Asn Leu Lys Asp Ser Gly Val Gln Val Val Gly Leu Arg Pro
        35                  40                  45

Gly Ser Ala Ser Ala Lys Lys Ala Glu Asn Ala Gly Leu Ala Val Ala
    50                  55                  60

Ser Val Glu Asp Ala Val Lys Gln Ala Asp Val Ile Met Ile Leu Ala
65                  70                  75                  80

Pro Asp Glu His Gln Ala Arg Leu Tyr Asn Glu Gln Ile Ala Pro Asn
                85                  90                  95

Ile Lys Gln Gly Ala Ala Leu Ala Phe Ala His Gly Phe Asn Ile His
            100                 105                 110

Phe Glu Gln Ile Thr Pro Arg Ala Asp Leu Asp Val Ile Met Ile Ala
        115                 120                 125

Pro Lys Gly Pro Gly His Leu Val Arg Ser Thr Tyr Thr Gln Gly Gly
    130                 135                 140

Gly Val Pro Ser Leu Ile Ala Val Tyr Gln Asn Ala Ser Gly Arg Ala
145                 150                 155                 160

Lys Glu Leu Ala Leu Ser Tyr Ala Ser Ala Asn Gly Gly Gly Arg Ala
                165                 170                 175

Gly Ile Ile Glu Thr Thr Phe Arg Glu Glu Thr Glu Thr Asp Leu Phe
            180                 185                 190

Gly Glu Gln Ala Val Leu Cys Gly Gly Ala Thr Ala Leu Val Gln Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Arg Tyr Ser Ile Ser Asn Thr Ala Glu Tyr
                245                 250                 255

Gly Asp Leu Thr Arg Gly Pro Arg Ile Val Thr Glu Gln Thr Lys Gln
            260                 265                 270

Glu Met Lys Lys Ile Leu Arg Glu Ile Gln Thr Gly Glu Phe Ala Arg
        275                 280                 285

Glu Phe Ile Leu Glu Asn Gln Ala Gly Ala Ala Thr Leu Lys Ala Lys
    290                 295                 300

Arg Arg Leu Gly Arg Glu His Leu Ile Glu Ser Val Gly Ala Arg Leu
305                 310                 315                 320

Arg Asp Met Met Pro Trp Ile Lys Ala Asn Arg Ile Val Asp Thr Ser
                325                 330                 335

Lys Asn

<210> SEQ ID NO 32
<211> LENGTH: 1017
<212> TYPE: DNA

<213> ORGANISM: Methylococcus capsulatus

<400> SEQUENCE: 32

```
atgcagattt actacgacaa agacgccgac ctttccatca tccagggaaa gaaggttgcc      60
atcatcggct acggctcgca gggccacgcc cacgccaaca acctcaagga ttccggagtg     120
caggtcgtgg tggggctgcg tccgggttcg gcttccgcca agaaggccga gaacgccggc     180
ctcgcggtcg cctcggtcga ggatgcggtc aaacaggcgg acgtcatcat gatcctggcg     240
ccggacgagc atcaggcccg cctctacaat gaacagatcg cgccgaacat caagcagggc     300
gccgccctcg ccttcgccca cggcttcaac atccacttcg agcagatcac cccgcgcgcc     360
gacctcgacg tgatcatgat cgcgcccaag ggtcccggcc atctggtacg ttccacctac     420
acccagggcg gcggcgtgcc ctcgctgatc gccgtgtacc agaatgccag cgggcgcgcc     480
aaggaactcg cgctgtccta tgcttcggcc aatggcggcg gtcgggctgg tatcatcgag     540
accaccttcc gcgaagagac cgaaaccgat ctgttcggcg aacaggccgt cctgtgtggc     600
ggcgccaccg cactggtgca ggcgggtttc gagacgctgg tcgaagccgg ttatgcgccc     660
gagatggcct atttcgagtg tctgcacgaa ctcaagctga tcgtcgacct gatgtacgaa     720
ggcggcatcg ccaacatgcg ttattcgatc tccaatacgg cagagtacgg cgacctgacc     780
cgtggtccgc gcatcgtcac cgagcagacc aagcaggaaa tgaagaaaat cctgcgcgag     840
atccagaccg cgaattcgc ccgtgagttc attttggaaa accaggccgg agccgccacc     900
ctgaaagcga aacgccgtct cggccgagag catctcatcg agagcgtggg cgccaggctg     960
cgcgacatga tgccgtggat caaggccaac cgcattgtgg acacgagcaa gaactga      1017
```

<210> SEQ ID NO 33
<211> LENGTH: 562
<212> TYPE: PRT
<213> ORGANISM: Methylococcus capsulatus

<400> SEQUENCE: 33

```
Met Thr Asp Lys His Pro Arg Pro His Ser Gln Val Val Asp Gly
1               5                  10                  15

Met Glu Arg Ala Pro Ser Arg Ala Met Leu His Ala Val Gly Phe Ala
            20                  25                  30

Asp Ala Asp Phe Ala Lys Pro Gln Ile Gly Ile Ala Ser Thr Trp Ala
        35                  40                  45

Met Val Thr Pro Cys Asn Met His Ile Asn Lys Leu Ala Glu Asp Ala
    50                  55                  60

Ala Arg Gly Val Asp Gly Gly Gly Lys Ala Val Ile Phe Asn Thr
65                  70                  75                  80

Ile Thr Ile Ser Asp Gly Ile Ser Met Gly Thr Glu Gly Met Lys Tyr
                85                  90                  95

Ser Leu Val Ser Arg Glu Val Ile Ala Asp Ser Ile Glu Thr Val Val
            100                 105                 110

Ala Cys Gln Gly Tyr Asp Gly Val Ala Ile Gly Gly Cys Asp Lys
        115                 120                 125

Asn Met Pro Gly Cys Leu Ile Ala Leu Ala Arg Leu Asn Arg Pro Ala
    130                 135                 140

Val Phe Val Tyr Gly Gly Thr Ile Leu Pro Gly Cys His Asp Gly Lys
145                 150                 155                 160

Lys Leu Asp Val Val Ser Val Phe Glu Ala Val Gly Ala Arg Ala Asn
                165                 170                 175
```

-continued

His Arg Ile Asp Asp Ala Glu Leu His Ala Ile Glu Ser Asn Ala Ile
                180                 185                 190

Pro Gly Pro Gly Ser Cys Gly Gly Met Tyr Thr Ala Asn Thr Met Ala
            195                 200                 205

Ser Ala Ile Glu Ala Leu Gly Met Ser Leu Pro Gly Ser Ser Ala Gln
        210                 215                 220

Val Ala Ile Ser Arg Ala Lys Glu Leu Asp Cys Glu Arg Ala Gly Ala
225                 230                 235                 240

Gln Val Leu Lys Leu Leu Asp Leu Gly Leu Lys Pro Arg Asp Ile Met
                245                 250                 255

Thr Lys Lys Ala Phe Glu Asn Ala Ile Thr Val Val Ile Ala Leu Gly
            260                 265                 270

Gly Ser Thr Asn Ala Val Leu His Leu Leu Ala Met Ala Asn Ala Cys
        275                 280                 285

Gly Val Asp Leu Lys Leu Asp Asp Phe Thr Arg Ile Gly Arg Lys Val
        290                 295                 300

Pro Met Leu Ala Asp Leu Lys Pro Ser Gly Arg Tyr Ser Met Ala Glu
305                 310                 315                 320

Leu Val Glu Ile Gly Gly Ile Gln Pro Leu Met Lys Thr Leu Leu Asp
                325                 330                 335

Ala Gly Leu Leu His Gly Asp Cys Met Thr Val Thr Gly Lys Thr Leu
            340                 345                 350

Glu Glu Asn Leu Ala Asp Ala Pro Asp Tyr Pro Ala Gly Gln Asp Met
        355                 360                 365

Ile Arg Ser Leu Asp Asn Pro Ile Lys Lys Asp Ser His Leu Val Ile
        370                 375                 380

Leu Lys Gly Asn Leu Ala Pro Glu Gly Ala Val Ala Lys Ile Thr Gly
385                 390                 395                 400

Lys Glu Gly Leu Ser Phe Thr Gly Thr Ala Arg Val Phe Asp Cys Glu
                405                 410                 415

Glu Ala Ala Leu Thr Ala Ile Leu Asp Gly Thr Ile Val Lys Gly Asp
            420                 425                 430

Val Ile Val Ile Arg Tyr Glu Gly Pro Lys Gly Gly Pro Gly Met Arg
        435                 440                 445

Glu Met Leu Ser Pro Thr Ser Ala Val Met Gly Lys Gly Leu Gly Lys
        450                 455                 460

Glu Val Ala Leu Ile Thr Asp Gly Arg Phe Ser Gly Gly Thr His Gly
465                 470                 475                 480

Phe Val Val Gly His Ile Thr Pro Glu Ala Tyr Thr Gly Gly Pro Leu
                485                 490                 495

Ala Ile Val Arg Asp Gly Asp Thr Ile Thr Ile Asp Ala Glu Thr Arg
            500                 505                 510

Glu Leu Ser Leu His Val Thr Asp Asp Glu Ile Gly Arg Arg Leu Ala
        515                 520                 525

Gln Trp Thr Gln Pro Ala Pro Arg Tyr Thr Lys Gly Val Leu Ala Lys
        530                 535                 540

Tyr Ala Arg Leu Val Ser Pro Ala Ser Glu Gly Ala Val Thr Asp Asp
545                 550                 555                 560

Gly Leu

<210> SEQ ID NO 34
<211> LENGTH: 1689
<212> TYPE: DNA
<213> ORGANISM: Methylococcus capsulatus

<400> SEQUENCE: 34

```
atgaccgaca agcaccccg tccccattcg tcccaggtcg tcgacggcat ggagcgcgcc      60
ccgagccgcg cgatgctgca cgccgtcggc ttcgccgatg ccgacttcgc caaaccgcag    120
atcggcatcg cttccacctg ggcgatggtg acgccgtgca acatgcacat caacaagctc    180
gccgaggacg cagcacgcgg cgtcgacggc ggcggcggca aggcagtgat cttcaacacc    240
atcaccattt ccgacggcat ctcgatgggc accgaaggaa tgaaatactc cctcgtgtcg    300
cgggaagtca tcgccgactc gatcgaaacc gtggtggcct gtcagggtta tgacggcgtg    360
gtcgccatcg gcggctgcga caagaacatg cccggctgcc tgatcgccct cgcccgcctc    420
aaccgtccgg cggtgttcgt ctatggcggc accatcctgc cgggctgcca cgacggcaag    480
aagctggacg tggtgtcggt gttcgaagcg gtcggcgccc cgccaaccac ccgcatcgac    540
gatgccgaac tgcacgccat cgaatccaat gccatccccg gtccgggctc ctgcggtggc    600
atgtataccg ccaacaccat ggcctccgcc atcgaggcat tagggatgag cctgccgggc    660
agttcggccc aggtggccat ttcccgcgcc aaggaactgg attgcgagcg ggccggcgcg    720
caggtcctca gctcctgga cctggggctc aaaccccgcg acatcatgac caagaaggcg    780
ttcgagaacg ccatcacggt ggtgatcgcc ctgggcggct ccaccaacgc cgtgctgcac    840
ctcctggcca tggccaacgc ctgcggcgtc gacctgaagc tcgacgattt cacccgcatc    900
gggcgcaaag tgccgatgct ggcggatctg aaacccagcg gcagatactc catggccgaa    960
ctggtggaaa tcgccggcat ccagccgctg atgaagacct tgctggacgc gggactcctg   1020
cacggcgact gcatgaccgt aaccggcaag accctggaag aaaacctggc cgacgcgccc   1080
gactacccgg ccggacaaga catgatccgg tcgctggaca cccccatcaa aaaggacagc   1140
catctggtga tcctcaaggg caacctggcg ccggaaggcg cggtcgccaa gatcaccggc   1200
aaggaaggac tgagcttcac cggcaccgcc cgcgtattcg actgcgagga agcggcgctc   1260
acggccatcc tcgacggcac gatcgtgaaa ggcgacgtca tcgtcatccg ctatgaaggc   1320
cccaagggcg ccccggcat gcgcgagatg ctctcgccga cctcggcggt catgggcaag   1380
ggattgggca aggaggtcgc cctcatcacc gacgccgct tttccggcgg cacccacggc   1440
ttcgtggtcg ccacatcac gccggaagcc tacaccggcg gccccctggc gatcgtccgg   1500
gacggcgata ccatcaccat cgacgccgag acccgcgaat tgagcctgca cgtcaccgac   1560
gatgaaatcg ccggcgcct ggcgcagtgg actcaaccgg cgccgcgcta caccaagggc   1620
gtgctggcca aatacgccag gttggtgagc ccggcctcgg aaggcgccgt caccgacgac   1680
ggcctctga                                                           1689
```

<210> SEQ ID NO 35
<211> LENGTH: 549
<212> TYPE: PRT
<213> ORGANISM: Methylococcus capsulatus

<400> SEQUENCE: 35

```
Met Gly Thr Val Glu Pro Gly Ala Ile Gly Gln His Leu Leu Ala Cys
1               5                   10                  15

Leu Tyr Gln Ala Gly Val Gly His Ile Phe Gly Val Pro Gly Asp Tyr
            20                  25                  30

Val Leu Gly Phe Tyr Asp Leu Met Ala Lys Gly Pro Val Arg His Ile
        35                  40                  45

Gly Thr Thr Arg Glu Asp Thr Ala Ala Phe Ala Ala Asp Gly Tyr Ala
```

```
                50                  55                  60
        Arg Cys Arg Gly Met Gly Ala Leu Ala Val Thr Tyr Gly Val Gly Ala
        65                  70                  75                  80

Leu Asn Thr Val Asn Ala Val Ala Gly Ala Tyr Ala Glu Ser Ser Pro
                            85                  90                  95

Val Val Val Ile Ser Gly Ala Pro Gly Val Arg Glu Gln Arg Glu Asp
                        100                 105                 110

Pro Leu Ile His His Arg Phe Gly Pro Phe Arg Phe Gln Arg Glu Ile
                    115                 120                 125

Phe Glu Arg Ile Thr Cys Ala Ala Val Val Leu Asp Asp Pro Val Ile
                130                 135                 140

Ala Phe Arg Gln Val Glu Arg Ala Leu Ala Ala Arg Gln His Cys
        145                 150                 155                 160

Lys Pro Val Tyr Ile Glu Ile Pro Ala Asp Arg Val Met Ala Pro Gly
                        165                 170                 175

Tyr Pro Ile Pro Gln Glu Thr Pro Glu Thr Pro Ser Ser Asp Asp Ser
                    180                 185                 190

Ala Leu Ala Glu Ala Val Ala Glu Ala Ala Glu Leu Leu Gly Arg Ala
                195                 200                 205

Val Ser Pro Val Ile Leu Ala Gly Val Glu Leu His Arg Arg Gly Leu
        210                 215                 220

Gln Asp Ala Leu Val Gly Leu Val Glu Gln Ala Arg Leu Pro Val Ala
        225                 230                 235                 240

Ala Thr Leu Thr Gly Lys Ser Val Phe Ala Glu Arg His Pro Ala Tyr
                        245                 250                 255

Leu Gly Val Tyr Glu Gly Ala Met Ser Thr Glu Asn Ala Arg Tyr Met
                    260                 265                 270

Val Glu Gln Ser Asp Leu Leu Met Leu Gly Val Thr Leu Asn Asp
                275                 280                 285

Val Asp Thr Gly Ile Tyr Thr Ala Arg Leu Asp Pro Gln Arg Ile Val
        290                 295                 300

Arg Ala Ala Gln Asn Glu Val Val Ile Arg His His Arg Tyr Pro Arg
        305                 310                 315                 320

Val Leu Leu Ala Asp Phe Val Thr Ala Leu Ala Arg Ser Val Lys Ala
                        325                 330                 335

Arg Gly Glu Ala Phe Pro Met Pro Ala Gly Pro Glu Pro Trp Asp Phe
                    340                 345                 350

Pro Ala Pro Asp Arg Pro Met Thr Ile Ala Arg Leu Val Glu Arg Leu
                355                 360                 365

Asp Arg Ala Leu Thr Ser Asp Met Ile Val Val Cys Asp Val Gly Asp
        370                 375                 380

Cys Leu Phe Ala Ala Thr Asp Leu Arg Val His Glu Arg Ser Glu Phe
        385                 390                 395                 400

Leu Ala Ser Ala Phe Tyr Thr Ser Met Gly Phe Ala Val Pro Ala Ala
                        405                 410                 415

Leu Gly Ala Gln Ile Ala Arg Pro Asp His Arg Ala Leu Ile Leu Val
                    420                 425                 430

Gly Asp Gly Ala Phe Gln Met Thr Gly Thr Glu Leu Ser Thr His Ala
                435                 440                 445

Arg Leu Gly Leu Ala Pro Ile Val Val Leu Asp Asn Arg Gly Tyr
        450                 455                 460

Ser Thr Glu Arg Phe Ile Leu Asp Gly Ala Phe Asn Asp Ile Ala Asp
        465                 470                 475                 480
```

```
Trp Arg Phe His Arg Leu Gly Glu Val Phe Gly Pro Leu Gln Gly Tyr
            485                 490                 495

Asp Ala Pro Asp Glu Ala Ala Phe Glu Asn Ala Leu Ser Glu Ala Leu
        500                 505                 510

Val Asn Arg Asn Met Pro Ser Leu Ile Asn Val Arg Leu Ser Pro Gly
        515                 520                 525

Asp Ala Ser Ile Ala Met Lys Arg Leu Ala Gly His Leu Gln Cys Arg
        530                 535                 540

Val Lys Gly Glu Gly
545

<210> SEQ ID NO 36
<211> LENGTH: 1650
<212> TYPE: DNA
<213> ORGANISM: Methylococcus capsulatus

<400> SEQUENCE: 36
atgggcacgg ttgagcctgg cgctatcgga caacatctgc tcgcctgcct ttaccaggcg      60
ggcgtcgggc acatcttcgg cgttcccggc gattacgtgc tgggcttcta tgatctgatg     120
gccaaaggtc ccgtccggca tatcgggacc acgcgggagg acaccgccgc cttcgccgcc     180
gacggctatg cccgctgccg gggcatgggc gcgctggcgg tgacttacgg ggtcggtgcg     240
ctcaacaccg tcaacgccgt cgccggcgcc tatgcggaat cctcgccggt ggtggtcatc     300
agcggtgcgc gggggtgcg cgagcaaagg gaagacccgt tgatccacca ccgcttcggg     360
ccgttccggt tccagcgcga gatattcgaa cggatcacct gcgccgccgt ggtgctggac     420
gatccggtga tcgccttccg gcaggtggag cgtgcgctcg cggccgcccg tcagcactgc     480
aagccggtgt acatcgagat tcccgccgac cgggtgatgg cgccgggata tccgattcca     540
caggaaaccc cggaaacgcc ttccagcgac gattcggccc tggcggaggc ggtcgccgag     600
gccgcggagc tcctgggccg tgcggtgtcg ccggtgatcc ttgcaggcgt cgagttgcac     660
cggcgagggc tccaggacgc cctcgtcggc ctcgtcgagc aggcgcgcct gccggtggcg     720
gcgaccttga ccggcaagtc ggtgttcgcc gagcgccatc ccgcctatct ggggtgtac     780 gagggtgcga tgagcacgga aaacgcgcgc tacatggtcg agcagtccga cctcctgctg     840
atgctcgggg tcacgctgaa cgatgtcgac acgggcatct acacgcgcg tctcgatccg     900 cagcgcatcg tccgcgcagc ccagaacgag gtcgtgattc gccatcaccg ctatccccgc     960
gtcctgctcg cggacttcgt cacggccctg gcgcggtccg tcaaggcccg ggcgaggcg    1020 tttccgatgc cggcggggcc ggaaccgtgg gactttcccg cgccggaccg gccgatgacg    1080
atcgcccggc tggtggagcg gctcgaccgc gcgctgacct ccgacatgat cgtagtgtgc    1140
gacgtcggcg actgcctgtt cgcagccacc gacctgcgcg tgcacgagcg cagcgaattc    1200
ctggcgtccg ccttctatac ctcgatgggg ttcgcggtgc ccgccgccct cggggcccag    1260
atcgcccgtc cggaccaccg ggcgctgatc ctggtcggcg acggtgcctt ccagatgacc    1320
ggaacggagc tgtcgaccca tgcccgtctc ggcctggcgc ccatcgtggt ggtgctcgac    1380
aatcgcggtt acagcaccga gcgcttcatc ctcgacggag ccttcaacga catcgccgac    1440
tggcgcttcc accggctggg cgaggtgttc ggccccctac agggctacga cgcgcccgac    1500
gaagcggcgt tcgaaaacgc gctcagcgaa gcgctggtca accgaaacat gccgagcctc    1560
atcaacgtcc gtctttcccc cggcgatgcc tcgatagcca tgaagcgtct cgccgggcat    1620
ctgcagtgcc gggtcaaggg cgagggctga                                      1650
```

<210> SEQ ID NO 37
<211> LENGTH: 590
<212> TYPE: PRT
<213> ORGANISM: Methylosinus trichosporium

<400> SEQUENCE: 37

```
Met Ala Arg Lys Met Thr Gly Ala Glu Met Val Val Glu Ala Leu Lys
1               5                   10                  15

Asp Gln Gly Val Glu Ile Ile Phe Gly Tyr Pro Gly Gly Ala Val Leu
            20                  25                  30

Pro Ile Tyr Asp Ala Leu Phe His Gln Glu Lys Val Gln His Ile Leu
        35                  40                  45

Val Arg His Glu Gln Gly Ala Ala His Ala Ala Glu Gly Tyr Ala Arg
50                  55                  60

Ser Ser Gly Lys Val Gly Val Leu Leu Val Thr Ser Gly Pro Gly Ala
65                  70                  75                  80

Thr Asn Thr Ile Thr Gly Leu Thr Asp Ala Leu Met Asp Ser Ile Pro
                85                  90                  95

Val Val Cys Ile Thr Gly Gln Val Pro Thr His Leu Ile Gly Ser Asp
            100                 105                 110

Ala Phe Gln Glu Cys Asp Thr Val Gly Ile Thr Arg His Cys Thr Lys
        115                 120                 125

His Asn Tyr Leu Val Lys Ser Val Asp Asp Leu Pro Arg Ile Leu His
130                 135                 140

Glu Ala Phe Tyr Val Ala Ser Ser Gly Arg Pro Gly Pro Val Val Ile
145                 150                 155                 160

Asp Ile Pro Lys Asp Val Gln Phe Ala Ser Gly Thr Tyr Thr Gly Pro
                165                 170                 175

Arg Asn Val His His Lys Thr Tyr Gln Pro Lys Leu Glu Gly Asp Thr
            180                 185                 190

Glu Ser Ile Arg Arg Ala Val Lys Met Met Ala Ala Lys Arg Pro
        195                 200                 205

Ile Phe Tyr Thr Gly Gly Gly Val Ile Asn Ser Gly Pro Ala Ala Ser
210                 215                 220

Thr Leu Leu Arg Glu Leu Val Ser Leu Thr Gly Phe Pro Ile Thr Ser
225                 230                 235                 240

Thr Leu Met Gly Leu Gly Ala Tyr Pro Gly Ser Gly Pro Asn Trp Leu
                245                 250                 255

Gly Met Leu Gly Met His Gly Thr Phe Glu Ala Asn Asn Ala Met His
            260                 265                 270

Asp Cys Asp Leu Met Ile Ala Val Gly Ala Arg Phe Asp Asp Arg Ile
        275                 280                 285

Thr Gly Arg Leu Asp Ala Phe Ser Pro Gly Ser Lys Lys Ile His Ile
290                 295                 300

Asp Ile Asp Arg Ser Ser Ile Asn Lys Asn Val Lys Ile Asp Leu Pro
305                 310                 315                 320

Ile Val Gly Asp Cys Gly His Val Leu Glu Ser Leu Val Arg Val Trp
                325                 330                 335

Arg Ser Glu Ala Met His Ala Glu Lys Gln Pro Leu Asp Gly Trp Trp
            340                 345                 350

Lys Thr Ile Asp His Trp Arg Glu Arg Lys Ser Leu Ala Phe Arg Asn
        355                 360                 365

Ser Asp Lys Val Ile Lys Pro Gln Tyr Ala Val Gln Arg Leu Tyr Ala
```

```
              370             375             380
Leu Thr Lys Asp Arg Asp Pro Tyr Ile Thr Thr Glu Val Gly Gln His
385                 390                 395                 400

Gln Met Trp Ala Ala Gln His Tyr His Phe Asp Glu Pro Asn Arg Trp
                405                 410                 415

Met Thr Ser Gly Gly Leu Gly Thr Met Gly Tyr Gly Leu Pro Ala Ala
                420                 425                 430

Ile Gly Ala Gln Leu Ala His Pro Lys Ser Leu Val Val Asp Ile Ala
                435                 440                 445

Gly Glu Ala Ser Ile Leu Met Asn Ile Gln Glu Met Ser Thr Ala Ile
                450                 455                 460

Gln Tyr Arg Leu Pro Val Lys Val Phe Ile Leu Asn Asn Glu Tyr Met
465                 470                 475                 480

Gly Met Val Arg Gln Trp Gln Glu Leu Leu His Gly Gly Arg Tyr Ser
                485                 490                 495

His Ser Tyr Ser Glu Ala Leu Pro Asp Phe Val Lys Leu Ala Glu Ala
                500                 505                 510

Phe Gly Gly Lys Gly Ile Arg Cys Ser Asp Pro Ala Glu Leu Asp Ser
                515                 520                 525

Ala Ile Leu Glu Met Ile Asp Tyr Asp Gly Pro Val Ile Phe Asp Cys
530                 535                 540

Leu Val Glu Lys Asn Glu Asn Cys Phe Pro Met Ile Pro Ser Gly Lys
545                 550                 555                 560

Ala His Asn Asp Met Leu Leu Ala Asp Leu Gly Asp Asp Ala Gly Val
                565                 570                 575

Glu Leu Gly Ser Ile Ile Asp Glu Lys Gly Lys Met Leu Val
                580                 585                 590
```

<210> SEQ ID NO 38
<211> LENGTH: 1773
<212> TYPE: DNA
<213> ORGANISM: Methylosinus trichosporium

<400> SEQUENCE: 38

```
atggccagaa aaatgaccgg agcggaaatg gtcgtcgaag ccctgaagga tcagggcgtc    60
gagattatct tcggctatcc cggcggcgcc gtgcttccga tctatgacgc gctcttccac   120
caggagaagg tgcagcacat tctcgtgcgc acgagcagg gcgccgccca tgcggccgag   180
ggctatgcgc gctcctccgg caaggtcggc gtgctgctgg tcacctccgg acccggcgcc   240
accaacacca tcaccggcct caccgatgcg ctgatggact ccattcccgt ggtctgcatc   300
accggccagg tgccgacgca tctcatcggc tcggacgcct tcaagagtg cgatacggtc   360
ggcatcaccc gtcactgcac caagcataat tatctggtga agagcgtcga cgatctgccg   420
cgcattctgc acgaggcctt ctatgtcgcc tcgagcgggc ggccgggccc tgtggtcatc   480
gacatcccca aggatgtgca attcgccagc ggaacctata ccggcccgcg caacgtccat   540
cacaagacct atcagcccaa gctcgagggc gacacggagt ctatccgccg cgccgtgaag   600
atgatggccg ccgccaagcg gccgatcttc tacaccggcg gcggcgtcat caattccggt   660
cccgcggcct cgacgctgct gcgcgagctg gtgtcgctga ccggctttcc gatcacctcg   720
accttgatgg gctcggcgc ctatccgggc tccggcccca attggctcgg catgctcggc   780
atgcacggca ccttcgaggc caataatgcg atgcatgatt gcgatctgat gatcgccgtc   840
ggcgcgcgtt tcgacgatcg catcaccgga cggctcgacg ccttctcgcc cggctcgaag   900
```

```
aagatccaca tcgatatcga tcgctcctcg atcaataaga atgtgaagat cgatctgccg    960
atcgtcggcg actgcggcca tgtgctggag agtctggtgc gcgtctggcg ctccgaggcg   1020
atgcacgccg agaagcagcc gctcgacggc tggtggaaga cgatcgacca ttggcgcgag   1080
cgcaagtcgc tcgccttccg caattcggac aaggtgatca agccgcaata cgccgtgcag   1140
cggctctatg cgctcaccaa ggatcgcgat ccctacatca cgacggaagt cggccagcat   1200
cagatgtggg ccgcgcagca ttatcatttc gacgagccca atcgctggat gacttccggc   1260
gggctcggca ccatgggcta tggtctgccg gcggcgatcg gcgcgcagct cgcgcatccg   1320
aaatcgctgg tcgtcgacat cgccggcgag gcctcgatcc tgatgaacat tcaggagatg   1380
tcgacggcga tccaatatcg gctgccggtg aaggtgttca tcctcaacaa tgaatatatg   1440
ggcatggtgc gccagtggca ggagctgctg cacggcgggc gctactcgca ctcctattcg   1500
gaggcgctgc ccgatttcgt gaagctcgcc gaagccttcg ggggcaaggg catccgctgc   1560
tcggacccgg cggagctcga tagcgcgatt ctcgagatga tcgactatga cgggccggtg   1620
atcttcgatt gtctcgtcga gaaaaacgag aattgcttcc cgatgatccc gtcgggcaag   1680
gcgcataacg acatgctgct cgccgatctc ggcgacgacg ccggcgtcga gctcggctcg   1740
atcatcgacg agaagggcaa gatgctggtg tga                               1773
```

<210> SEQ ID NO 39
<211> LENGTH: 548
<212> TYPE: PRT
<213> ORGANISM: Lactococcus lactis

<400> SEQUENCE: 39

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Pro Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Asn Thr
    210                 215                 220
```

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
            245                 250                 255

Tyr Asn Gly Lys Leu Ser Glu Pro Asn Leu Lys Glu Phe Val Glu Ser
        260                 265                 270

Ala Asp Phe Ile Leu Met Leu Gly Val Lys Leu Thr Asp Ser Ser Thr
    275                 280                 285

Gly Ala Phe Thr His His Leu Asn Glu Asn Lys Met Ile Ser Leu Asn
290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Gly Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Gly Phe Val Ser Val Met Lys Glu Ala
            500                 505                 510

Gln Ala Asp Pro Asn Arg Met Tyr Trp Ile Glu Leu Val Leu Ala Lys
        515                 520                 525

Glu Asp Ala Pro Lys Val Leu Lys Lys Met Gly Lys Leu Phe Ala Glu
530                 535                 540

Gln Asn Lys Ser
545

<210> SEQ ID NO 40
<211> LENGTH: 1647
<212> TYPE: DNA
<213> ORGANISM: Lactococcus lactis

<400> SEQUENCE: 40
atgtacaccg tgggcgacta tctgctggac cggctgcatg aactgggcat cgaggaaatc      60
ttcggcgtcc ccggcgacta taacctgcag ttcctggacc agatcatcag ccgcaaggac     120
atgaagtggg tgggcaacgc caacgagctg aacgcctcgt acatggcgga cggctatgcc     180
cggaccaaga aggccgcggc cttcctgacc accttcggcg tcggcgaact gagcgccgtg     240

```
aacggcctgg cgggctcgta cgccgagaac ctgccggtcg tggaaatcgt cggctccccc    300
accagcaagg tgcagaacga gggcaagttc gtccaccata ccctggccga cggcgacttc    360
aagcacttca tgaagatgca tgaaccggtg accgcggccc gcaccctgct gaccgccgag    420
aacgcgaccg tcgaaatcga ccgcgtgctg agcgcgctgc tgaaggagcg gaagccggtc    480
tatatcaacc tgcccgtcga cgtggcggcc gcgaaggccg agaagccgtc cctgcccctg    540
aagaaggaaa accccacctc gaacacctcc gaccaggaga tcctgaacaa gatccaggaa    600
agcctgaaga cgccaagaa gccgatcgtg atcaccggcc acgagatcat ctcgttcggc     660
ctggaaaaca ccgtcaccca gttcatctcc aagaccaagc tgccgatcac caccctgaac    720
ttcggcaaga gctcggtgga cgagaccctg ccctcgttcc tgggcatcta aacggcaag    780 ctgtccgaac cgaacctgaa ggagttcgtg gaaagcgcgg acttcatcct gatgctgggc    840
gtcaagctga ccgactccag caccggcgcc ttcacccacc atctgaacga aacaagatg    900 atctcgctga acatcgacga gggcaagatc ttcaacgaat ccatccagaa cttcgacttc    960
gaaagcctga tctcgtccct gctggacctg tccggcatcg agtacaaggg caagtatatc   1020
gacaagaagc aggaagactt cgtcccgagc aacgcgctgc tgtcgcagga ccgcctgtgg   1080
caggccgtgg agaacctgac ccagagcaac gagaccatcg tcgcggaaca gggcacctcg   1140
ttcttcggcg ccagctcgat cttcctgaag ccgaagtcgc acttcatcgg ccagcccctg   1200
tggggctcca tcggctacac cttccccgcc gcgctgggct cgcagatcgc ggacaaggaa   1260
tcccggcatc tgctgttcat cggcgacggc agcctgcagc tgaccgtgca ggagctgggc   1320
ctggccatcc gcgaaaagat caacccgatc tgcttcatca tcaacaacga cggctatacc   1380
gtcgagcggg aaatccacgg cccgaaccag tcgtacaacg acatccccat gtggaactat   1440
tccaagctgc cggagagctt cggcgccacc gaggaacgcg tcgtgtccaa gatcgtccgg   1500
accgagaacg agttcgtcag cgtgatgaag gaagcccagg cggaccccaa ccggatgtac   1560
tggatcgagc tggtgctggc gaaggaagac gccccgaagg tcctgaagaa gatgggcaag   1620
ctgttcgccg aacagaacaa gagctga                                       1647
```

<210> SEQ ID NO 41
<211> LENGTH: 563
<212> TYPE: PRT
<213> ORGANISM: Saccharomyces cerevisiae

<400> SEQUENCE: 41

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
```

-continued

```
            115                 120                 125
Ser Ala Asn Ile Ser Glu Thr Thr Ser Met Ile Thr Asp Ile Ala Thr
            130                 135                 140
Ala Pro Ser Glu Ile Asp Arg Leu Ile Arg Thr Thr Phe Ile Thr Gln
145                 150                 155                 160
Arg Pro Ser Tyr Leu Gly Leu Pro Ala Asn Leu Val Asp Leu Lys Val
                165                 170                 175
Pro Gly Ser Leu Leu Glu Lys Pro Ile Asp Leu Ser Leu Lys Pro Asn
            180                 185                 190
Asp Pro Glu Ala Glu Lys Glu Val Ile Asp Thr Val Leu Glu Leu Ile
            195                 200                 205
Gln Asn Ser Lys Asn Pro Val Ile Leu Ser Asp Ala Cys Ala Ser Arg
            210                 215                 220
His Asn Val Lys Lys Glu Thr Gln Lys Leu Ile Asp Leu Thr Gln Phe
225                 230                 235                 240
Pro Ala Phe Val Thr Pro Leu Gly Lys Gly Ser Ile Asp Glu Gln His
                245                 250                 255
Pro Arg Tyr Gly Gly Val Tyr Val Gly Thr Leu Ser Lys Gln Asp Val
                260                 265                 270
Lys Gln Ala Val Glu Ser Ala Asp Leu Ile Leu Ser Val Gly Ala Leu
            275                 280                 285
Leu Ser Asp Phe Asn Thr Gly Ser Phe Ser Tyr Ser Tyr Lys Thr Lys
            290                 295                 300
Asn Val Val Glu Phe His Ser Asp Tyr Val Lys Val Lys Asn Ala Thr
305                 310                 315                 320
Phe Leu Gly Val Gln Met Lys Phe Ala Leu Gln Asn Leu Leu Lys Val
                325                 330                 335
Ile Pro Asp Val Val Lys Gly Tyr Lys Ser Val Pro Val Pro Thr Lys
                340                 345                 350
Thr Pro Ala Asn Lys Gly Val Pro Ala Ser Thr Pro Leu Lys Gln Glu
            355                 360                 365
Trp Leu Trp Asn Glu Leu Ser Lys Phe Leu Gln Glu Gly Asp Val Ile
            370                 375                 380
Ile Ser Glu Thr Gly Thr Ser Ala Phe Gly Ile Asn Gln Thr Ile Phe
385                 390                 395                 400
Pro Lys Asp Ala Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
                420                 425                 430
Asp Pro Asn Lys Arg Val Ile Leu Phe Ile Gly Asp Gly Ser Leu Gln
            435                 440                 445
Leu Thr Val Gln Glu Ile Ser Thr Met Ile Arg Trp Gly Leu Lys Pro
            450                 455                 460
Tyr Leu Phe Val Leu Asn Asn Asp Gly Tyr Thr Ile Glu Lys Leu Ile
465                 470                 475                 480
His Gly Pro His Ala Glu Tyr Asn Glu Ile Gln Thr Trp Asp His Leu
                485                 490                 495
Ala Leu Leu Pro Ala Phe Gly Ala Lys Lys Tyr Glu Asn His Lys Ile
            500                 505                 510
Ala Thr Thr Gly Glu Trp Asp Ala Leu Thr Thr Asp Ser Glu Phe Gln
            515                 520                 525
Lys Asn Ser Val Ile Arg Leu Ile Glu Leu Lys Leu Pro Val Phe Asp
            530                 535                 540
```

Ala Pro Glu Ser Leu Ile Lys Gln Ala Gln Leu Thr Ala Ala Thr Asn
545                 550                 555                 560

Ala Lys Gln

<210> SEQ ID NO 42
<211> LENGTH: 1692
<212> TYPE: DNA
<213> ORGANISM: Saccharomyces cerevisiae

<400> SEQUENCE: 42

| | | | |
|---|---|---|---|
| atgtcggaaa tcaccctggg caagtacctg ttcgagcggc tgaagcaggt caacgtcaac | 60 |
| accatcttcg gcctgcccgg cgacttcaac ctgagcctgc tggacaagat ctacgaggtc | 120 |
| gacggcctgc gctgggccgg caacgcgaac gaactgaacg ccgcgtacgc cgcggacggc | 180 |
| tatgcccgga tcaagggcct gtcggtcctg gtgaccacct tcggcgtggg cgagctgtcg | 240 |
| gccctgaacg catcgccgg ctcctacgcg aacacgtcg gcgtgctgca tgtcgtgggc | 300 |
| gtcccgagca tctcggccca ggcgaagcag ctgctgctgc accataccct gggcaacggc | 360 |
| gacttcaccg tgttccaccg catgtccgcc aacatcagcg agaccacctc gatgatcacc | 420 |
| gacatcgcca ccgcgccgag cgaaatcgac cgcctgatcc ggaccacctt catcacccag | 480 |
| cggccgtcgt acctgggcct gcccgccaac ctggtcgacc tgaaggtgcc gggcagcctg | 540 |
| ctggagaagc ccatcgacct gtcgctgaag ccgaacgacc ccgaggccga aaaggaagtc | 600 |
| atcgacaccg tgctggaact gatccagaac agcaagaacc cggtcatcct gtccgacgcc | 660 |
| tgcgcgagcc gccacaacgt gaagaaggag acccagaagc tgatcgacct gacccagttc | 720 |
| ccggccttcg tcaccccct gggcaagggc tccatcgacg agcagcatcc gcggtacggc | 780 |
| ggcgtctatg tgggcaccct gagcaagcag gacgtcaagc aggccgtgga aagcgcggac | 840 |
| ctgatcctgt cggtgggcgc cctgctgtcc gacttcaaca ccggctcctt cagctactcg | 900 |
| tataagacca gaacgtcgt ggagttccat tcggactacg tcaaggtgaa gaacgcgacc | 960 |
| ttcctgggcg tccagatgaa gttcgccctg cagaacctgc tgaaggtgat cccggacgtc | 1020 |
| gtgaagggct ataagtccgt cccggtgccc accaagaccc ccgccaacaa gggcgtcccg | 1080 |
| gcgtcgaccc ccctgaagca ggaatggctg tggaacgagc tgtccaagtt cctgcaggaa | 1140 |
| ggcgacgtga tcatctcgga gaccggcacc tccgcgttcg gcatcaacca gaccatcttc | 1200 |
| ccgaaggacg cctacggcat cagccaggtc ctgtggggct cgatcggctt caccaccggc | 1260 |
| gccaccctgg gcgccgcgtt cgccgcggag gaaatcgacc gaacaagcg cgtcatcctg | 1320 |
| ttcatcggcg acggctccct gcagctgacc gtgcaggaaa tcagcaccat gatccggtgg | 1380 |
| ggcctgaagc cctacctgtt cgtgctgaac aacgacggct ataccatcga gaagctgatc | 1440 |
| cacggcccgc atgcggaata caacgagatc cagacctggg accacctggc cctgctgccc | 1500 |
| gccttcggcg cgaagaagta tgaaaaccat aagatcgcca ccaccggcga gtgggacgcg | 1560 |
| ctgaccaccg actccgagtt ccagaagaac agcgtcatcc gcctgatcga gctgaagctg | 1620 |
| ccggtgttcg acgcccccga aagcctgatc aagcaggcgc agctgaccgc cgcgaccaac | 1680 |
| gccaagcagt ga | 1692 |

<210> SEQ ID NO 43
<211> LENGTH: 635
<212> TYPE: PRT
<213> ORGANISM: Saccharomyces cerevisiae

<400> SEQUENCE: 43

```
Met Ala Pro Val Thr Ile Glu Lys Phe Val Asn Gln Glu Arg His
1               5                   10                  15

Leu Val Ser Asn Arg Ser Ala Thr Ile Pro Phe Gly Glu Tyr Ile Phe
                20                  25                  30

Lys Arg Leu Leu Ser Ile Asp Thr Lys Ser Val Phe Gly Val Pro Gly
            35                  40                  45

Asp Phe Asn Leu Ser Leu Leu Glu Tyr Leu Tyr Ser Pro Ser Val Glu
        50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
                405                 410                 415
```

Gln Ser Ser Ile Ile Thr Gln Val His Leu Gln Lys Thr Met Pro Lys
            420                 425                 430

Phe Leu Asn Pro Gly Asp Val Val Cys Glu Thr Gly Ser Phe Gln
        435                 440                 445

Phe Ser Val Arg Asp Phe Ala Phe Pro Ser Gln Leu Lys Tyr Ile Ser
450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
        515                 520                 525

Asn Ile Pro Leu Glu Val Ile Ile Trp Asn Asn Gly Tyr Thr Ile
        530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
        595                 600                 605

Glu Val Lys Leu Gly Leu Asp Phe Pro Glu Gln Leu Lys Cys Met
610                 615                 620

Val Glu Ala Ala Ala Leu Lys Arg Asn Lys Lys
625                 630                 635

<210> SEQ ID NO 44
<211> LENGTH: 1908
<212> TYPE: DNA
<213> ORGANISM: Saccharomyces cerevisiae

<400> SEQUENCE: 44 atggccccccg tcaccatcga gaagttcgtc aaccaggaag agcggcatct ggtgtccaac      60
cggagcgcga ccatcccgtt cggcgagtac atcttcaagc gcctgctgag catcgacacc     120
aagtcggtgt tcggcgtgcc gggcgacttc aacctgagcc tgctggagta cctgtatagc     180
ccctcggtcg aatcggccgg cctgcgctgg gtgggcacct gcaacgaact gaacgccgcg     240
tacgccgcgg acggctactc ccggtatagc aacaagatcg gctgcctgat caccacctat     300
ggcgtcggcg aactgtcggc gctgaacggc atcgcgggct ccttcgccga gaacgtgaag     360
gtcctgcaca tcgtgggcgt cgccaagtcg atcgactccc gcagctcgaa cttctcggac     420
cggaacctgc accatctggt cccgcagctg catgactcca acttcaaggg ccccaaccac     480
aaggtgtacc atgacatggt gaaggaccgc gtcgcgtgct ccgtggccta tctggaggac     540
atcgaaaccg cctgcgacca ggtggacaac gtcatccggg acatctacaa gtatagcaag     600
ccgggttaca tcttcgtccc cgcggacttc gccgacatgt ccgtgacctg cgacaacctg     660
gtgaacgtcc cgcgcatcag ccagcaggac tgcatcgtgt accctccga aaaccagctg     720 agcgacatca tcaacaagat cacctcgtgg atctactcca gcaagacccc ggccatcctg     780
ggcgacgtct tgaccgaccg gtatggcgtg agcaacttcc tgaacaagct gatctgcaag     840
accggcatct ggaacttctc gaccgtcatg ggcaagtcgg tgatcgacga atccaacccg     900

```
acctacatgg gccagtataa cggcaaggaa ggcctgaagc aggtctacga gcacttcgaa    960
ctgtgcgacc tggtcctgca tttcggcgtg gacatcaacg agatcaacaa cggccactac   1020
accttcacct ataagccgaa cgcgaagatc atccagttcc atcccaacta catccgcctg   1080
gtggacaccc ggcagggcaa cgaacagatg ttcaagggca tcaacttcgc cccgatcctg   1140
aaggagctgt ataagcgcat cgacgtcagc aagctgtcgc tgcagtacga cagcaacgtg   1200
acccagtata ccaacgagac catgcggctg aagaccccca ccaacggcca gtcgtccatc   1260
atcacccagg tccacctgca gaagaccatg ccgaagttcc tgaacccggc gacgtcgtg    1320
gtctgcgaga ccggctcctt ccagttcagc gtgcgcgact tcgcgttccc gagccagctg   1380
aagtacatct cgcagggctt cttcctgtcc atcggcatgg ccctgcccgc cgcgctgggc   1440
gtcggcatcg cgatgcagga ccactcgaac gcccatatca acggcggcaa cgtgaaggaa   1500
gactacaagc cgcggctgat cctgttcgaa ggcgacggcg ccgcgcagat gaccatccag   1560
gagctgtcca ccatcctgaa gtgcaacatc ccgctggaag tcatcatctg aacaacaac    1620
ggctacacca tcgagcgcgc catcatgggc cccacccgga gctataacga cgtgatgtcg   1680
tggaagtgga ccaagctgtt cgaagcgttc ggcgacttcg acggcaagta caccaactcc   1740
accctgatcc agtgcccgag caagctggcc ctgaagctgg aggaactgaa gaactcgaac   1800
aagcgctccg gcatcgagct gctggaagtc aagctgggcg agctggactt ccccgaacag   1860
ctgaagtgca tggtggaggc cgcggccctg aagcggaaca agaagtga              1908

<210> SEQ ID NO 45
<211> LENGTH: 563
<212> TYPE: PRT
<213> ORGANISM: Saccharomyces cerevisiae

<400> SEQUENCE: 45

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190
```

```
Asp Ala Glu Ser Glu Lys Glu Val Ile Asp Thr Ile Leu Ala Leu Val
            195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
            245                 250                 255

Pro Arg Tyr Gly Gly Val Tyr Val Thr Leu Ser Lys Pro Glu Val
        260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
            325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
            370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
            405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
            485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 46
<211> LENGTH: 1692
<212> TYPE: DNA
<213> ORGANISM: Saccharomyces cerevisiae

<400> SEQUENCE: 46
```

-continued

| | |
|---|---|
| atgagcgaga tcaccctggg caagtacctg ttcgagcggc tgaagcaggt caacgtcaac | 60 |
| accgtcttcg gcctgcccgg cgacttcaac ctgagcctgc tggacaagat ctacgaggtc | 120 |
| gaaggcatgc gctgggcggg caacgccaac gagctgaacg ccgcgtacgc cgcggacggc | 180 |
| tatgcccgga tcaagggcat cgtcgtgcatc atcaccacct tcggcgtggg cgagctgtcc | 240 |
| gccctgaacg gcatcgcggg cagctacgcc gaacacgtcg gcgtgctgca tgtcgtgggc | 300 |
| gtcccgagca tctcggccca ggcgaagcag ctgctgctgc accatacccct gggcaacggc | 360 |
| gacttcaccg tgttccaccg catgtccgcg aacatcagcg agaccaccgc catgatcacc | 420 |
| gacatcgcca ccgcgccggc cgaaatcgac cgctgcatcc ggaccaccta cgtcacccag | 480 |
| cggcccgtgt atctgggcct gccggccaac ctggtcgacc tgaacgtgcc cgcgaagctg | 540 |
| ctgcagaccc cgatcgacat gtcgctgaag cccaacgacg ccgagtccga aaaggaagtc | 600 |
| atcgacacca tcctggcgct ggtcaaggac gccaagaacc cggtgatcct ggcggacgcc | 660 |
| tgctgctccc gccacgacgt caaggccgag accaagaagc tgatcgacct gacccagttc | 720 |
| cccgccttcg tgaccccgat gggcaagggc tccatcgacg aacagcatcc gcggtacggc | 780 |
| ggcgtctatg tgggcaccct gagcaagccc gaagtcaagg aagccgtgga agcgccgac | 840 |
| ctgatcctgt cggtcggcgc cctgctgtcc gacttcaaca ccggctcctt cagctactcg | 900 |
| tataagacca agaacatcgt ggagttccac agcgaccaca tgaagatccg caacgccacc | 960 |
| ttccccggcg tccagatgaa gttcgtgctg cagaagctgc tgaccaccat cgccgacgcc | 1020 |
| gcgaagggct acaagccggt cgcggtgccc gcccggaccc cggcgaacgc cgcggtcccc | 1080 |
| gcctcgaccc cgctgaagca ggaatggatg tggaaccagc tgggcaactt cctgcaggaa | 1140 |
| ggcgacgtcg tgatcgcgga aaccggcacc tccgccttcg gcatcaacca gaccaccttc | 1200 |
| ccgaacaaca cctacggcat cagccaggtg ctgtggggct cgatcggctt caccaccggc | 1260 |
| gccaccctgg gcgccgcgtt cgccgcggag gaaatcgacc gaagaagcg cgtcatcctg | 1320 |
| ttcatcggcg acggcagcct gcagctgacc gtgcaggaaa tctcgaccat gatccggtgg | 1380 |
| ggcctgaagc cctacctgtt cgtcctgaac aacgacggct ataccatcga agctgatc | 1440 |
| cacgccccga aggcccagta caacgaaatc cagggctggg accatctgtc gctgctgccc | 1500 |
| accttcggcg ccaaggacta tgagacccat cgcgtggcga ccaccggcga atgggacaag | 1560 |
| ctgaccccagg acaagtcgtt caacgacaac tccaagatcc ggatgatcga gatcatgctg | 1620 |
| cccgtcttcg acgcgccgca gaacctggtg aacaggcca agctgaccgc cgcgaccaac | 1680 |
| gcgaagcagt ga | 1692 |

<210> SEQ ID NO 47
<211> LENGTH: 1048
<212> TYPE: PRT
<213> ORGANISM: Clostridium acetobutylicum

<400> SEQUENCE: 47

```
Met Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
```

-continued

```
               65                  70                  75                  80
          Ser Ala Ile Asn Ala Ile Ala Gly Ala Tyr Ala Glu Gln Val Pro Val
                              85                  90                  95

Val Lys Ile Thr Gly Ile Pro Thr Ala Lys Val Arg Asp Asn Gly Leu
                             100                 105                 110

Tyr Val His His Thr Leu Gly Asp Gly Arg Phe Asp His Phe Phe Glu
                             115                 120                 125

Met Phe Arg Glu Val Thr Val Ala Glu Ala Leu Leu Ser Glu Glu Asn
                   130                 135                 140

Ala Ala Gln Glu Ile Asp Arg Val Leu Ile Ser Cys Trp Arg Gln Lys
          145                 150                 155                 160

Arg Pro Val Leu Ile Asn Leu Pro Ile Asp Val Tyr Asp Lys Pro Ile
                             165                 170                 175

Asn Lys Pro Leu Lys Pro Leu Leu Asp Tyr Thr Ile Ser Ser Asn Lys
                         180                 185                 190

Glu Ala Ala Cys Glu Phe Val Thr Glu Ile Val Pro Ile Ile Asn Arg
                   195                 200                 205

Ala Lys Lys Pro Val Ile Leu Ala Asp Tyr Gly Val Tyr Arg Tyr Gln
          210                 215                 220

Val Gln His Val Leu Lys Asn Leu Ala Glu Lys Thr Gly Phe Pro Val
          225                 230                 235                 240

Ala Thr Leu Ser Met Gly Lys Gly Val Phe Asn Glu Ala His Pro Gln
                             245                 250                 255

Phe Ile Gly Val Tyr Asn Gly Asp Val Ser Ser Pro Tyr Leu Arg Gln
                         260                 265                 270

Arg Val Asp Glu Ala Asp Cys Ile Ile Ser Val Gly Val Lys Leu Thr
                   275                 280                 285

Asp Ser Thr Thr Gly Gly Phe Ser His Gly Phe Ser Lys Arg Asn Val
                   290                 295                 300

Ile His Ile Asp Pro Phe Ser Ile Lys Ala Lys Gly Lys Lys Tyr Ala
          305                 310                 315                 320

Pro Ile Thr Met Lys Asp Ala Leu Thr Glu Leu Thr Ser Lys Ile Glu
                             325                 330                 335

His Arg Asn Phe Glu Asp Leu Asp Ile Lys Pro Tyr Lys Ser Asp Asn
                         340                 345                 350

Gln Lys Tyr Phe Ala Lys Glu Lys Pro Ile Thr Gln Lys Arg Phe Phe
                     355                 360                 365

Glu Arg Ile Ala His Phe Ile Lys Glu Lys Asp Val Leu Leu Ala Glu
                   370                 375                 380

Gln Gly Thr Cys Phe Phe Gly Ala Ser Thr Ile Gln Leu Pro Lys Asp
          385                 390                 395                 400

Ala Thr Phe Ile Gly Gln Pro Leu Trp Gly Ser Ile Gly Tyr Thr Leu
                             405                 410                 415

Pro Ala Leu Leu Gly Ser Gln Leu Ala Asp Gln Lys Arg Arg Asn Ile
                         420                 425                 430

Leu Leu Ile Gly Asp Gly Ala Phe Gln Met Thr Ala Gln Glu Ile Ser
                     435                 440                 445

Thr Met Leu Arg Leu Gln Ile Lys Pro Ile Ile Phe Leu Ile Asn Asn
                   450                 455                 460

Asp Gly Tyr Thr Ile Glu Arg Ala Ile His Gly Arg Glu Gln Val Tyr
          465                 470                 475                 480

Asn Asn Ile Gln Met Trp Arg Tyr His Asn Val Pro Lys Val Leu Gly
                             485                 490                 495
```

```
Pro Lys Glu Cys Ser Leu Thr Phe Lys Val Gln Ser Glu Thr Glu Leu
            500                 505                 510

Glu Lys Ala Leu Leu Val Ala Asp Lys Asp Cys Glu His Leu Ile Phe
        515                 520                 525

Ile Glu Val Val Met Asp Arg Tyr Asp Lys Pro Glu Pro Leu Glu Arg
530                 535                 540

Leu Ser Lys Arg Phe Ala Asn Gln Asn Asn Gly Tyr Ala Arg Ile Asn
545                 550                 555                 560

Gly Ile Gly Ala Ile Leu Thr Thr Phe Gly Val Gly Glu Leu Ser Ala
                565                 570                 575

Ile Asn Ala Ile Ala Gly Ala Tyr Ala Glu Gln Val Pro Val Val Lys
            580                 585                 590

Ile Thr Gly Ile Pro Thr Ala Lys Val Arg Asp Asn Gly Leu Tyr Val
        595                 600                 605

His His Thr Leu Gly Asp Gly Arg Phe Asp His Phe Phe Glu Met Phe
    610                 615                 620

Arg Glu Val Thr Val Ala Glu Ala Leu Leu Ser Glu Glu Asn Ala Ala
625                 630                 635                 640

Gln Glu Ile Asp Arg Val Leu Ile Ser Cys Trp Arg Gln Lys Arg Pro
                645                 650                 655

Val Leu Ile Asn Leu Pro Ile Asp Val Tyr Asp Lys Pro Ile Asn Lys
            660                 665                 670

Pro Leu Lys Pro Leu Leu Asp Tyr Thr Ile Ser Ser Asn Lys Glu Ala
        675                 680                 685

Ala Cys Glu Phe Val Thr Glu Ile Val Pro Ile Ile Asn Arg Ala Lys
    690                 695                 700

Lys Pro Val Ile Leu Ala Asp Tyr Gly Val Tyr Arg Tyr Gln Val Gln
705                 710                 715                 720

His Val Leu Lys Asn Leu Ala Glu Lys Thr Gly Phe Pro Val Ala Thr
                725                 730                 735

Leu Ser Met Gly Lys Gly Val Phe Asn Glu Ala His Pro Gln Phe Ile
            740                 745                 750

Gly Val Tyr Asn Gly Asp Val Ser Ser Pro Tyr Leu Arg Gln Arg Val
        755                 760                 765

Asp Glu Ala Asp Cys Ile Ile Ser Val Gly Val Lys Leu Thr Asp Ser
    770                 775                 780

Thr Thr Gly Gly Phe Ser His Gly Phe Ser Lys Arg Asn Val Ile His
785                 790                 795                 800

Ile Asp Pro Phe Ser Ile Lys Ala Lys Gly Lys Lys Tyr Ala Pro Ile
                805                 810                 815

Thr Met Lys Asp Ala Leu Thr Glu Leu Thr Ser Lys Ile Glu His Arg
            820                 825                 830

Asn Phe Glu Asp Leu Asp Ile Lys Pro Tyr Lys Ser Asp Asn Gln Lys
        835                 840                 845

Tyr Phe Ala Lys Glu Lys Pro Ile Thr Gln Lys Arg Phe Phe Glu Arg
    850                 855                 860

Ile Ala His Phe Ile Lys Glu Lys Asp Val Leu Leu Ala Glu Gln Gly
865                 870                 875                 880

Thr Cys Phe Phe Gly Ala Ser Thr Ile Gln Leu Pro Lys Asp Ala Thr
                885                 890                 895

Phe Ile Gly Gln Pro Leu Trp Gly Ser Ile Gly Tyr Thr Leu Pro Ala
            900                 905                 910
```

-continued

```
Leu Leu Gly Ser Gln Leu Ala Asp Gln Lys Arg Arg Asn Ile Leu Leu
            915                 920                 925

Ile Gly Asp Gly Ala Phe Gln Met Thr Ala Gln Glu Ile Ser Thr Met
        930                 935                 940

Leu Arg Leu Gln Ile Lys Pro Ile Ile Phe Leu Ile Asn Asn Asp Gly
945                 950                 955                 960

Tyr Thr Ile Glu Arg Ala Ile His Gly Arg Glu Gln Val Tyr Asn Asn
                965                 970                 975

Ile Gln Met Trp Arg Tyr His Asn Val Pro Lys Val Leu Gly Pro Lys
            980                 985                 990

Glu Cys Ser Leu Thr Phe Lys Val  Gln Ser Glu Thr Glu  Leu Glu Lys
        995                1000                1005

Ala Leu  Leu Val Ala Asp Lys  Asp Cys Glu His Leu  Ile Phe Ile
    1010                1015                1020

Glu Val  Val Met Asp Arg Tyr  Asp Lys Pro Glu Pro  Leu Glu Arg
    1025                1030                1035

Leu Ser  Lys Arg Phe Ala Asn  Gln Asn Asn
    1040                1045
```

<210> SEQ ID NO 48
<211> LENGTH: 3147
<212> TYPE: DNA
<213> ORGANISM: Clostridium acetobutylicum

<400> SEQUENCE: 48

```
atgaagtcgg aatacaccat cggccgctat ctgctggacc gcctgagcga gctgggcatc    60
cgccacatct tcggcgtccc cggcgactac aacctgtcgt tcctggacta catcatggag   120
tataagggca tcgactgggt cggcaactgc aacgaactga cgccggcta cgccgcggac   180 ggctatgccc gcatcaacgg catcggcgcg atcctgacca ccttcggcgt cggcgagctg   240
tccgccatca cgccatcgc gggcgcctac gcggaacagg tgccggtcgt gaagatcacc   300
ggcatcccca ccgccaaggt ccgcgacaac ggcctgtatg tgcaccatac cctgggcgac   360
ggccgcttcg accacttctt cgagatgttc cgggaagtca ccgtggccga ggcgctgctg   420
agcgaggaaa acgccgcgca ggaaatcgac cgcgtgctga tctcgtgctg cgccagaag    480 cggccggtcc tgatcaacct gcccatcgac gtgtacgaca agccgatcaa caagccgctg   540
aagcccctgc tggactatac catcagctcg aacaaggaag ccgcgtgcga gttcgtcacc   600
gagatcgtgc cgatcatcaa cgcgccaag aagcccgtca tcctggcgga ctacggcgtg   660
taccggtatc aggtccagca cgtgctgaag aacctggcgg agaagaccgg cttcccggtc   720
gccaccctgt cgatgggcaa gggcgtgttc aacgaagccc atccgcagtt catcggcgtc   780
tacaacggcg acgtgtccag ccctatctg cgccagcggg tcgacgaggc cgactgcatc   840
atctcggtcg gcgtgaagct gaccgactcc accaccggcg gcttctccca cggcttcagc   900
aagcgcaacg tgatccatat cgacccgttc tccatcaagg ccaagggcaa gaagtacgcg   960
cccatcacca tgaaggacgc cctgaccgaa ctgacctcga gatcgagca ccggaacttc  1020 gaagacctgg acatcaagcc gtacaagtcc gacaaccaga gtatttcgc gaaggagaag  1080 cccatcaccc agaagcgctt cttcaacgga tcgccatt tcatcaagga agggacgtc  1140 ctgctggcgg aacagggcac ctgcttcttc ggcgccagca ccatccagct gccgaaggac  1200
gcgaccttca tcgccagcc cctgtgggc tccatcggct acaccctgcc ggccctgctg  1260
ggcagccagc tggcggacca gaagcgtcgc aacatcctgc tgatcggcga cggcgccttc  1320
```

```
cagatgaccg cgcaggagat ctcgaccatg ctgcgcctgc agatcaagcc gatcatcttc   1380
ctgatcaaca acgacggcta caccatcgag cgcgccatcc acggccggga acaggtgtac   1440
aacaacatcc agatgtggcg gtatcataac gtcccgaagg tgctgggccc caaggaatgc   1500
agcctgacct tcaaggtcca gtcggagacc gaactggaga aggccctgct ggtcgccgac   1560
aaggactgcg agcacctgat cttcatcgaa gtcgtgatgg accgctacga caagccggag   1620
cccctggaac gcctgtccaa gcggttcgcc aaccagaaca acggctatgc gcggatcaac   1680
ggcatcggcg ccattttaac caccttcggc gtgggcgagc tgagcgcgat caacgcgatc   1740
gccggcgcct acgcggagca ggtgccggtg gtcaaaatta ccggcatccc caccgcgaag   1800
gtgcgggaca acggcctgta cgtccatcac accctgggcg acggccggtt cgaccatttc   1860
ttcgaaatgt tccgggaggt gaccgtcgcc gaggcgctgc tgtcggaaga gaacgcggcc   1920
caggagatcg accgcgtcct gatcagctgc tggcggcaga agcgccccgt gctgatcaac   1980
ctgccgatcg acgtctatga caagcccatc aacaagcccc tgaagccgct gctggactac   2040
accatctcgt ccaacaagga agccgcctgc gagttcgtca ccgaaatcgt ccccatcatc   2100
aaccgcgcga agaagccggt gatcctggcc gactatggcg tctatcggta tcaggtgcag   2160
catgtcctga agaacctggc cgaaaagacc ggcttccccg tggccaccct gagcatgggc   2220
aagggcgtct tcaacgaggc gcaccccag ttcatcggcg tgtataacgg cgacgtgagc   2280
tcgccgtacc tgcggcagcg cgtggacgaa gccgactgca tcatcagcgt cggcgtcaag   2340
ctgaccgact cgaccaccgg cggcttctcg cacggcttct cgaagcggaa cgtcatccac   2400
atcgacccgt tctcgatcaa ggcgaagggc aagaagtatg ccccgatcac catgaaggac   2460
gcgctgaccg aactgaccag caagatcgaa catcgcaact tcgaggacct ggacatcaag   2520
ccctacaagt cggacaacca gaagtacttc gccaaggaaa agccgattac tcagaagcgc   2580
ttcttcgagc gcatcgcgca cttcatcaag gaaaaggacg tcctgctggc cgagcaaggc   2640
acctgcttct tcggtgcgtc gaccatccag ctgcccaagg acgccacctt catcggccag   2700
ccgctgtggg gctcgatcgg ctataccctg cccgcgctgc tgggctccca gctggccgat   2760
caaaaacgtc gcaatatttt actgatcggc gacggcgcgt tccagatgac cgcccaggag   2820
atcagcacca tgctgcggct gcagatcaag cccattatct tcctgattaa caacgacggc   2880
tataccatcg aacgggcgat ccacggccgc gagcaggtct ataataatat tcaaatgtgg   2940
cggtatcata atgtgcccaa ggtcctgggc ccgaaggaat gctcgctgac cttcaaggtg   3000
cagagcgaaa ccgagctgga aaaggccctg ctggtcgccg ataaggactg cgaacatctg   3060
atcttcatcg aggtggtcat ggaccggtat gacaagcccg aacccctgga acggctgagc   3120
aagcgcttcg cgaaccagaa caactga                                       3147
```

<210> SEQ ID NO 49
<211> LENGTH: 360
<212> TYPE: PRT
<213> ORGANISM: Saccharomyces cerevisiae

<400> SEQUENCE: 49

```
Met Ser Tyr Pro Glu Lys Phe Glu Gly Ile Ala Ile Gln Ser His Glu
 1               5                   10                  15

Asp Trp Lys Asn Pro Lys Lys Thr Lys Tyr Asp Pro Lys Pro Phe Tyr
                20                  25                  30

Asp His Asp Ile Asp Ile Lys Ile Glu Ala Cys Gly Val Cys Gly Ser
            35                  40                  45
```

```
Asp Ile His Cys Ala Ala Gly His Trp Gly Asn Met Lys Met Pro Leu
 50                  55                  60
Val Val Gly His Glu Ile Val Gly Lys Val Val Lys Leu Gly Pro Lys
 65                  70                  75                  80
Ser Asn Ser Gly Leu Lys Val Gly Gln Arg Val Gly Val Gly Ala Gln
                 85                  90                  95
Val Phe Ser Cys Leu Glu Cys Asp Arg Cys Lys Asn Asp Asn Glu Pro
                100                 105                 110
Tyr Cys Thr Lys Phe Val Thr Thr Tyr Ser Gln Pro Tyr Glu Asp Gly
            115                 120                 125
Tyr Val Ser Gln Gly Gly Tyr Ala Asn Tyr Val Arg Val His Glu His
    130                 135                 140
Phe Val Val Pro Ile Pro Glu Asn Ile Pro Ser His Leu Ala Ala Pro
145                 150                 155                 160
Leu Leu Cys Gly Gly Leu Thr Val Tyr Ser Pro Leu Val Arg Asn Gly
                165                 170                 175
Cys Gly Pro Gly Lys Lys Val Gly Ile Val Gly Leu Gly Gly Ile Gly
            180                 185                 190
Ser Met Gly Thr Leu Ile Ser Lys Ala Met Gly Ala Glu Thr Tyr Val
    195                 200                 205
Ile Ser Arg Ser Ser Arg Lys Arg Glu Asp Ala Met Lys Met Gly Ala
210                 215                 220
Asp His Tyr Ile Ala Thr Leu Glu Glu Gly Asp Trp Gly Glu Lys Tyr
225                 230                 235                 240
Phe Asp Thr Phe Asp Leu Ile Val Val Cys Ala Ser Ser Leu Thr Asp
                245                 250                 255
Ile Asp Phe Asn Ile Met Pro Lys Ala Met Lys Val Gly Gly Arg Ile
            260                 265                 270
Val Ser Ile Ser Ile Pro Glu Gln His Glu Met Leu Ser Leu Lys Pro
    275                 280                 285
Tyr Gly Leu Lys Ala Val Ser Ile Ser Tyr Ser Ala Leu Gly Ser Ile
290                 295                 300
Lys Glu Leu Asn Gln Leu Leu Lys Leu Val Ser Glu Lys Asp Ile Lys
305                 310                 315                 320
Ile Trp Val Glu Thr Leu Pro Val Gly Glu Ala Gly Val His Glu Ala
                325                 330                 335
Phe Glu Arg Met Glu Lys Gly Asp Val Arg Tyr Arg Phe Thr Leu Val
            340                 345                 350
Gly Tyr Asp Lys Glu Phe Ser Asp
    355                 360

<210> SEQ ID NO 50
<211> LENGTH: 1083
<212> TYPE: DNA
<213> ORGANISM: Saccharomyces cerevisiae

<400> SEQUENCE: 50
atgtcttatc ctgagaaatt tgaaggtatc gctattcaat cacacgaaga ttggaaaaac      60
ccaaagaaga caaagtatga cccaaaacca ttttacgatc atgacattga cattaagatc    120
gaagcatgtg gtgtctgcgg tagtgatatt cattgtgcag ctggtcattg gggcaatatg    180
aagatgccgc tagtcgttgg tcatgaaatc gttggtaaag ttgtcaagct agggcccaag    240
tcaaacagtg ggttgaaagt cggtcaacgt gttggtgtag gtgctcaagt cttttcatgc    300
ttggaatgtg accgttgtaa gaatgataat gaaccatact gcaccaagtt tgttaccaca    360
```

-continued

```
tacagtcagc cttatgaaga cggctatgtg tcgcagggtg gctatgcaaa ctacgtcaga    420
gttcatgaac attttgtggt gcctatccca gagaatattc catcacattt ggctgctcca    480
ctattatgtg gtggtttgac tgtgtactct ccattggttc gtaacggttg cggtccaggt    540
aaaaaagttg gtatagttgg tcttggtggt atcggcagta tgggtacatt gatttccaaa    600
gccatggggg cagagacgta tgttatttct cgttcttcga gaaaaagaga agatgcaatg    660
aagatgggcg ccgatcacta cattgctaca ttagaagaag gtgattgggg tgaaaagtac    720
tttgacacct tcgacctgat tgtagtctgt gcttcctccc ttaccgacat tgacttcaac    780
attatgccaa aggctatgaa ggttggtggt agaattgtct caatctctat accagaacaa    840
cacgaaatgt tatcgctaaa gccatatggc ttaaaggctg tctccatttc ttacagtgct    900
ttaggttcca tcaaagaatt gaaccaactc ttgaaattag tctctgaaaa agatatcaaa    960
atttgggtgg aaacattacc tgttggtgaa gccggcgtcc atgaagcctt cgaaaggatg   1020
gaaaagggtg acgttagata tagatttacc ttagtcggct acgacaaaga attttcagac   1080
tag                                                                 1083
```

```
<210> SEQ ID NO 51
<211> LENGTH: 351
<212> TYPE: PRT
<213> ORGANISM: Methylosinus trichosporium

<400> SEQUENCE: 51
```

```
Met Ser Thr Lys Ala Tyr Ala Val Ala Ser Ala Glu Ala Leu Phe Gly
1               5                   10                  15

Pro Leu Ala Ile Glu Arg Arg Ala Leu Gly Pro Glu Asp Val Glu Ile
            20                  25                  30

Asp Ile Leu Tyr Cys Gly Val Cys His Ser Asp Leu His Thr Ala Arg
        35                  40                  45

Ser Glu Trp Pro Gly Thr Arg Tyr Pro Cys Val Pro Gly His Glu Ile
    50                  55                  60

Val Gly Arg Val Thr Ala Val Gly Ala Lys Val Thr Lys Phe Ser Val
65                  70                  75                  80

Gly Asp Leu Ala Ala Val Gly Cys Met Val Asp Ser Cys Arg Arg Cys
                85                  90                  95

Leu Ser Cys Asp Asp Gly Leu Glu Gln Tyr Cys Glu His Gly Phe Thr
            100                 105                 110

Ala Thr Tyr Asn Gly Pro Ile Tyr Gly Ser Gly Glu Asn Thr Phe Gly
        115                 120                 125

Gly Tyr Ser Glu Lys Ile Val Val Asp Ala His Phe Val Leu Ala Ile
    130                 135                 140

His His Ser Glu Thr Gln Leu Ala Gly Val Ala Pro Leu Leu Cys Ala
145                 150                 155                 160

Gly Ile Thr Thr Trp Ser Pro Leu Lys His Trp Gly Val Gly Pro Gly
                165                 170                 175

Lys Ser Val Gly Ile Val Gly Ile Gly Gly Leu Gly His Met Gly Val
            180                 185                 190

Lys Leu Ala His Ala Leu Gly Ala His Val Val Ala Phe Thr Thr Ser
        195                 200                 205

Pro Ser Lys Arg Asp Ala Ala Leu Ala Leu Gly Ala Asp Glu Val Val
    210                 215                 220

Val Ser Thr Asp Pro Ala Ala Met Ala Ala Arg Ala Gly Ser Leu Asp
225                 230                 235                 240
```

```
Phe Ile Leu Asp Thr Val Ala Val Ala His Asp Leu Asp Ala Tyr Val
                245                 250                 255

Asn Leu Leu Lys Arg Asp Gly Ala Leu Val Leu Val Gly Val Pro Ala
            260                 265                 270

Thr Pro His Pro Ser Pro Ser Ala Gly Gly Leu Ile Phe Lys Arg Arg
        275                 280                 285

Gln Val Ala Gly Ser Leu Ile Gly Gly Val Lys Glu Thr Gln Glu Met
    290                 295                 300

Leu Asp Phe Cys Ala Glu Arg Gly Ile Val Ala Asp Ile Glu Thr Ile
305                 310                 315                 320

Ala Met Gln Gln Ile Glu Thr Ala Tyr Ala Arg Met Leu Lys Asn Asp
                325                 330                 335

Val Lys Tyr Arg Phe Val Ile Asp Met Ala Thr Leu Lys Ala Ala
            340                 345                 350

<210> SEQ ID NO 52
<211> LENGTH: 1056
<212> TYPE: DNA
<213> ORGANISM: Methylosinus trichosporium

<400> SEQUENCE: 52
atgtccacca aagcctatgc cgttgcgtcc gccgaggcgc tcttcggccc gctcgcgatc     60
gagcgccgcg cgctcgggcc cgaggatgta gagatcgaca tcctctattg cggcgtctgc    120
cattccgatc tgcacacggc gcgcagtgaa tggccgggca cgcgctaccc atgcgtcccg    180
ggccacgaga ttgtcggccg cgtcaccgct gtcggcgcga aggtgacgaa attttcggtc    240
ggcgatctcg ccgccgtcgg ctgcatggtc gacagctgcc ggcgatgctt gtcctgcgac    300
gacgggctcg aacaatattg cgagcacggt ttcaccgcca cctataacgg cccgatctac    360
ggctcgggcg agaacacctt tggcggctat tcggagaaaa tcgtcgtcga cgcgcatttc    420
gtgctggcga tccaccattc tgagacgcag cttgccggag tcgcgccgct gctctgcgcc    480
ggcatcacca cttggtcgcc gctcaagcat gggggtgtcg gcccgggaaa atcggtcggc    540
atcgtcggca tcggcgggct cggccatatg ggggtcaagc tcgcccatgc gctcggcgcc    600
catgtcgtcg ccttcaccac ctcgccgtca aagcgcgacg cggccctcgc gctcggcgcc    660
gacgaggtcg tcgtctccac agatcctgcc gctatggcgg cgcgggcggg aagcctcgac    720
ttcattctcg atacggtcgc cgtcgcccat gacctcgacg cttatgtgaa tctgttgaag    780
cgcgatggcg ctctggtgct cgtcggcgtg ccggcgacgc cgcatccctc gccatcggcg    840
ggcgggttga tcttcaagcg cgcgccaggtc gccggctcgc tgatcggcgg cgtaaaggag    900
acgcaggaga tgctcgactt ctgcgccgag cgcggcattg tcgcggacat agagacgatc    960
gccatgcagc agatcgagac cgcctatgcg cgcatgctga agaatgatgt gaaataccgc   1020
ttcgtcatcg acatggcgac gctgaaggcg gcgtga                              1056

<210> SEQ ID NO 53
<211> LENGTH: 342
<212> TYPE: PRT
<213> ORGANISM: Methylococcus capsulatus

<400> SEQUENCE: 53

Met Lys Ala Trp Val Ile Asp Arg Ile Gly Pro Leu Asp Ser Ser Arg
1               5                   10                  15

Thr Leu Leu Arg Ala Thr Asp Leu Pro Val Pro Glu Pro Gly Pro Gly
            20                  25                  30
```

```
Glu Ile Leu Leu Gln Val Ala Val Cys Gly Val Cys His Thr Glu Ile
            35                  40                  45

Asp Glu Ile Glu Gly Arg Thr Ala Pro Pro Arg Leu Pro Val Val Pro
 50                  55                  60

Gly His Gln Ala Val Gly Arg Ile Ala Ala Leu Gly Ser Gly Val Ala
 65                  70                  75                  80

Glu Phe Ala Leu Gly Asp Arg Val Gly Val Ala Trp Ile Phe Ser Ala
                85                  90                  95

Cys Gly Glu Cys Glu Phe Cys Arg Ser Gly Arg Glu Asn Leu Cys Phe
            100                 105                 110

Ala Phe Cys Ala Thr Gly Arg Asp Val Asp Gly Tyr Ala Gln Tyr
            115                 120                 125

Met Thr Val Pro Ala Ala Phe Ala Phe Arg Ile Pro Glu Gly Phe Thr
130                 135                 140

Asp Ala Glu Ala Ala Pro Leu Leu Cys Ala Gly Ala Ile Gly Tyr Arg
145                 150                 155                 160

Ser Leu Asn Leu Ser Gly Leu Lys Asn Gly Gln Pro Leu Gly Leu Thr
                165                 170                 175

Gly Phe Gly Ala Ser Ala His Leu Val Leu Met Met Ala Arg Tyr Arg
            180                 185                 190

Phe Pro Asp Ser Glu Val Tyr Val Phe Ala Arg His Pro Glu Glu Arg
            195                 200                 205

Ala Phe Ala Leu Gln Leu Gly Ala Val Trp Ala Gly Asp Thr Ala Asp
            210                 215                 220

Ile Ala Pro Ala Pro Leu Ala Ala Ile Ile Asp Thr Thr Pro Ala Trp
225                 230                 235                 240

Lys Pro Val Val Ala Ala Leu Ala Asn Leu Ala Pro Gly Gly Arg Leu
                245                 250                 255

Val Val Asn Ala Ile Arg Lys Ala Pro Asp Asp Arg Ala Cys Leu Ala
            260                 265                 270

Glu Leu Asp Tyr Ala Arg His Leu Trp Met Glu Arg Glu Ile Lys Ser
            275                 280                 285

Val Ala Asn Val Ala Arg Ser Asp Val Ala Gly Phe Leu Ala Leu Ala
        290                 295                 300

Ala Glu Met Gly Ile Arg Pro Glu Thr Glu Glu Tyr Pro Phe Glu Asp
305                 310                 315                 320

Ala Asp Arg Ala Leu Leu Asp Leu Lys Gln Arg Ile Arg Gly Ala
                325                 330                 335

Lys Val Leu Arg Val Thr
            340

<210> SEQ ID NO 54
<211> LENGTH: 1029
<212> TYPE: DNA
<213> ORGANISM: Methylococcus capsulatus

<400> SEQUENCE: 54
atgaaagctt gggtgatcga ccgaatcggc ccgctggact cgtcgcgaac tctgctacgc      60
gccaccgacc tcccggtgcc ggagcccggc cctggcgaaa tcctgctgca ggtggcggtt     120
tgcggcgtct gccacaccga atcgacgag atcgagggcc gcaccgcgcc gccgcgcctg      180
ccggtcgtgc ccgacacca gcggtcggt cggatcgcgg ctctcggctc cggcgtggcg      240
gaattcgctt tgggcgaccg cgtcggcgtg gcctggatct tttctgcctg cggagaatgc     300
```

```
gaattctgcc ggtcgggacg ggagaacctc tgtttcgcat tctgtgccac cgggcgcgat    360
gtcgacggcg gctacgccca gtacatgacc gtcccggcgg cctttgcttt ccgcattccg    420
gagggattca ccgatgccga agcggcgccg cttctgtgcg ccggcgccat cggttaccgt    480
tcgctcaatc tcagcgggct gaaaaacggc cagccgctgg ggctcaccgg gttcggggct    540
tccgcccatc tggtgctgat gatggcccgg taccggtttc ccgattcgga agtctatgtc    600
tttgcgcgtc atcccgagga gcgcgcgttc gcgctgcagc tgggcgcggt ctgggccggc    660
gacaccgcgg acattgctcc cgccccgctg ccgccatca tcgacacgac gccggcgtgg    720
aagccggtgg tcgcagcgct cgccaacctc gctcccggtg ccggctggt cgttaatgcg    780
atccgcaagg cgccggacga tcgcgcctgt ctcgccgaac tcgactatgc ccggcacttg    840
tggatggaac gggaaatcaa gtcggtcgcc aacgtggcgc gcagtgacgt ggccgggttc    900
ctggcgctgg cggcggaaat gggcatccgt cccgagacgg aggagtaccc gttcgaggat    960
gccgaccggg cgctgctcga cctcaagcaa cgccggattc gcggggcgaa ggtgttgcgg   1020
gtgacttga                                                            1029
```

<210> SEQ ID NO 55
<211> LENGTH: 355
<212> TYPE: PRT
<213> ORGANISM: Methylococcus capsulatus

<400> SEQUENCE: 55

```
Met Pro Thr Ala Lys Ala Tyr Ala Ala Phe Ser Ala Asp Ser Ala Leu
1               5                   10                  15

Ala Pro Phe Val Leu Gln Arg Arg Asp Pro Leu Pro Gln Asp Ile Arg
            20                  25                  30

Ile Gly Ile Leu Tyr Cys Gly Val Cys His Ser Asp Leu His Gln Ala
        35                  40                  45

Arg Asn Glu Trp Asn Ala Thr Thr Tyr Pro Cys Val Pro Gly His Glu
    50                  55                  60

Ile Val Gly Lys Val Leu Glu Val Gly Arg Ser Val Thr Lys Phe Lys
65                  70                  75                  80

Pro Gly Asp Thr Val Ala Val Gly Cys Met Val Asp Ser Cys Arg Thr
                85                  90                  95

Cys Pro Asn Cys Val Asp Ala Leu Glu Gln His Cys Glu His Gly Pro
            100                 105                 110

Val Phe Thr Tyr Asn Ser Pro Asp Pro His Gly Gly Met Thr Phe
        115                 120                 125

Gly Gly Tyr Ala Glu Ser Ile Val Val Asp Glu Ala Phe Val Leu Arg
    130                 135                 140

Ile Pro Asp Gly Leu Asp Leu Ala Ala Ala Pro Leu Leu Cys Ala
145                 150                 155                 160

Gly Ile Thr Thr Tyr Ser Pro Leu Arg His Trp Lys Val Gly Ala Gly
                165                 170                 175

Gln Arg Val Gly Val Val Gly Leu Gly Gly Leu Gly His Met Ala Leu
            180                 185                 190

Lys Phe Ala His Thr Phe Gly Ala Glu Thr Val Leu Phe Thr Thr Thr
        195                 200                 205

Pro Asp Lys Ala Glu Asp Ala Arg Arg Leu Gly Ala Asp Glu Val Val
    210                 215                 220

Val Ser Arg Asp Pro Glu Ala Met Ala Arg Gln Ala Gly Arg Phe Asp
225                 230                 235                 240
```

```
Phe Ile Leu Asp Thr Val Ser Ala Pro His Asp Ile Asp Ala Tyr Leu
                245                 250                 255

Asn Leu Leu Arg Arg Asp Gly Thr Leu Thr Leu Val Gly Val Pro Pro
            260                 265                 270

Gln Gly Val Gln Val Met Pro Phe Ser Leu Ile Gly Gly Arg Arg Arg
        275                 280                 285

Leu Ala Gly Ser Leu Ile Gly Ile Arg Glu Thr Gln Glu Met Leu
    290                 295                 300

Asp Phe Cys Gly Glu His Gly Ile Val Cys Asp Ile Glu Leu Ile Pro
305                 310                 315                 320

Ile Gln Gly Ile Asn Asp Ala Phe Glu Arg Met Leu Lys Ser Asp Val
                325                 330                 335

Lys Tyr Arg Phe Val Ile Asp Met Ala Thr Leu Asn Gly Glu Ser Ser
            340                 345                 350

Gly Gly Arg
        355

<210> SEQ ID NO 56
<211> LENGTH: 1068
<212> TYPE: DNA
<213> ORGANISM: Methylococcus capsulatus

<400> SEQUENCE: 56
atgcctacag ccaaagccta tgccgctttt tccgcagact cggcgctggc gccgttcgtc      60
ctgcagcggc gcgaccccact gccccaggac atccgcatcg aatcctgta ctgcggtgtc     120 tgccattccg acctgcacca ggcacgcaat gagtggaatg cgaccacata tccttgtgtg    180
ccaggccatg agatcgtcgg caaggtcctt gaagtcggcc gcagcgtgac gaagttcaag    240
cccggcgaca cggtcgcggt gggctgcatg gtggattcct gccggacctg cccgaactgc    300
gtggacgccc tggaacagca ctgcgagcac ggccccgtct caacctacaa cagccccgat    360
ccgcacggcg gcggcatgac cttcggtggc tatgccgaga gcatcgtggt cgacgaggcc    420
ttcgtgctgc ggataccgga cggactggac ctcgcggccg ccgccccgct gttgtgcgcc    480
gggattacca cctattcgcc cctgcggcac tggaaagtgg gggcgggtca gcgggtcggg    540
gtcgtcggtc tgggtggact gggacacatg gcgctcaagt tcgcgcatac cttcggcgcc    600
gaaacggtgc tgttcacgac gacgccggac aaggcggagg atgcccgtcg gctgggagcg    660
gacgaggtcg tcgtgtcgag ggatcccgag gccatggcgc ggcaggccgg ccggttcgat    720
ttcatcctcg acaccgtctc ggcgccccat gacatcgatg cctatctgaa cctgctgagg    780
cgggacggca cgctgaccct ggtcggcgta cctccgcaag gggtacaggt catgcccttc    840
agcctgatcg gcgggcgccg cgcactggct ggttcattga tcggcggcat ccgggaaacc    900
caggagatgc tggatttctg cggcgaacac ggcatcgtct gcgacatcga gctgattccg    960
atccaaggaa tcaacgacgc cttcgagcgc atgctcaaaa gcgacgtgaa ataccgtttc   1020
gtgatcgaca tggcgacgct gaacggggag tcgtccggag gcgatga                 1068

<210> SEQ ID NO 57
<211> LENGTH: 348
<212> TYPE: PRT
<213> ORGANISM: Saccharomyces cerevisiae

<400> SEQUENCE: 57

Met Ser Ile Pro Glu Thr Gln Lys Ala Ile Ile Phe Tyr Glu Ser Asn
1               5                   10                  15
```

```
Gly Lys Leu Glu His Lys Asp Ile Pro Val Pro Lys Pro Asn
             20                  25                  30

Glu Leu Leu Ile Asn Val Lys Tyr Ser Gly Val Cys His Thr Asp Leu
                 35                  40                  45

His Ala Trp His Gly Asp Trp Pro Leu Pro Thr Lys Leu Pro Leu Val
 50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
            115                 120                 125

Tyr Ala Thr Ala Asp Ala Val Gln Ala Ala His Ile Pro Gln Gly Thr
            130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
            195                 200                 205

Glu Leu Phe Thr Ser Leu Gly Gly Glu Val Phe Ile Asp Phe Thr Lys
210                 215                 220

Glu Lys Asp Ile Val Ser Ala Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Val Lys Ser
            275                 280                 285

Ile Ser Ile Val Gly Ser Tyr Val Gly Asn Arg Ala Asp Thr Arg Glu
            290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
            325                 330                 335

Gln Ile Ala Gly Arg Tyr Val Val Asp Thr Ser Lys
            340                 345

<210> SEQ ID NO 58
<211> LENGTH: 1047
<212> TYPE: DNA
<213> ORGANISM: Saccharomyces cerevisiae

<400> SEQUENCE: 58
atgagcatcc ccgagaccca gaaggccatc atcttctacg agagcaacgg caagctggaa      60
cataaggaca tcccggtgcc caagcccaag ccgaacgaac tgctgatcaa cgtgaagtac     120
agcggcgtct gccacaccga cctgcacgcg tggcatggcg actggccgct gcccaccaag     180
ctgcccctgg tgggcggcca tgaaggcgcc ggcgtcgtgg tcggcatggg cgagaacgtc     240
```

```
aagggctgga agatcggcga ctacgcgggc atcaagtggc tgaacggcag ctgcatggcc    300
tgcgagtatt gcgaactggg caacgaatcg aactgcccgc acgcggacct gtccggctac    360
acccatgacg gcagcttcca ggagtatgcc accgcggacg ccgtgcaggc cgcgcacatc    420
ccgcagggca ccgacctggc ggaggtggcc cccatcctgt gcgccggcat caccgtctac    480
aaggcgctga agagcgccaa cctgcgcgcg ggccattggg ccgcgatctc gggcgccgcc    540
ggtggcctgg ctccctggc cgtgcagtac gcgaaggcga tgggctaccg cgtcctgggc    600
atcgacggcg gtccgggcaa ggaagagctg ttcacctccc tgggcggcga agtgttcatc    660
gacttcacca aggagaagga catcgtcagc gccgtggtca aggcgaccaa cggcggcgcc    720
cacggcatca tcaacgtgtc ggtctccgaa gccgcgatcg aggcgtcgac ccgctactgc    780
cgggccaacg gcaccgtggt cctggtgggc ctgcccgcgg gcgccaagtg cagctcggac    840
gtcttcaacc atgtggtcaa gagcatctcg atcgtgggct cgtatgtcgg caaccgcgcc    900
gacacccgcg aggccctgga cttcttcgcc cgtggcctgg tcaagtcccc gatcaaggtg    960
gtcggcctgt ccagcctgcc cgagatctac gaaaagatgg agaagggcca gatcgccggc    1020
cgctatgtgg tcgacacctc caagtga                                        1047
```

<210> SEQ ID NO 59
<211> LENGTH: 509
<212> TYPE: PRT
<213> ORGANISM: Methylococcus capsulatus

<400> SEQUENCE: 59

```
Met Leu Gln Lys Tyr Ile Glu Lys Ile Leu Arg Ala Arg Val Tyr Asp
1               5                   10                  15

Val Ala Gln Glu Thr Pro Leu Asp Pro Ala Pro Gly Leu Ser Arg Arg
            20                  25                  30

Leu Asp Asn Thr Val Leu Ile Lys Arg Glu Asp Leu Gln Pro Val Phe
        35                  40                  45

Ser Phe Lys Leu Arg Gly Ala Tyr Asn Lys Ile Ala Ser Leu Thr Pro
    50                  55                  60

Glu Ala Arg Ala Ala Gly Val Ile Ala Ala Ser Ala Gly Asn His Ala
65                  70                  75                  80

Gln Gly Val Ala Leu Ala Ala Gln Arg Leu Gly Ile Arg Ala Val Ile
                85                  90                  95

Val Met Pro Cys Thr Thr Pro His Ile Lys Val Asp Ala Val Arg Asn
            100                 105                 110

Arg Gly Gly Glu Val Val Leu His Gly Asp Ala Tyr Asp Glu Ala Tyr
        115                 120                 125

Glu His Ala Leu Glu Leu Ala Arg Asp Gln Cys Leu Thr Phe Val His
    130                 135                 140

Pro Tyr Asp Asp Pro Glu Val Ile Ala Gly Gln Gly Thr Ile Gly Met
145                 150                 155                 160

Glu Ile Leu Arg Gln His Gln Asp Ala Ile His Ala Ile Phe Val Pro
                165                 170                 175

Val Gly Gly Gly Gly Leu Ile Ala Gly Ile Ala Ala Tyr Val Lys Phe
            180                 185                 190

Val Arg Pro Asp Ile Arg Val Ile Gly Val Glu Pro Val Asp Ser Asp
        195                 200                 205

Cys Leu His Arg Ala Leu Lys Ala Lys Arg Arg Val Ile Leu Lys Gln
    210                 215                 220

Val Gly Leu Phe Ala Asp Gly Val Ala Val Lys Gln Val Gly Lys Glu
```

```
                        225                 230                 235                 240
            Pro Phe His Leu Ala His Gln Trp Val Asp Glu Val Thr Val Asp
                                245                 250                 255

Thr Asp Glu Ile Cys Ala Ala Ile Lys Asp Ile Phe Asp Asp Thr Arg
                                260                 265                 270

Ser Ile Ala Glu Pro Ala Gly Ala Leu Gly Ile Ala Gly Leu Lys Lys
                                275                 280                 285

Tyr Val Ala Glu Thr Gly Ile Lys Asn Ala Cys Leu Val Ala Ile Glu
                                290                 295                 300

Ser Gly Ala Asn Ile Asn Phe Asp Arg Leu Arg His Val Ala Glu Arg
            305                 310                 315                 320

Ala Glu Ile Gly Glu Lys Arg Glu Leu Leu Leu Ala Val Thr Ile Pro
                                325                 330                 335

Glu Arg Pro Gly Ser Phe Leu Glu Phe Cys Arg Val Leu Gly Arg Arg
                                340                 345                 350

Asn Ile Thr Glu Phe Asn Tyr Arg Phe Phe Asp Glu Lys Ala Ala Gln
                                355                 360                 365

Val Phe Val Gly Leu Pro Val Ala Ser Gly Ala Ile Asp Arg Glu Ser
                        370                 375                 380

Leu Val Arg Glu Phe Glu Arg Gln Gly Phe Gly Val Leu Asp Leu Thr
            385                 390                 395                 400

Gly Asn Glu Leu Ala Ile Glu His Ile Arg Tyr Met Val Gly Gly His
                                405                 410                 415

Ala Pro Lys Leu Leu Asp Glu Gln Val Tyr Ser Phe Glu Phe Pro Glu
                                420                 425                 430

Arg Pro Gly Ala Leu Leu Arg Phe Leu Ser Ile Met Gly Gly Arg Trp
                                435                 440                 445

Asn Ile Ser Leu Phe His Tyr Arg Asn His Gly Ala Ala Phe Gly Arg
                                450                 455                 460

Val Leu Met Gly Ile Gln Val Pro Lys Pro Glu Arg Lys Ala Phe Arg
            465                 470                 475                 480

Glu Phe Leu Glu Ala Ile Gly Tyr Ala Phe Lys Glu Glu Thr Gln Asn
                                485                 490                 495

Pro Ala Tyr Arg Leu Phe Ala Gly Gly Ser Glu Arg Gly
                                500                 505

<210> SEQ ID NO 60
<211> LENGTH: 1530
<212> TYPE: DNA
<213> ORGANISM: Methylococcus capsulatus

<400> SEQUENCE: 60
atgctgcaaa aatacataga gaagattctg cgcgcccgtg tctacgacgt tgcccaggag      60 acccccgctgg acccggcgcc cggcctgtcg cggcggctgg acaacacggt gctgatcaag    120
cgcgaggacc tgcagccggt gttctcgttc aagctgcgcg cgcctacaa caagatcgcc     180 tcgctcacac ccgaggcgcg cgcggccggc gtgatcgcgg cctccgccgg caaccacgcc    240
cagggcgtgg cactggcggc gcagcggctg gcatccgcg ccgtgatcgt gatgccttgc     300
accaccccgc atatcaaggt cgatgcggtg cgcaaccgag gcggtgaggt cgtactgcat    360
ggcgacgcct atgacgaagc ctacgaacat gcgctggaac tggcccgcga ccagtgcctg    420
accttcgtcc accctacga cgatccggaa gtcatcgccg gcaaggcac catcggcatg      480 gaaatcctgc gccagcacca ggacgccatc cacgccatct tcgtgcctgt gggcggcggc    540
```

```
ggattgatcg ccggcatcgc cgcctacgtc aagttcgtgc gcccggacat ccgcgtcatc      600
ggcgtggaac cagtggactc cgactgcctg caccgggcgc tgaaagccaa gcggcgggtg      660
atcctgaagc aggtgggcct gttcgccgac ggcgtcgcgg tgaagcaggt cggcaaggaa      720
ccgttccatc tcgcccacca gtgggtggac gaggtcgtga ccgtcgacac cgacgaaatc      780
tgcgccgcca tcaaggacat cttcgacgac acccgctcca tcgccgagcc ggcgggcgcg      840
ctgggcatcg ccgggctcaa gaaatacgtg ccgaaacag gaatcaagaa cgcgtgcctg       900
gtggcgatcg aaagcggcgc caacatcaac ttcgaccggc tgcgccacgt cgctgagcgc      960
gccgagatcg cgaaaagcg cgaactgctg ctggcagtga cgatcccga gcggcccggc       1020 agcttcctcg aattctgccg ggtgctgggc cgccgcaaca tcaccgaatt caactaccgc      1080
ttcttcgacg aaaaggccgc ccaggtgttc gtcggcctcc cggtggcgag cggcgcgatc      1140
gaccgcgaaa gcctggtccg cgaattcgaa cgccagggtt tcggcgtgct cgacctgacc      1200
ggcaacgaac tcgccatcga acacatccgc tacatggtcg gcggccacgc gccgaaactg      1260
ctggacgaac aggtctacag cttcgaattc cccgagcgac ccggcgcgct gctgcgcttc      1320
ctgtccatca tgggcgggcg ctggaacatc agcctgttcc attaccgcaa ccacggcgcc      1380
gccttcggcc gggtactgat gggcatccag gtgccgaaac cggaacgcaa ggccttccgg      1440
gaattcctcg aagccatcgg ctacgccttc aaggaggaaa cccaaaatcc cgcctaccgg      1500
ctgttcgcgg ggggcagcga gcgggggtga                                      1530
```

<210> SEQ ID NO 61
<211> LENGTH: 514
<212> TYPE: PRT
<213> ORGANISM: Methylococcus capsulatus

<400> SEQUENCE: 61

```
Met His Asp Arg Leu Ile Ile Phe Asp Thr Thr Leu Arg Asp Gly Glu
1               5                   10                  15

Gln Ser Pro Gly Ala Ser Met Thr Arg Asp Glu Lys Val Arg Ile Ala
            20                  25                  30

Arg Ala Leu Glu Arg Leu Lys Val Asp Val Ile Glu Ala Gly Phe Pro
        35                  40                  45

Ala Ala Ser Pro Gly Asp Phe Glu Ala Val Gln Ala Val Ala Arg Thr
    50                  55                  60

Ile Lys Asp Ser Arg Val Cys Gly Leu Ala Arg Ala Leu Asp Arg Asp
65                  70                  75                  80

Ile Asp Arg Ala Gly Glu Ala Leu Lys Asp Ala Gln Arg Ala Arg Ile
                85                  90                  95

His Thr Phe Ile Ala Thr Ser Pro Ile His Met Arg His Lys Leu Gln
            100                 105                 110

Met Ser Pro Asp Gln Val Val Glu Tyr Ala Val Lys Ala Val Lys Arg
        115                 120                 125

Ala Arg Gln Tyr Thr Asp Val Glu Phe Ser Pro Glu Asp Ala Gly
    130                 135                 140

Arg Ser Glu Glu Asp Phe Leu Cys Arg Ile Leu Glu Ala Val Ile Asp
145                 150                 155                 160

Ala Gly Ala Thr Thr Leu Asn Ile Pro Asp Thr Val Gly Tyr Ala Phe
                165                 170                 175

Pro Glu Gln Phe Gly His Met Ile Gly Arg Leu Ile Glu Arg Ile Pro
            180                 185                 190

Asn Ser Asp Lys Ala Val Phe Ser Val His Cys His Asn Asp Leu Gly
```

```
                195                 200                 205
Leu Ala Val Ala Asn Ser Leu Ala Ala Val Leu His Gly Ala Arg Gln
    210                 215                 220

Val Glu Cys Thr Ile Asn Gly Leu Gly Glu Arg Ala Gly Asn Ala Ala
225                 230                 235                 240

Leu Glu Glu Ile Val Met Ala Val Arg Thr Arg Lys Asp Ile Phe Pro
                245                 250                 255

Cys His Thr Asp Ile Glu Thr Arg Glu Ile Val Ala Cys Ser Lys Leu
            260                 265                 270

Val Ser Ser Ile Thr Gly Phe Pro Ile Gln Pro Asn Lys Ala Ile Val
        275                 280                 285

Gly Ala Asn Ala Phe Ala His Glu Ser Gly Ile His Gln Asp Gly Val
    290                 295                 300

Leu Lys Ser Arg Glu Thr Tyr Glu Ile Met Ser Ala Glu Asp Val Gly
305                 310                 315                 320

Trp Ser Thr Asn Arg Met Val Leu Gly Lys His Ser Gly Arg Asn Ala
                325                 330                 335

Phe Arg Thr Arg Met Gln Glu Leu Gly Ile Glu Phe Ala Ser Glu Glu
            340                 345                 350

Glu Leu Asn Ser Val Phe Gln Arg Phe Lys Val Leu Ala Asp Lys Lys
        355                 360                 365

His Glu Ile Phe Asp Glu Asp Leu Gln Ala Leu Ile Thr Glu Ala Gly
    370                 375                 380

Ala Glu Ala Glu Asp Glu Arg Val Lys Leu Val Ala Leu Arg Val Cys
385                 390                 395                 400

Ser Glu Thr Gly Glu Ile Pro His Ala Gln Val Thr Ile Lys Val Asp
                405                 410                 415

Asn Glu Glu Arg Thr Gly Thr Ser Ser Gly Gly Ala Val Asp Ala
            420                 425                 430

Ser Leu Lys Ala Ile Glu Ser Leu Leu His Thr Asp Thr Ala Leu Thr
        435                 440                 445

Leu Tyr Ser Val Asn Asn Ile Thr Ser Gly Thr Asp Ala Gln Gly Glu
    450                 455                 460

Val Thr Val Arg Leu Glu Lys Gly Gly Arg Ile Val Asn Gly Gln Gly
465                 470                 475                 480

Ala Asp Thr Asp Ile Val Ile Ala Ser Lys Ala Tyr Val Asn Ala
                485                 490                 495

Val Asn Lys Leu Leu Ala Pro Ile Gln Arg Thr His Pro Gln Val Gly
            500                 505                 510

Asp Val
```

<210> SEQ ID NO 62
<211> LENGTH: 1545
<212> TYPE: DNA
<213> ORGANISM: Methylococcus capsulatus

<400> SEQUENCE: 62

```
atgcacgaca gactgatcat tttcgacacg accttgcgcg acggagagca gagccccggc    60
gcgtccatga cccgcgatga aaaggtccgc atcgcccggg cgctggagcg tctgaaggtc   120
gacgtcatcg aggcgggctt tcccgccgcc agccccggcg atttcgaggc cgtccaggcc   180
gtggcccgga ccatcaagga cagcagggtc tgcggcctgg cccgcgccct cgaccgcgac   240
atcgaccgcg ccggcgaagc cctcaaggac gcccagcgcg cccgcatcca caccttcatc   300
```

```
gccacctcgc ccatccacat gcggcacaag ctgcagatgt cgcccgacca ggtggtggaa    360
tacgcggtca aggccgtcaa gcgggcccgc cagtacaccg acgacgtgga attctcgccc    420
gaggacgccg gacgctccga ggaggatttc ctctgccgca tcctggaagc cgtgatcgat    480
gcgggggcga ccacgctgaa catccccgac accgtcggct acgccttccc ggaacagttc    540
gggcacatga tcggccggct gatcgagcgg attccgaact ccgacaaggc cgtgttctcg    600
gttcactgcc acaacgacct gggactggcg gtcgccaatt cgctggccgc cgtgctgcac    660
ggcgcgcgcc aggtggaatg caccatcaac gggctgggcg agcgggccgg caacgccgcg    720
ctggaagaga tcgtcatggc ggtgcgcacc cgtaaagaca tcttcccctg ccacaccgac    780
atcgagacac gggaaatcgt ggcctgctcc aaactggtct ccagcatcac cggtttcccg    840
atccagccca acaaggccat cgtcggcgcc aacgccttcg cccacgagtc gggcatccac    900
caggacggtg tgctcaagag ccgggaaacc tacgagatca tgagcgccga ggacgtgggg    960
tggagcacca accgcatggt gctgggcaaa cattccggcc gcaacgcgtt ccgtacccgg   1020
atgcaggaac tcggcatcga gttcgcctcg gaagaggaac tgaactcggt gttccagcgc   1080
ttcaaggtgc tggccgacaa gaagcacgag atcttcgacg aggacctcca ggccctcatc   1140
accgaagccg gcgcagaagc cgaagacgaa cgggtcaagc tggtcgcgct gcgggtctgc   1200
tcggaaacgg gcgagattcc ccacgcccag gtcaccatca aggtggacaa cgaggaacgc   1260
accggcacat cgagcggcgg cggcgccgtg gacgccagcc tcaaggccat cgaatcgctg   1320
ctgcacacgg acaccgcgct gacgctgtac tcggtcaaca acatcaccag cggcaccgac   1380
gcccagggcg aggtcaccgt gcggctcgag aaaggcgggc gcatcgtcaa cggccagggc   1440
gccgataccg acatcgtgat cgcctcggcc aaggcctacg tcaacgccgt gaacaagctg   1500
ctggcgccca tccagcgcac ccacccgcaa gtcggggatg tgtga                   1545
```

<210> SEQ ID NO 63
<211> LENGTH: 470
<212> TYPE: PRT
<213> ORGANISM: Methylococcus capsulatus

<400> SEQUENCE: 63

```
Met Ser Gly Lys Thr Leu Tyr Asp Lys Leu Trp Asp Asp His Val Val
1               5                   10                  15

His Val Asp Ala Asp Gly Ser Cys Leu Ile Tyr Ile Asp Arg His Leu
            20                  25                  30

Ile His Glu Val Thr Ser Pro Gln Ala Phe Glu Gly Leu Arg Met Ala
        35                  40                  45

Gly Arg Val Pro Trp Arg Val Asp Ala Asn Leu Ala Val Ala Asp His
    50                  55                  60

Asn Val Pro Thr Ala Asp Arg Asp Arg Gly Ile Ala Asp Pro Val Ser
65                  70                  75                  80

Arg Leu Gln Val Glu Thr Leu Asp Lys Asn Cys Ala Asp Phe Gly Ile
                85                  90                  95

Thr Glu Phe Ala Met Asp Asp Val Arg Gln Gly Ile Val His Val Ile
            100                 105                 110

Gly Pro Glu Gln Gly Ala Thr Leu Pro Gly Met Thr Ile Val Cys Gly
        115                 120                 125

Asp Ser His Thr Ser Thr His Gly Ala Phe Gly Ala Leu Ala Phe Gly
    130                 135                 140

Ile Gly Thr Ser Glu Val Glu His Val Leu Ala Thr Gln Cys Leu Val
145                 150                 155                 160

```

```
Gln Arg Lys Ala Lys Asn Met Leu Val Arg Val Gln Gly Lys Leu Ala
                165                 170                 175
Pro Gly Val Thr Ala Lys Asp Leu Val Leu Ala Val Ile Gly Arg Ile
            180                 185                 190
Gly Thr Ala Gly Gly Thr Gly Tyr Thr Ile Glu Phe Ala Gly Glu Ala
        195                 200                 205
Ile Arg Gly Leu Ser Met Glu Gly Arg Met Thr Val Cys Asn Met Ala
    210                 215                 220
Ile Glu Ala Gly Ala Arg Ala Gly Leu Val Val Asp Glu Val Thr
225                 230                 235                 240
Leu Asp Tyr Leu Glu Gly Arg Pro Phe Ala Pro Gly Ala Leu Trp
                245                 250                 255
Glu Arg Ala Val Glu Ala Trp Lys Asp Leu His Ser Asp Pro Asp Ala
            260                 265                 270
Val Phe Asp Lys Val Val Glu Ile Asp Ala Ala Ser Ile Lys Pro Gln
        275                 280                 285
Val Thr Trp Gly Thr Ser Pro Glu Gln Val Pro Val Asp Ala Glu
    290                 295                 300
Val Pro Asp Pro Ala Thr Glu Ala Asp Pro Val Arg Arg Glu Ser Met
305                 310                 315                 320
Glu Arg Ala Leu Gln Tyr Met Asp Leu Leu Pro Gly Thr Pro Ile Gly
                325                 330                 335
Ala Ile Arg Val Asp Arg Val Phe Ile Gly Ser Cys Thr Asn Ala Arg
            340                 345                 350
Ile Glu Asp Leu Arg Ala Ala Ala Glu Val Val Arg Gly His Lys Arg
        355                 360                 365
Ala Ala Ser Val Lys Gln Ala Leu Val Val Pro Gly Ser Gly Leu Val
    370                 375                 380
Lys Arg Gln Ala Glu Gln Gly Leu Asp Lys Val Phe Leu Glu Ala
385                 390                 395                 400
Gly Phe Glu Trp Arg Asp Pro Gly Cys Ser Met Cys Leu Ala Met Asn
                405                 410                 415
Ala Asp Arg Leu Glu Pro Gly Glu Arg Cys Ala Ser Thr Ser Asn Arg
            420                 425                 430
Asn Phe Glu Gly Arg Gln Gly Tyr Gly Gly Arg Thr His Leu Val Ser
        435                 440                 445
Pro Ala Met Ala Ala Ala Ala Ile His Gly His Phe Val Asp Ile
    450                 455                 460
Thr Glu Gly Gly Arg Ala
465                 470

<210> SEQ ID NO 64
<211> LENGTH: 1413
<212> TYPE: DNA
<213> ORGANISM: Methylococcus capsulatus

<400> SEQUENCE: 64
atgagcggaa aacccttta cgacaagctg tgggacgacc acgtcgtgca tgtcgatgcg    60
gacggatcgt gcctgatcta catcgatcgt catctaatcc acgaggtgac ctcgcctcag   120
gcattcgaag gctgcggat ggcggggcgt gtaccctggc gggtggatgc caatcttgcg   180
gtggccgacc acaacgtccc caccgccgac cgcgacaggg gtatcgccga tccggtgtcg   240
cgcctgcagg tggaaaccct ggacaagaac tgcgccgatt tcggcatcac cgaattcgcg   300
```

```
atggacgacg tgcgccaggg tatcgtgcat gtgatcgggc ccgagcaggg cgcgaccctg    360
ccgggcatga ccatcgtttg cggcgattcg catacttcga ctcacggtgc tttcggggcg    420
ctcgccttcg ggatcggcac ttccgaggtc gagcacgtac tggccacgca atgcctggtg    480
cagcgcaagg cgaagaacat gctggtccgc gtccagggca agctggcgcc gggcgtgacg    540
gcgaaagatc tggtactggc ggtcatcggc cgtatcggaa ccgccggcgg caccggctac    600
accatcgaat cgctggcga agccattcgc ggcctgtcga tggaaggccg atgacggtc     660
tgcaacatgg cgatcgaggc gggcgcacgt gccggcctgg tggcggtgga cgaagtcacg    720
ctcgactatc tcgagggccg cccgttcgct ccggcgggcg cgttgtggga gcgggcggtc    780
gaggcatgga aagacctgca cagcgatccg gatgcggtat cgacaaggt cgtcgagatc     840
gatgccgcca gcatcaagcc gcaggtgacc tggggaactt cgccggaaca ggtcgtgccg    900
gtggatgccg aggtgcccga cccggccacg gaagccgatc ccgtgcggcg ggaaagcatg    960
gagcgggcgc tgcagtacat ggatctcctg ccgggcacgc caatcggcgc gatccgggtc   1020
gatcgggtgt tcatcggctc ctgcaccaat gccaggatcg aggatctgcg cgccgcggcg   1080
gaagtcgtcc gggggcacaa gcgcgctgcc agcgtgaagc aggcactggt ggtgcccggc   1140
tcgggtttgg tcaagcggca ggcggagcag gaggggctgg acaaggtgtt cctcgaggcc   1200
ggtttcgaat ggcgcgaccc gggttgttcc atgtgtctgg cgatgaacgc cgaccgcctg   1260
gaacccggcg agcgttgcgc ctcgacctcc aaccggaatt ttgaggggcg ccagggctat   1320
ggcgggcgta cccatctggt gagtccggcc atggcggctg cggcggccat tcacgggcat   1380
ttcgtcgaca tcaccgaagg agggcgcgca tga                                1413
```

<210> SEQ ID NO 65
<211> LENGTH: 212
<212> TYPE: PRT
<213> ORGANISM: Methylococcus capsulatus

<400> SEQUENCE: 65

```
Met Lys Pro Phe Lys Lys Phe Thr Ser Arg Val Val Pro Leu Asp Arg
1               5                   10                  15

Ala Asn Val Asp Thr Asp Ala Ile Ile Pro Lys Gln Phe Leu Lys Ser
            20                  25                  30

Ile Arg Arg Ser Gly Phe Gly Pro Tyr Leu Phe Asp Glu Trp Arg Tyr
        35                  40                  45

Leu Asp Arg Gly Glu Pro Asp Met Asp Cys Ser His Arg Pro Leu Asn
    50                  55                  60

Pro Glu Phe Val Leu Asn Leu Pro Cys Tyr Ala Gly Ala Arg Ile Leu
65                  70                  75                  80

Leu Ala Arg Lys Asn Phe Gly Cys Gly Ser Ser Arg Glu His Ala Pro
                85                  90                  95

Trp Ala Leu Glu Asp Tyr Gly Phe Arg Ala Ile Ile Ala Pro Ser Phe
            100                 105                 110

Ala Asp Ile Phe Tyr Asn Asn Cys Phe Lys Asn Gly Ile Leu Pro Ile
        115                 120                 125

Val Leu Asp Glu Ala Thr Val Asp Arg Leu Phe Ser Glu Ala Gly Pro
    130                 135                 140

Gly Phe Glu Leu Thr Val Asp Leu Glu Ser Gln Thr Val Ala Thr Pro
145                 150                 155                 160

Phe Gly Glu Thr Phe His Phe Asp Val Asp Ala Ser Arg Lys His Arg
                165                 170                 175
```

```
Leu Leu Asn Gly Leu Asp Asp Ile Gly Leu Thr Leu Gln His Ala Asp
            180                 185                 190

Ala Ile Arg Ala Tyr Glu Ala Arg Arg Lys Ser Ala Pro Trp Leu
        195                 200                 205

Phe Ala Val Pro
    210

<210> SEQ ID NO 66
<211> LENGTH: 639
<212> TYPE: DNA
<213> ORGANISM: Methylococcus capsulatus

<400> SEQUENCE: 66
atgaagcctt tcaagaaatt cacttcgcga gtcgtgccgt ggaccgcgc caatgtcgac      60 accgacgcca tcattcccaa gcagttcctg aagtccatcc gccgcagcgg gttcggtccc     120
tatctgttcg acgagtggcg ttacctggac cgtggcgagc ccgacatgga ttgcagccac     180
cgtccgctca acccggagtt cgtgctcaac ctgcccctgtt acgccggcgc caggatattg    240
ctggcccgca agaacttcgg ctgtggctcc tcgcgcgagc atgcgccctg gcgctggag     300 gattacggct ccgcgccat catcgcgccg agtttcgccg atatcttcta caacaactgc     360
ttcaagaacg gcatcctgcc catcgtgctc gacgaggcca cggtcgaccg gctgttttagc   420 gaggccgggc ccggcttcga gctcaccgtc gacctggagt cgcagaccgt ggcgacgccg    480
ttcggcgaga ccttccattt cgacgtggat gcctcccgca agcatcgtct gctgaacggc    540
ctggacgaca tcggtctgac ccttcagcat gccgatgcca tccgcgccta cgaagccgcc    600
cgcaggaagt ccgcaccctg gctgtttgcc gtccccttga                           639

<210> SEQ ID NO 67
<211> LENGTH: 559
<212> TYPE: PRT
<213> ORGANISM: Zymomonas mobilis

<400> SEQUENCE: 67

Met Ser Tyr Thr Val Gly Thr Tyr Leu Ala Ala Leu Val Gln Ile Gly
1               5                   10                  15

Leu Lys His His Phe Ala Val Ala Gly Asp Tyr Asn Leu Val Leu Leu
            20                  25                  30

Asp Asn Leu Leu Leu Asn Lys Asn Met Glu Gln Val Tyr Cys Cys Asn
        35                  40                  45

Glu Leu Asn Cys Gly Phe Ser Ala Glu Gly Tyr Ala Arg Ala Lys Ala
    50                  55                  60

Asp Ala Ala Ala Val Val Thr Tyr Ser Val Gly Ala Leu Ser Ala Phe
65                  70                  75                  80

Asp Ala Ile Gly Gly Ala Tyr Ala Glu Asn Leu Pro Val Ile Leu Ile
                85                  90                  95

Ser Gly Ala Pro Asn Asn Asn Asp His Ala Ala Gly His Val Leu His
            100                 105                 110

His Ala Leu Gly Lys Thr Asp Tyr His Tyr Gln Leu Glu Met Ala Lys
        115                 120                 125

Asn Ile Thr Ala Ala Ala Glu Ala Ile Tyr Thr Pro Glu Glu Ala Pro
    130                 135                 140

Ala Lys Ile Asp His Val Ile Lys Thr Ala Leu Arg Glu Lys Lys Pro
145                 150                 155                 160

Val Tyr Leu Glu Ile Ala Cys Asn Ile Ala Ser Met Pro Cys Ala Ala
                165                 170                 175
```

Pro Gly Pro Ala Ser Ala Leu Phe Asn Asp Glu Ala Ser Asp Glu Ala
          180                 185                 190

Ser Leu Asn Ala Ala Val Glu Glu Thr Leu Lys Phe Ile Ala Asn Arg
        195                 200                 205

Asp Lys Val Ala Val Leu Val Gly Ser Lys Leu Arg Ala Ala Gly Ala
210                 215                 220

Glu Glu Ala Ala Val Lys Phe Ala Asp Ala Leu Gly Gly Ala Val Ala
225                 230                 235                 240

Thr Met Ala Ala Ala Lys Ser Phe Phe Gln Lys Lys Thr Ala Leu His
                245                 250                 255

Arg Tyr Leu Met Gly Glu Val Ser Tyr Pro Gly Val Glu Lys Thr Met
            260                 265                 270

Lys Glu Ala Asp Ala Val Ile Ala Leu Ala Pro Val Phe Asn Asp Tyr
        275                 280                 285

Ser Thr Thr Gly Trp Thr Asp Ile Pro Asp Pro Lys Lys Leu Val Leu
        290                 295                 300

Ala Glu Pro Arg Ser Val Val Asn Gly Val Arg Phe Pro Ser Val
305                 310                 315                 320

His Leu Lys Asp Tyr Leu Thr Arg Leu Ala Gln Lys Val Ser Lys Lys
                325                 330                 335

Thr Gly Ala Leu Asp Phe Phe Lys Ser Leu Asn Ala Gly Glu Leu Lys
            340                 345                 350

Lys Ala Ala Pro Ala Asp Pro Ser Ala Pro Leu Val Asn Ala Glu Ile
        355                 360                 365

Ala Arg Gln Val Glu Ala Leu Leu Thr Pro Asn Thr Thr Val Ile Ala
    370                 375                 380

Glu Thr Gly Asp Ser Trp Phe Asn Ala Gln Arg Met Lys Leu Pro Asn
385                 390                 395                 400

Gly Ala Arg Val Glu Tyr Glu Met Gln Trp Gly His Ile Gly Trp Ser
                405                 410                 415

Val Pro Ala Ala Phe Gly Tyr Ala Val Gly Ala Pro Glu Arg Arg Asn
            420                 425                 430

Ile Leu Met Val Gly Asp Gly Ser Phe Gln Leu Thr Ala Gln Glu Val
        435                 440                 445

Ala Gln Met Val Arg Leu Lys Leu Pro Val Ile Phe Leu Ile Asn
    450                 455                 460

Asn Tyr Gly Tyr Thr Ile Glu Val Met Ile His Asp Gly Pro Tyr Asn
465                 470                 475                 480

Asn Ile Lys Asn Trp Asp Tyr Ala Gly Leu Met Glu Val Phe Asn Gly
                485                 490                 495

Asn Gly Tyr Asp Ser Gly Ala Gly Lys Gly Leu Lys Ala Lys Thr
            500                 505                 510

Gly Gly Glu Leu Ala Glu Ala Ile Lys Val Ala Leu Ala Asn Thr Asp
        515                 520                 525

Gly Pro Thr Leu Ile Glu Cys Phe Ile Gly Arg Glu Asp Cys Thr Glu
    530                 535                 540

Glu Leu Val Lys Trp Gly Lys Arg Val Ala Ala Arg Gln Gln Pro
545                 550                 555

<210> SEQ ID NO 68
<211> LENGTH: 1905
<212> TYPE: DNA
<213> ORGANISM: Zymomonas mobilis

<400> SEQUENCE: 68

```
tatcgctcat gatcgcgaca tgttctgata ttttcctcta aaaaagataa aaagtcttt     60
cgcttcggca gaagaggttc atcatgaaca aaaattcggc attttaaaa atgcctatag   120
ctaaatccgg aacgacactt tagaggtttc tgggtcatcc tgattcagac atagtgtttt   180
gaatatatgg agtaagcaat gagttatact gtcggtacct atttagcggc gcttgtccag   240
attggtctca agcatcactt cgcagtcgcg ggcgactaca acctcgtcct tcttgacaac   300
ctgcttttga acaaaaacat ggagcaggtt tattgctgta acgaactgaa ctgcggtttc   360
agtgcagaag ttatgctcg tgccaaagcg acgcagcag ccgtcgttac ctacagcgtc    420
ggtgcgcttt ccgcatttga tgctatcggt ggcgccatg cagaaaacct tccggttatc    480
ctgatctccg gtgctccgaa caacaatgat cacgctgctg gtcacgtgtt gcatcacgct   540
cttggcaaaa ccgactatca ctatcagttg aaatggcca agaacatcac ggccgcagct   600
gaagcgattt acaccccaga agaagctccg gctaaaatcg atcacgtgat taaaactgct   660
cttcgtgaga agaagccggt ttatctcgaa atcgcttgca acattgcttc catgccctgc   720
gccgctcctg gaccggcaag cgcattgttc aatgacgaag ccagcgacga agcttctttg   780
aatgcagcgg ttgaagaaac cctgaaattc atcgccaacc gcgacaaagt tgccgtcctc   840
gtcggcagca agctgcgcgc agctggtgct gaagaagctg ctgtcaaatt tgctgatgct   900
ctcggtggcg cagttgctac catggctgct gcaaaaagct tcttccagaa gaaaccgca    960
ttacatcggt acctcatggg tgaagtcagc tatccgggcg ttgaaaagac gatgaaagaa  1020
gccgatgcg ttatcgctct ggctcctgtc ttcaacgact actccaccac tggttggacg  1080
gatattcctg atcctaagaa actggttctc gctgaaccgc gttctgtcgt cgttaacggc  1140
gttcgcttcc ccagcgttca tctgaaagac tatctgaccc gtttggctca gaaagttcc   1200
aagaaaaccg gtgctttgga cttcttcaaa tccctcaatg caggtgaact gaagaaagcc  1260
gctccggctg atccgagtgc tccgttggtc aacgcagaaa tcgcccgtca ggtcgaagct  1320
cttctgaccc cgaacacgac ggttattgct gaaaccggtg actcttggtt caatgctcag  1380
cgcatgaagc tcccgaacgg tgctcgcgtt gaatatgaaa tgcagtgggg tcacatcggt  1440
tggtccgttc ctgccgcctt cggttatgcc gtcggtgctc cggaacgtcg caacatcctc  1500
atggttggtg atggttcctt ccagctgacg gctcaggaag tcgctcagat ggttcgcctg  1560
aaactgccgg ttatcatctt cttgatcaat aactatggtt acaccatcga agttatgatc  1620
catgatggtc cgtacaacaa catcaagaac tgggattatg ccggtctgat ggaagtgttc  1680
aacggtaacg gtggttatga cagcggcgct ggtaaaggcc tgaaggctaa accggtggc   1740
gaactggcag aagctatcaa ggttgctctg gcaaacaccg acggcccaac cctgatcgaa  1800
tgcttcatcg gtcgtgaaga ctgcactgaa gaattggtca aatggggtaa gcgcgttgct  1860
gcccgccaac agccgtaagc ctgttaacaa gctcctctag ttttt               1905
```

<210> SEQ ID NO 69
<211> LENGTH: 383
<212> TYPE: PRT
<213> ORGANISM: Zymomonas mobilis

<400> SEQUENCE: 69

```
Met Ala Ser Ser Thr Phe Tyr Ile Pro Phe Val Asn Glu Met Gly Glu
 1               5                  10                  15

Gly Ser Leu Glu Lys Ala Ile Lys Asp Leu Asn Gly Ser Gly Phe Lys
            20                  25                  30
```

Asn Ala Leu Ile Val Ser Asp Ala Phe Met Asn Lys Ser Gly Val Val
            35                  40                  45

Lys Gln Val Ala Asp Leu Leu Lys Ala Gln Gly Ile Asn Ser Ala Val
 50                  55                  60

Tyr Asp Gly Val Met Pro Asn Pro Thr Val Thr Ala Val Leu Glu Gly
 65                  70                  75                  80

Leu Lys Ile Leu Lys Asp Asn Asn Ser Asp Phe Val Ile Ser Leu Gly
                 85                  90                  95

Gly Gly Ser Pro His Asp Cys Ala Lys Ala Ile Ala Leu Val Ala Thr
                100                 105                 110

Asn Gly Gly Glu Val Lys Asp Tyr Glu Gly Ile Asp Lys Ser Lys Lys
                115                 120                 125

Pro Ala Leu Pro Leu Met Ser Ile Asn Thr Thr Ala Gly Thr Ala Ser
130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
                180                 185                 190

Met Asp Ala Leu Thr His Ala Phe Glu Ala Tyr Ser Ser Thr Ala Ala
                195                 200                 205

Thr Pro Ile Thr Asp Ala Cys Ala Leu Lys Ala Ala Ser Met Ile Ala
                210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Tyr
                260                 265                 270

Tyr Asn Leu Pro His Gly Val Cys Asn Ala Val Leu Leu Pro His Val
                275                 280                 285

Leu Ala Tyr Asn Ala Ser Val Val Ala Gly Arg Leu Lys Asp Val Gly
                290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
                340                 345                 350

Leu Ala Asp His Ala Leu Lys Asp Ala Cys Ala Leu Thr Asn Pro Arg
                355                 360                 365

Gln Gly Asp Gln Lys Glu Val Glu Glu Leu Phe Leu Ser Ala Phe
370                 375                 380

<210> SEQ ID NO 70
<211> LENGTH: 1747
<212> TYPE: DNA
<213> ORGANISM: Zymomonas mobilis

<400> SEQUENCE: 70
aaaggcaaaa tcggtaacca catctcaatt attaaacaat acttcataat aaaaagacaa     60 cttttttcata atttgcataa gtcttgatgt aaaaaatata tatttagaaa gaacaagcag   120

```
ccttgctcat caccgctgtc gcgagtagaa aaatctcggc tttcagaaaa agaggccgct    180
tcgttaaaca gactataaat gtgctggaat aaagcgaacc ccttgatctg ataaaactga    240
tagacatatt gcttttgcgc tgcccgattg ctgaaaatgc gtaaaggtg attttactcg     300
ttttcaggaa aaactttgag aaaacgtctc gaaaacggga ttaaaacgca aaacaatag    360
aaagcgattt cgcgaaaatg gttgttttcg ggttgttgct ttaaactagt atgtagggtg    420
aggttatagc tatggcttct tcaacttttt atattccttt cgtcaacgaa atgggcgaag    480
gttcgcttga aaagcaatc aaggatctta acggcagcgg ctttaaaaat gcgctgatcg     540
tttctgatgc tttcatgaac aaatccggtg ttgtgaagca ggttgctgac ctgttgaaag    600
cacagggtat taattctgct gtttatgatg gcgttatgcc gaacccgact gttaccgcag    660
ttctggaagg ccttaagatc ctgaaggata caattcaga cttcgtcatc tccctcggtg     720
gtggttctcc ccatgactgc gccaaagcca tcgctctggt cgcaaccaat ggtggtgaag    780
tcaaagacta cgaaggtatc gacaaatcta agaaacctgc cctgcctttg atgtcaatca    840
acacgacggc tggtacggct tctgaaatga cgcgtttctg catcatcact gatgaagtcc    900
gtcacgttaa gatggccatt gttgaccgtc acgttacccc gatggtttcc gtcaacgatc    960
ctctgttgat ggttggtatg ccaaaaggcc tgaccgccgc caccggtatg gatgctctga   1020
cccacgcatt tgaagcttat tcttcaacgg cagctactcc gatcaccgat gcttgcgcct   1080
tgaaggctgc gtccatgatc gctaagaatc tgaagaccgc ttgcgacaac ggtaaggata   1140
tgccagctcg tgaagctatg gcttatgccc aattcctcgc tggtatggcc ttcaacaacg   1200
cttcgcttgg ttatgtccat gctatggctc accagttggg cggctactac aacctgccgc   1260
atggtgtctg caacgctgtt ctgcttccgc atgttctggc ttataacgcc tctgtcgttg   1320
ctggtcgtct gaaagacgtt ggtgttgcta tgggtctcga tatcgccaat ctcggtgata   1380
aagaaggcgc agaagccacc attcaggctg ttcgcgatct ggctgcttcc attggtattc   1440
cagcaaatct gaccgagctg ggtgctaaga agaagatgt gccgcttctt gctgaccacg    1500
ctctgaaaga tgcttgtgct ctgaccaacc cgcgtcaggg tgatcagaaa gaagttgaag   1560
aactcttcct gagcgctttc taatttcaaa acaggaaaac ggttttccgt cctgtcttga   1620
ttttcaagca aacaatgcct ccgatttcta atcggaggca tttgttttg tttattgcaa    1680
aaacaaaaaa tattgttaca aattttaca ggctattaag cctaccgtca taataattt     1740
gccattt                                                             1747

<210> SEQ ID NO 71
<211> LENGTH: 511
<212> TYPE: PRT
<213> ORGANISM: Marinobacter algicola

<400> SEQUENCE: 71

Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
            35                  40                  45

Gly Gly Ile His Leu Leu Ile Arg Gly Asn Lys Arg His Pro Ala Ala
        50                  55                  60

Arg Glu Arg Phe Leu Asn Glu Ile Ala Ser Ser Val Phe Glu Arg
65                  70                  75                  80
```

```
Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
            115                 120                 125

Ser Ala Ala Ser Val Asn Phe Arg Glu Glu Leu Asp Lys Ala Leu Lys
130                 135                 140

Ile Asn Thr Leu Cys Leu Glu Asn Val Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
            195                 200                 205

Leu Leu Gln Asp Lys Ile Ser Asp Val Lys Ala Arg Tyr Ser Gly Lys
            210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
                260                 265                 270

Ser Ile Ile Glu Ser Ala Leu Glu Glu Pro Ser Pro Gly Trp Ile Glu
            275                 280                 285

Gly Val Lys Val Ala Asp Ala Ile Ile Leu Ala Tyr Ala Arg Glu Lys
            290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
            355                 360                 365

Lys Thr Asn Tyr Ala Ala Tyr Asp Gln Leu Phe Tyr Arg Arg Pro Thr
            370                 375                 380

Lys Pro Phe Val Ala Val Asn Arg Lys Leu Phe Asp Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
            435                 440                 445

Arg Asn Asp Ser Leu Met Ala Leu Ala Ser Arg Met Gly Glu Leu Asp
450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala
```

<210> SEQ ID NO 72
<211> LENGTH: 1477
<212> TYPE: DNA
<213> ORGANISM: Marinobacter algicola

<400> SEQUENCE: 72

```
atggcgaccc agcagcagca gaacggcgcc tcggcgagcg gcgtcctgga acagttgcgc    60
gggaagcatg tcctgataac cggtaccacc ggtttccttg gcaaggtagt cctggaaaag   120
ctgatccgca cagtcccgga catcggcggc atccacctcc tgatccgggg caacaagagg   180
catccggccg cccgtgaacg gttcttgaac gagatcgcca gcagttcggt cttcgagcgt   240
ctgcgccacg acgacaacga ggccttcgaa accttcctgg aagaaagggt gcactgtata   300
accggagagg tcaccgagag tcgtttcggc cttaccccgg agcgcttccg cgcgctggcg   360
ggtcaggtgg acgccttcat caattcggcc gcctccgtca acttccgcga ggaactggac   420
aaggcgctga agatcaatac gctgtgcctg gagaatgtcg cggcccttgc tgaactcaac   480
agtgcgatgg cggtcatcca ggtttcgacc tgctacgtta acggcaagaa tagcgggcag   540
atcaccgaat cggtcatcaa gcccgcgggg gagtccatcc cgcgtagcac cgatgggtac   600
tatgaaatcg aagaattggt gcacctgctg caggacaaaa tcagcgatgt gaaggcccga   660
tactccggga aggttctgga aaaaaaattg gtggacctag catccgggga agccaataac   720
tacgggtgga gcgatacata taccttcacc aagtggctgg gcgaacagct cctcatgaag   780
gccctgagcg gcagatcgct gaccatcgtg cggccgtcga tcatcgagtc ggcattggaa   840
gagcccagcc cggggtggat tgaaggcgtc aaggtcgccg atgccatcat actggcctac   900
gcgagggaga aggtatcgct cttcctggca agcggagcg catcatcga cgtcatccca   960
gtggatctgg tggccaattc gatcattctg tccctggcgg aggcgctctc cggttcgggc   1020
cagcggcgta tctatcagtg ctgcagcggc ggctcgaacc ccatctccct cgggaagttc   1080
atcgactatc tgatggcgga ggcgaagacc aactacgcgg cctacgatca gctgttctac   1140
cgccgcccca ccaagccgtt cgtggccgtc aaccgcaaac tcttcgacgt cgtcgtgggc   1200
ggcatgcggg tcccgctctc gatcgcgggc aaagccatgc gcctggcggg acaaaaccgc   1260
gaactgaagg tcctgaagaa tctggatacg acccggtccc tggccaccat tttcgggttc   1320
tacaccgctc cggactacat ctttcgcaat gacagcctga tggccctggc ctcgcgcatg   1380
ggcgagctgg accgcgtgtt gttccccgtt gacgcccgtc agatcgactg gcagctgtat   1440
ctgtgcaaaa tccacctcgg cgggctgaat cggtacg                            1477
```

<210> SEQ ID NO 73
<211> LENGTH: 475
<212> TYPE: PRT
<213> ORGANISM: Psychrobacter articus

<400> SEQUENCE: 73

Met Arg Leu Leu Thr Ala Val Asp Gln Leu Phe Leu Leu Leu Glu Ser
1               5                   10                  15

Arg Lys His Pro Met His Val Gly Gly Leu Phe Leu Phe Glu Leu Pro
                20                  25                  30

Glu Asn Ala Asp Ile Ser Phe Val His Gln Leu Val Lys Gln Met Gln
            35                  40                  45

Asp Ser Asp Val Pro Pro Thr Phe Pro Phe Asn Gln Val Leu Glu His
        50                  55                  60

```
Met Met Phe Trp Lys Glu Asp Lys Asn Phe Asp Val Glu His His Leu
 65                  70                  75                  80

His His Val Ala Leu Pro Lys Pro Ala Arg Val Arg Glu Leu Leu Met
                 85                  90                  95

Tyr Val Ser Arg Glu His Gly Arg Leu Leu Asp Arg Ala Met Pro Leu
                100                 105                 110

Trp Glu Cys His Val Ile Glu Gly Ile Gln Pro Glu Thr Glu Gly Ser
                115                 120                 125

Pro Glu Arg Phe Ala Leu Tyr Phe Lys Ile His His Ser Leu Val Asp
            130                 135                 140

Gly Ile Ala Ala Met Arg Leu Val Lys Lys Ser Leu Ser Gln Ser Pro
145                 150                 155                 160

Asn Glu Pro Val Thr Leu Pro Ile Trp Ser Leu Met Ala His His Arg
                165                 170                 175

Asn Gln Ile Asp Ala Ile Phe Pro Lys Glu Arg Ser Ala Leu Arg Ile
                180                 185                 190

Leu Lys Glu Gln Val Ser Thr Ile Lys Pro Val Phe Thr Glu Leu Leu
            195                 200                 205

Asn Asn Phe Lys Asn Tyr Asn Asp Asp Ser Tyr Val Ser Thr Phe Asp
210                 215                 220

Ala Pro Arg Ser Ile Leu Asn Arg Arg Ile Ser Ala Ser Arg Arg Ile
225                 230                 235                 240

Ala Ala Gln Ser Tyr Asp Ile Lys Arg Phe Asn Asp Ile Ala Glu Arg
                245                 250                 255

Ile Asn Ile Ser Lys Asn Asp Val Val Leu Ala Val Cys Ser Gly Ala
                260                 265                 270

Ile Arg Arg Tyr Leu Ile Ser Met Asp Ala Leu Pro Ser Lys Pro Leu
            275                 280                 285

Ile Ala Phe Val Pro Met Ser Leu Arg Thr Asp Asp Ser Ile Ala Gly
            290                 295                 300

Asn Gln Leu Ser Phe Val Leu Ala Asn Leu Gly Thr His Leu Asp Asp
305                 310                 315                 320

Pro Leu Ser Arg Ile Lys Leu Ile His Arg Ser Met Asn Asn Ser Lys
                325                 330                 335

Arg Arg Phe Arg Arg Met Asn Gln Ala Gln Val Ile Asn Tyr Ser Ile
            340                 345                 350

Val Ser Tyr Ala Trp Glu Gly Ile Asn Leu Ala Thr Asp Leu Phe Pro
            355                 360                 365

Lys Lys Gln Ala Phe Asn Leu Ile Ile Ser Asn Val Pro Gly Ser Glu
            370                 375                 380

Lys Pro Leu Tyr Trp Asn Gly Ala Arg Leu Glu Ser Leu Tyr Pro Ala
385                 390                 395                 400

Ser Ile Val Phe Asn Gly Gln Ala Met Asn Ile Thr Leu Ala Ser Tyr
                405                 410                 415

Leu Asp Lys Met Glu Phe Gly Ile Thr Ala Cys Ser Lys Ala Leu Pro
                420                 425                 430

His Val Gln Asp Met Leu Met Leu Ile Glu Glu Leu Gln Leu Leu
                435                 440                 445

Glu Ser Val Ser Lys Glu Leu Glu Phe Asn Gly Ile Thr Val Lys Asp
            450                 455                 460

Lys Ser Glu Lys Lys Leu Lys Lys Leu Ala Pro
465                 470                 475
```

<210> SEQ ID NO 74
<211> LENGTH: 1428
<212> TYPE: DNA
<213> ORGANISM: Psychrobacter articus

<400> SEQUENCE: 74

```
atgcgcctgc tgaccgccgt cgaccagctg ttcctgctgc tggagtcccg caagcacccg      60
atgcacgtgg gcggcctgtt cctgttcgaa ctgccggaga cgccgacat ctcgttcgtc     120
caccagctgg tgaagcagat gcaggactcc gacgtcccgc ccaccttccc cttcaaccag    180
gtgctggaac acatgatgtt ctggaaggag acaagaact tcgacgtcga acaccatctg     240
caccatgtgg ccctgccgaa gcccgcgcgc gtccgggagc tgctgatgta cgtgtcccgc    300
gaacacggcc ggctgctgga ccgcgcgatg ccgctgtggg aatgccatgt catcgagggc    360
atccagccgg aaaccgaggg cagccccgag cggttcgccc tgtatttcaa gatccaccat    420
cgctggtcg acggcatcgc cgcgatgcgc ctggtgaaga gagcctgtc gcagtcgccg     480
aacgaacccg tgaccctgcc gatctggagc ctgatggccc accatcggaa ccagatcgac    540
gcgatcttcc caaggagcg gagcgccctg cgcatcctga aggaacaggt ctcgaccatc    600
aagccggtgt tcaccgagct gctgaacaac ttcaagaact acaacgacga ctcgtatgtc    660
tccaccttcg acgcgccccg cagcatcctg aaccgccgga tcagcgcctc gcgccggatc    720
gccgcgcagt cgtacgacat caagcggttc aacgacatcg ccgaacgcat caacatctcc    780
aagaacgacg tcgtgctggc cgtgtgcagc ggcgcgatcc gccgctacct gatcagcatg    840
gacgcgctgc cgagcaagcc cctgatcgcc ttcgtcccga tgtcgctgcg caccgacgac    900
tccatcgcgg gcaaccagct gtcgttcgtg ctggccaacc tgggcaccca cctggacgac    960
ccctgtccc ggatcaagct gatccatcgc tccatgaaca acagcaagcg ccggttccgc   1020
cggatgaacc aggcccaggt catcaactac agcatcgtgt cgtatgcctg ggagggcatc   1080
aacctggcga ccgacctgtt cccgaagaag caggccttca acctgatcat ctcgaacgtg   1140
ccgggcagcg agaagcccct gtactggaac ggcgcgcgcc tggaaagcct gtatccggcc   1200
tcgatcgtgt tcaacggcca ggccatgaac atcaccctgg cgtcctacct ggacaagatg   1260
gagttcggca tcaccgcctg cagcaaggcg ctgccgcacg tccaggacat gctgatgctg   1320
atcgaggaag agctgcagct gctggagtcc gtcagcaagg aactggagtt caacggcatc   1380
accgtgaagg acaagtcgga aaagaagctg aagaagctgg ccccgtga            1428
```

<210> SEQ ID NO 75
<211> LENGTH: 461
<212> TYPE: PRT
<213> ORGANISM: Rhodococcus opacus

<400> SEQUENCE: 75

```
Met Ser Val Met Ser Pro Thr Glu Ala Met Phe Val Leu Phe Glu Thr
1               5                   10                  15

Pro Ser His Pro Met His Met Gly Ala Leu Glu Leu Phe Glu Pro Pro
                20                  25                  30

Arg Glu Ser Gly Pro Asp His Ala Arg Leu Met Phe Glu Ala Leu Ile
            35                  40                  45

Ser Gln Glu Gly Ala Ser Asp Thr Phe Arg Arg Ala Val Arg Pro
        50                  55                  60

Leu Arg Gly Ala Ser Tyr Pro Trp Trp Ser Val Asp Asp Arg Val Asp
65                  70                  75                  80
```

Leu Gly Tyr His Val Arg His Thr Ala Val Pro Gly Arg Gly Arg Met
                85                  90                  95

Glu Asp Leu Leu Ser Leu Val Ser Gln Met His Gly Met Pro Leu Asp
            100                 105                 110

Pro Gln His Pro Met Trp Glu Ile His Val Ile Glu Gly Leu Ala Asp
        115                 120                 125

Gly Arg Thr Ala Val Phe Ser Lys Ile His Leu Ser Leu Met Asp Gly
    130                 135                 140

Pro Ala Gly Leu Arg Leu Leu His His Ala Leu Ser Thr Asp Pro Asp
145                 150                 155                 160

Ala Arg Asp Cys Pro Ala Pro Trp Thr Pro Gly Val Ser Gly Thr Ser
                165                 170                 175

Arg Arg Glu Ser Ala Leu Pro Val Ala Ala Val Arg Ala Gly Val Arg
            180                 185                 190

Ala Ala Thr Ser Ile Val Gly Val Leu Pro Ala Leu Ala Lys Val Ala
        195                 200                 205

Tyr Asp Gly Val Arg Asp Gln His Leu Thr Leu Pro Leu Gln Ser Pro
    210                 215                 220

Pro Thr Met Leu Asn Val Pro Val Gly Arg Ala Arg Lys Leu Ala Ala
225                 230                 235                 240

Arg Ser Trp Pro Ile Arg Arg Leu Val Ser Val Ala Ala Ala Ala Arg
                245                 250                 255

Thr Thr Ile Asn Ala Val Val Leu Ala Met Cys Ser Gly Ala Leu Arg
            260                 265                 270

His Tyr Leu Val Glu Gln Tyr Ala Leu Pro Glu Ala Pro Leu Thr Ala
        275                 280                 285

Met Leu Pro Val Pro Leu Asp Leu Gly Gly Thr Met Ile Gly Pro Arg
    290                 295                 300

Gly Arg Asp His Gly Val Gly Ala Met Val Val Gly Leu Ala Thr Asp
305                 310                 315                 320

Glu Ala Asp Pro Ala Ala Arg Leu Ala Arg Ile Ser Glu Ser Val Glu
                325                 330                 335

His Thr Asn Arg Val Phe Gly Ala Leu Ser His Thr Gln Phe Gln Val
            340                 345                 350

Met Ser Ala Leu Ala Ile Ser Pro Ile Leu Leu Glu Pro Val Arg Arg
        355                 360                 365

Phe Val Asp Asp Thr Pro Pro Pro Phe Asn Val Met Ile Ser Tyr Met
    370                 375                 380

Pro Gly Pro Ser Arg Pro Arg Tyr Trp Asn Gly Ala Arg Leu Asp Ala
385                 390                 395                 400

Val Tyr Pro Ala Pro Thr Val Leu Gly Gly Gln Ala Leu Ser Ile Thr
                405                 410                 415

Leu Thr Ser Arg Ser Gly Gln Leu Asp Val Gly Val Gly Asp Arg
            420                 425                 430

Gln Ala Val Pro His Leu Gln Arg Ile Ile Thr His Leu Glu Thr Ser
        435                 440                 445

Leu Thr Asp Leu Glu Asn Ala Val Ala Ala Ser Gly Thr
    450                 455                 460

<210> SEQ ID NO 76
<211> LENGTH: 1386
<212> TYPE: DNA
<213> ORGANISM: Rhodococcus opacus

<400> SEQUENCE: 76

```
atgtccgtga tgtccccgac cgaggcgatg ttcgtcctgt tcgagacccc gagccacccg    60
atgcacatgg gcgcgctgga gctgttcgag ccgccgcgcg agtcgggccc ggaccacgcc   120
cgcctgatgt tcgaggcgct gatctcccag gaaggcgcca gcgacacctt ccgccggcgc   180
gccgtccggc cgctgcgcgg cgcgtcgtac ccctggtggt ccgtcgacga ccgggtggac   240
ctgggctatc acgtccgcca taccgccgtg ccgggccggg ccgcatggga ggacctgctg   300
tcgctggtgt cccagatgca cggcatgccc tggaccccgc agcacccat gtgggagatc    360
catgtcatcg aaggcctggc cgacggccgc accgcggtgt tcagcaagat ccatctgtcg   420
ctgatggacg gccggccgg cctgcggctg ctgcaccatg cgctgagcac cgacccggac    480
gcccgcgact gccccgcgcc gtggaccccc ggcgtcagcg gcacctcgcg gcgcgaatcg   540
gccctgccgg tcgccgcggt gcgggcgggc gtgcgcgccg cgacctccat cgtcggcgtg   600
ctgcccgccc tggcgaaggt cgcctacgac ggcgtgcggg accagcacct gaccctgccg   660
ctgcagagcc cgcccaccat gctgaacgtc ccgtgggcc gggcccgcaa gctggccgcg    720
cggagctggc cgatccggcg cctggtctcg gtggccgcgg ccgcgcgcac caccatcaac   780
gccgtcgtgc tggcgatgtg ctcgggcgcc ctgcgccact acctggtcga gcagtatgcc   840
ctgccggaag cgcccctgac cgccatgctg cccgtgccgc tggacctggg cggcaccatg   900
atcggcccgc gtgccgcga ccacggcgtc ggcgcgatgg tcgtgggcct ggcgaccgac    960
gaggccgacc ccgccgcgcg gctggcccgc atcagcgagt cggtcgaaca caccaaccgc  1020
gtgttcggcg cgctgtccca tacccagttc caggtcatgt ccgccctggc gatcagcccg  1080
atcctgctgg aacccgtccg gcgcttcgtg gacgacaccc cgccccgtt caacgtgatg   1140
atctcgtaca tgccgggtcc gtcccggccg cgctattgga acggcgcgcg gctggacgcc  1200
gtctaccccg cgccgaccgt gctgggcggc caggccctga gcatcaccct gacctcccgc  1260
agcggccagc tggacgtcgg cgtcgtgggc gaccggcagg ccgtgccgca cctgcagcgc  1320
atcatcaccc atctggagac ctccctgacc gacctggaaa acgccgtggc cgcgagcggc  1380
acctga                                                              1386
```

<210> SEQ ID NO 77
<211> LENGTH: 451
<212> TYPE: PRT
<213> ORGANISM: Rhodococcus opacus

<400> SEQUENCE: 77

```
Met Pro Val Thr Asp Ser Ile Phe Leu Leu Gly Glu Ser Arg Glu His
1               5                   10                  15

Pro Met His Val Gly Ser Leu Glu Leu Phe Thr Pro Pro Asp Asp Ala
            20                  25                  30

Gly Pro Asp Tyr Val Lys Ser Met His Glu Thr Leu Leu Lys His Thr
        35                  40                  45

Asp Val Asp Pro Thr Phe Arg Lys Lys Pro Ala Gly Pro Val Gly Ser
    50                  55                  60

Leu Gly Asn Val Trp Trp Ala Asp Glu Ser Asp Val Asp Leu Glu Tyr
65                  70                  75                  80

His Val Arg His Ser Ala Leu Pro Ala Pro Tyr Arg Val Arg Glu Leu
                85                  90                  95

Leu Thr Leu Thr Ser Arg Leu His Gly Thr Leu Leu Asp Arg His Arg
            100                 105                 110

Pro Leu Trp Glu Met Tyr Leu Ile Glu Gly Leu Ser Asp Gly Arg Phe
```

|   |   |   |   |   | 115 |   |   |   |   | 120 |   |   |   |   | 125 |   |
|---|---|---|---|---|---|---|---|---|---|---|---|---|---|---|---|---|

Ala Ile Tyr Thr Lys Leu His His Ser Leu Met Asp Gly Val Ser Gly
130                 135                 140

Leu Arg Leu Leu Met Arg Thr Leu Ser Thr Asp Pro Asp Val Arg Asp
145                 150                 155                 160

Ala Pro Pro Pro Trp Asn Leu Pro Arg Pro Ala Ala Asn Gly Ala
                165                 170                 175

Ala Pro Asp Leu Trp Ser Val Val Asn Gly Val Arg Arg Thr Val Gly
            180                 185                 190

Asp Val Ala Gly Leu Ala Pro Ala Ser Leu Arg Ile Ala Arg Thr Ala
        195                 200                 205

Met Gly Gln His Asp Met Arg Phe Pro Tyr Glu Ala Pro Arg Thr Met
    210                 215                 220

Leu Asn Val Pro Ile Gly Gly Ala Arg Arg Phe Ala Ala Gln Ser Trp
225                 230                 235                 240

Pro Leu Glu Arg Val His Ala Val Arg Lys Ala Ala Gly Val Ser Val
                245                 250                 255

Asn Asp Val Val Met Ala Met Cys Ala Gly Ala Leu Arg Gly Tyr Leu
            260                 265                 270

Glu Glu Gln Asn Ala Leu Pro Asp Glu Pro Leu Ile Ala Met Val Pro
        275                 280                 285

Val Ser Leu Arg Asp Gln Gln Ala Asp Ala Gly Gly Asn Ala Val
    290                 295                 300

Gly Val Thr Leu Cys Asn Leu Ala Thr Asp Val Asp Asp Pro Ala Glu
305                 310                 315                 320

Arg Leu Thr Ala Ile Ser Ala Ser Met Ser Gln Gly Lys Glu Leu Phe
                325                 330                 335

Gly Ser Leu Thr Ser Met Gln Ala Leu Ala Trp Ser Ala Val Asn Met
            340                 345                 350

Ser Pro Ile Ala Leu Thr Pro Val Pro Gly Phe Val Arg Phe Thr Pro
        355                 360                 365

Pro Pro Phe Asn Val Ile Ile Ser Asn Val Pro Gly Pro Arg Lys Thr
    370                 375                 380

Met Tyr Trp Asn Gly Ser Arg Leu Asp Gly Ile Tyr Pro Thr Ser Val
385                 390                 395                 400

Val Leu Asp Gly Gln Ala Leu Asn Ile Thr Leu Thr Thr Asn Gly Gly
                405                 410                 415

Asn Leu Asp Phe Gly Val Ile Gly Cys Arg Arg Ser Val Pro Ser Leu
            420                 425                 430

Gln Arg Ile Leu Phe Tyr Leu Glu Ala Ala Leu Gly Glu Leu Glu Ala
        435                 440                 445

Ala Leu Leu
    450

<210> SEQ ID NO 78
<211> LENGTH: 1356
<212> TYPE: DNA
<213> ORGANISM: Rhodococcus opacus

<400> SEQUENCE: 78
atgccggtca ccgactccat cttcctgctg gcgaaagcc gcgagcaccc gatgcacgtg      60
ggctccctgg aactgttcac ccccccggac gacgccggcc cggactacgt caagtcgatg     120
cacgagaccc tgctgaagca taccgacgtg gaccccacct ccgcaagaa gccggcgggc     180

```
cccgtcggct cgctgggcaa cgtgtggtgg gccgacgagt ccgacgtcga cctggaatac      240
cacgtgcgcc atagcgcgct gccggccccc tatcgcgtcc gggaactgct gaccctgacc      300
tcgcggctgc acggcaccct gctggaccgc catcggccgc tgtgggagat gtacctgatc      360
gaaggcctga cgacggccg cttcgccatc tataccaagc tgcaccatag cctgatggac       420
ggcgtctcgg gcctgcgcct gctgatgcgg accctgtcga ccgacccgga cgtgcgcgac      480
gccccgcccc cgtggaacct gccgcggccc gccgcggcca acggcgcggc cccggacctg      540
tggtcggtcg tgaacggcgt ccgccggacc gtcggcgacg tggccggcct ggcgcccgcc      600
tccctgcgca tcgcgcggac cgcgatgggc cagcacgaca tgcgcttccc gtacgaggcg      660
ccccggacca tgctgaacgt gccgatcggc ggcgcccgcc ggttcgcggc ccagtcctgg      720
cccctggaac gcgtccatgc cgtgcggaag gcggccggcg tcagcgtgaa cgacgtcgtg      780
atggccatgt gcgcgggcgc cctgcgcggc tatctggagg aacagaacgc gctgccggac      840
gagcccctga tcgcgatggt cccggtgtcc ctgcgggacg aacagcaggc ggacgccggc      900
ggcaacgccg tcggcgtgac cctgtgcaac ctggcgaccg acgtcgacga ccccgccgag      960
cgcctgaccg cgatcagcgc ctcgatgtcc cagggcaagg aactgttcgg cagcctgacc     1020
tcgatgcagg cgctggcctg gtcggcggtg aacatgtccc cgatcgccct gaccccggtc     1080
cccggcttcg tgcggttcac ccccccgccc ttcaacgtca tcatcagcaa cgtgccgggc     1140
ccccgcaaga ccatgtactg gaacggctcc cggctggacg gcatctatcc gaccagcgtc     1200
gtgctggacg gccaggccct gaacatcacc ctgaccacca acggcggcaa cctggacttc     1260
ggcgtcatcg gctgccgccg gtccgtgccg agcctgcagc gcatcctgtt ctacctggaa     1320
gcggccctgg gcgagctgga agcggccctg ctgtga                                1356
```

<210> SEQ ID NO 79
<211> LENGTH: 464
<212> TYPE: PRT
<213> ORGANISM: Rhodococcus opacus

<400> SEQUENCE: 79

```
Met Pro Leu Pro Met Ser Pro Leu Asp Ser Met Phe Leu Leu Gly Glu
1               5                   10                  15

Ser Arg Glu His Pro Met His Val Gly Gly Val Glu Ile Phe Gln Leu
            20                  25                  30

Pro Glu Gly Ala Asp Thr Tyr Asp Met Arg Ala Met Leu Asp Arg Ala
        35                  40                  45

Leu Ala Asp Gly Asp Gly Ile Val Thr Pro Arg Leu Ala Lys Arg Ala
    50                  55                  60

Arg Arg Ser Phe Ser Ser Leu Gly Gln Trp Ser Trp Glu Thr Val Asp
65                  70                  75                  80

Asp Ile Asp Leu Gly His His Ile Arg His Asp Ala Leu Pro Ala Pro
                85                  90                  95

Gly Gly Glu Ala Glu Leu Met Ala Leu Cys Ser Arg Leu His Gly Ser
            100                 105                 110

Leu Leu Asp Arg Ser Arg Pro Leu Trp Glu Met His Leu Ile Glu Gly
        115                 120                 125

Leu Ser Asp Gly Arg Phe Ala Val Tyr Thr Lys Ile His His Ala Val
    130                 135                 140

Ala Asp Gly Val Thr Ala Met Lys Met Leu Arg Asn Ala Leu Ser Glu
145                 150                 155                 160

Asn Ser Asp Asp Arg Asp Val Pro Ala Pro Trp Gln Pro Arg Gly Pro
```

```
                    165                 170                 175
Arg Pro Gln Arg Thr Pro Ser Ser Lys Gly Phe Ser Leu Ser Gly Leu
            180                 185                 190

Ala Gly Ser Thr Leu Arg Thr Ala Arg Glu Thr Val Gly Glu Val Ala
            195                 200                 205

Gly Leu Val Pro Ala Leu Ala Gly Thr Val Ser Arg Ala Phe Arg Asp
210                 215                 220

Gln Gly Gly Pro Leu Ala Leu Ser Ala Pro Lys Thr Pro Phe Asn Val
225                 230                 235                 240

Pro Ile Thr Gly Ala Arg Gln Phe Ala Ala Gln Ser Trp Pro Leu Glu
                245                 250                 255

Arg Leu Arg Leu Val Ala Lys Leu Ser Asp Ser Thr Ile Asn Asp Val
                260                 265                 270

Val Leu Ala Met Ser Ser Gly Ala Leu Arg Ser Tyr Leu Glu Asp Gln
                275                 280                 285

Asn Ala Leu Pro Ala Asp Pro Leu Ile Ala Met Val Pro Val Ser Leu
            290                 295                 300

Lys Ser Gln Arg Glu Ala Ala Thr Gly Asn Asn Ile Gly Val Leu Met
305                 310                 315                 320

Cys Asn Leu Gly Thr His Leu Arg Glu Pro Ala Asp Arg Leu Glu Thr
                325                 330                 335

Ile Arg Thr Ser Met Arg Glu Gly Lys Glu Ala Tyr Gly Ser Met Thr
                340                 345                 350

Ala Thr Gln Ile Leu Ala Met Ser Ala Leu Gly Ala Ala Pro Ile Gly
            355                 360                 365

Ala Ser Met Leu Phe Gly His Asn Ser Arg Val Arg Pro Pro Phe Asn
            370                 375                 380

Leu Ile Ile Ser Asn Val Pro Gly Pro Ser Ser Pro Leu Tyr Trp Asn
385                 390                 395                 400

Gly Ala Arg Leu Asp Ala Ile Tyr Pro Leu Ser Val Pro Val Asp Gly
                405                 410                 415

Gln Gly Leu Asn Ile Thr Cys Thr Ser Asn Asp Asp Ile Ile Ser Phe
            420                 425                 430

Gly Val Thr Gly Cys Arg Ser Ala Val Pro Asp Leu Lys Ser Ile Pro
            435                 440                 445

Ala Arg Leu Gly His Glu Leu Arg Ala Leu Glu Arg Ala Val Gly Ile
        450                 455                 460

<210> SEQ ID NO 80
<211> LENGTH: 1395
<212> TYPE: DNA
<213> ORGANISM: Rhodococcus opacus

<400> SEQUENCE: 80
atgcccctgc cgatgtcccc cctggactcc atgttcctgc tgggcgaaag ccgcgagcac      60
ccgatgcacg tgggcggcgt cgaaatcttc cagctgcccg agggcgccga cacctacgac     120
atgcgggcga tgctggaccg cgccctggcg gacggcgacg gcatcgtcac cccgcggctg     180
gccaagcgcg cgcgccggtc gttcagctcg ctgggccagt ggtcctggga aaccgtggac     240
gacatcgacc tgggccacca tatccggcac gacgccctgc cggcccctgg cggcgaggcc     300
gaactgatgg cgctgtgctc gcgcctgcac ggctccctgc tggaccgcag ccggccgctg     360
tgggagatgg atctgatcga aggcctgagc gacggccgct cgccgtccta taccaagatc     420
caccatgccg tcgcggacgg cgtgaccgcc atgaagatgc tgcggaacgc gctgagcgag     480
```

```
aactcggacg accgcgacgt gccggccccc tggcagccgc gtggcccgcg gccccagcgc      540 acccctcca gcaagggctt ctccctgagc ggcctggccg gctcgaccct gcggaccgcg      600
cgcgagaccg tcggcgaagt ggccggcctg gtcccggccc tggcgggcac cgtgagccgg      660
gccttccgcg accagggcgg cccgctggcc ctgtcggcgc cgaagacccc cttcaacgtc      720
cccatcaccg gcgcccgcca gttcgccgcg cagtcgtggc cgctggaacg cctgcggctg      780
gtggccaagc tgtcggactc caccatcaac gacgtcgtgc tggccatgtc gtccggcgcg      840
ctgcggtcct acctggagga ccagaacgcc ctgccggcgg acccctgat cgcgatggtc       900 ccggtgtccc tgaagagcca gcgcgaagcc gcgaccggca caacatcgg cgtcctgatg       960 tgcaacctgg gcacccacct gcgggagccg gccgaccgcc tggaaaccat ccggaccagc     1020
atgcgcgagg gcaaggaagc ctatggctcg atgaccgcga cccagatcct ggccatgtcc     1080
gcgctgggcg ccgcgccgat cggcgccagc atgctgttcg ccataactc gcgcgtccgg      1140 ccgcccttca acctgatcat ctccaacgtg ccgggcccca gctcgccgct gtactggaac     1200
ggcgcccgcc tggacgcgat ctatccgctg agcgtccccg tggacggcca gggcctgaac     1260
atcacctgca cctcgaacga cgacatcatc tccttcggcg tcaccggctg ccggtccgcc     1320
gtgccggacc tgaagagcat ccccgcgcgc ctgggccatg agctgcgggc cctggaacgc     1380
gcggtgggca tctga                                                      1395
```

<210> SEQ ID NO 81
<211> LENGTH: 468
<212> TYPE: PRT
<213> ORGANISM: Rhodococcus opacus

<400> SEQUENCE: 81

```
Met Ala Pro Thr Asp Ser Leu Phe Leu Leu Gly Glu Ser Arg Glu His
1               5                   10                  15

Pro Met His Val Gly Gly Leu Ala Val Phe Thr Pro Ala Glu Gly Ser
            20                  25                  30

Ser Ala Ala Asp Val Arg Ala Met Phe Asp Ala Ala Leu Val Gly Asp
        35                  40                  45

Arg Val Ala Ala Pro Phe Arg Lys Arg Ala Arg Ser Val Thr Ser
    50                  55                  60

Leu Gly Gln Trp Gly Trp Asp Thr Leu Arg Asp Asp Glu Val Asp Leu
65                  70                  75                  80

Glu His His Val Arg Arg Asp Ala Leu Pro Gln Pro Gly Gly Met Ala
                85                  90                  95

Glu Leu Met Thr Leu Val Ser Arg Leu His Gly Thr Leu Leu Asp Arg
            100                 105                 110

Ser Arg Pro Leu Trp Glu Met His Leu Ile Glu Gly Leu Ala Asp Gly
        115                 120                 125

Arg Tyr Ala Val Tyr Thr Lys Ile His His Ala Leu Ala Asp Gly Ala
    130                 135                 140

Ser Ala Met Arg Leu Leu Arg Asp Ser Met Ser Glu Asp Pro His Arg
145                 150                 155                 160

Arg Asn Met Pro Thr Pro Trp Gln Pro Arg Asn Pro Leu Ser Ala Val
                165                 170                 175

Pro Asp Ala Gly Val Ala Val Thr Pro Gly Pro Gly Ser Ala Leu Pro
            180                 185                 190

Ala Met Ala Trp Asp Ala Ala Arg Ser Ala Ala Gly Glu Val Ala Gly
        195                 200                 205
```

Leu Leu Pro Ala Ala Leu Gly Thr Val Asp Arg Ala Leu His Gly Lys
    210                 215                 220

Gly Gly Ala Leu Ser Leu Thr Ala Pro His Thr Leu Phe Asn Val Pro
225                 230                 235                 240

Ile Ser Gly Ala Arg His Val Ala Ala Arg Ser Phe Pro Ile Glu Arg
                245                 250                 255

Ile Arg Leu Leu Ala Lys His Ala Asp Ala Thr Ile Asn Asp Ile Val
            260                 265                 270

Leu Thr Met Cys Ala Gly Thr Leu Arg Ala Tyr Leu His Thr Arg Asp
        275                 280                 285

Ala Leu Pro Asp Asn Pro Leu Ile Ala Met Val Pro Val Ser Leu Arg
    290                 295                 300

Ala Pro Glu Thr Gly Thr Gly Asp Arg Ala Pro Gly Gly Asn Arg Val
305                 310                 315                 320

Gly Val Leu Met Cys Asn Leu Ala Thr His Leu Pro Asp Pro Ala His
                325                 330                 335

Arg Leu Glu Thr Val Arg Asn Cys Met Asn Glu Gly Lys Ala Ala Leu
            340                 345                 350

Gln Ala Met Ser Pro Ala Gln Val Leu Ala Met Ser Ala Leu Gly Ala
        355                 360                 365

Ala Pro Leu Gly Val Glu Met Phe Leu Gly Arg Arg Gly Pro Leu Arg
    370                 375                 380

Pro Pro Phe Asn Val Val Ile Ser Asn Val Ala Gly Pro Arg Thr Pro
385                 390                 395                 400

Leu Tyr Trp Asn Gly Ala Arg Leu Glu Ser Leu Tyr Pro Leu Ser Ile
                405                 410                 415

Pro Thr Thr Gly Gln Ala Leu Asn Ile Thr Cys Thr Ser Ser Asp Asp
            420                 425                 430

Gln Ile Val Phe Gly Leu Thr Gly Cys Arg Arg Thr Val Pro Asp Leu
        435                 440                 445

His Pro Met Leu Asp Gln Leu Asp Ala Glu Leu Asp Leu Leu Glu Thr
    450                 455                 460

Ala Val Gly Leu
465

<210> SEQ ID NO 82
<211> LENGTH: 1407
<212> TYPE: DNA
<213> ORGANISM: Rhodococcus opacus

<400> SEQUENCE: 82
atggccccga ccgactccct gttcctgctg ggcgaatccc gcgagcaccc gatgcacgtg      60
ggcggcctgg cggtcttcac cccggcggag ggcagctcgg ccgcggacgt ccgcgccatg     120
ttcgacgccg cgctggtcgg cgaccgggtg gccgcgccgt tccgcaagcg ggcccgccgg     180
agcgtgacct cgctgggcca gtggggctgg acaccctgc gcgacgacga ggtcgacctg      240
gaacaccatg tgcgccggga cgccctgccg cagccgggtg gcatggcgga actgatgacc     300
ctggtctccc gcctgcatgg caccctgctg accgcagcc ggcgctgtg ggagatgcac       360 ctgatcgaag gcctggccga cggccggtac gcggtgtata ccaagatcca ccatgccctg    420
gcggacggcg ccagcgcgat cgccctgctg cgggactcga tgtccgagga cccgcatcgc    480
cggaacatgc cgacccctg gcagccgcgc aaccccctgt cggccgtccc ggacgccggc    540
gtcgcggtga ccccggccc cggcagcgcc ctgcccgcga tggcctggga cgccgcgcgc    600

```
tccgccgcgg gcgaagtcgc cggcctgctg ccggccgcgc tgggcaccgt ggaccgggcc    660
ctgcacggca agggcggcgc cctgtccctg accgcgccgc ataccctgtt caacgtcccc    720
atcagcggcg cccgccacgt ggccgcgcgg tcgttcccga tcgagcgcat ccggctgctg    780
gccaagcatg ccgacgcgac catcaacgac atcgtgctga ccatgtgcgc cggcaccctg    840
cgcgcgtacc tgcacacccg cgacgccctg ccggacaacc ccctgatcgc gatggtcccg    900
gtgagcctgc gcgcccccga aaccggcacc ggcgaccgcg cccctggcgg caaccgggtc    960
ggcgtgctga tgtgcaacct ggccacccac ctgccggacc ccgcgcatcg cctggagacc   1020
gtccggaact gcatgaacga aggcaaggcc gcgctgcagg ccatgtcgcc ggcgcaggtc   1080
ctggccatgt ccgcgctggg cgccgcgccg ctgggcgtgg agatgttcct gggccgccgg   1140 ggcccccctgc gcccgccctt caacgtcgtg atctcgaacg tggcgggccc gcgcaccccc   1200
ctgtactgga acggcgcccg gctggaatcc ctgtatccgc tgagcatccc caccaccggc   1260
caggccctga acatcacctg cacctccagc gacgaccaga tcgtcttcgg cctgaccggc   1320
tgccgccgga ccgtgccgga cctgcacccc atgctggacc agctggacgc ggagctggac   1380
ctgctggaaa ccgcggtcgg cctgtga                                       1407
```